US012350048B2

(12) United States Patent
Agulto et al.

(10) Patent No.: US 12,350,048 B2
(45) Date of Patent: Jul. 8, 2025

(54) MANAGEMENT OF PSYCHIATRIC OR MENTAL CONDITIONS USING DIGITAL REALITY WITH COGNITIVE BEHAVIORAL TECHNIQUE

(71) Applicants: BehaVR, LLC, Elizabethtown, KY (US); FrontAct Co., Ltd., Tokyo (JP)

(72) Inventors: Roward Agulto, Elizabethtown, KY (US); Jillian Ahrens, Elizabethtown, KY (US); Eleanor Anderson, Elizabethtown, KY (US); Todd Grinnell, Marlborough, MA (US); Robert Hayes, Marlborough, MA (US); Shannon Hooper, Elizabethtown, KY (US); Katie Howarth, Elizabethtown, KY (US); Marc Recasens, Elizabethtown, KY (US); Bayley Taple, Elizabethtown, KY (US); Risa Weisberg Hawkins, Elizabethtown, KY (US); Sarah Zadd, Elizabethtown, KY (US); Gazeleh Vakili, Marlborough, MA (US); Nicholas DeMartinis, III, Marlborough, MA (US)

(73) Assignees: BehaVR, LLC; FrontAct Co., Ltd., Tokyo (JP)

( * ) Notice: Subject to any disclaimer, the term of this patent is extended or adjusted under 35 U.S.C. 154(b) by 81 days.

(21) Appl. No.: 18/380,153

(22) Filed: Oct. 13, 2023

(65) Prior Publication Data

US 2024/0148296 A1    May 9, 2024

Related U.S. Application Data

(60) Provisional application No. 63/415,860, filed on Oct. 13, 2022.

(51) Int. Cl.
*A61B 5/16*     (2006.01)
*A61B 5/00*     (2006.01)

(52) U.S. Cl.
CPC ............ *A61B 5/165* (2013.01); *A61B 5/4035* (2013.01)

(58) Field of Classification Search
CPC .............................. A61B 5/4035; A61B 5/165
See application file for complete search history.

(56) References Cited

U.S. PATENT DOCUMENTS

2023/0056779 A1* 2/2023 Alam .................... G16H 40/67

* cited by examiner

*Primary Examiner* — Kesha Frisby
(74) *Attorney, Agent, or Firm* — Morgan, Lewis & Bockius LLP

(57) ABSTRACT

Systems, methods, and devices for implementing cognitive behavioral therapy to help a subject to manage a psychiatric or mental condition of the subject are provided. Interactive digital reality (DR) activities are provided through an interactive DR scene, each configured for a subject to practice a specific reframing technique. In some embodiments, a method also includes providing one or more additional psychotherapeutic or psychoeducational techniques. Through the practice of satisfying conditions associated with each interactive DR activity, the systems, methods, and devices help a subject to manage a psychiatric or mental condition of the subject, such as by getting better at recognizing and/or challenging an anxious thought as the thought occurs, and/or by reframing the anxious thought into more a different thought using the interactive DR scene.

44 Claims, 93 Drawing Sheets

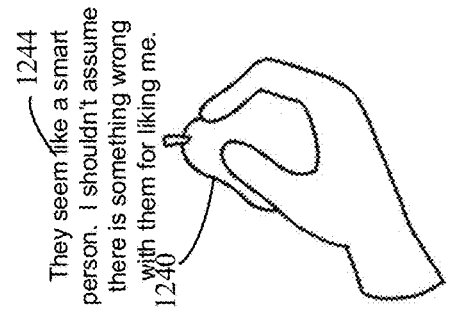
Fig. 12D
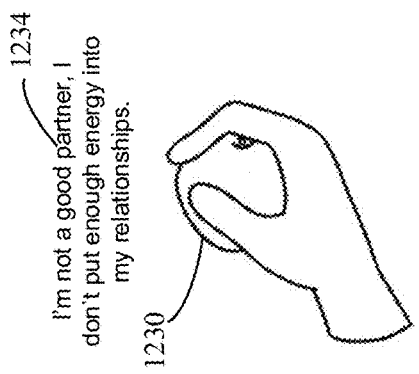
Fig. 12C
Fig. 12A
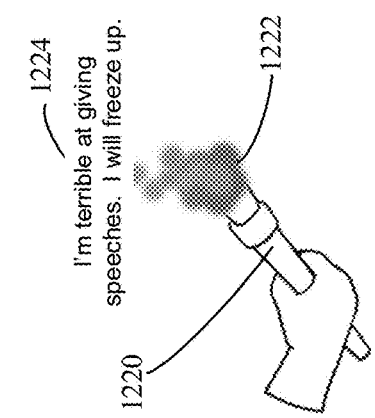
Fig. 12B
Fig. 11
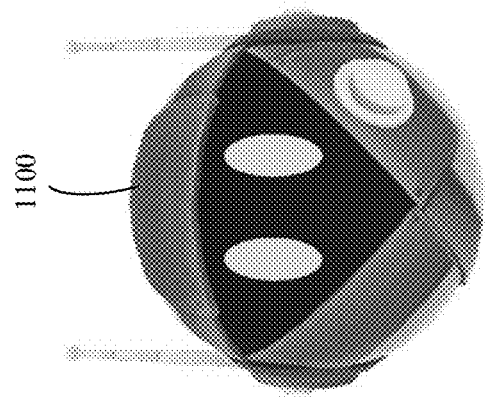

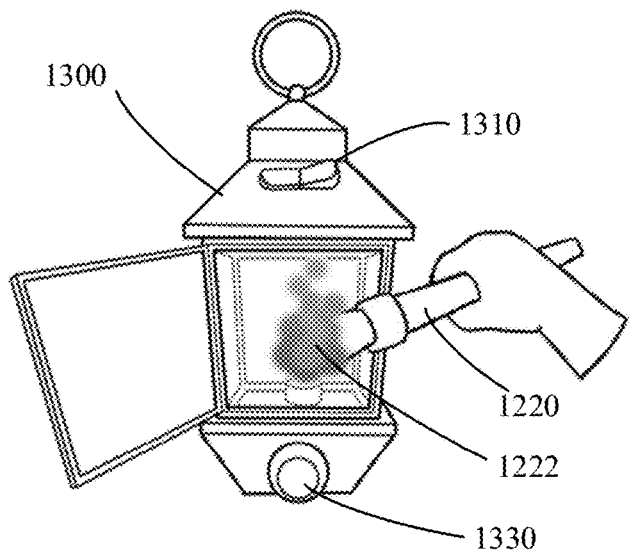 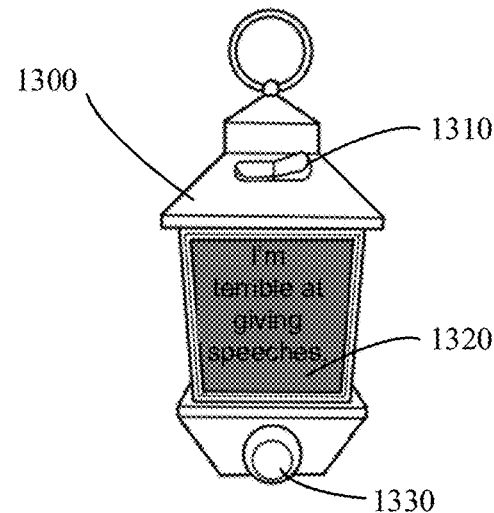
Fig. 13A          Fig. 13B
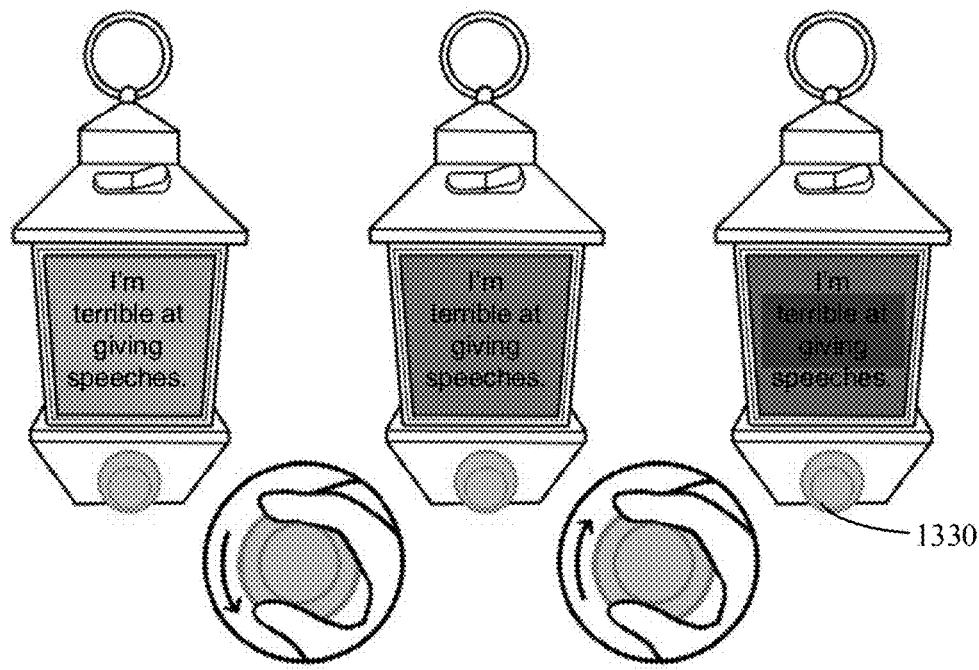
Fig. 13C

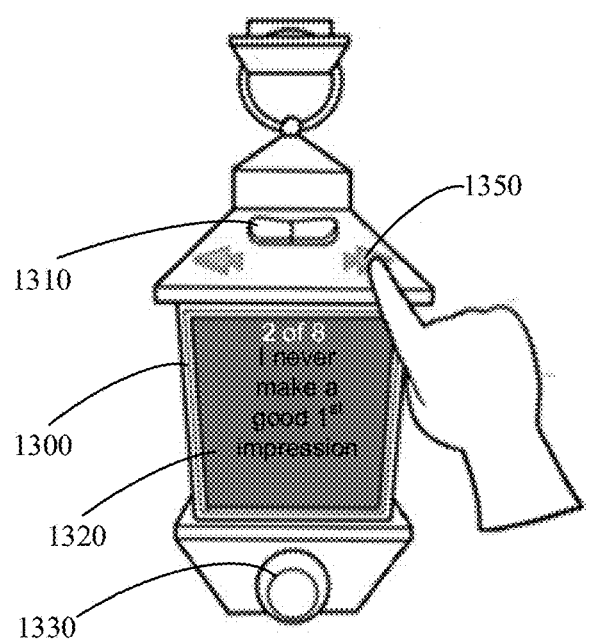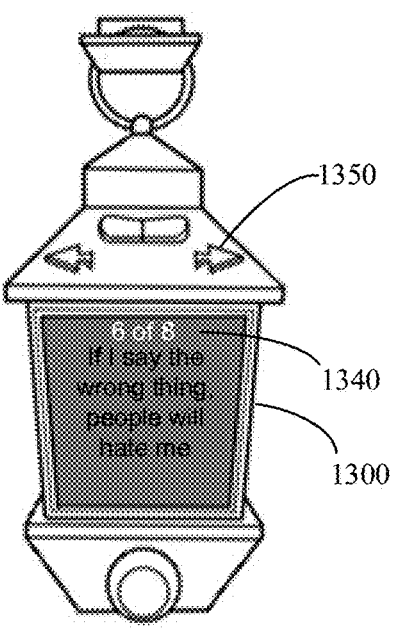
Fig. 13D  Fig. 13E
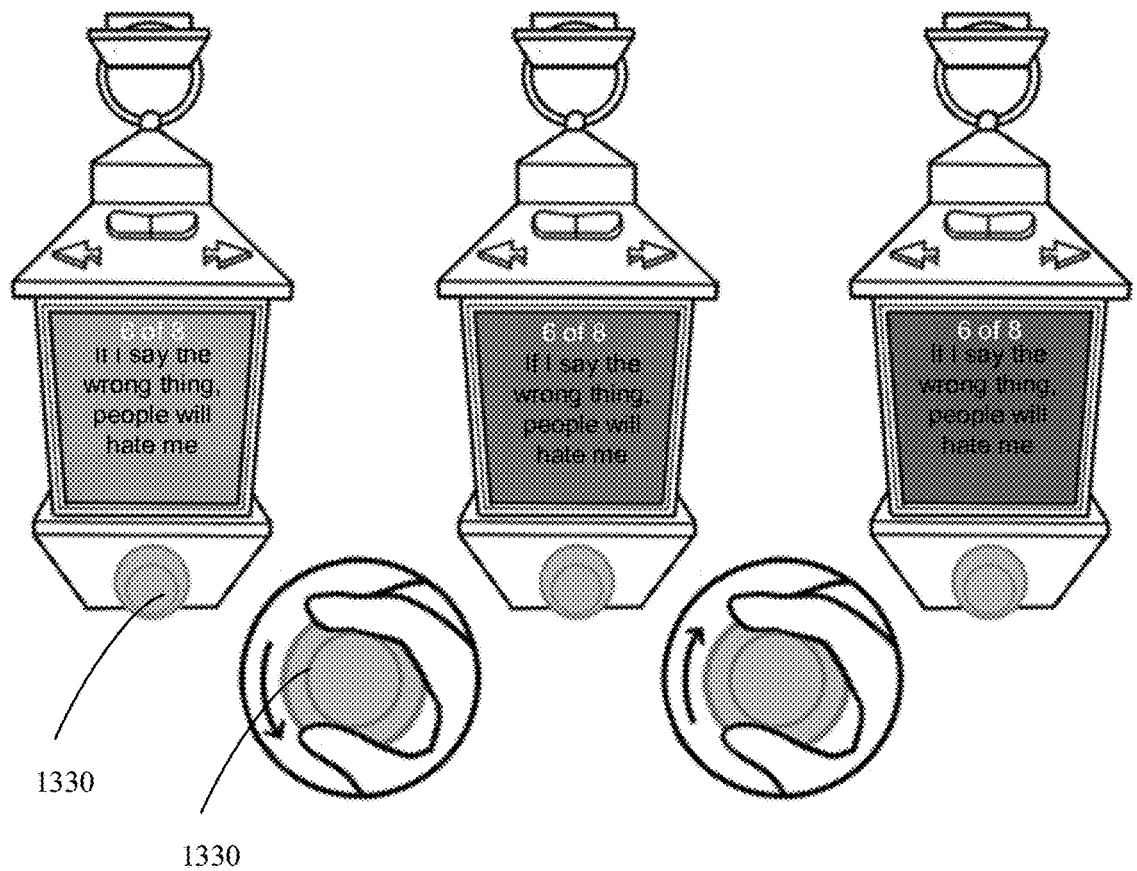
Fig. 13F

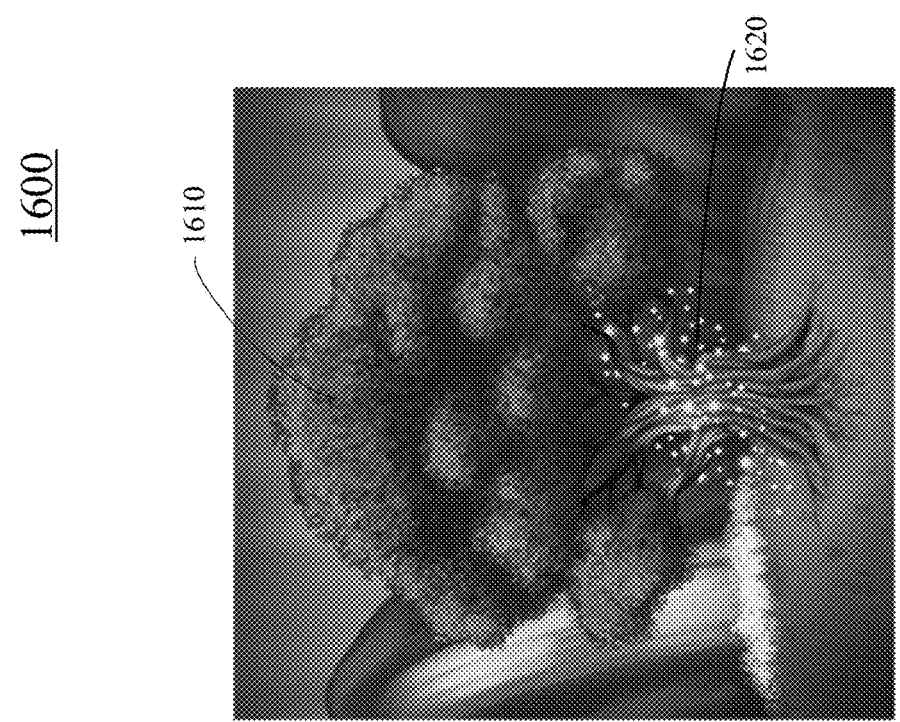
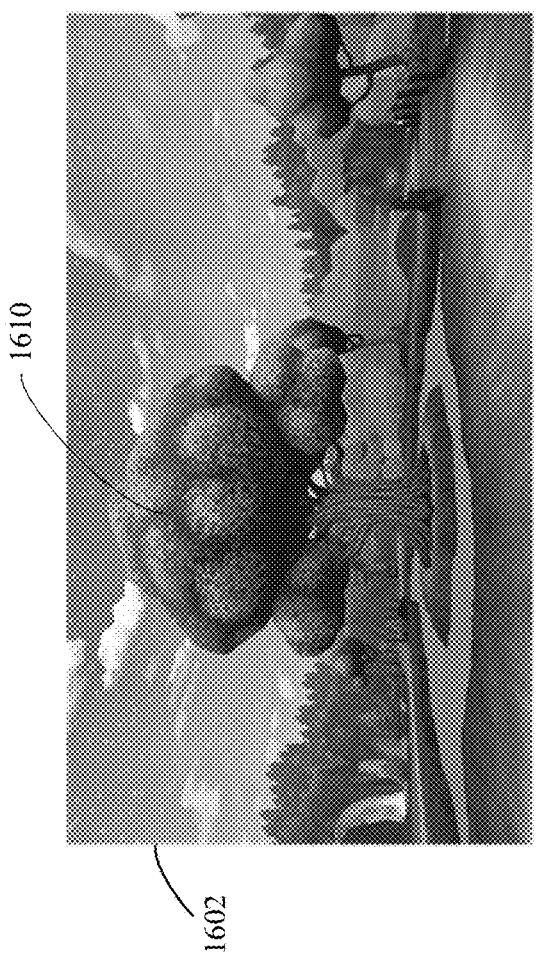
Fig. 16A
Fig. 16B
Fig. 16C

I should not compare myself to other's.

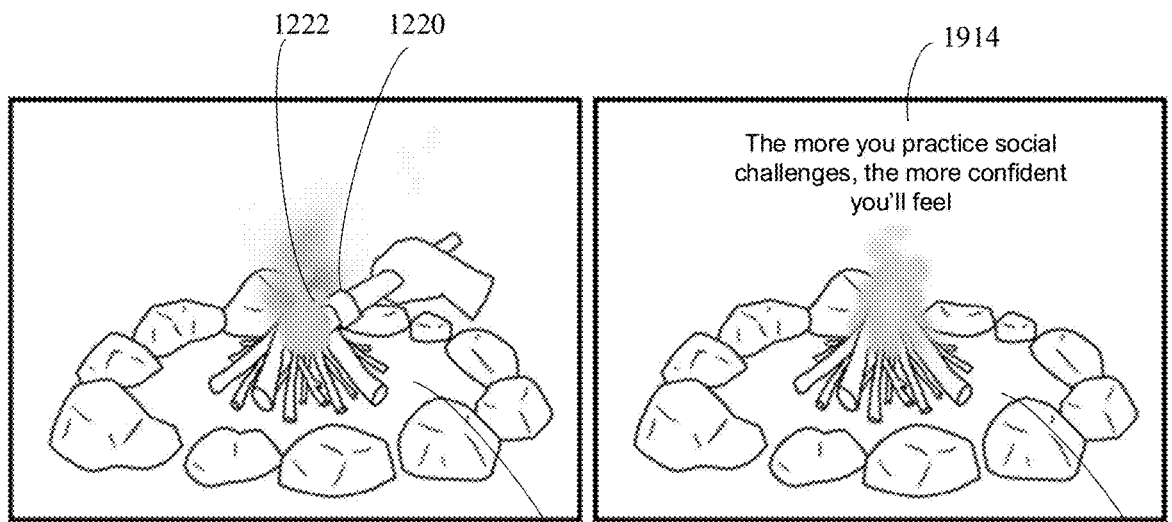
Fig. 19H
Fig. 19I
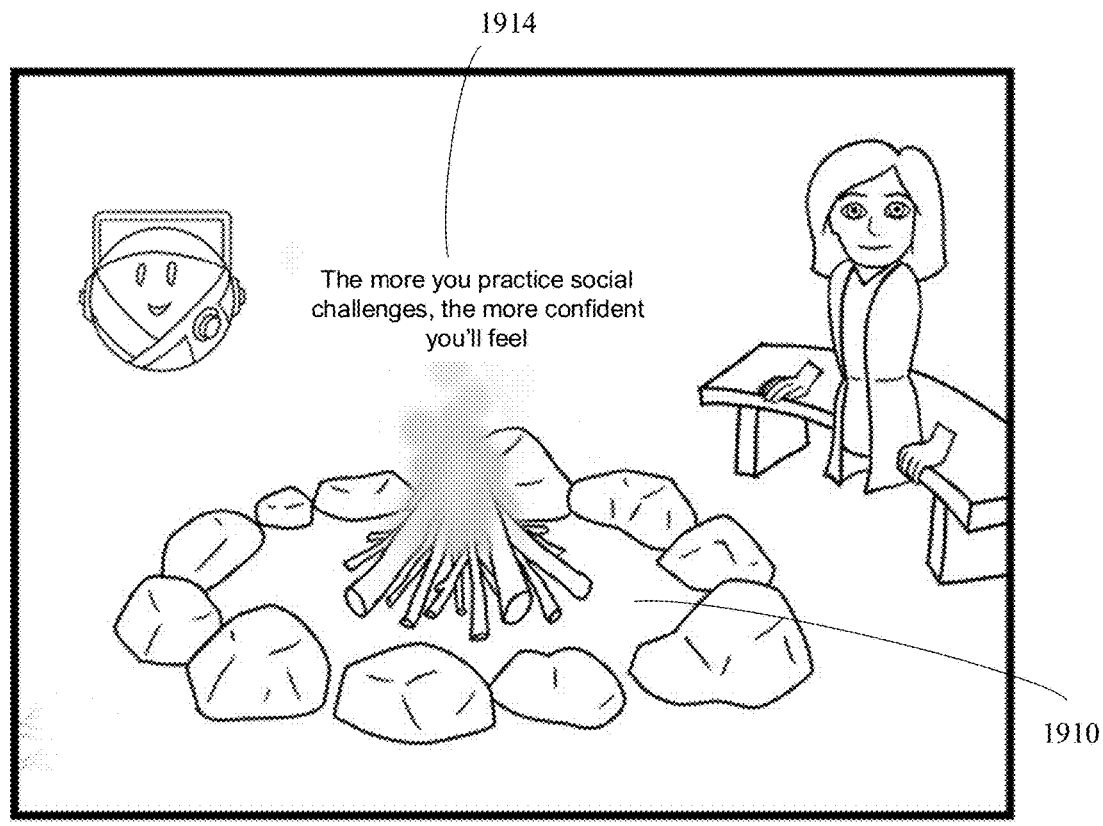
Fig. 19J

2200

| Time Period | Exemplary Lesson | Exemplary Content |
|---|---|---|
| 1 | Introduction to Cognitive Reframing: Part 1 | Users are introduced to the Woods of Wisdom for the first time, and learn about linking emotions and behaviors to anxious thoughts. |
| | Introduction to Cognitive Reframing: Part 2 | Users learn how to identify different types of anxious thoughts, and practice labeling thoughts. |
| | How to Record Thoughts | Users learn how to record both anxious thoughts and positive thoughts/affirmations in DR. They also unlock the ability to log thoughts via App. |
| 2 | Gathering Evidence | Users practice a reframing activity, such as by reframing a thought by gathering evidence for and against the thought. |
| 3 | Usefulness & Core Beliefs | Users practice identifying the usefulness and core belief activity associated with an anxious thought, such as by testing the usefulness of that core belief as it relates to them achieving his/her goals. |
| 4 | Creating Space | Users practice defusion activity, such as by learning how to create cognitive distance between themselves and his/her thoughts. |

Fig. 22

| Key<br>R = required<br>O = optional | | Psychoeducation | Social Challenge | Mindfulness | Cognitive Reframing | Goal Setting |
|---|---|---|---|---|---|---|
| Week 1 | Chapter 1 | (R) Intro to program and intro to CBT + psychoeducation (~15 min) | | | | |
| Week 1 | Chapter 2 | (R) Intro to Mindfulness | | (R) Mindfulness | | |
| Week 1 | Chapter 3 | (R) Intro to Goals | | (O) Mindfulness | | (R) Long term goal setting<br>(O) Short term goal setting in PWA |
| Week 2 | Chapter 4 | (R) Intro to Exposure and Social Challenges | (R) Fear ladder activity and first challenge | (R) Mindfulness | | (O) Long term + short term goal setting |
| Week 2 | Chapter 5 | | (R) SC practice | (R) Mindfulness | | (O) Long term + short term goal setting |
| Week 2 | Chapter 6 | | (R) SC practice | (O) Mindfulness | | (O) Long term + short term goal setting |
| Week 3 | Chapter 7 | (R) Intro to Cognitive Reframing Part 1 | (R) SC practice | (O) Mindfulness | (R) Woods of Wisdom Tutorial + Anxious thoughts and linking emotions/behaviors | (O) Long term + short term goal setting |
| Week 3 | Chapter 8 | (R) Intro to Cognitive Reframing Part 2 | (R) SC practice | (O) Mindfulness | (R) CR Session – Label Types + Practice | (O) Long term + short term goal setting |
| Week 3 | Chapter 9 | | (R) SC practice | (O) Mindfulness | (R) CR practice | (O) Long term + short term goal setting |
| Week 4 | Chapter 10 | | (R) SC practice | (O) Mindfulness | (R) CR Tutorial | (O) Long term + short term goal setting |
| Week 4 | Chapter 11 | (R) Gathering Evidence | (R) SC practice | (O) Mindfulness | (R) CR practice | (O) Long term + short term goal setting |
| Week 4 | Chapter 12 | | (R) SC practice | (O) Mindfulness | (O) CR practice | (O) Long term + short term goal setting |

| | | | | | |
|---|---|---|---|---|---|
| Week 5 | Chapter 13 | | (R) SC practice | (O) Mindfulness | (R) CR tutorial | (O) Long term goal setting<br>(R) Short term goal setting |
| Week 5 | Chapter 14 | (R) Usefulness | (R) SC practice | (O) Mindfulness | (R) CR practice | (O) Long term + short term goal setting |
| Week 5 | Chapter 15 | | (R) SC practice | (O) Mindfulness | (O) CR practice | (O) Long term + short term goal setting |
| Week 6 | Chapter 16 | | (R) SC practice | (O) Mindfulness | (O) CR practice | (O) Long term + short term goal setting |
| Week 6 | Chapter 17 | | (R) SC practice | (O) Mindfulness | (O) CR practice | (O) Long term + short term goal setting |
| Week 6 | Chapter 18 | | (R) SC practice | (O) Mindfulness | (O) CR practice | (O) Long term + short term goal setting |
| Week 7 | Chapter 19 | | (R) SC practice | (O) Mindfulness | (O) CR practice | (O) Long term + short term goal setting |
| Week 7 | Chapter 20 | | (R) SC practice | (O) Mindfulness | (O) CR practice | (O) Long term + short term goal setting |
| Week 7 | Chapter 21 | | (R) SC practice | (O) Mindfulness | (O) CR practice | (O) Long term + short term goal setting |
| Week 8 | Chapter 22 | (R) Maintenance + Values | (R) SC practice | (O) Mindfulness | (O) CR practice | (O) Long term + short term goal setting |
| Week 8 | Chapter 23 | | (R) SC practice | | | |
| Week 8 | Chapter 24 | (R) Graduation | | (O) Mindfulness | (O) CR practice | (O) Long term + short term goal setting |

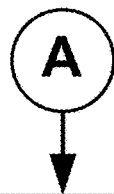

2523 — Present, on the display, an interactive digital reality (DR) scene comprising (i) a first affordance region associated with a plurality of interactive DR activities and (ii) a second affordance region different from the first affordance region and associated with a ledger of activity performed by the subject during the plurality of interactive DR activities and persistently displayed during the plurality of interactive DR activities. A first interactive DR activity in the plurality of activities comprises detecting, by the one or more processors, the selection by the subject of a respective recording object in one or more recording objects at the first affordance region, forming, by the one or more processors, a first corresponding evidence construct associated with the subject in one or more evidence constructs. The first corresponding evidence construct is associated with a first statement uttered by the subject during the first interactive DR activity. There is presented on the display, at the first affordance region, a first visualization of the first corresponding evidence construct. There is updating, on the display, at the second affordance region, the ledger with a second visualization of the first corresponding evidence construct different from the first visualization of the first corresponding evidence construct.

2524 — The forming the first corresponding evidence construct further comprises: converting the first corresponding evidence construct into a corresponding evidence text. The first visualization comprises the corresponding evidence text at or adjacent to the recording object that records the corresponding evidence construct.

2526 — Each respective evidence construct is contained in or represented by the one or more recording objects selected by the subject.

2528 — The forming the first corresponding evidence construct further comprises presenting, on the display, the one or more evidence constructs associated with a first sentiment and the one or more evidence constructs associated with a second sentiment in a DR sorting area of the first affordance region. The one or more evidence constructs associated with the first sentiment are separated from the one or more evidence constructs associated with the second sentiment. The subject discards any evidence construct in the one or more evidence constructs associated with the first sentiment and/or the one or more evidence constructs associated with the second sentiment that is deemed not objective by the subject.

Fig. 29C

MANAGEMENT OF PSYCHIATRIC OR MENTAL CONDITIONS USING DIGITAL REALITY WITH COGNITIVE BEHAVIORAL TECHNIQUE

CROSS-REFERENCE TO RELATED APPLICATION

The present Application claims priority to U.S. Provisional Patent Application No. 63/415,860, entitled "Management of Psychiatric or Mental Conditions Using Digital Reality with Cognitive Behavioral Technique," filed Oct. 13, 2022, which is hereby incorporated by reference in its entirety for all purposes.

TECHNICAL FIELD

The present disclosure relates to systems, methods, and devices for providing digital reality based activities. More particularly, the present disclosure relates to systems, methods, and devices that use digital reality with cognitive behavioral techniques to allow for management of psychiatric or mental conditions exhibited by a subject.

BACKGROUND

Demand to access mental health care facilities and services that improve the mental health of patients is at an all-time high. However, evidence cannot be found that this increased access to mental health care facilities has also led to decreases in the prevalence of mental health issues. In fact, mental health problems in patients have increased in recent years. See Mojtabai et al., "Trends in Psychological Distress, Depressive Episodes and Mental-Health Treatment-Seeking in the United States: 2001-2012," Journal of Affective Disorders, 174, pg. 556.

Furthermore, increased demand to mental health care facilities causes a proportional increase in demand for health care practitioners and professionals to provide services at the mental health care facilities. Accordingly, health care practitioners and professionals are subjected to increased stress, both psychological and physiological, that prevents them from providing optimal service. See Ruiz-Fernandez et al., 2020, "Compassion Fatigue, Burnout, Compassion Satisfaction and Perceived Stress in Healthcare Professionals During the COVID-19 Health Crisis in Spain," Journal of Clinical Nursing, 29(21-22), pg. 4321-4430.

Conventional solutions to improving mental health are laborious and resource intensive for all parties involved. For instance, conventional solutions often require time-consuming and expensive in-person meetings between a clinician and a patient. Moreover, these in-person meetings do not readily allow a clinician to observe the patient in situations that expose an underlying mental health issue of the patient given the intimate and private nature of in-person meetings with the clinician.

Furthermore, conventional solutions lack satisfactory efficacy for treatment of certain mental health issues. For instance, while conventional in-person cognitive and/or behavioral exposure techniques have generally shown some efficacy, they lack significant efficacy, particularly for post-traumatic stress disorders (PTSD), social anxiety disorder (SAD), and panic disorder. See Carpenter et al., 2018, Cognitive Behavioral Therapy for Anxiety and Related Disorders: A Meta-analysis of Randomized Placebo-controlled Trails," Depression and Anxiety, 25(56), pg. 502.

Coinciding with this, interactive computer implemented gaming and services are expanding. However, prior solutions to marry therapeutic services to improve mental health with computer implemented gaming has been unsatisfactory. One cause of such dissatisfaction is the requirement that a therapist be present with a patient during a computer implemented therapeutic gaming session. See Freeman et al., 2017, "Virtual Reality in the Assessment, Understanding, and Treatment of Mental Health Disorders," Psychological Medicine, 47(14), pg. 2393. This requirement is burdensome on the temporal, spatial, and financial resources available to both the patient and the medical practitioner.

Moreover, another dissatisfaction with prior solutions to marry therapeutic services and/or computer implemented gaming is a requirement for users to have experience with therapeutic services and/or computer implemented gaming in order to obtain adequate services. For instance, such prior solutions lack a mechanism that allows for unskilled users to successfully complete a computer implemented therapeutic service without having prior experience with either therapeutic services and/or computer implemented gaming.

As such, there is a need for systems, methods, and devices that improve the mental health of subjects without overly burdening the subjects or their medical practitioners and/or allow for efficient utilization by the subject.

SUMMARY

The present disclosure addresses the need in the art discussed above with systems, methods, and devices that make use of interactive digital reality activities, for example, one or more digital cognitive behavioral techniques implemented through a plurality of interactive digital reality activities to improve the ability of subjects to manage their psychiatric or mental conditions using a display device.

In one aspect, the present disclosure provides improved systems, methods, and devices for implementing cognitive behavioral therapy (CBT) to help a subject to manage a psychiatric or mental condition of the subject. In some embodiments, implementing CBT provided by the systems, methods, and devices of the present disclosure includes implementing techniques such as a cognitive reframing technique and/or a cognitive defusion technique. In some embodiments, to further help a subject to manage a psychiatric or mental condition, the systems, methods, and devices of the present disclosure provide CBT for the subject at least in part through a client application accessible through a display of an electronic device, optionally, with one or more other psychotherapeutic and/or psychoeducational techniques including exposure therapy, mindfulness-based intervention, behavioral activation, psychoeducational intervention, or a combination thereof.

In some embodiments, the systems, methods, and devices of the present disclosure provide for a respective interactive digital reality (DR) activity through an implementation of a CBT activity within an interactive DR scene. Accordingly, in some embodiments, the systems, methods, and devices of the present disclosure provide one or more self-applied cognitive reframing sessions for the subject within the interactive DR scene.

In some embodiments, one or more interactive DR activities in the plurality of interactive activities allows for the subject to identify a negative thought or statement, such as a first statement that is uttered (e.g., spoken) by the subject when interacting with the interactive DR scene or a predetermined thought or statement provided by the systems, methods, and devices of the present disclosure. In some embodiments, the one or more interactive DR activities in the plurality of interactive activities provided by the systems, methods, and devices of the present disclosure allows the subject to disrupt a native cognitive pattern associated with formation of the negative thought or statement by the subject with a new cognitive pattern associated with a formation of a positive or adaptive thought or statement when interacting with the interactive DR scene.

In some embodiments, the one or more interactive DR activities in the plurality of interactive activities provide for an implementation of CBT activity within the interactive DR scene by having the subject self-identify evidence for a thought spoken by the subject (e.g., a statement provided by the subject). In some embodiments, the systems, methods, and devices of the present disclosure evaluate if the self-identified evidence provided by the subject during the one or more interactive DR activities in the plurality of interactive activities is sufficient to reframe the thought provided by the subject. In some embodiment, one or more interactive DR activities in the plurality of interactive activities allows the subject to reframe the thought in order to improve the psychiatric or mental condition exhibited by the subject, such as by modulating harm expectancy and/or a perception of control associated with the thought for the subject.

Turning to more specific aspects of the present disclosure, in some embodiments, a method of the present disclosure is implemented at a computer system associated with the subject. The computer system includes one or more processors and a display for presenting at least a digital reality (DR) scene and/or activity. The computer system also includes an input mechanism for receiving one or more inputs from an end-user of the computer system, such as an audio recorder for recording one or more audios from the subject. The computer system further includes a memory coupled to the one or more processors. The memory includes one or more programs configured to be executed by the one or more processors. In some embodiments, the computer system includes one or more speakers or headphones for presenting auditory aspects of an interactive DR scene, such as one or more instructions for interacting with the interactive DR scene and/or feedback based on the interactions by the subject with the interactive DR scene. In some embodiments, the computer system includes one or more biometric sensors to collect measurable biometric signals associated with a physiological or psychological state of the subject.

An aspect of the present disclosure is directed to providing a method that implements CBT within an interactive DR scene.

In some embodiments, a method for management of a psychiatric or mental condition is provided at a computer system associated with a subject. The computer system includes one or more processors, a display, an audio recorder, and a memory coupled to the one or more processors. The memory includes one or more programs configured to be executed by the one or more processors.

In some embodiments, the psychiatric or mental condition is a clinically diagnosed mental disorder or a sub-clinically diagnosed mental disorder.

In some embodiments, the psychiatric or mental condition includes being stressed in a social setting, fearing a social setting, or being overwhelmed in a social setting.

In some embodiments, the psychiatric or mental condition is a clinically diagnosed mental disorder. Moreover, the clinically diagnosed mental disorder is an anxiety disorder, a mood disorder, a psychotic disorder, an eating disorder, an impulse control disorder, an addiction disorder, a personality disorder, an obsessive-compulsive disorder, or a post-traumatic stress disorder.

In some embodiments, the psychiatric or mental condition is a clinically diagnosed mental disorder. Moreover, the clinically diagnosed mental disorder is an anxiety disorder. Moreover, the anxiety disorder includes a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

In some embodiments, the psychiatric or mental condition is a clinically diagnosed mental disorder. Furthermore, the clinically diagnosed mental disorder is a mood disorder. Moreover, in some such embodiments, the mood disorder includes a depression disorder, a bipolar disorder, or a cyclothymic disorder.

In some embodiments, the depression disorder is major depressive disorder.

In some embodiments, the psychiatric or mental condition is a clinically diagnosed mental disorder. Additionally, the clinically diagnosed mental disorder is a psychotic disorder. Moreover, in some such embodiments the psychotic disorder includes a schizophrenia disorder, a delusion disorder, or a hallucination disorder.

In some embodiments, the psychiatric or mental condition is a clinically diagnosed mental disorder. Moreover, in some such embodiments the clinically diagnosed mental disorder is an eating disorder, and the eating disorder includes anorexia nervosa, bulimia nervosa, or binge eating disorder.

In some embodiments, the psychiatric or mental condition is a clinically diagnosed mental disorder. Moreover, the clinically diagnosed mental disorder is an impulse control disorder. Additionally, the impulse control disorder includes a pyromania disorder, a kleptomania disorder, or a compulsive gambling disorder.

In some embodiments, the psychiatric or mental condition is a clinically diagnosed mental disorder. Moreover, the clinically diagnosed mental disorder is an addiction disorder, in which the addiction disorder includes an alcohol use disorder or a substance abuse disorder.

In some embodiments, the psychiatric or mental condition is a clinically diagnosed mental disorder that is a personality disorder. In some such embodiments, the personality disorder comprises an antisocial personality disorder, an obsessive-compulsive personality disorder, or a paranoid personality disorder.

In some embodiments, presenting, on the display, an interactive digital reality (DR) scene that includes a first affordance region and a second affordance region. The first affordance region is associated with a plurality of interactive DR activities. Moreover, the second affordance region is different from the first affordance region and is associated with a ledger of activity performed by the subject during the plurality of interactive DR activities and persistently displayed during the plurality of interactive DR activities. Furthermore, a first interactive DR activity in the plurality of interactive DR activities includes detecting, by the one or more processors, a selection by the subject of a respective recording object in one or more recording objects at the first affordance region. Moreover, the first interactive DR activity includes forming, by the one or more processors, a first corresponding evidence construct associated with the subject in one or more evidence constructs, in which the first corresponding evidence construct is associated with a first statement uttered by the subject during the first interactive DR activity. Furthermore, the first interactive DR activity includes presenting, on the display, at the first affordance region, a first visualization of the first corresponding evidence construct, and updating, on the display, at the second affordance region, the ledger with a second visualization of the first corresponding evidence construct different from the first visualization of the first corresponding evidence construct.

In some embodiments, the forming the first corresponding evidence construct further includes. converting the first corresponding evidence construct into a corresponding evidence text. Moreover, the first visualization includes the corresponding evidence text at or adjacent to the recording object that records the corresponding evidence construct.

In some embodiments, each respective evidence construct is contained in or represented by the one or more recording objects selected by the subject.

In some embodiments, the forming the first corresponding evidence construct further includes presenting, on the display, the one or more evidence constructs associated with a first sentiment and the one or more evidence constructs associated with a second sentiment in a DR sorting area of the first affordance region. Furthermore, the one or more evidence constructs associated with the first sentiment are separated from the one or more evidence constructs associated with the second sentiment. Moreover, the forming the first corresponding evidence construct includes discarding, by the subject, any evidence construct in the one or more evidence constructs associated with the first sentiment and/or the one or more evidence constructs associated with the second sentiment that is deemed not objective by the subject.

In some embodiments, the presenting allows the subject to read the one or more evidence constructs associated with the first sentiment and the one or more evidence constructs associated with the second sentiment.

In some embodiments, a corresponding evidence text converted from the first corresponding evidence construct is presented at or adjacent to the respective DR recording object that records the corresponding evidence construct.

In some embodiments, the first interactive activity includes presenting, on the display, a DR measurement object indicative of whether the one or more evidence constructs associated with the first sentiment exceed the one or more evidence constructs associated with the second sentiment.

In some embodiments, the one or more evidence constructs associated with the first sentiment exceed the one or more evidence constructs associated with the second sentiment when a quality of the one or more evidence constructs associated with the first sentiment exceeds a quality of the one or more evidence constructs associated with the second sentiment, and/or when a quantity of the one or more evidence constructs associated with the first sentiment exceeds a quantity of the one or more evidence constructs associated with the second sentiment.

In some embodiments, the DR measurement object simulates a balance scale within a DR weighting area of the first interactive DR scene.

In some embodiments, the one or more evidence constructs associated with the first sentiment are generated prior to, concurrently with, or subsequent to the one or more one or more evidence constructs associated with the second sentiment.

In some embodiments, the one of the first and second sentiments is a positive sentiment and the other of the first and second sentiments is a negative sentiment.

In some embodiments, one of the first and second sentiments is an arousing sentiment and the other of the first and second sentiments is a negative or neutral sentiment.

In some embodiments, the interactive DR scene further includes a third affordance region different from the first affordance region and the second affordance region, in which the third affordance region includes a chart depicting a progression of the subject through the plurality of interactive DR activities.

In some embodiments, the third affordance region is persistently displayed with the second affordance region during the plurality of interactive DR activities.

In some embodiments, the chart depicts the progression of the subject linearly through each interactive DR activity in the plurality of interactive DR activities.

In some embodiments, the chart is dynamically updated, by the one or more progressors, to indicate a current status of the progression of the subject through the plurality of interactive DR activities.

In some embodiments, further presenting, on the display, at the first affordance region, a second interactive DR activity in the plurality of interactive DR activities.

In some embodiments, a second interactive DR activity in the plurality of interactive DR activities includes obtaining, in electronic form, a first assessment of the subject, the first assessment comprising an identification of a corresponding plurality of tags associated with the first statement.

In some embodiments, the corresponding plurality of tags includes a first set of tags associated with the first sentiment and a second set of tags associated with the second sentiment.

In some embodiments, a third interactive DR activity in the plurality of interactive DR activities includes obtaining, in electronic form, a second assessment of the subject. Moreover, the second assessment includes a determination when the subject satisfies a threshold validation in change for the psychiatric or mental condition exhibited by the subject.

In some embodiments, the threshold validation in change for the psychiatric or mental condition exhibited by the subject includes a threshold change in diagnosis status for the psychiatric or mental condition exhibited by the subject, a threshold change in subjective distress of the subject caused by the corresponding challenge, a threshold change in cognitive symptoms of the subject, a threshold change in mindfulness state of the subject, or a combination thereof.

In some embodiments, determining whether the subject satisfies a threshold condition associated with each interactive DR activity in the plurality of interactive DR activities, in which each respective threshold condition defines a criterion that must be achieved in order for the respective threshold condition to be deemed satisfied.

In some embodiments, the subject satisfies a respective threshold condition when the one or more evidence constructs associated with the positive sentiment exceeds the one or more evidence constructs associated with the negative sentiment.

In some embodiments, the determining is further performed by one or more models and/or a medical practitioner associated with the subject.

In some embodiments, the determining is further performed by one or more models. The one or more models includes a logistic regression model, a neural network model, a support vector machine model, a Naive Bayes model, a nearest neighbor model, a random forest model, a decision tree model, a boosted trees model, a multinomial logistic regression model, a linear model, a linear regression model, a Gradient Boosting model, a mixture model, a hidden Markov model, a Gaussian model, a linear discriminant model, or any combinations thereof.

In some embodiments, the determining is further performed by one or more models. In some such embodiments, the one or models is a concordance-index model.

In some embodiments, the threshold condition includes an absence, a presence, a deactivation, an activation, or a value for one or more physiological markers.

In some embodiments, the one or more physiological markers includes a threshold value for skin conductance (SC), a threshold heart rate (HR), a threshold blood volume pulse (BVP), or any combination thereof.

In some embodiments, the threshold condition includes a deactivation of the parasympathetic nervous system (PNS).

In some embodiments, the threshold condition includes an activation of the sympathetic nervous system (SNS).

In some embodiments, the method includes obtaining, on the display, at the second affordance region, when the subject is deemed to satisfy the threshold condition associated with each interactive DR activity in the plurality of interactive DR activities, by the one or more recording objects, a second corresponding evidence construct associated with a second statement uttered by the subject in the one or more evidence constructs. In some such embodiments, the second statement is a reframing of the first statement.

In some embodiments, the method includes further updating, by the one or more processors, on the display, at the second affordance region, the ledger with a third visualization of the second corresponding evidence construct associated and, at a user profile associated with the subject, a historical record of the ledger. In some such embodiments, the third visualization is displayed adjacent to the first visualization, which indicates an improvement in the management of the psychiatric or mental condition by the subject.

In some embodiments, when the subject is deemed not to satisfy the threshold condition, the method further includes repeating the forming to generate one or more additional evidence constructs, each additional evidence associated with the first or second sentiment. Moreover, the method includes repeating the determining based on the one or more additional evidence constructs together with the one or more evidence constructs associated with the first sentiment and the one or more evidence constructs associated with the second sentiment. Moreover, in some such embodiments, the method alternatively includes presenting, on the display, an additional interactive DR activity in the plurality of interactive DR activities configured to help the subject to reframe the first statement.

Yet another aspect of the present disclosure is directed to providing non-transitory computer readable storage medium storing one or more programs. The one or more programs includes instructions, which when executed by a computer system cause the computer system to perform a method of the present disclosure.

Yet another aspect of the present disclosure is directed to providing use of a computer system for improving an ability of a subject to manage a psychiatric or mental condition exhibited by the subject. The computer system includes one or more processors, a display, and a memory coupled to the one or more processors. In some embodiments, the computer system includes audio speakers and/or a microphone. The memory includes one or more programs, configured to be executed by the one or more processors, that implement a method of the present disclosure.

Yet another aspect of the present disclosure is directed to providing a device for implementing CBT to help a subject to manage a psychiatric or mental condition of the subject. The device is configured to improve an ability of a subject to manage a psychiatric or mental condition of the subject. Furthermore, the device includes one or more processors and a memory coupled to the one or more processors. The memory includes one or more programs configured to be executed by the one or more processors. The one or more programs are configured to cause the computer system to perform the methods of the present disclosure. In some embodiments, the device includes a display and/or audio circuitry. In some embodiments, the device includes an objective lens in optical communication with a two-dimensional pixelated detector.

Yet another aspect of the present disclosure is directed to providing regimens for implementing CBT and/or additional educational or therapeutical sessions (e.g., education on CBT, mindfulness session, exposure therapeutical session) to help a subject to manage a psychiatric or mental condition of the subject.

Yet another aspect of the present disclosure is directed to providing a method implemented at a computer system associated with the subject. The computer system includes one or more processors and a display for presenting at least a digital reality (DR) scene and/or activity. The computer system also includes an input mechanism for receiving one or more inputs from an end-user of the computer system, such as an audio recorder for recording one or more audios from the subject. The computer system further includes a memory coupled to the one or more processors. The memory includes one or more programs configured to be executed by the one or more processors. In some embodiments, the computer system includes one or more speakers or headphones for presenting auditory aspects of an interactive DR scene, such as one or more instructions for interacting with the interactive DR scene and/or feedback based on the interactions by the subject with the interactive DR scene. In some embodiments, the computer system includes one or more biometric sensors to collect measurable biometric signals associated with a physiological or psychological state of the subject.

An aspect of the present disclosure is directed to providing a method that implements CBT within an interactive DR scene. In some embodiments, the method includes obtaining, in electronic form, a first statement from the subject. In some embodiments, the method includes providing, via the display, a first interactive DR activity for a subject to practice a first CBT technique, such as a gathering evidence technique. In some embodiments, the method includes presenting, on the display, a DR thought-recording object for the subject to speak a second statement to the DR thought-recording object, and recording the second statement. In some embodiments, the method includes updating, on the display, a DR wellbeing object from a first display state to a second display state based at least in part on the second statement, thereby indicating an improvement in the management of the psychiatric or mental condition by the subject.

In some embodiments, additionally or optionally, the method includes presenting, on the display, one or more additional DR scenes or one or more portals to the one or more additional scenes. In some embodiments, each additional scene is configured for use in an educational or therapeutical session. In some embodiments, the one or more additional DR scenes include an educational DR interactive scene configured to educate the subject, a DR interactive DR scene configured for the subject to practice a different CBT technique, a DR interactive scene configured for the subject to practice a mindfulness session, a DR interactive scene configured for the subject to practice an exposure therapeutical session, or any combination thereof.

To obtain, in electronic form, a first statement from the subject, in some embodiments, the method includes presenting, on the display, a DR thought-recording object. Accordingly, in some embodiments, the method records the first statement when the subject interacts with (e.g., speaks to) the DR thought-recording object. In some embodiments, the method includes presenting, on the display, a DR vessel object with a selection feature. In some embodiments, the selection feature allows the subject to browse through a plurality of prestored statements until the subject selects a first prestored statement and designates the first prestored statement to be the first statement. In some embodiments, the method includes allowing the subject to record a first statement using a client application associated with a client device (e.g., a companion application, or app), and then obtains the first statement from the client application, such as by utilizing a communication network.

In some embodiments, the method includes converting the first statement into a text, and presenting, on the display, the DR thought-recording object, the text at or adjacent to the DR thought-recording object, and/or a DR thought-category feature. Accordingly, this displaying of the text within the DR scene helps the subject visualize the first statement for contemplation by the subject and/or a medical practitioner associated with the subject, thereby improving implementation of CBT through the DR scene.

In some embodiments, the DR thought-category feature indicates a corresponding category, in a plurality of categories, associated with the first statement. In some embodiments, indicating the corresponding category helps the subject conceptualize a fact that a thought, such as the first statement, is possibly distorted, inaccurate, or not useful for the subject. Accordingly, the provision of the plurality of categories to place the first statement in helps the subject notice their thoughts in the real world external to the DR scene, such as by raising awareness to the thinking patterns of the subject.

In some embodiments, the method includes presenting, on the display, the DR vessel object representative of containing, carrying and/or transporting of a statement associated with a thought, and associates, on the display and by the subject, the DR vessel object with the first statement. Additionally or optionally, in some embodiments, the method includes presenting, on the display, the DR vessel object and the text at or adjacent to the DR vessel object. In some embodiments, the method includes using, by the subject, a DR thought-impact feature to assign a level of impact of the first statement on the subject. In some embodiments, the method includes rendering the DR vessel object to indicate a level of impact of the first statement on the subject.

In some embodiments, to provide the first interactive DR activity for a subject to practice a gathering evidence CBT technique, the method includes presenting, on the display, a first interactive DR scene. In some embodiments, the first interactive DR scene includes a first plurality of DR evidence-recording objects, a second plurality of DR evidence-recording objects different than the first plurality of DR evidence-recording objects, a DR wellbeing object in a corresponding first display state indicative of a current mental or emotional wellbeing of the subject (e.g., a state associated with the first statement), or a combination thereof.

In some embodiments, in providing the first interactive DR activity, the method also includes generating one or more evidence constructs associated with a first sentiment and one or more evidence constructs associated with a second sentiment. In some embodiments, generating of an evidence construct associated with the first or second sentiment is achieved by detecting a selection by the subject of a respective DR evidence-recording object in either the first or second plurality of DR evidence-recording objects, and recording a corresponding evidence construct spoken by the subject. In some embodiments, the corresponding evidence construct is associated with either the first sentiment when the respective DR evidence-recording object is selected from the first plurality of DR evidence-recording objects or the second sentiment when the respective DR evidence-recording object is selected from the second plurality of DR evidence-recording objects. In some embodiments, the detecting of a selection by the subject and the recording of a corresponding evidence construct are repeated by the method until a threshold selection of any DR evidence-recording object in either the first or second plurality of DR evidence-recording objects is detected, such as no selection.

In some embodiments, the method includes converting, prior to the repeating of the detecting of a selection by the subject and the recording of a corresponding evidence construct, the recorded corresponding evidence into a corresponding evidence text, and presenting, on the display, the corresponding evidence text at or adjacent to the respective DR evidence-recording object that records the corresponding evidence.

In some embodiments, the method includes presenting, on the display, the one or more evidence constructs associated with the first sentiment and the one or more evidence constructs associated with the second sentiment in a DR sorting area of the first interactive DR scene. The one or more evidence constructs associated with the first sentiment is separated from the one or more evidence constructs associated with the second sentiment. In some embodiments, the method includes discarding, by the subject, any evidence construct in the one or more evidence constructs associated with the first sentiment and the one or more evidence constructs associated with the second sentiment that is deemed not objective by the subject.

In some embodiments, in generating one or more evidence constructs associated with a first sentiment and one or more evidence constructs associated with a second sentiment, the method further includes determining whether the subject satisfies a threshold sentiment condition. In some embodiments, the determining of whether the subject satisfies a threshold sentiment condition is based at least in part on the one or more evidence constructs associated with the first sentiment and the one or more evidence constructs associated with the second sentiment. In some embodiments, the method includes presenting, on the display, a DR measurement object indicative of whether the one or more evidence constructs associated with the first sentiment exceed the one or more evidence constructs associated with the second sentiment, thereby satisfying the threshold sentiment condition.

In some embodiments, the method includes repeating the generating evidence construct process to generate one or more additional evidence constructs, each additional evidence associated with the first or second sentiment. The method also includes the determining process, in which the determination is based at least in part on the one or more additional evidence constructs together with the one or more evidence constructs associated with the first sentiment and the one or more evidence constructs associated with the second sentiment.

In some embodiments, the presenting of a DR thought-recording object for the subject to speak a second statement to the DR thought-recording object and recording the second statement are performed when the subject is deemed to satisfy the threshold sentiment condition. In some embodiments, the second statement is a reframing of the first statement. In some embodiments, the method also includes presenting, on the display, the DR vessel object, which allows for the DR vessel object to act as a digital representation of containing, carrying, and/or transporting of a statement associated with a thought, and allowing the subject to associate the DR vessel object with the second statement that is a reframing of the first statement. Additionally or optionally, in some embodiments, the method includes presenting, on the display, the DR vessel object and a text converted, or generated, from the second statement at or adjacent to the DR vessel object.

In some embodiments, in updating a DR wellbeing object from a first display state to a second display state, the method includes updating an appearance of the DR wellbeing object based at least in part on the second statement, thereby indicating an improvement in the management of the psychiatric or mental condition exhibited by the subject.

Another aspect of the present disclosure is directed to providing a method that implements CBT within an interactive DR scene. In some embodiments, the method includes obtaining, in electronic form, a first statement from the subject. In some embodiments, the method includes providing, via the display, a second interactive DR activity configured for a subject to a practice usefulness and core beliefs CBT technique. In some embodiments, the method includes presenting, on the display, a DR thought-recording object in order for the subject to speak a second statement to the DR thought-recording object, and recording the second statement. In some embodiments, the method includes updating, on the display, a DR wellbeing object from a first to second display state based at least in part on the second statement, thereby indicating an improvement in the management of the psychiatric or mental condition by the subject. In some embodiments, additionally or optionally, the method includes presenting, on the display, one or more additional DR scenes or one or more portals to the one or more additional scenes, each additional scene configured for use in an educational or therapeutical session.

In some embodiments, the obtaining of the first statement from the subject, the presenting of the DR thought-recording object for the subject to speak the second statement to the DR thought-recording object, the recording of the second statement, the updating of the DR wellbeing object from a first display state to a second display state, and/or the presenting of one or more additional DR scenes or one or more portals to the one or more additional DR scenes are the same as or similar to those of the method in the first aspect, and therefore description of such are omitted to avoid redundancy.

In some embodiments, to provide a second interactive DR activity for a subject to practice a usefulness and core beliefs CBT technique, the method includes presenting, on the display, a second interactive DR scene. In some embodiments, the second interactive DR scene includes a DR map, a DR moving object, a plurality of DR belief objects, or a combination thereof. The DR map includes a starting point, a destination, and one or more stops between the starting point and the destination. The DR moving object is configured to move along the DR map. Each respective DR belief object in the plurality of DR belief objects is associated with a corresponding core belief in a plurality of core beliefs. The method also includes detecting a selection of a first DR belief object in the plurality of DR belief objects by the subject. The first DR belief object is associated with a first corresponding core belief that best represents the first statement. In some embodiments, the method further includes regulating movement of the DR moving object along the DR map based at least in part on the first corresponding core belief.

In regulating the movement of the DR moving object along the DR map, in some embodiments, the method includes placing, responsive to instructions provided by the subject, the selected first DR belief object on the DR belief-recording object, and placing, responsive to instructions provided by the subject, the DR belief-recording object along with the selected first DR belief object on the DR moving object. In some embodiments, the method includes presenting, on the display when the DR moving object reaches a DR loading station, one or more cargo items for the subject to load to the DR moving object. In some embodiments, this regulating the movement of the DR moving object provides a gamification to the CBT technique, which improves interaction by the subject that, in turn, provides an improvement in the management of the psychiatric or mental condition exhibited by the subject.

In regulating the movement of the DR moving object along the DR map, in some embodiments the method includes prompting, when the DR moving object reaches a stop in the one or more stops, the subject to select whether the first corresponding core belief is useful or harmful in helping achieve the short-term goal associated with the stop. In some embodiments, the method includes pulling, in response to user instructions to pull provided by the subject, a DR switch object in a direction based on whether the subject considers the first corresponding core belief useful or harmful. In some embodiments, the pulling sends the DR moving object to a first path in which the DR moving object encounters the one or more DR obstacles when the subject indicates that the first corresponding core belief is harmful, or to a second path in which the DR moving object encounters one or more resources that enables the DR moving object to move toward the destination. In some embodiments, the method includes imposing, when the subject indicates that the first corresponding core belief is harmful, one or more DR obstacles to obstruct movement of the DR moving object along the DR map.

In some embodiments the method includes determining when the subject satisfies the threshold sentiment condition based on whether the DR moving object reaches the destination. In some embodiments the method also includes inverting, responsive to instructions provided by the subject, the first corresponding core belief to generate an inverted core belief. In some embodiments, the method further includes regulating movement of the DR moving object along the DR map based at least in part on the inverted core belief. In some embodiments, the method includes rewarding the subject with a DR gift.

Yet another aspect of the present disclosure is directed to a method that implements CBT within an interactive DR scene. In some embodiments, the method includes obtaining, in electronic form, a first statement from the subject, providing, via the display, a third interactive DR activity for a subject to practice a create space CBT technique, presenting, on the display, a DR thought-recording object for the subject to speak a second statement to the DR thought-recording object, recording the second statement, and updating, on the display, a DR wellbeing object from a first display state to a second display state based at least in part on the second statement, or a combination thereof, thereby indicating an improvement in the management of the subject's psychiatric or mental condition. In some embodiments, additionally or optionally, the method includes presenting, on the display, one or more additional DR scenes or one or more portals to the one or more DR additional scenes, each DR additional scene configured for use in an educational or therapeutical session.

In some embodiments, the obtaining of the first statement from the subject, the presenting of the DR thought-recording object for the subject to speak the second statement to the DR thought-recording object, the recording of the second statement, the updating of the DR wellbeing object from the first display state to the second display state, or the presenting of one or more additional DR scenes or one or more portals to the one or more additional scenes, or any combination thereof, is the same as or similar to those steps of the method in the first interactive DR scene, and therefore description of such are omitted to avoid redundancy.

In some embodiments, to provide a third interactive DR activity for a subject to practice a create space CBT technique, the method includes presenting, on the display, a third interactive DR scene. The third interactive DR scene includes the DR thought-recording object, the DR vessel object, a DR thought-indicative object, a plurality of DR third-person-recording objects, a DR word-recording object, or a combination thereof. The method also includes activating the DR thought-indicative object with the first statement of the subject. The method further includes generating a plurality of third-person statements to feed the DR thought-indicative object. In some embodiments, a third-person statement is generated by presenting a third statement at or adjacent to the DR thought-indicative object, where the third statement is the first statement of the subject but presented in a name of a third person, detecting a selection by the subject of a respective DR third-person-recording object in the plurality of DR third-person-recording objects, recording a corresponding third-person statement when the subject speaks to the respective DR third-person-recording object in the name of the third person, or a combination thereof. In some embodiments, the detecting of the selection and the recording of the corresponding third-person statement are repeated until no selection of any DR third-person-recording object in the plurality of DR third-person-recording objects is detected, thereby generating the plurality of third-person statements. In some embodiments, the plurality of third-person statements includes one or more third statements spoken by the subject in the name of the third person and one or more fourth statements spoken by the subject in the name of the third person. Each of the one or more fourth statements negates a third statement in the one or more statements spoken by the subject in the name of the third person.

In some embodiments, the method includes playing back the recorded corresponding third-person statement to the subject. In some embodiments, the method includes providing an explanation to the subject of an effect of generating the plurality of third-person statements.

In some embodiments, in providing the third interactive DR activity, the method also includes generating, by the subject using the DR word-recording object, a DR construct to counter the plurality of third-person statements. To do so, in some embodiments, the method includes instructing the subject to identify for a single word or phrase that signifies an anxiety response to the plurality of third-person statements. In some embodiments, the method includes presenting, on the display, the DR word-recording object for the subject to speak the single word or phrase to the DR word-recording object. In some embodiments, the DR construct is generated in an amount that depends on a number of times the subject speaks the single word or phrase.

In some embodiments, the method includes providing an explanation to the subject of an effect of repeating the single word or phrase. Additionally or optionally, in some embodiments, the method includes converting the single word or phrase spoken by the subject into a text, and presenting the text at or adjacent the DR word-recording object. In some embodiments, the method includes regulating an appearance of the text in accordance with the amount of the DR construct or the number of times the subject speaks the single word or phrase.

In some exemplary embodiments, the method includes detecting a movement of the DR word-recording object by the subject to the DR thought-indicative object. In some embodiments, the method includes regulating the DR thought-indicative object in response to the detecting of a movement of the DR word-recording object by the subject. In some embodiments, the regulating of the DR thought-indicative object deactivates the DR thought-indicative object, erases the plurality of third-person statements from the display, or both.

In some embodiments, in providing the third interactive DR activity, the method further includes generating, by the subject using the DR thought-recording object and/or the DR vessel object, an advisory statement that counters the plurality of third-person statements. In some embodiments, the generating of an advisory statement is achieved by presenting, on the display, a third-person avatar associated with the plurality of third-person statements, detecting a selection by the subject of the DR thought-recording object, and recording the advisory statement when the subject speaks to the DR thought-recording object and advises the third-person avatar.

In some embodiments, the method includes activating the DR thought-indicative object with the advisory statement. In some embodiments, the method includes converting the advisory statement into a text and presenting the text at or adjacent the DR thought-indicative object.

In some embodiments, the method includes swapping, on the display, a position of the subject with a position of the third-person avatar, and playing back the advisory statement to the subject. In some embodiments, the method includes determining if the subject satisfies the threshold sentiment condition based at least in part on the advisory statement.

Yet another aspect of the present disclosure is directed to providing a method that implements CBT within an interactive DR scene. In some embodiments, via a display, the method provides an educational DR interactive scene to educate the subject. In some embodiments, the educational DR interactive scene includes one or more topics such as education on cognitive behavioral therapy, mindfulness, goal setting, exposure therapy, cognitive reframing CBT technique, gathering evidence CBT technique, usefulness CBT technique, or any combination thereof.

In some embodiments, to provide an educational DR interactive scene, the method includes presenting, on the display, a DR host within a first interactive DR scene to greet the subject when the subject enters the first interactive DR scene. In some embodiments, the presenting the DR host includes guiding the subject to learn how to associate one or more emotions and/or one or more behaviors with an anxious thought or a triggering event.

In some embodiments, the guiding of the subject to learn how to associate the one or more emotions and/or one or more behaviors with the anxious thought or the triggering event includes presenting, on the display, a first designated site within the first interactive DR scene. The first designated site includes a DR educational-vessel object that includes a selection feature to allow the subject to browse through a plurality of prestored statements until the subject finds a prestored statement that relates to a recent thought of the subject and/or a thought-impact feature to assign a level of impact of the recent thought on the subject. In some embodiments, the guiding of the subject to learn how to associate the one or more emotions and/or one or more behaviors with the anxious thought or the triggering event includes asking, by the DR host and prior to the subject selecting any prestored statement in the plurality of prestored statements, the subject to consider a recent anxious situation and to recall any thoughts that came up responsive to recalling the recent anxious situation. In some embodiments, the guiding of the subject to learn how to associate the one or more emotions and/or one or more behaviors with the anxious thought or the triggering event includes presenting, on the display, a text of a corresponding prestored statement in the plurality of prestored statements at or adjacent the DR educational-vessel object while the subject browses through the plurality of prestored statements. In some embodiments, the guiding of the subject to learn how to associate the one or more emotions and/or one or more behaviors with the anxious thought or the triggering event includes detecting an action performed by the subject on the DR selection feature.

In some embodiments, the guiding of the subject to learn how to associate the one or more emotions and/or one or more behaviors with the anxious thought or the triggering event also includes presenting, on the display, a second designated site within the first interactive DR scene. The second designed site includes a plurality of words or phrases for the subject to select. In some embodiments, the guiding of the subject to learn how to associate the one or more emotions and/or one or more behaviors with the anxious thought or the triggering event includes asking, by the DR host and prior to the subject selecting any word or phrase, the subject what the subject felt and/or did at the time when the recent thought came up. In some embodiments, the guiding of the subject to learn how to associate the one or more emotions and/or one or more behaviors with the anxious thought or the triggering event includes transforming a word or phrase selected by the subject into one or more DR animated creatures that surrounds the DR educational-vessel object.

In some embodiments, the guiding of the subject to learn how to associate the one or more emotions and/or one or more behaviors with the anxious thought or the triggering event further includes describing, by the DR host, how one or more thoughts, one or more emotions, one or more behaviors, or a combination thereof are connected.

In providing the educational DR interactive scene, in some embodiments, the method also includes guiding the subject to learn how to label anxious thoughts. The guiding of the subject to learn how to label anxious thoughts includes introducing, by the DR host, a plurality of types of anxious thoughts or cognitive distortions, and presenting, on the display, a DR miniature environment, and a type-selection object. The DR miniature environment includes a miniature version of the DR wellbeing object and its surrounding environment and/or a miniature version of an avatar of the subject.

In some embodiments, the guiding of the subject to learn how to label an anxious thought includes detecting a selection of a respective type in a plurality of types of anxious thoughts or cognitive distortions by the subject using the type-selection object. In some embodiments, the guiding further includes replacing, on the display, the DR miniature environment with a corresponding distortion miniature environment indicative of the respective type in the plurality of types of anxious thoughts or cognitive distortions. In some embodiments, the detecting of a selection by the subject and/or the replacing of the DR miniature environment is repeated until no selection of any type in the plurality of types of anxious thoughts or cognitive distortions is detected.

In some embodiments, the guiding of the subject to learn how to label anxious thoughts includes allowing the subject to select one or more types in the plurality of types of anxious thoughts or cognitive distortions that apply to a recent thought. In some embodiments, the guiding of the subject to learn how to label anxious thoughts includes presenting one or more labels indicative of the selected one or more types that apply to the recent thought on the DR educational-vessel object. In some embodiments, the allowing of the subject to select one or more types is repeated for a predetermined number of times or as the subject desires.

In some embodiments, the guiding of the subject to learn how to label the one or more anxious thoughts includes highlighting the type or types in the plurality of types of anxious thoughts or cognitive distortions that have been selected the most by the subject. In some embodiments, the guiding of the subject to learn how to label anxious thoughts includes determining if the types selected by the subject exhibit a predetermined thinking pattern.

In providing the educational DR interactive scene, in some embodiments, the method further includes guiding the subject to learn how to record thoughts. The guiding of the subject to learn how to record thoughts includes presenting, on the display, a journal menu object. In some embodiments, the journal menu object includes a recording feature. The method also includes detecting a selection of the recording feature by the subject, and presenting, on the display, a portal object, the DR educational-vessel object, a DR thought-recording object, or a combination thereof. The DR educational-vessel object includes a selection feature to allow the subject to select whether the subject wants to record an anxious thought or a positive thought. The method further includes recording a training statement representing a thought when the subject places the DR thought-recording object adjacent to the mouth of the subject and stopping recording when the subject puts the DR thought-recording object away from the mouth of the subject.

In some embodiments, the guiding of the subject to learn how to record thoughts includes converting the recorded training statement into an eleventh text, and presenting, on the display, the DR thought-recording object, the eleventh text at or adjacent to the DR thought-recording object, and/or a thought-category feature at or adjacent to the DR thought-recording object. The thought-category feature indicates a corresponding category, in a plurality of categories, associated with the recorded training statement.

In some embodiments, the guiding of the subject to learn how to record thoughts includes associating, on the display and by the subject, the DR educational-vessel object with the recorded training statement. In some embodiments, the guiding of the subject to learn how to record thoughts includes presenting, on the display, the DR educational-vessel object and the eleventh text at or adjacent to the DR educational-vessel object. In some embodiments, the guiding of the subject to learn how to record thoughts includes rendering at least a portion of the DR educational-vessel object in a color indicative of the recorded training statement.

In some embodiments, the guiding of the subject to learn how to record thoughts includes using, by the subject, a DR thought-impact feature on the DR educational-vessel object to assign a level of impact of the recorded training statement on the subject. In some embodiments, the guiding of the subject includes rendering the DR educational-vessel object to indicate a level of impact of the recorded training statement on the subject.

In some embodiments, the method includes presenting, on the display and in response to a completion of the recorded training statement, the DR portal object for transporting the DR educational-vessel object and the DR thought-recording object.

Yet another aspect of the present disclosure is directed to a method that implements CBT within an interactive DR scene. The method includes obtaining, in electronic form, a first statement from the subject. The method further includes providing, via the display, one or more interactive DR activities configured to help the subject to reframe the first statement. The obtaining of the first statement from the subject the same as or similar to that of the method in the first aspect. In some embodiments, the one or more interactive DR activities include a first interactive DR activity for a subject to practice a gather evidence CBT technique, a second interactive DR activity configured for a subject to practice a usefulness and core beliefs CBT technique, a third interactive DR activity for a subject to practice a create space CBT technique, a fourth interactive DR activity for a subject to practice a CBT technique, or any combination thereof.

In some embodiments, additionally or optionally, the method includes presenting, on the display, a DR thought-recording object for the subject to speak a second statement to the DR thought-recording object and recording the second statement. In some embodiments, the method further includes updating, on the display, a DR wellbeing object from a first display state to a second display state based at least in part on the second statement. From this, the method indicates an improvement in the management of the psychiatric or mental condition by the subject. In some embodiments, these steps are the same as or substantially similar to those of the another aspect of the present disclosure (e.g., a method for implementing a first interactive DR activity), and therefore descriptions of such are omitted to avoid redundancy.

In some embodiments, additionally or optionally, the method includes presenting, on the display, one or more additional DR scenes or one or more portals to the one or more additional DR scenes, each additional DR scene configured for use in an educational or therapeutical session. In some embodiments, the one or more additional DR scenes include an educational DR interactive scene to educate the subject, a DR interactive scene configured for the subject to practice a mindfulness session, a DR interactive scene configured for the subject to practice an exposure therapeutical session, or any combination thereof.

Yet another aspect of the present disclosure is directed to providing non-transitory computer readable storage medium storing one or more programs. The one or more programs includes instructions, which when executed by a computer system cause the computer system to perform a method of the present disclosure.

Yet another aspect of the present disclosure is directed to providing use of a computer system for improving an ability of a subject to manage a psychiatric or mental condition exhibited by the subject. The computer system includes one or more processors, a display, and a memory coupled to the one or more processors. In some embodiments, the computer system includes audio speakers and/or a microphone. The memory includes one or more programs, configured to be executed by the one or more processors, that implement a method of the present disclosure.

Yet another aspect of the present disclosure is directed to providing a device for implementing CBT to help a subject to manage a psychiatric or mental condition of the subject. The device is configured to improve an ability of a subject to manage a psychiatric or mental condition of the subject. Furthermore, the device includes one or more processors and a memory coupled to the one or more processors. The memory includes one or more programs configured to be executed by the one or more processors. The one or more programs are configured to cause the computer system to perform the methods of the present disclosure. In some embodiments, the device includes a display and/or audio circuitry. In some embodiments, the device includes an objective lens in optical communication with a two-dimensional pixelated detector.

Yet another aspect of the present disclosure is directed to providing regimens for implementing CBT and/or additional educational or therapeutical sessions (e.g., education on CBT, mindfulness session, exposure therapeutical session) to help a subject to manage a psychiatric or mental condition of the subject.

BRIEF DESCRIPTION OF THE DRAWINGS

FIG. 11 illustrates an exemplary DR assistant, in accordance with an embodiment of the present disclosure.

FIGS. 12A, 12B, 12C, and 12D illustrate various exemplary DR recordable objects, in accordance with some embodiments of the present disclosure.

FIGS. 13A, 13B, 13C, 13D, 13E, 13F, and 13G illustrate exemplary DR vessel objects, in accordance with some embodiments of the present disclosure.

FIGS. 16A, 16B, and 16C collectively illustrate an exemplary DR wellbeing object, in accordance with some embodiments of the present disclosure.

FIGS. 19A, 19B, 19C, 19D, 19E, 19F, 19G, 19H, 19I, and 19J illustrate a third exemplary DR activity configured for a subject to practice still another CBT technique, in accordance with some embodiments of the present disclosure.

FIG. 22 illustrates an exemplary regimen, in accordance with some embodiments of the present disclosure.

FIGS. 23A and 23B collectively illustrate another exemplary regimen, in accordance with some embodiments of the present disclosure.

FIGS. 28A, 28B, 28C, 28D, 28E, 28F, 28G, 28H, 28I, 28J, 28K, 28L, 28M, 28N, 28O, 28P, 28Q, 28R, 28S, 28T, 28U, and 28V illustrate a variety of exemplary interactive DR activities configured for a subject to practice one or more CBT techniques, in accordance with some embodiments of the present disclosure.

FIGS. 29A, 29B, 29C, 29D, 29E, 29F, 29G, and 29H illustrate a method for management of a psychiatric or mental condition in accordance with the present disclosure in which optional elements are indicated by dashed boxes.

Figure 1:
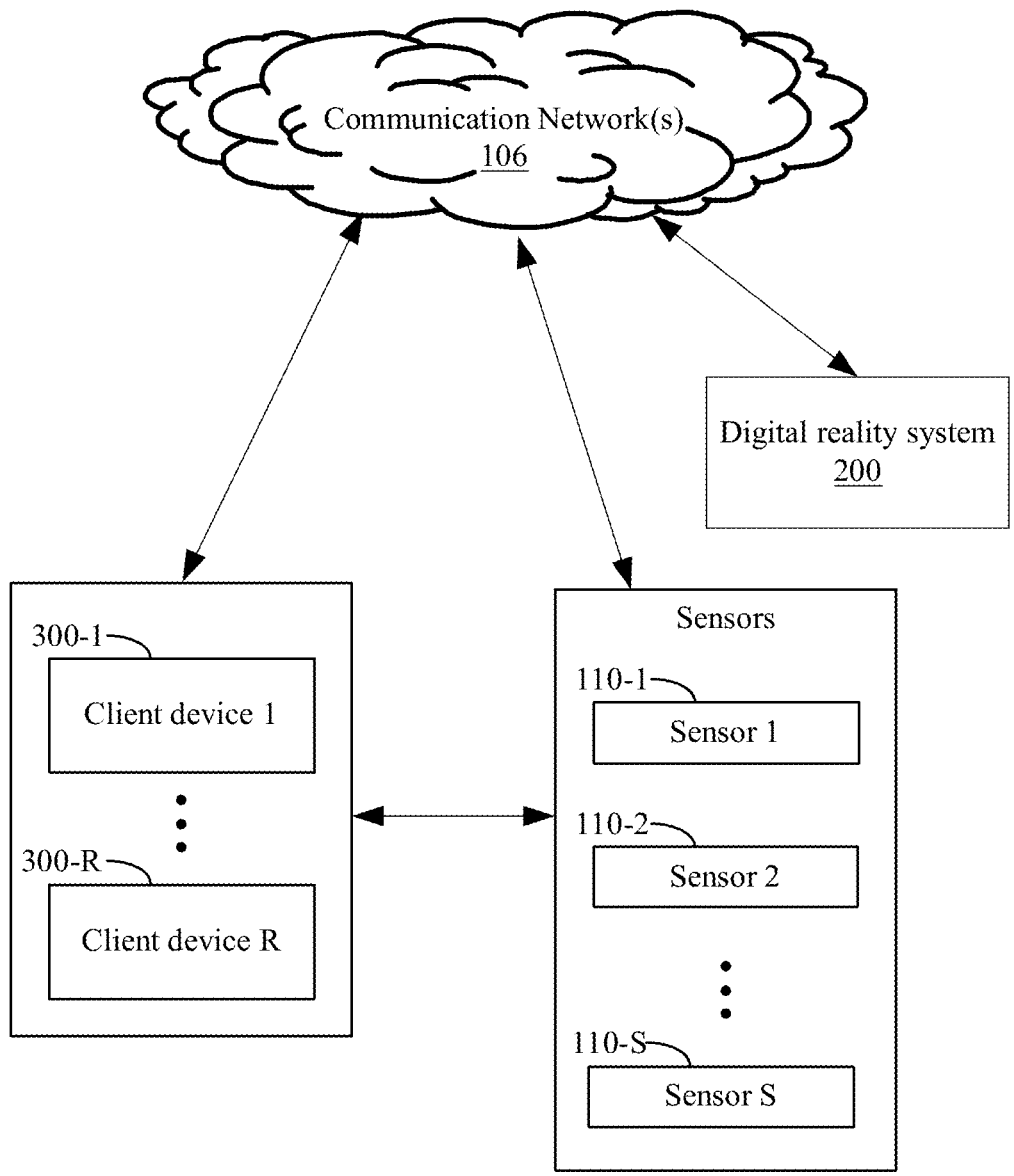
FIG. 1 illustrates a block diagram illustrating an embodiment of a system for displaying an interactive digital reality (DR) scene, in accordance with an embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The systems, methods, and devices of the present disclosure are configured to implement cognitive behavioral therapy (CBT) techniques within one or more interactive digital reality (DR) scenes through a plurality of interactive DR activities of the one or more interactive DR scenes in order to help a subject to manage their psychiatric or mental condition. For instance, in various embodiments, the systems, methods, and devices are configured to provide one or more interactive DR activities provided through an interactive DR scene, in which each interactive DR activity is configured to allow a subject to implement a particular CBT technique or aspect of the particular CBT technique when interacting with the interactive DR scene. As a non-limiting example, in some embodiments, a first interactive DR activity is configured to implement a cognitive reframing CBT technique by interacting with the subject through the interactive DR scene in order to reframe a first thought represented by a first statement into a second, more beneficial, thought, for instance, reframing the first statement into a second statement representing the second thought. As yet another non-limiting example, in some embodiments, the one or more interactive DR activities include a second interactive DR activity configured for a subject to practice a gather evidence CBT technique, a third interactive DR activity configured for a subject to practice a usefulness and core beliefs CBT technique, a fourth interactive DR activity for a subject to practice a create space CBT technique, or any combination thereof.

In some embodiments, the systems, methods, and devices of the present disclosure implement the CBT technique along with one or more other psychotherapeutic and/or psychoeducational techniques through the plurality of interactive DR activities within the interactive DR scene. Examples of other psychotherapeutic and/or psychoeducational techniques include, but are not limited to, exposure therapy, mindfulness-based intervention, behavioral activation, and/or psychoeducational interventions. In some embodiments, a psychotherapeutic and/or psychoeducational technique is presented before, after, or intermittently with an interactive DR activity (e.g., the first, second or third interactive DR activity).

In some embodiments, a goal of the plurality of interactive DR activities provided by the systems, methods, and devices of the present disclosure is to collectively implement a new thinking pattern for a subject by having the subject engage with the interactive DR scene, such as by generating a higher number of a first set of evidence constructs (e.g., reframed thoughts and/or positive affirmations) compared to unresolved anxious thoughts for the subject, either with an interactive DR scene or in a real-world, physical environment. Accordingly, by utilizing the systems, methods, and devices of the present disclosure, the new thinking pattern of the subject is better at recognizing and/or challenging anxious thoughts as they occur (e.g., in real-time), rather than letting the anxious thoughts overwhelm the consciousness of the subject, which is an exhibition by the subject of an anxiety condition.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For instance, a first interactive digital reality activity could be termed a second interactive digital reality activity, and, similarly, a second interactive digital reality activity could be termed a first interactive digital reality activity, without departing from the scope of the present disclosure. The first interactive digital reality activity and the second interactive digital reality activity are both interactive digital reality activities, but they are not the same interactive digital reality activity.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The description herein includes example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The description herein, for purpose of explanation, is described with reference to specific implementations. However, the illustrative discussions are not intended to be exhaustive or to limit the implementations to the precise forms disclosed. Many modifications and variations are possible in view of the disclosed teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. Where particular values are described in the application and claims, unless otherwise stated, the term "about" means within an acceptable error range for the particular value. The term "about" can have the meaning as commonly understood by one of ordinary skill in the art. The term "about" can refer to ±10%. The term "about" can refer to ±5%.

As used herein, the term "equally spaced" means that a distance from a first feature to a corresponding second feature is the same for successive pairs of features unless expressly stated otherwise.

As used herein, the term "dynamically" means an ability to update a program while the program is currently running.

Additionally, the terms "client," "patient," "subject," and "user" are used interchangeably herein unless expressly stated otherwise.

Furthermore, the terms "healthcare professional," "medical practitioner," and "clinician" are used interchangeably herein unless expressly stated otherwise.

Moreover, the terms "avatar" and "player character" are used interchangeably herein unless expressly stated otherwise.

In addition, the terms "therapy" and "treatment" are used interchangeably herein unless expressly stated otherwise.

In some embodiments, the terms "statement," "phrase," and "utterance" are used interchangeably herein unless expressly stated otherwise.

Furthermore, the terms "activity" and "technique" are used interchangeably herein unless expressly stated otherwise.

Moreover, as used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier.

For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,000$; $n \geq 200,000$; $n \geq 500,000$, $n \geq 1 \times 10^6$, $n \geq 5 \times 10^6$, or $n \geq 1 \times 10^7$. In some embodiments n is between 10,000 and $1 \times 10^7$, between 100,000 and $5 \times 10^6$, or between 500,000 and $1 \times 10^6$.

Furthermore, when a reference number is given an "$i^{th}$" denotation, the reference number refers to a generic component, set, or embodiment. For instance, a digital reality scene termed "digital reality scene i" refers to the $i^{th}$ digital reality scene in a plurality of digital reality scenes (e.g., a digital reality scene 40-$i$ in a plurality of digital reality scenes 40). In the present disclosure, unless expressly stated otherwise, descriptions of devices and systems will include implementations of one or more computers.

As used herein, the term "DR" is an abbreviation of digital reality, which can be any virtual reality, any augmented reality, any mixed reality, or the like.

As used herein, the term "miniature," "small version," or the like is used to differentiate an object in a DR scene from the same object rendered in another DR scene, to differentiate an object in a portion of a DR scene from the same object rendered in another portion of the same DR scene, to differentiate an object from its surroundings, or the like. A miniature object or a small version of an object can be, but do not necessarily have to be, always small in size when displayed. For instance, in some embodiments, if a closer look is desirable or beneficial, the DR miniature environment or a portion of it is enlarged or even rendered over the entire display.

1. Systems

Figure 2A:
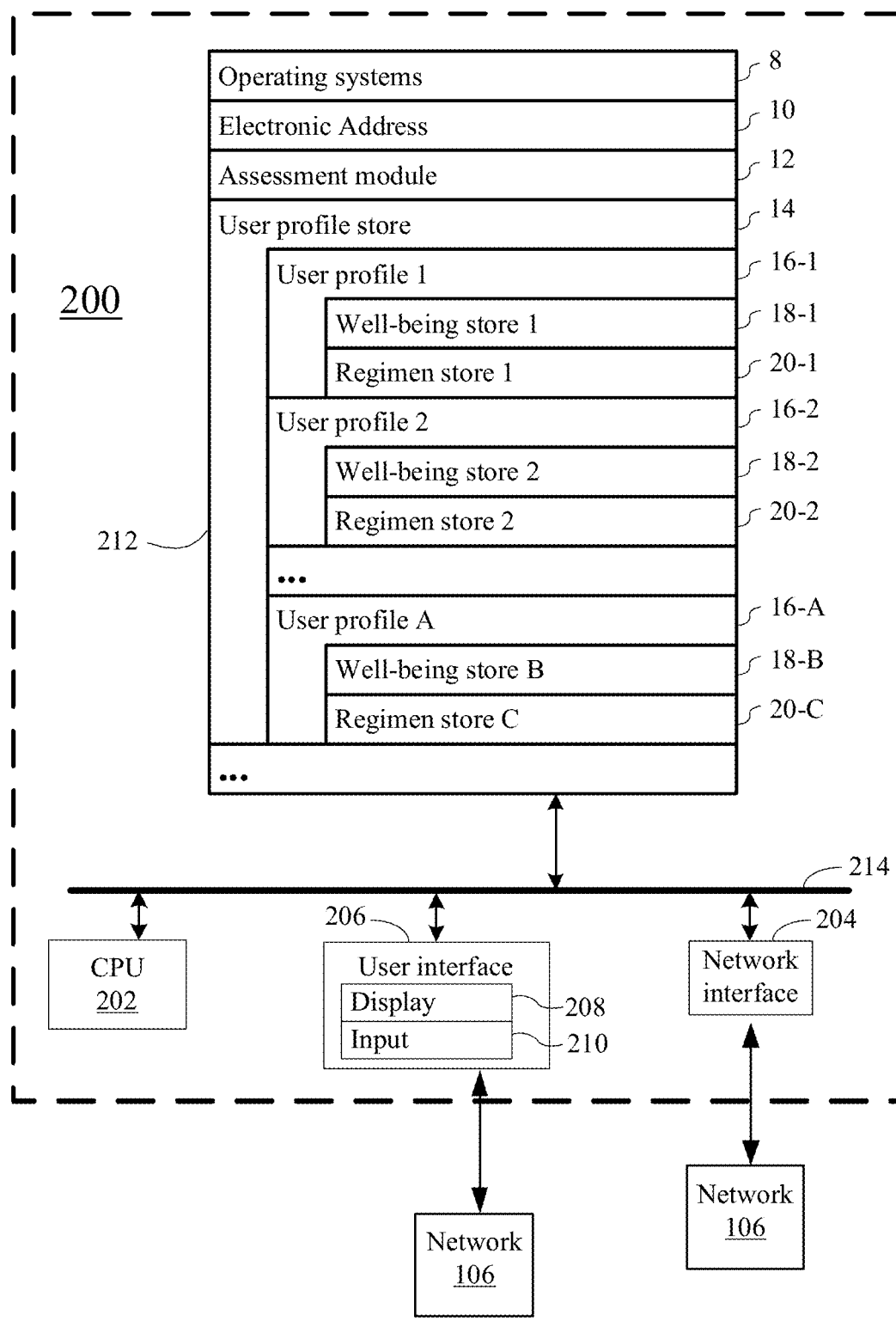
FIGS. 2A and 2B collectively illustrate a DR host system for facilitating a DR experience, in accordance with an embodiment of the present disclosure.
Figure 2B:
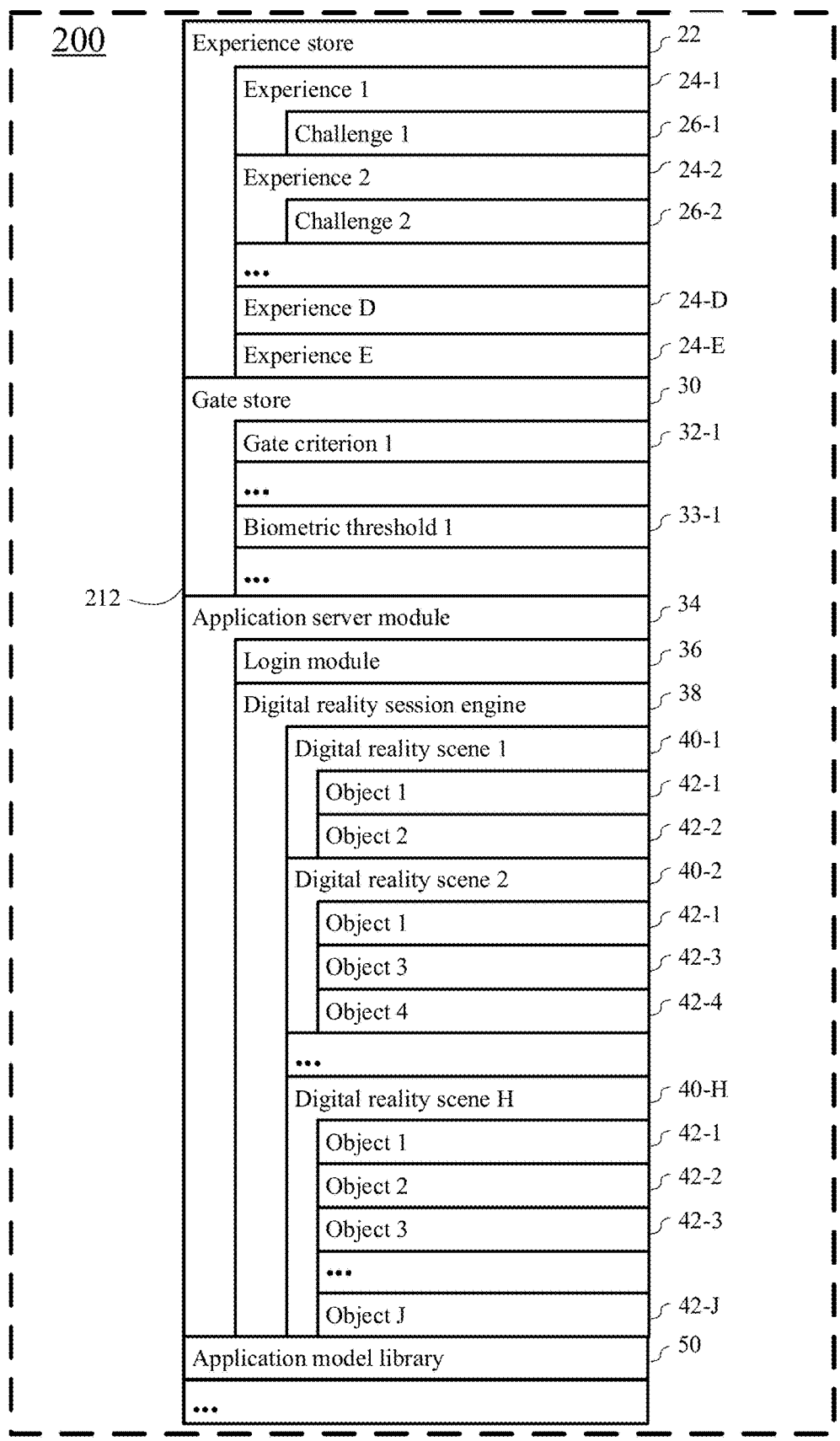
Figure 3:
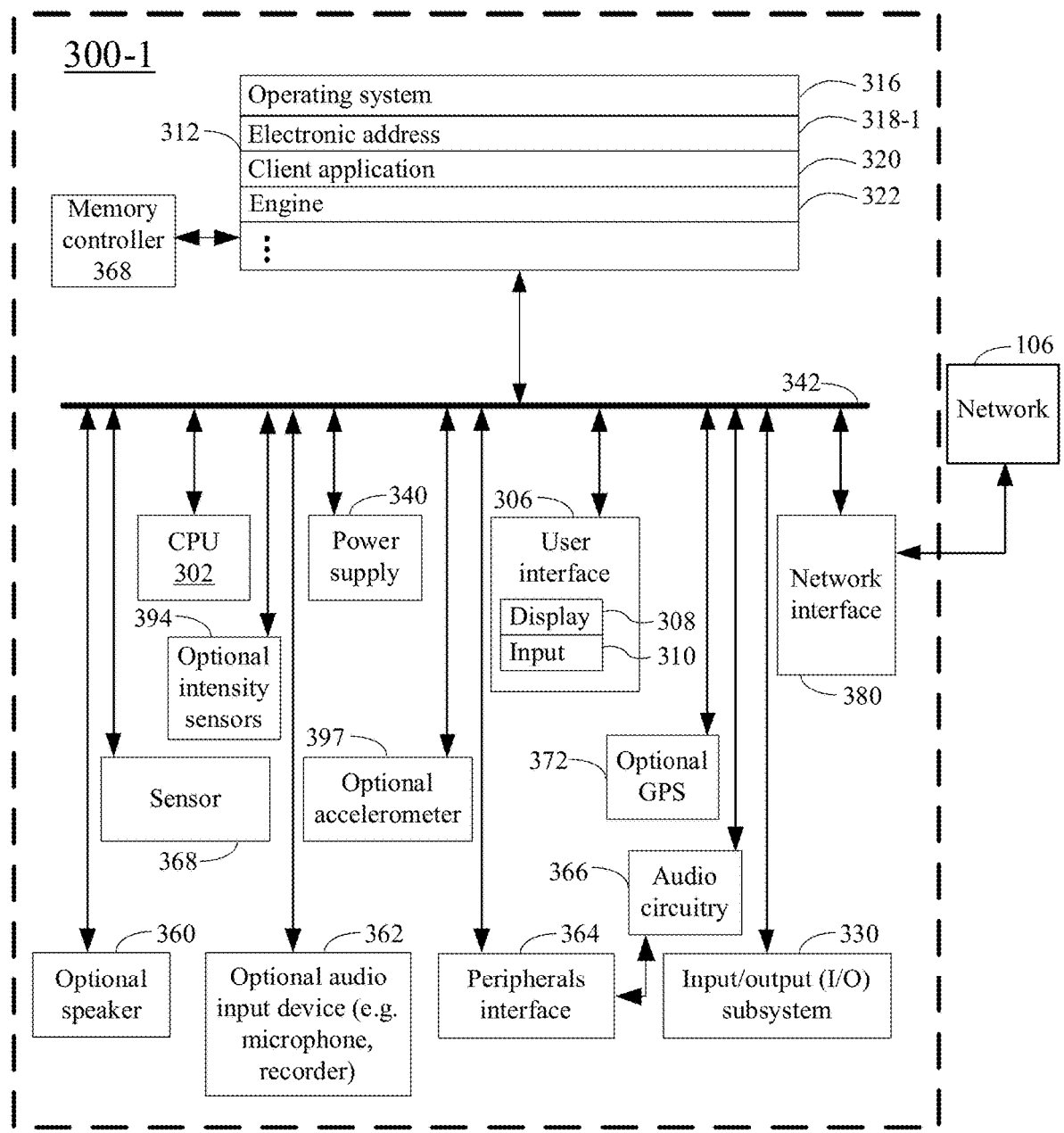
FIG. 3 illustrates a client device for displaying an interactive DR scene, in accordance with an embodiment of the present disclosure.

Exemplary systems of the present disclosure are described herein with respect to FIGS. 1-3.

1.1. Client-Server System

FIG. 1 depicts a block diagram of a distributed client-server system (e.g., distributed client-server system 100) according to some embodiments of the present disclosure. The system 100 facilitates implementing a CBT technique through an interactive DR activity for a subject within an interactive DR scene in order to improve an ability of the subject to manage a psychiatric or mental condition, such as a clinically diagnosed mental disorder, a sub-clinically diagnosed medical disorder, an undiagnosed condition (one that has not been diagnosed for the subject by a medical practitioner), or a combination thereof. The system 100 includes a digital reality system (e.g., digital reality system 200) and one or more client devices 300 (e.g., a first client device 300-1, a second client device 300-2, . . . , a $R^{th}$ client device 300-R, etc.) in communication with the digital reality system 200 through a communication network (e.g., communication network 106). In some embodiments, each client device 300 is associated with at least one subject (e.g., a subject).

Additionally or optionally, in some embodiments, the system 100 includes a plurality of sensors, such as sensor 110-1, sensor 110-2, . . . , sensor 110-S of FIG. 1. The plurality of sensors 110 includes at least one biometric sensor (e.g., sensor 110-1 and/or sensor 110-2 being a biometric sensor or including a biometric sensor) configured to capture biometric data of a subject. In some embodiments, one or more sensors 110 in the plurality of sensors are incorporated into a client device 300 or are components of the client device. In some embodiments, the one or more sensors 110 are in communication with one or more client devices (e.g., through ANT+ or Bluetooth or network interface of the client device). For example, in some embodiments, data captured by the one or more sensors 110 is sent to and/or aggregated in the one or more client devices. In some embodiments, the one or more sensors 110 are in communication with a remote system, e.g., connected to the digital reality system 200 via the communication network 106. For instance, in some embodiments, data captured by the one or more sensors is sent to the remote system, which collects, stores, processes, or a combination thereof the captured biometric data.

In some embodiments, the system 100 facilitates providing a regimen of interactive DR activities for a population of subjects. In some embodiments, at least one subject in the population of subjects exhibits a psychiatric or mental condition. In some embodiments, each subject in the population of subjects exhibits a psychiatric or mental condition.

In some embodiments the psychiatric or mental condition is diagnosed by a combination of clinical symptoms based on the Diagnostic and Statistical Manual of Mental Disorders (DSM) ("The Diagnostic and statistical manual of mental disorders," Fifth Edition (DSM-5), Arlington: American Psychiatric Publishing 21, 591-643, which is hereby incorporated by reference in its entirety for all purposes) or the International Classification of Diseases (Maercker et al., 2013, "Proposals for mental disorders specifically associated with stress in the International Classification of Diseases-11" The Lancet 381, pp. 1683-1685, which is hereby incorporated by reference in its entirety for all purposes).

In some embodiments, the regimen is prepared at the digital reality system 200 and then provided to a subject through a graphical user interface (GUI) displayed on a display (e.g., display 308 of FIG. 3) of a respective client device 300. In some embodiments, a medical practitioner (e.g., clinician) associated with a subject prepares the regimen at a first client device (e.g., the client device 300-1) and the subject performs the regimen at a second client device (e.g., the client device 300-2), which does not require the subject to use the same client device 300 as the medical practitioner. However, the present disclosure is not limited thereto. For instance, in some embodiments, the medical practitioner associated with the subject prepares the regimen at the first client device 300-1 and the subject performs the regimen at the first client device. Moreover, in some embodiments, the regimen is prepared by a model (e.g., model of application library 50 of FIG. 2B), such as by a first model without human interference.

Examples of the communication network 106 includes, but is not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments, the communication network 106 optionally includes the Internet, one or more local area networks (LANs), one or more wide area networks (WANs), other types of networks, or a combination of such networks.

It should be noted that the exemplary topology shown in FIG. 1 merely serves to describe the features of an embodiment of the present disclosure in a manner that will be readily understood to one of skill in the art. Other topologies of the system 100 are possible. For instance, in some embodiments, any of the illustrated devices and systems can, in fact, constitute several computer systems that are linked together in a network or be one or more virtual machines and/or containers in a cloud-computing environment. Moreover, rather than relying on a physical communications network 106, the illustrated devices and systems may wirelessly transmit information between each other.

1.2. Digital Reality System

FIGS. 2A and 2B depict an exemplary digital reality system 200 for implementing a CBT technique through one or more interactive DR activities in a plurality of interactive DR activities within an interactive DR scene in order to improve an ability of a subject to manage a psychiatric or mental condition exhibited by the subject. In various embodiments, the digital reality system 200 includes one or more processing units (CPUs) 202, a network or other communications interface 204, and a memory 212.

The memory 212 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. The memory 212 may optionally include one or more storage devices remotely located from the CPU(s) 202.

The memory 212, or alternatively the non-volatile memory device(s) within memory 212, includes a non-transitory computer readable storage medium. Access to the memory 212 by other components of the digital reality system 200, such as the CPU(s) 202, is, optionally, controlled by a controller. In some embodiments, the memory 212 includes mass storage that is remotely located with respect to the CPU(s) 202. In other words, some data stored in the memory 212 may in fact be hosted on devices that are external to the digital reality system 200, but that can be electronically accessed by the digital reality system 200 over an Internet, intranet, or other form of network 106 or electronic cable using communication interface 204.

In some embodiments, the memory 212 of the digital reality system 200 for implementing a CBT technique within an interactive DR scene in order to improve an ability of a subject to manage a psychiatric or mental condition exhibited by the subject stores:

an optional operating system 8 (e.g., ANDROID, iOS, DARWIN, RTXC, LINUX, UNIX, OS X, WINDOWS, or an embedded operating system such as VxWorks) that includes procedures for handling various basic system services;

an electronic address 10 associated with the digital reality system 200 that identifies the digital reality system 200;

an optional assessment module 12 for obtaining an assessment of a subject;

a user profile store 14 for retaining information associated with a population of users (e.g., user of client devices 300 of FIG. 1), including a user profile 16 for each user in the population of users, the user profile 16 including a corresponding well-being store 18 and a regimen store 20 associated with a subject of the user profile 16;

an experience store 22 including a plurality of experiences (e.g., first experience 24-1, second experience 24-2, . . . , experience 24-I of FIG. 2B), each experience 24 for social exposure therapy including a corresponding challenge 26, experience 24 for other psychotherapeutic and/or psychoeducational techniques may or may not include a corresponding challenge 26;

a gate store 30 including a plurality of gate criteria (e.g., first gate criterion 32-1, second gate criterion 32-2, ..., gate criterion G 32-G of FIG. 2B), each gate criterion 32 representing a condition for user interaction;

an application server module 34 that facilitates providing a plurality of digital reality scenes 40 to a population of client devices 300, the application server module 34 including a login module 36 for accessing a digital reality scene 40 and a digital reality session engine 38 that facilitates providing a plurality of digital reality scenes (e.g., first digital reality scene 40-1, second digital reality scene 40-2, ..., digital reality scene H 40-H of FIG. 2B) for a population of users (e.g., client devices 300); and an application model library 50 that retains one or more models for providing an evaluation of a characteristic of a respective input, such as providing a first evaluation of whether completion of a corresponding challenge 26 satisfies one or more corresponding gate criteria 32 (e.g., determining whether a subject satisfies a threshold condition associated with each interactive DR activity in the plurality of interactive DR activities).

An electronic address 10 is associated with the digital reality system 200. The electronic address 10 is utilized to at least uniquely identify the digital reality system 200 from other devices and components of the distributed system 100 (e.g., uniquely identify digital reality system 200 from client device 300-1, client device 300-2, ..., or client device 300-R of FIG. 1). For instance, in some embodiments, the electronic address 10 is utilized to receive a request from a client device 300 to participate in a respective digital reality scene via a login module 36 of an application server module 34.

Figure 27:
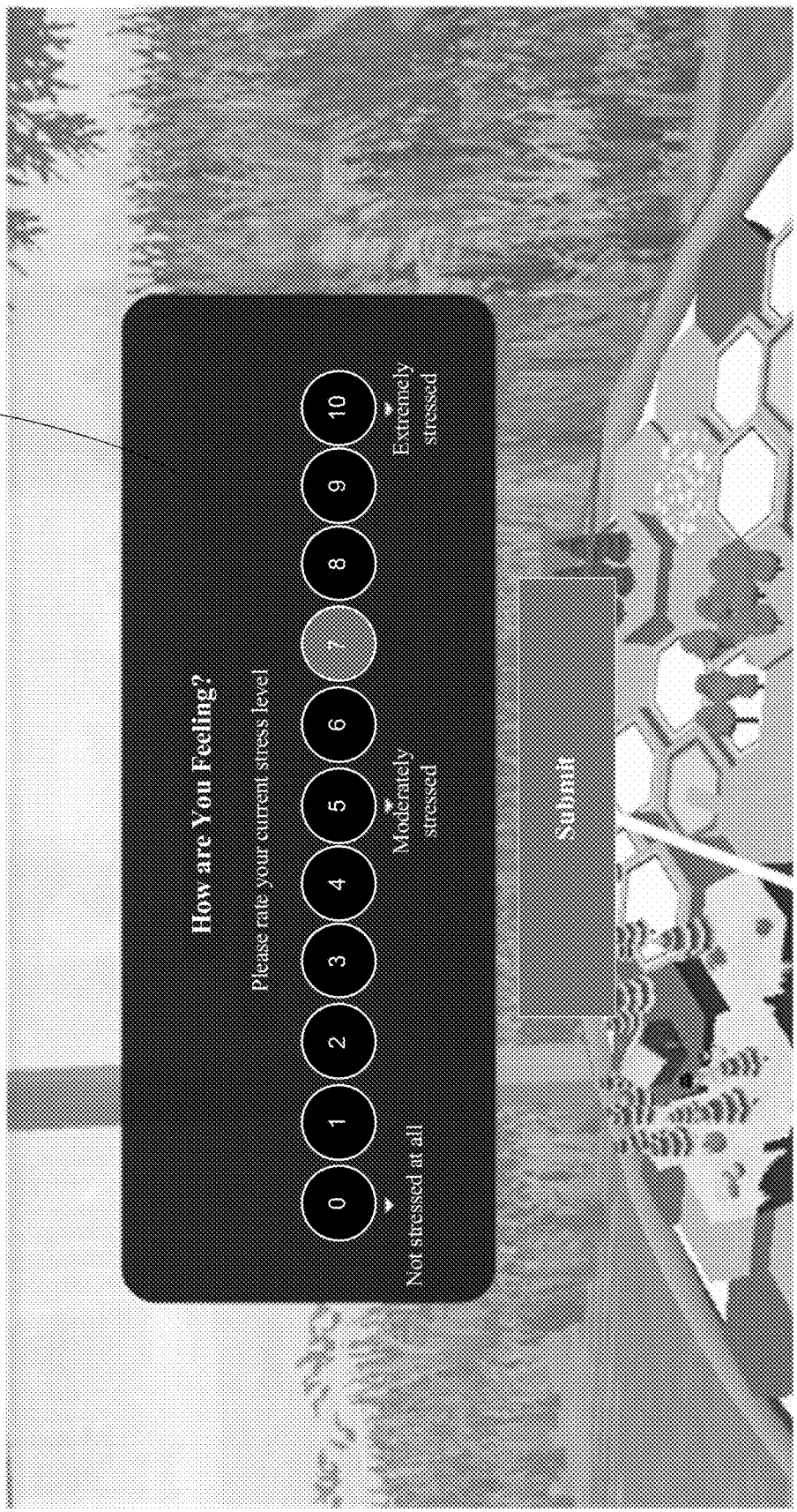
FIG. 27 illustrates an exemplary subjective unit of distress (SUDS) for a subject to track stress levels, in accordance with some embodiments of the present disclosure.

In some embodiments, an assessment module 12 facilitates obtaining an assessment from a subject (e.g., assessment 2710 of FIG. 27), such as a user of a respective client device 300 or a medical practitioner associated with the user. In some embodiments, the assessment module 12 includes one or more assessments that is communicated to the respective client device (e.g., via communications network 106 of FIG. 1). For instance, in some embodiments, the assessment module 12 stores a standardized assessment that is provided to each subject. The standardized assessment provides a uniform assessment to each subject. In some embodiments, by utilizing a standardized assessment, the assessments obtained from multiple users is normalized, such as in order to optimize identification of a plurality of proposed experiences (e.g., from experiences 24 of experience store 22 of FIG. 2B) between different users.

In some embodiments, the assessment includes one or more prompts answered by a subject. In some embodiments, through the answers to the one or more prompts provided by the subject, an identification of a plurality of proposed experiences is obtained for the subject. For instance, in some embodiments, an assessment for a social anxiety psychiatric or medical condition includes asking a user of a client device (e.g., client device 300-1) a question and providing multiple predetermined answers (e.g., none, mild, moderate, or severe). Accordingly, a user selection of a first answer from the predetermined answers forms the basis for the identification of the plurality of proposed experiences 24.

In some embodiments, the assessment module 12 forms a respective assessment based on a set of prompts in the one or more prompts. For instance, in some embodiments, the one or more prompts includes at least three prompts, and the assessment module 12 selects a first prompt and a second prompt, but not a third prompt, to generate an assessment for a first subject. In some embodiments, the assessment module 12 selects the first prompt and the third prompt, but not the second prompt, to generate the assessment for the first subject and/or a second subject. Accordingly, in some embodiments, the assessment module 12 allows for dynamically generating and/or updating an assessment provided to a subject based at least in part on the one or more prompts stored by the assessment module 12. However, the present disclosure is not limited thereto.

In some embodiments, the assessment module 12 includes one or more authorization criteria associated with approving an assessment obtained from a subject. For instance, in some embodiments, the assessment is provided to a first subject of a first client device 300-1, in which the first subject exhibits a psychiatric or mental condition. In such embodiments, obtaining the assessment from the first subject is conditioned on satisfying a first authorization criterion. This first authorization criterion is associated with the first subject obtaining an authorization of the assessment from a medical practitioner associated with the subject. By way of example, in some embodiments, the first authorization criterion requires that the medical practitioner validate a certain aspect of the assessment, such as a truthfulness of the assessment. Accordingly, in some such embodiments, by adding a level of human authorization, the digital reality system 200 ensures that a subject that exhibits a psychiatric or mental condition improves their ability to manage the psychiatric or mental condition when utilizing the systems, methods, and devices of the present disclosure by providing honest answers to the assessment. In this way, in some such embodiments, the assessment module 12 prevents the subject from distorting the assessment, which would result implementation of CBT techniques for the subject that might not improve the ability of the subject to manage their psychiatric or mental condition. However, the present disclosure is not limited thereto.

A user profile store 14 retains a plurality of user profiles 16. In some embodiments, each respective user profile 16 is associated with a corresponding user of the digital reality system 200, such as a user of a client device 300 that exhibits a psychiatric or mental condition and/or a medical practitioner associated with the user. For instance, in some embodiments, a respective user first customizes their profile (e.g., first user profile 16-1) at a client device 300 by making a selection of a plurality of user login information, such as a password, an address (e.g., E-mail address, physical address, etc.), a personal name (e.g., a given name, a username, etc.), and the like. In some embodiments, the respective user provides, or is collected by the client device 300 (e.g., using optional GPS, using sensor 110, etc.), one or more demographic characteristics (e.g., an age of the user, a weight of the user, a height of the user, a gender of the user, year of education of the user, etc.) and/or one or more geographic characteristics (e.g., a region associated with the user, a physical address associated with the user, etc.). However, the present disclosure is not limited thereto. In some embodiments, the user profile uniquely identifies the respective user, which allows for storing and/or evaluating historical information about the respective user based on various interactive DR activities engaged with by the respective subject. In this way, each user profile 16 allows the digital reality system 200 to retain login information, privacy information (e.g., which psychiatric or mental condition is exhibited by a corresponding subject associated with a respective user profile 16), user information, biographical data, performance information, assessment response information, other preferences, or a combination thereof, such as in order to tailor one or more interactive DR activities presented to the respective subject within an interactive DR scene provided by the digital reality system 200. In some embodiments, a login name associated with a respective user is the same as the username displayed for the user. In other embodiments, a login name associated with a respective user is different from the username displayed for the user (e.g., displayed usernames with a digital reality scene 40 are different from associated user logins). In some embodiments, the user profile 16 includes some or all of a corresponding medical record of the subject associated with the user profile 16. For instance, in some embodiments, the corresponding medical record of the subject is obtained from a client device associated with a medical practitioner of the subject (e.g., via communication network 106), which forms a basis for information of the user profile 16. In some embodiments, the digital reality system 200 stores a plurality of avatar information, including a plurality of traits for each avatar user, and/or a contact list of contacts within a digital reality scene 40. Accordingly, the systems, methods, and devices of the present disclosure allow for personalizing a DR scene 40 and/or an interactive DR activity based on the information associated with the user using the user profile 16. By way of example, in some embodiments, a subject provides an age of the subject and, in accordance with the age of the subject, an appearance and/or an intensity level (e.g., a difficulty level) of a non-player character associated with a digital reality scene is modified to result in an implementation of CBT techniques appropriate for the age of the subject in order to improve the ability of the subject to manage their psychiatric or mental condition. However, the present disclosure is not limited thereto.

Additionally, in some embodiments, each user profile 16 includes a well-being store (e.g., first user profile 16-1 includes first well-being store 18-1, second user profile 16-2 includes second well-being store 18-2, . . . , user profile A 16-A includes well-being store B 18-B, etc.). In some embodiments, the well-being store 18 retains a plurality of health information associated with the subject, such as an indication of a clinical diagnosis for a psychiatric or mental condition, a plurality of insurance information associated with an insurance provider of a corresponding subject, an electronic medical record, and the like. In some embodiments, the well-being store 18 includes a status of a treatment administered to a subject, such as a result of a previous treatment for the psychiatric or mental condition, a result of a previous regimen 20 provided to the subject, and the like.

In some embodiments, the well-being store 18 includes a plurality of biometric data elements that is associated with the respective user. For instance, in some embodiments, a set of biometric data elements is obtained when presenting a digital reality scene 40 on a client device 300, and a plurality of biometric data elements from the set of biometric data elements (e.g., the first set of biometric data elements) is retained by the well-being store 18. As a non-limiting example, in some embodiments, the plurality of biometric data elements retained by the well-being store 18 includes a heart rate of the subject (e.g., a baseline heart rate, one or more heart rate zones of the subject, etc.). In some embodiments, the plurality of biometric data elements retained by the well-being store 18 includes a blood pressure of the subject (e.g., a baseline systolic blood pressure, a threshold diastolic blood pressure, etc.). Furthermore, in some embodiments, the plurality of biometric data elements includes a plurality of spatiotemporal data elements, which describe a spatial and temporal aspect of the user when interacting with a digital reality scene. Non-limiting examples of the plurality of spatiotemporal data elements includes an area of a portion of an eye of the user, a change in a position of the eye of the subject when addressing the corresponding challenge 26, a count of occurrences of the eye of the user at a predetermined reference position, and the like. However, the present disclosure is not limited thereto. In some embodiments, the plurality of biometric data includes one or more resting-state functional magnetic resonance imaging connectivity (rsfMRI) scans of the subject. Etkin et al., 2019, "Using fMRI connectivity to define a treatment-resistant form of post-traumatic stress disorder," Science Translational Medicine 11, eaal3236, which is hereby incorporated by reference in its entirety for all purposes.

In some embodiments, the well-being store 18 includes one or more annotations. In some embodiments, each annotation is associated with the corresponding subject participating in a digital reality scene 40 and/or one or more assessments obtained from the subject. For instance, in some embodiments, the one or more assessments obtained from the subject that are stored by the well-being store 18 include a first assessment for obtaining the identification of the plurality of proposed experiences and/or a second assessment based on a proposed experience 24 conducted by the user. In some embodiments, the one or more annotations include a first annotation provided by the medical practitioner associated with the subject. In some embodiments, the one or more annotations includes a second annotation provided by the subject.

In some embodiments, each user profile includes a regimen store (e.g., first user profile 16-1 includes first regimen store 20-1, second user profile 16-2 includes second regimen store 20-2, . . . , user profile A 16-A includes regimen store C 20-C, etc.) that retains information associated with a corresponding subject. By way of example, in some embodiments, the information retained by the regimen store of the user profile includes a plurality of sessions of a corresponding user interacting with the digital reality system. In some embodiments, the plurality of sessions includes an exposure session, a cognitive behavioral therapy session, a mindfulness based cognitive therapy session, or a combination thereof. From this, the user profile allows the systems, methods, and devices of the present disclosure to track various parameters associated with improving an ability of a subject to manage their psychiatric or mental condition.

In some embodiments, by retaining a well-being store 18 and a regimen store 20 with each user profile 16, the digital reality system 200 allows each subject associated with a user profile to interact with the digital reality system 200 when and where the subject desires without losing their progress in improving their ability of manage their psychiatric or mental condition.

In some embodiments, a gate or criterion store 30 facilitates retaining a plurality of criteria 32 (e.g., gate criterion 32-1, gate criterion 32-2, . . . ). In some embodiments, a gate criterion 32 is used to determine whether a challenge associated with an experience has been successfully completed by a subject, to identify a subsequent challenge for a subject to take, to determine whether a category has been successfully completed by a subject, to identify a subsequent category for a subject to take, to determine whether a subject is ready to reframe a thought, or any combination thereof. In some embodiments, a gate criterion sets a condition for determining whether a category has been successfully completed, and/or for identifying a subsequent category or categories for a subject to take. In some embodiments, a gate criterion sets a condition precedent for executing a category or a condition that must be achieved in order to deem the category complete. In some embodiments, a gate criterion sets a condition for a subject to reframe a thought or a statement. In some embodiments, the criterion store 30 also includes a plurality of biometric thresholds (e.g., biometric threshold 33-1, . . . ). In some embodiments, a biometric threshold sets a condition for determining whether a challenge associated with an experience has been successfully completed, and/or for identifying a subsequent challenge for a subject to take. In some embodiments, a biometric threshold sets a condition precedent for executing a challenge associated with an experience or a condition that must be achieved in order to deem the challenge associated with the experience complete. In some embodiments, a biometric threshold sets a condition precedent for reframing a thought. However, the present disclosure is not limited thereto. In some embodiments, each gate criterion is associated with a corresponding threshold condition that is associated with a respective interactive DR activity (e.g., interactive DR activity 2810-1 of FIG. 28B, interactive DR activity 2810-1 of FIG. 17A, activity 2810-1 of FIG. 18A, interactive DR activity 2810-2 of FIG. 28E, etc.)

While FIG. 2B illustrates gate criteria and biometric thresholds separately, it should be noted that, in some embodiments, gate criteria and biometric thresholds are arranged in the criterion store in other ways. For instance, in some embodiments, a category is associated with a gate criterion that includes one or more biometric thresholds for determining whether the challenge(s) of one or more experiences associated with the category has been successfully completed. In such embodiments, the criterion store includes separate biometric thresholds. Moreover, while FIG. 2B illustrates only gate criteria and biometric thresholds, it should be noted that, in some embodiments, the criterion store includes other criteria. For instance, in some embodiments, the criterion store includes at least one criterion for emergent termination of a social challenge or session. Further, in some embodiments, a criterion, either a gate criterion, a biometric threshold, or any other type, is a standard criterion applicable to multiple subjects or a personalized criterion specifically designed for a single subject. In some embodiments, the criterion store includes at least one standard criterion. In some embodiments, the criterion store includes at least one personalized criterion. In some embodiments, the criterion store includes both standard and personalized criteria.

In some embodiments, the digital reality system 200 includes an application server module 34 that facilitates providing access to a digital reality scene 40 for a user of a client device 300. In some embodiments, the application server module 34 sends each respective client device 300 data elements associated with a digital reality scene 40 when there is a request for such data elements by the respective client device 300, such as when the user logs into a client application 320 at the client device 300. For instance, in some embodiments, a login module 36 of the application server 34 verifies the information provided by the user of the client device 300 against the information stored in a user profile 16 to ensure the correct user is requesting access to a digital reality scene 40. Accordingly, a population of users employ the client devices 300 to access the application server module 34 at the digital reality system 200 and to interact with a digital reality scene 40 that is hosted by the digital reality system 200.

In some embodiments, the application server module 34 also facilitates allowing the user of the client device 300 to configure a digital reality scene 40 in accordance with a determination that the user is a medical practitioner and/or an administrator of the client device 300. For instance, a user interface of a client device allows the user to configure a number of non-player characters (NPCs) associated with one or more challenges 26. Examples of NPCs include other avatars associated with a digital reality scene 40 that the subject interacts with in (e.g., a coffee shop barista, a guest at a party, a co-worker, a transit worker, a menu narrator, a computer implemented communications agent, etc.).

Each respective digital reality scene 40 defines a digital domain for use by a population of users. A digital reality scene broadly means any space (e.g., digital space and/or real-world space) where digital reality content (e.g., an avatar, a digital reality object, etc.) is presented to a user, for instance, through a display of a client device. For example, in some embodiments, a digital reality scene 40 includes an avatar creation client application, a video game, a social networking website or forum, a messaging client application, or any other client application including a digital representation, such as a digital object.

In some embodiments, a digital reality scene 40 is configured for exposing a subject to a therapy technique for improving the psychiatric or mental condition of the subject by having the subject perform a plurality of interactive DR activities. For instance, in some embodiments, the therapy for improving the psychiatric or mental condition of the subject is a cognitive therapy. As a non-limiting example, in some such embodiments, the cognitive therapy is cognitive behavioral therapy (CBT) or mindfulness based cognitive therapy (MBCT), such as a mindfulness-based stress reduction therapy. Accordingly, in some embodiments, the digital reality scene is configured for exposing the subject to a cognitive reframing training, a mindfulness training, and/or other educational or therapeutical trainings. Additional details and information regarding exposing a subject to cognitive therapy is found at Segal et al., 2018, "Mindfulness-based Cognitive Therapy for Depression," Guilford Publications, print; Hayes et al., 2018, "Process-based CBT: The Science and Core Clinical Competencies of Cognitive Behavior Therapy," New Harbinger Publications, print, each of which is hereby incorporated by reference in its entirety for all purposes.

Specifically, a respective digital reality scene 40 includes a plurality of objects (e.g., first object 42-1, second object 42-2, . . . , object J 42-J of digital reality scene H 40-H of FIG. 2B) that populates the respective digital reality scene 40. In some embodiments, the plurality of objects 42 includes a plurality of player character objects 42 (e.g., avatars) that represent and/or is controlled by the user, a plurality of NPC objects 42 that represent NPC in the respective digital reality scene that the user cannot directly control, and a plurality of scene objects 42 (e.g., objects that are not player character objects 42 or NPC objects 42, such as bodies of water in a digital reality scene 40, buildings, and furniture in the digital reality scene 40, etc.). As used herein, a digital reality scene refers to any space (e.g., digital space and/or real-world space) where digital reality content (e.g., an avatar, a digital reality object, etc.) is presented to a user through a display (e.g., a display of a client device 300). As a non-limiting example, in some embodiments, the plurality of scene objects 42 includes one or more DR recording objects, one or more DR thought-recording objects, one or more DR features (e.g., a thought-category DR feature, a thought-impact DR feature, etc.), one or more DR maps, one or more DR moving objects, one or more DR belief objects, one or more DR belief-recording object, one or more DR thought-indicative objects, one or more DR third-person-recording objects, one or more DR word-recording objects, one or more DR wellbeing objects, or a combination thereof.

However, the present disclosure is not limited thereto. For instance, in some embodiments, the object 42 includes one or more characters (e.g., written characters, spoken characters, etc.) that is comprehensible by a user in the digital reality scene 40, such a video or text. Collectively, the plurality of objects 42 enables a user of a client device 300 to actively interact with the digital reality scene 40, such as one or more users that is online and interacting in the digital reality scene 40 and form the respective digital reality scene 40.

Each respective object 42 includes a plurality of attributes that describe not only how a respective object 42 interacts with a digital reality scene 40, such as with other objects 42 in the digital reality scene 40, but also how the respective object 42 interacts with other users in the digital reality scene 40. In some embodiments, one or more attributes of an object 42 that is modified or varied include a mass of the object 42, a volume of the object 42, a coefficient of friction of the object 42, a state of matter of the object 42, a rigidity of a body of the object 42, a position of the object 42, a health value of the object 42 (e.g., hit points of the object 42, energy points of the object, etc.), joints of the object 42, and the like. As a non-limiting example, consider a first attribute that describes a response to a collision with a respective object 42 (e.g., a hardness of the object 42, an adhesiveness of the object 42, etc.).

In some embodiments, one or more attributes associated with a respective object 42 is the same for each user in a digital reality scene 40. For example, in some embodiments, if a respective object 42 has an attribute that makes the respective object 42 interactive with users, each user in the digital reality scene 40 is able to interact with the respective object 42. On the other hand, if the respective object 42 has an attribute that makes the respective object 42 interactive for a select group of users, such as those subjects that have an indication in a user profile 16 of exhibiting a psychiatric or mental condition, only the users in the select group of users are allowed to interact with the respective object 42. For example, in some embodiments, an administrator user of a digital reality scene 40 restricts interaction with a specific object 42 for all users except for the administer user or one or more particular users, such as those exhibiting a psychiatric or mental condition.

In some embodiments, the digital reality system 200 includes an application model library 50 that stores one or more models (e.g., classifiers, regressors, etc.). In some embodiments, the model is implemented as an artificial intelligence engine. For instance, in some embodiments, the model includes one or more gradient boosting models, one or more random forest models, one or more neural networks (NN), one or more regression models, one or more Naïve Bayes models, one or more machine learning algorithms (MLA), or a combination thereof. In some embodiments, an MLA or a NN is trained from a training data set (e.g., a first training data set including the user profile store 14, the experience store 22, the gate store 30, the application server module logs 34, or a combination thereof) that includes one or more features identified from a data set. By way of example, in some embodiments, the training data set includes data associated with a first user profile 16-1 and data associated with user tendencies in when confronted with an experience 24 in a digital reality scene 40. Accordingly, in some embodiments, a first model is a neural network classification model, a second model is a Naïve Bayes classification model, and the like. Furthermore, in some embodiments, the model includes decision tree algorithm, a neural network algorithm, a support vector machine (SVM) algorithm, and the like. Moreover, in some embodiments, the model described herein is a logistic regression algorithm, a neural network algorithm, a convolutional neural network algorithm, a support vector machine (SVM) algorithm, a Naïve Bayes algorithm, a nearest neighbor algorithm, a boosted trees algorithm, a random forest algorithm, a decision tree algorithm, a clustering algorithm, or a combination thereof.

In some embodiments, a model is utilized to normalize a value or data set, such as by transforming the value or a set of values to a common frame of reference for comparison purposes. For example, in some embodiments, when one or more pixel values corresponding to one or more pixels in a respective image is normalized to a predetermined statistic (e.g., a mean and/or standard deviation of one or more pixel values across one or more images), the pixel values of the respective pixels are compared to the respective statistic so that the amount by which the pixel values differ from the statistic is determined.

In some embodiments, an untrained model (e.g., "untrained classifier" and/or "untrained neural network") includes a machine learning model or algorithm, such as a classifier or a neural network, that has not been trained on a target dataset. In some embodiments, training a model (e.g., training a neural network) refers to the process of training an untrained or partially trained model (e.g., an untrained or partially trained neural network). For instance, consider the case of a plurality of training samples comprising a corresponding plurality of images (e.g., images capture when presenting a digital reality scene on a display of a client device 300), discussed below. The plurality of images is applied as collective input to an untrained or partially trained model, in conjunction with a corresponding measured indication of one or more objects (e.g., scene objects 42) for each respective image (hereinafter training dataset) to train the untrained or partially trained model on indications that identify objects related to morphological classes, thereby obtaining a trained model. Moreover, it will be appreciated that the term "untrained model" does not exclude the possibility that transfer learning techniques are used in such training of the untrained or partially trained model. For instance, Fernandes et al., 2017, "Transfer Learning with Partial Observability Applied to Cervical Cancer Screening," Pattern Recognition and Image Analysis: $8^{th}$ Iberian Conference Proceedings, 243-250, which is hereby incorporated by reference in its entirety for all purposes, provides non-limiting examples of such transfer learning. In instances where transfer learning is used, the untrained model described above is provided with additional data over and beyond that of the primary training dataset. That is, in non-limiting examples of transfer learning embodiments, the untrained model receives (i) the plurality of images and the measured indications for each respective image ("primary training dataset") and (ii) additional data. In some embodiments, this additional data is in the form of parameters (e.g., coefficients, weights, and/or hyperparameters) that were learned from another, auxiliary training dataset. Moreover, while a description of a single auxiliary training dataset has been disclosed, it will be appreciated that there is no limit on the number of auxiliary training datasets that may be used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The parameters learned from the first auxiliary training dataset (by application of a first model to the first auxiliary training dataset) may be applied to the second auxiliary training dataset using transfer learning techniques (e.g., a second model that is the same or different from the first model), which in turn may result in a trained intermediate model whose parameters are then applied to the primary training dataset and this, in conjunction with the primary training dataset itself, is applied to the untrained model. Alternatively, a first set of parameters learned from the first auxiliary training dataset (by application of a first model to the first auxiliary training dataset) and a second set of parameters learned from the second auxiliary training dataset (by application of a second model that is the same or different from the first model to the second auxiliary training dataset) may each individually be applied to a separate instance of the primary training dataset (e.g., by separate independent matrix multiplications) and both such applications of the parameters to separate instances of the primary training dataset in conjunction with the primary training dataset itself (or some reduced form of the primary training dataset such as principal components or regression coefficients learned from the primary training set) may then be applied to the untrained model in order to train the untrained model. In some instances, additionally or alternatively, knowledge regarding objects related to morphological classes derived from an auxiliary training dataset is used, in conjunction with the object and/or class-labeled images in the primary training dataset, to train the untrained model.

As used herein, the term "model" refers to a machine learning model or algorithm.

In some embodiments, a model is an unsupervised learning algorithm. One example of an unsupervised learning algorithm is cluster analysis.

In some embodiments, a model is supervised machine learning. Nonlimiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level classifier).

Neural networks. In some embodiments, the model is a neural network (e.g., a convolutional neural network and/or a residual neural network). Neural network algorithms, also known as artificial neural networks (ANNs), include convolutional and/or residual neural network algorithms (deep learning algorithms). Neural networks can be machine learning algorithms that may be trained to map an input data set to an output data set, where the neural network includes an interconnected group of nodes organized into multiple layers of nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning algorithm (DNN) can be a neural network comprising a plurality of hidden layers, e.g., two or more hidden layers. Each layer of the neural network can comprise a number of nodes (or "neurons"). A node can receive input that comes either directly from the input data or the output of nodes in previous layers, and perform a specific operation, e.g., a summation operation. In some embodiments, a connection from an input to a node is associated with a parameter (e.g., a weight and/or weighting factor). In some embodiments, the node may sum up the products of all pairs of inputs, xi, and their associated parameters. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in performing the methods disclosed herein. Examples can include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. Convolutional and/or residual neural networks can be used for analyzing an image of a subject in accordance with the present disclosure.

For instance, a deep neural network model includes an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in *Advances in Neural Information Processing Systems* 2, Pereira, Burges, Bottou, Weinberger, eds., pp. 1097-1105, Curran Associates, Inc.;

Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference in its entirety for all purposes.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, New York, each of which is hereby incorporated by reference in its entirety for all purposes.

Support vector machines. In some embodiments, the model is a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety for all purposes. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes algorithms. In some embodiments, the model is a Naive Bayes algorithm. Naïve Bayes classifiers suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference in its entirety for all purposes. A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference in its entirety for all purposes.

Nearest neighbor algorithms. In some embodiments, a model is a nearest neighbor algorithm. Nearest neighbor models can be memory-based and include no model to be fit. For nearest neighbors, given a query point $x_0$ (a first image), the k training points $x_{(r)}$, r, . . . , k (here the training images) closest in distance to $x_0$ are identified and then the point $x_0$ is classified using the k nearest neighbors. In some embodiments, the distance to these neighbors is a function of the values of a discriminating set. In some embodiments, Euclidean distance in feature space is used to determine distance as $d_{(i)} = \|x_{(i)} - x_{(O)}\|$. In some embodiments, when the nearest neighbor algorithm is used, the value data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference in its entirety for all purposes.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference in its entirety for all purposes. In some embodiments, the number of distance calculations needed to solve the k-nearest neighbor model is such that a computer is used to solve the model for a given input because it cannot be mentally performed.

Random forest, decision tree, and boosted tree algorithms. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference in its entirety for all purposes. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety for all purposes. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses a regression algorithm. A regression algorithm can be any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, An Introduction to Categorical Data Analysis, 1996, Chapter 5, pp. 103-144, John Wiley & Son, New York, which is hereby incorporated by reference in its entirety for all purposes. In some embodiments, the model makes use of a regression model disclosed in Hastie et al., 2001, *The Elements of Statistical Learning*, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis algorithms. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the model (e.g., a linear classifier) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety for all purposes. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in a training dataset. If distance is a good measure of similarity, then the distance between reference entities in the same cluster can be significantly less than the distance between the reference entities in different clusters. However, clustering may not use a distance metric. For example, a nonmetric similarity function s(x, x') can be used to compare two vectors x and x'. s(x, x') can be a symmetric function whose value is large when x and x' are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering includes unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

The term "classification" can refer to any number(s) or other characters(s) that are associated with a particular property of a sample. For example, a "+" symbol (or the word "positive") can signify that a sample is classified as having a desired outcome or characteristic, whereas a "−" symbol (or the word "negative") can signify that a sample is classified as having an undesired outcome or characteristic. In another example, the term "classification" refers to a respective outcome or characteristic (e.g., high risk, medium risk, low risk). In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff value refers to a value above which results are excluded. In some embodiments, a threshold value is a value above or below which a particular classification applies. Either of these terms can be used in either of these contexts.

One of skill in the art will readily appreciate other models that are applicable to the systems, methods, and devices of the present disclosure. In some embodiments, the systems, methods, and devices of the present disclosure utilize more than one model to provide an evaluation (e.g., arrive at an evaluation given one or more inputs) with an increased accuracy. For instance, in some embodiments, each respective model arrives at a corresponding evaluation when provided a respective data set. Accordingly, each respective model can independently arrive at a result and then the result of each respective model is collectively verified through a comparison or amalgamation of the models. From this, a cumulative result is provided by the models. However, the present disclosure is not limited thereto.

In some embodiments, a respective model is tasked with performing a corresponding activity. As a non-limiting example, in some embodiments, the task performed by the respective model includes, but is not limited to, diagnosing a mental disorder, generating a manifestation of a corresponding challenging in the form of an experience 24 associated with a digital reality scene 40, identifying each category in a plurality of categories of an assessment obtained from an subject, conducting a validation of the assessment obtained from the subject, conducting a further validation of another validation by a medical practitioner of the assessment obtained from the subject, generating a respective gate criterion, generating a respective biometric threshold, generating an exposure progression including a plurality of categories arranged in an order, determining whether a challenge has been successfully completed, identifying a subsequent challenge for a subject to take, determining whether a category has been successfully completed, identifying a subsequent category for a subject to take, determining whether a subject is ready to reframe a thought, or any combination thereof. In some embodiments, each respective model of the present disclosure makes use of 10 or more parameters, 100 or more parameters, 1000 or more parameters, 10,000 or more parameters, or 100,000 or more parameters. In some embodiments, each respective model of the present disclosure cannot be mentally performed.

Each of the above identified modules and applications correspond to a set of executable instructions for performing one or more functions described above and the methods described in the present disclosure. These modules (e.g., sets of instructions) need not be implemented as separate software programs, procedures or modules, and thus various subsets of these modules are, optionally, combined or otherwise re-arranged in various embodiments of the present disclosure. In some embodiments, the memory 212 optionally stores a subset of the modules and data structures identified above. Furthermore, in some embodiments, the memory 212 stores additional modules and data structures not described above.

It should be appreciated that FIGS. 2A and 2B illustrates only an example of the digital reality system 200, and that the digital reality system 200 optionally has more or fewer components than shown, optionally combines two or more components, or optionally has a different configuration or arrangement of the components. The various components shown in FIGS. 2A and 2B are implemented in hardware, software, firmware, or a combination thereof, including one or more signal processing and/or application specific integrated circuits. Moreover, the digital reality system 200 can be a single device that includes all the functionality of the digital reality system 200. The client device 300 can also be a combination of multiple devices. For instance, in some embodiments, the functionality of the digital reality system 200 is spread across any number of networked computers and/or reside on each of several networked computers and/or by hosted on one or more virtual machines and/or containers at a remote location accessible across a communications network (e.g., communications network 106, network interface 204, or both). One of skill in the art will appreciate that a wide array of different computer topologies is possible for the digital reality system 200, and other devices and systems of the preset disclosure, and that all such topologies are within the scope of the present disclosure.

1.3. Client Device

Referring to FIG. 3, an exemplary client device 300 is provided (e.g., first client device 300-1). A client device 300 includes one or more processing units (CPUs) 302, one or more network or other communication interfaces 380, a memory 312 (e.g., random access memory and/or non-volatile memory) optionally accessed by one or more controllers, and one or more communication busses 342 interconnecting the aforementioned components.

In some embodiments, a client device 300 includes a mobile device, such as a mobile phone (e.g., smart phone), a tablet, a laptop computer, a wearable device such as a smart watch, and the like. In such embodiments, a respective digital reality scene 40 that is accessible through the client device 300 includes an augmented reality scene. In some embodiments, the respective digital reality scene accessible through the client device 300 includes a mixed reality scene. However, the present disclosure is not limited thereto. For instance, in some embodiments, the client device 300 is a desktop computer or other similar device that communicates with one or more wearable devices (e.g., wearable display). In some embodiments, the client device 300 is a standalone device that is dedicated to providing a digital reality scene 40 of the systems, methods, and devices of the present disclosure. Further, in some embodiments, each client device 300 enables a respective subject to provide information related to the respective subject (e.g., subject preferences, subject feedback, etc.).

In some embodiments, the client device 300 includes a user interface 306. The user interface 306 typically includes a display device 308 for presenting media, such as a digital reality scene 40. In some embodiments, the display device 308 is utilized for receiving instructions from the subject operating the client device 300. In some embodiments, the display device 308 is optionally integrated within the client device 300 (e.g., housed in the same chassis as the CPU 302 and memory 312), such as a smart device (e.g., smart phone). In some embodiments, the client device 300 includes one or more input device(s) 310, which allow the subject to interact with the client device 300. In some embodiments, the one or more input devices 310 include a keyboard, a mouse, one or more cameras (e.g., an objective lens in communication with a two-dimensional pixelated detector) configured to determine a position of an object during an epoch (e.g., track a hand of a subject across space and/or time), other input mechanisms, or a combination thereof. Alternatively, or in addition, in some embodiments, the display device 308 includes a touch-sensitive surface, e.g., where display 308 is a touch-sensitive display or client device 300 includes a touch pad.

In some embodiments, the client device 300 includes an input/output (I/O) subsystem 330 for interfacing with one or more peripheral devices with the client device 300. For instance, in some embodiments, audio is presented through an external device (e.g., speakers, headphones, etc.) that receives audio information from the client device 300 and/or a remote device (e.g., digital reality system 200), and presents audio data based on this audio information. In some embodiments, the input/output (I/O) subsystem 330 also includes, or interfaces with, an audio output device, such as speakers or an audio output for connecting with speakers, earphones, or headphones. In some embodiments, the input/output (I/O) subsystem 330 also includes voice recognition capabilities (e.g., to supplement or replace an input device 310).

In some embodiments, the client device 300 also includes one or more sensors (e.g., an accelerometer, a magnetometer, a proximity sensor, a gyroscope, etc.), an image capture device (e.g., a camera device or an image capture module and related components), a location module (e.g., a Global Positioning System (GPS) receiver or other navigation or geolocation system module/device and related components), a speaker, a microphone, an audio recorder, or a combination thereof, and the like.

In some embodiments, the one or more input device(s) 310 includes a keyboard, a mouse, and/or other input buttons (e.g., one or more sliders, one or more joysticks, one or more radio buttons, etc.). Alternatively, or in addition, in some embodiments, the display device 308 includes a touch-sensitive surface, e.g., where display 308 is a touch-sensitive display 308 or a respective client device 300 includes a touch pad.

In some embodiments, a pose of the client device 300 is determined based on one or more characteristics, such as one or more local characteristics at the client device 300 (e.g., an acceleration of the client device) and/or one or more proximate characteristics near the client device 300 that are associated with a respective region of interest, such as a hand of a subject using the client device 300 or a controller of the client device 300. For instance, in some embodiments, the one or more proximate characteristics associated with the respective region of interest include an appearance of the region of interest. By way of example, in some embodiments a respective proximate characteristic is associated with a shape of the region of interest (e.g., a hand of a subject changing from an open fist to a clenched fist, etc.), a color of the region of interest (e.g., evaluating a color of an article of clothing worn by the subject), a reflectance of the region of interest, or the like. In some embodiments, the one or more proximate characteristics associated with a respective region of interest is derived from information derived from a previous session of a respective digital reality scene (e.g., information retained by regimen store of a corresponding user profile), such as a workflow for implementing one or more CBT techniques. In some embodiments, the one or more proximate characteristics associated with a respective region of interest is based on a reference databased including a plurality of characteristics having an association with a predetermined region of interest. Additional details and information regarding determining pose based on characteristics of a region of interest is found at Oe et al., 2005, "Estimating Camera Position and Posture by Using Feature Landmark Database," Scandinavian Conference on Image Analysis, pg. 171; Lee et al., 1998, "Fine Active Calibration of Camera Position/Orientation through Pattern Recognition," IEEE ISIE, print; Dettwiler et al., 1994, "Motion Tracking with an Active Camera," IEEE Transactions on Pattern Analysis and Machine Intelligence, 16(5), pg. 449; Kritikos et al., 2020, "Comparison between Full Body Motion Recognition Camera Interaction and Hand Controllers Interaction used in Virtual Reality Exposure Therapy for Acrophobia," Sensors, 20(5), pg. 1244, each of which is hereby incorporated by reference in its entirety for all purposes.

Furthermore, in some embodiments, the client device 300 includes a heads-up display (HUD) device, e.g., where the display 308 is head-mounted on the user such as a virtual reality headset that facilitates presenting a virtual reality scene 40, an augmented reality headset that facilitates presenting an augmented reality scene 40, or a mixed reality headset that facilitates presenting a mixed reality scene 40. However, the present disclosure is not limited thereto. In such embodiments, the client device 300 includes the input device(s) 310 such as a haptic feedback device. Accordingly, the HUD client device 300 provides the functionality of a virtual reality client device 300 with synchronized haptic and audio feedback, an augmented reality client device 300 with synchronized haptic and audio feedback, a mixed reality client device 300 with synchronized haptic and audio feedback, or a combination thereof.

Additionally, in some embodiments, the client device 300 includes, or is a component part of a digital reality kit for presenting a digital reality scene 40. Additional details and information regarding a digital reality kit is found at U.S. Patent Application Publication No. 2020/0121050 A1, entitled "Virtual Reality Kit," filed Oct. 18, 2019, which is hereby incorporated by reference in its entirety for all purposes.

In some embodiments, the client device 300 includes one or more digital reality components such a Pico Neo 3 pro (Pico Interactive Inc., San Francisco, California), Oculus Quest 2 (Oculus VR, Irvine, California), Snapchat Spectacles 3 (Snap Inc., Santa Monica, California), Google Cardboard (Google LLC, Mountain View, California), HTC VIVE Pro 2 (HTC Corporation, Taoyuan City, Taiwan), Apple Vision Pro (Apple Inc., Cupertino, California) or the like. One of skill in the art will appreciate that the present disclosure is not limited thereto.

In some embodiments, the client device 300 presents media to a user through the display 308. Examples of media presented by the display 308 include one or more images, a video, audio (e.g., waveforms of an audio sample), or a combination thereof. In typical embodiments, the one or more images, the video, the audio, or the combination thereof is presented by the display through a digital reality scene 40. In some embodiments, the audio is presented through an external device (e.g., speakers, headphones, etc.) that receives audio information from the client device 300, the digital reality system 200, or both, and presents audio data based on this audio information. In some embodiments, the user interface 306 also includes an audio output device, such as speakers or an audio output for connecting with speakers, earphones, or headphones. In some embodiments, the user interface 306 also includes an audio input device (e.g., a microphone), and optional voice recognition capabilities (e.g., to supplement or replace the keyboard). Optionally, the client device 300 includes an audio input device 362 (e.g., a microphone, recorder) to capture audio (e.g., speech from a user). In some embodiments, the audio input device 362 is a single omni-directional microphone.

In some embodiments, the client device 300 also includes one or more of: one or more sensors (e.g., accelerometer, magnetometer, proximity sensor, gyroscope); an image capture device (e.g., a camera device or module and related components); and/or a location module (e.g., a Global Positioning System (GPS) receiver or other navigation or geolocation device and related components). In some embodiments, the sensors include one or more hardware devices that detect spatial and motion information about the client device 300. Spatial and motion information can include information about a position of the client device 300, an orientation of the client device 300, a velocity of the client device 300, a rotation of the client device 300, an acceleration of the client device 300, or a combination thereof. For instance, in some embodiments, the sensors include one or more inertial measurement units (IMUs) that detect rotation of the user's head while the user is utilizing (e.g., wearing) the client device 300. In some embodiments, this rotation information is used (e.g., by client application 320 of FIG. 3 and/or digital reality session engine 38 of FIG. 2B) to adjust the images displayed on the display 308 of the client device 300. In some embodiments, each IMU includes one or more gyroscopes, one or more accelerometers, and/or one or more magnetometers that collect the spatial and motion information. In some embodiments, the sensors include one or more cameras positioned on the client device 300.

The memory 312 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. The memory 312 may optionally include one or more storage devices remotely located from the CPU(s) 302. The memory 312, or alternatively the non-volatile memory device(s) within memory 312, includes a non-transitory computer readable storage medium. Access to the memory 312 by other components of the client device 300, such as the CPU(s) 302 and the I/O subsystem 330, is, optionally, controlled by a controller. In some embodiments, the memory 312 can include mass storage that is remotely located with respect to the CPU 302. In other words, some data stored in the memory 312 may in fact be hosted on devices that are external to the client device 300, but that can be electronically accessed by the client device 300 over an Internet, intranet, or other form of network 106 or electronic cable using communication interface 380.

In some embodiments, the memory 312 of the client device 300 stores:
- an operating system 316 that includes procedures for handling various basic system services;
- an electronic address 318 associated with the client device 300 that identifies the client device 300 within a distributed system 100;
- a client application 320 for generating content for display through a graphical user interface presented on the display 308 of the client device 300; and
- an engine 322 that allows a client application 320 to operate in conjunction with the client device 300.

An electronic address 318 is associated with the client device 300, which is utilized to at least uniquely identify the client device 300 from other devices and components of the distributed system 100. In some embodiments, the electronic address 318 associated with the client device 300 is used to determine a source of an assessment provided by the client device 300 (e.g., receiving an assessment from the digital reality system 200 and communicating one or more responses based on the assessment).

In some embodiments, each client application 320 is a group of instructions that, when executed by a processor, generates content for presentation to the user, such as a virtual reality scene 40, an augmented reality scene 40, a mixed reality scene 40, or a combination thereof. In some embodiments, a client application 320 generates content in response to inputs received from the user through movement of the client device 300, such as the inputs 310 of the client device. Here, the client application 320 includes a gaming application, a conferencing application, a video playback application, or a combination thereof. For instance, in some embodiments, the client application 320 facilitates providing one or more sessions of a digital reality scene, such as the digital reality scene 40-1, 40-2, . . . , or 40-H of FIG. 2B. In some embodiments, the client application 320 is utilized to obtain an assessment from a subject that includes an identification of a plurality of proposed experiences 24. In some embodiments, the client application 320 is utilized to configure one or more criteria associated with an experience 24 or a digital reality scene 40.

In some embodiments, an engine 322 is a software module that allows a client application 320 to operate in conjunction with the client device 300. In some embodiments, the engine 322 receives information from the sensors on the client device 300 and provides the information to a client application 320. Based on the received information, the engine 322 determines media content to provide to the client device 300 for presentation to the user through the display 308 or the one or more audio devices, and/or a type of haptic feedback. For example, if the engine 322 receives information from the sensors 110 of the client device 300 indicating that the user has looked to the left, the engine 322 generates content for the display 308 that mirrors the user's movement in a digital reality scene 40. As another example, if the user hits a wall (e.g., in a digital reality scene 40), the engine 322 generates control signals for a haptic-feedback mechanism of the client device 300 to generate a vibration, and, optionally, audio that corresponds to the user action (e.g., sound of a human fist striking a wooden wall, or sound of a human fist hitting a Plexiglas wall, which would be different from the sound generated for the wooden wall). As yet another non-limiting example, in some embodiments, the engine 322 receives information from one or more sensors 110 in electronic communication with the client device 300, in which the one or more sensors obtain biometric data from a user of the client device 300 such as an instantaneous heart rate of the user captured during an epoch. In such embodiments, the engine 322 generates content for the display 308 that is responsive to the biometric data from the user, such as changing a color of a first object 42-1 in a digital reality scene 40 from a first color of orange to a second color of violet in order to reflect a lowering of the instantaneous heart rate of the user. However, the present disclosure is not limited thereto.

Similarly, in some embodiments, the engine 322 receives information from the sensors 110 of the client device 300 and provides the information from the sensors to a client application 320. Accordingly, in some embodiments, the application 320 uses the information to perform an action within a digital reality scene of the application 320. In this way, if the engine 322 receives information from the sensors 110 that the user has raised his or her hand, a simulated hand in the digital reality scene 40 lifts to a corresponding height. However, the present disclosure is not limited thereto.

In some embodiments, the engine 322 generates control signals for the haptic-feedback mechanism, which cause a haptic-feedback mechanism to create one or more haptic ques. As described supra, the information received by the engine 322 can also include information from the client device 300. For example, in some embodiments, one or more cameras (e.g., inputs 310, I/O subsystem 330 of FIG. 3) disposed on the client device 300 captures movements of the client device 300. In some such embodiments, the client application 320 utilizes this additional information to perform the action within a digital reality scene 40 of the client application 320.

In some embodiments, the engine 322 provides feedback to the user that the action was performed. In some embodiments, the provided feedback is visually provided through the display 308 of the client device 300, provided in an auditory manner through the one or more audio devices of the client device 300 (e.g., I/O subsystem 330), provided in a haptic manner via one or more of the haptic-feedback mechanisms of the client device 300, or a combination thereof.

Additional details and information regarding utilizing an engine (e.g., digital reality session engine 38 of FIG. 2B, engine 322 of FIG. 3) is found at U.S. Patent Application Publication No.: 2018/0254097 A1, entitled "Dynamic Multi-Sensory Simulation System for Effecting Behavior Change," filed Mar. 5, 2018; U.S. Patent Application Publication No.: 2020/0022632 A1, entitled "Digital Content Processing and Generation for a Virtual Environment," filed Jul. 16, 2019; and U.S. Patent Application Publication No.: 2020/0023157 A1, entitled "Dynamic Digital Content Delivery in a Virtual Environment," filed Jul. 16, 2019; each of which is hereby incorporated by reference in its entirety for all purposes.

Each of the above identified modules and applications correspond to a set of executable instructions for performing one or more functions described above and the methods described in the present disclosure. These modules (e.g., sets of instructions) need not be implemented as separate software programs, procedures or modules, and thus various subsets of these modules are, optionally, combined or otherwise re-arranged in various embodiments of the present disclosure. In some embodiments, the memory 312 optionally stores a subset of the modules and data structures identified above. Furthermore, in some embodiments, the memory 312 stores additional modules and data structures not described above.

It should be appreciated that FIG. 3 illustrates only an example of the client device 300, and that the client device 300 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits. Moreover, the client device 300 can be a single device that includes all the functionality of the client device 300. The client device 300 can also be a combination of multiple devices. For instance, the functionality of the client device 300 may be spread across any number of networked computers and/or reside on each of several networked computers and/or by hosted on one or more virtual machines and/or containers at a remote location accessible across a communications network (e.g., communications network 106, network interface 380, or both). One of skill in the art will appreciate that a wide array of different computer topologies is possible for the client device 300, and other devices and systems of the preset disclosure, and that all such topologies are within the scope of the present disclosure.

2. Methods

Now that exemplary devices and systems have been described, exemplary methods for improving an ability of a subject to manage a psychiatric or mental condition exhibited by the subject by implementing one or more CBT techniques using an interactive DR scene will be described. In some embodiments, the methods are performed at a computer system, such as the system 100, the digital reality system 200, the client device 300, or a combination thereof.

The methods of the present disclosure implement cognitive behavioral therapy (CBT) within an interactive DR scene through a plurality of interactive DR activities to help a subject to manage a psychiatric or mental condition of the subject. In some embodiments, the CBT includes techniques such as a cognitive reframing technique and cognitive defusion technique, which is implemented through the interactive DR scene. Additional details and information regarding the CBT is found at Cristea et al., 2018, "Why Cognitive Behavioral Therapy Is the Current Gold Standard of Psychotherapy," Frontiers in Psychiatry, 9, pg. 4, which is hereby incorporated by reference in its entirety for all purposes. Cognitive reframing is a psychological technique that includes identifying and then changing the way situations, experiences, events, ideas, emotions or a combination thereof are viewed by the subject, such as based on statements provided by the subject. Cognitive reframing is the process by which such situations or thoughts are challenged and then changed, which is allowed by completing the plurality of interactive DR activities. In the context of cognitive therapy, cognitive reframing is referred to as cognitive restructuring. Additional details and information regarding the cognitive reframing is found at Robson Jr et al., 2014, "A Concept Analysis of Cognitive Reframing," Journal of Theory Construction and Testing. 18 (2), which is hereby incorporated by reference in its entirety for all purposes.

In some embodiments, the methods combine one or more CBT techniques with one or more other psychotherapeutic and/or psychoeducational techniques, such as exposure therapy, mindfulness-based intervention, behavioral activation, psychoeducational interventions, or a combination thereof.

Mindfulness-based interventions (MBI) are effective in helping people cope with stress, anxiety and depression, and can positively affect physical health. Additional details and information regarding the MBIs is found at Wu et al., 2021, "Virtual Reality-Assisted Cognitive Behavioral Therapy for Anxiety Disorders: A Systematic Review and Meta-Analysis," Front Psychiatry, 12, pg. 575094, Garland et al., "Biobehavioral Mechanisms of Mindfulness as a Treatment for Chronic Stress: An RDoC Perspective," Chronic Stress (Thousand Oaks). 2017 February, 1:2470547017711912, and Hofmann et al., 2017, "Mindfulness-Based Interventions for Anxiety and Depression," Psychiatr. Clin. North Am., 40(4), pg. 739-749, each of which is hereby incorporated by reference in its entirety for all purposes.

In some embodiments, the CBT technique causes behavioral activation for the subject, such as by having the subject perform a first interactive DR activity associated with long-term and short-term goal settings within a client application, such as within an interactive DR scene. In some embodiments, both acceptance and commitment therapy (ACT) and behavioral activation (BA) are forms of CBT techniques effective for anxiety disorders and depression used by the systems, methods, and devices of the present disclosure. Additional details and information regarding the ACT and BA is found at Bluett et al., 2014, "Acceptance and commitment therapy for anxiety and OCD spectrum disorders: an empirical review.," J Anxiety Disord., 28(6), pg. 612-24; Zawn et al., 2021, "What is behavioral activation?," Medical News Today, Oct. 24, 2021, each of which is hereby incorporated by reference in its entirety for all purposes.

An example of a psychiatric or mental condition is post-traumatic stress disorder (PTSD). In some such embodiments, the severity of a subject's PTSD is measured before, during and/or after treatment, for instance, through an assessment with a Clinician-Administered PTSD Scale (CAPS) interview (See Weathers et al., 2018, "The Clinician-Administered PTSD Scale for DSM-5 (CAPS-5): Development and initial psychometric evaluation in military veterans," *Psychological Assessment* 30 383-395 and Weathers et al., 2001, "Clinician-Administered PTSD Scale: A review of the first ten years of research," Depression and Anxiety 13, pp. 132-156, each of which is hereby incorporated by reference in its entirety for all purposes), or self-reported PTSD Checklist (Forbes et al., 2001, "The validity of the PTSD checklist as a measure of symptomatic change in combat-related PTSD," Behaviour Research and Therapy 39, 977-986, and Blevins et al., 2015, "The post-traumatic stress disorder checklist for DSM-5 (PCL-5, each of which is hereby incorporated by reference in its entirety for all purposes): Development and initial psychometric evaluation," Journal of Traumatic Stress 28, 489-498). In some embodiments, application of the systems and methods of the present disclosure to a subject with PTSD causes an improvement in their score on such assessments, indicating that the severity of the PTSD has diminished, been alleviated, or has been treated by the systems and methods of the present disclosure.

Another example of a psychiatric or mental condition is depression. In some such embodiments, the severity of a subject's depression is measured before, during and/or after treatment, for instance, through assessment with a self-reported Beck Depression Inventory (Beck et al., 1996, "Beck depression inventory-II," San Antonio 78, 490-498). In some embodiments, application of the systems and methods of the present disclosure to a subject with depression causes an improvement in their score on this assessment, indicating that the severity of the depression has diminished, been alleviated, or has been treated by the systems and methods of the present disclosure.

In some other embodiments the severity of a subject's psychiatric or mental condition (e.g., depression, anxiety, etc.) is measured before, during and/or after treatment, for instance, through assessment with a Patient Health Questionnaire (Kroenke et al., 2010, "The patient health questionnaire somatic, anxiety, and depressive symptom scales: a systematic review," General Hospital Psychiatry 32, pp. 345-359, which is hereby incorporated by reference in its entirety for all purposes) or using the World Health Organization Quality of Life Scale (Skevington et al., 2004, "The World Health Organization's WHOQOL-BREF quality of life assessment: psychometric properties and results of the international field trial. A report from the WHOQOL group," Quality of life Research 13, 299-31, which is hereby incorporated by reference in its entirety for all purposes 0). In some embodiments, application of the systems and methods of the present disclosure to a subject with the psychiatric or mental condition causes an improvement in their score on this assessment, indicating that the severity of the psychiatric or mental condition (e.g., depression, anxiety, etc.) has diminished, been alleviated, or has been treated.

In some embodiments, a psychiatric or mental condition exhibited by a subject is a condition being stressed in a social setting, fearing a social setting, or being overwhelmed in a social setting, such as a clinically diagnosed mental disorder. In some embodiments, the clinically diagnosed mental disorder is an anxiety disorder such as a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject. In some embodiments, the clinically diagnosed mental disorder is a mood disorder such as a depression disorder, a bipolar disorder, or a cyclothymic disorder. For instance, in some embodiments, the depression disorder is a major depression disorder. In some embodiments, the clinically diagnosed mental disorder is a psychotic disorder such as a schizophrenia disorder, a delusion disorder, or a hallucination disorder. In some embodiments, the clinically diagnosed mental disorder is an eating disorder such as anorexia nervosa, bulimia nervosa, or binge eating disorder. In some embodiments, the clinically diagnosed mental disorder is an impulse control disorder such as a pyromania disorder, a kleptomania disorder, or a compulsive gambling disorder. In some embodiments, the clinically diagnosed mental disorder includes, but is not limited to, a personality disorder, an obsessive-compulsive disorder, or a post-traumatic stress disorder. In some embodiments, the clinically diagnosed mental disorder is an addiction disorder such as an alcohol use disorder or a substance abuse disorder. In some embodiments, the clinically diagnosed mental disorder is a personality disorder such as an antisocial personality disorder, an obsessive-compulsive personality disorder, or a paranoid personality disorder.

Non-limiting examples of psychiatric or mental conditions the addressed by the systems, methods, and devices of the present disclosure include, but are not limited to: stressful and/or overwhelmed feelings associated with social situations, such as excessive worry, excessive anxiety, avoidance of a feared situation, and the like; worry about everyday events associated with a general anxiety disorder, such as excessive worry, excessive anxiety, difficulty concentrating, and the like; persistent sadness, anxiousness, emptiness, or a combination thereof associated with a major depressive disorder; dysphoria, anhedonia, apathy, irritability, anger, avolition, lack of motivation, sleep dysregulation, decreased energy, fatigue, behavior disturbances and/or disruptions detrimental to daily function, agitation, restlessness, or a combination thereof, or a combination thereof.

For instance, in some embodiments, the methods are tailored for use in general wellness, e.g., for anyone seeking to improve their overall mental and/or emotional wellbeing. In some embodiments, the methods are tailored for treatment of mental health issues, such as sub-clinical mental health issues (e.g., for anyone burdened by ruminating thoughts which are detrimental to mental health and contribute to unwanted behavioral patterns. In some embodiments, the use of the systems and/or methods of the present disclosure provides a treatment of a psychiatric or mental condition exhibited by the subject. That is, in some embodiments, the present disclosure includes a method of treating a psychiatric or mental condition by using the systems and/or methods of the present disclosure. In some embodiments, the method of treating a psychiatric or mental condition includes a combination therapy and/or one or more adjunctive therapies with any psychiatric medication (e.g., a pharmaceutical composition that is administered to a subject in order to treat a psychiatric or mental condition exhibited by the subject). In some embodiments, the pharmaceutical composition includes at least one selected from the group consisting of: a selective serotonin reuptake inhibitor (SSRIs) pharmaceutical composition; a selective serotonin and norepinephrine inhibitors (SNRIs) pharmaceutical composition; a norepinephrine-dopamine reuptake inhibitor (NDRIs) pharmaceutical composition; a NMethyl-D-aspartate receptor antagonist pharmaceutical composition; a serotonergic pharmaceutical composition; a tricyclic antidepressant pharmaceutical composition; a monoamine oxidase inhibitor (MAOIs) pharmaceutical composition; a tetracyclic antidepressant pharmaceutical composition; a L-methylfolate pharmaceutical composition; a benzodiazepine pharmaceutical composition; and a beta-blocker pharmaceutical composition. In some embodiments, the pharmaceutical composition includes at least one selected from the group consisting of: chlorpromazine, perphenazine, trifluoperazine, mesoridazine, a fluphenazine, thiothixene, molindone, thioridazine, loxapine, haloperidol, aripiprazole, clozapine, ziprasidone, risperidone, quetiapine pharmaceutical composition, an olanzapine, citalopram, escitalopram, fluvoxamine, paroxetine, fluoxetine, sertraline, clomipramine, amoxapine, amitriptyline, desipramine, nortriptyline, doxepin, trimipramine, imipramine, protiptyline, desvenlafaxine, venlafaxine, duloxetine, lorazepam, buspirone, propranolol, clonazepam, chlordiazepoxide, oxazepam, atenolol, clorazepate, diazepam, lprazolam, amphetamine, dextroamphetamine, methylphenidate, lamotrigine, ketamine, and lithium.

In some embodiments, the methods for use in general wellness are self-administered by the subject without supervision of a health care worker (e.g., a medical practitioner) associated with the subject. For instance, in some embodiments, the methods of the present disclosure allow the subject to efficaciously perform CBT techniques through the plurality of interactive DR activities within the interactive DR scene 40. In some embodiments (e.g., when the subject prefers), the methods for use in general wellness are performed with supervision of a health care worker associated with the subject, or partly self-administered by the subject and partly supervised by the health care worker associated with the subject. In some embodiments, the methods for treatment of mental health issues are performed with supervision of the health care worker associated with the subject, or at least partly supervised by a health care worker associated with the subject.

Accordingly, the methods of the present disclosure are designed to implement CBT techniques within an interactive DR scene in order to improve an ability of a subject to manage a psychiatric or mental condition. The interactive DR experiences can be presented in various formats. For instance, in some embodiments, the methods provide the interactive DR experiences by: one or more psychoeducational mechanisms (e.g., videos); one or more CBT techniques implemented; one or more exposure therapy techniques; one or more mindfulness therapy techniques; or a combination thereof. In some embodiments, the methods provide the interactive DR experiences in one or more additional, optional, or alternative formats. For instance, in some embodiments, the methods allow a subject to access audio or digital mindfulness practices.

2.1. Exemplary Interactive DR Scenes

The present disclosure provides a number of different DR scenes configured for an interactive DR experiences to take place. In some embodiments, an interactive DR scenes configured to accommodate a single interactive DR experience. For instance, as a non-limiting example, an interactive DR scene is configured to accommodate one or more DR CBT technique practices and/or one or more DR mindfulness practices. In some embodiments, an interactive DR scene is further configured to accommodate a particular group of interactive DR experiences. For instance, as a non-limiting example, an interactive DR scene is configured for presenting two or more or all of psychoeducational videos, for practicing multiple interactive DR CBT technique activities, for practicing multiple DR mindfulness technique activities, or a combination thereof. In some embodiments, an interactive DR scene is further configured to accommodate one or more interactive DR experiences from different groups. For instance, as a non-limiting example, an interactive DR scene is configured for presenting a psychoeducational video (e.g., a cognitive or mindfulness psychoeducational video) and for practicing a corresponding DR activity (e.g., a DR CBT or mindfulness technique activity), or for practicing at least one DR cognitive technique activity and at least one DR mindfulness technique activity.

In some embodiments, an interactive DR scene includes no designated area, or include one or more designated areas. As used herein, a "designated area" refers to an area or a site within an interactive DR scene that is configured to accommodate a single interactive DR experience or multiple interactive experiences. For instance, as a non-limiting example, an interactive DR scene includes a designated area configured for practicing a DR CBT technique activity, a designated area for practicing a mindfulness activity, a designated area for presenting some or all of psychoeducational videos, or any combination thereof. In some embodiments, at least one Interactive DR scene does not have any designated areas, such as a menu interactive DR scene or a command line interface (CLI) DR scene. In various embodiments, each interactive DR scene has at least one designated area. In some embodiments, at least one interactive DR scene has more than two, more than three, more than four, more than five, more than six, more than seven, or more than eight designated areas. In some embodiments, at least one interactive DR scene has no more than two, no more than three, no more than four, no more than five, no more than six, no more than seven, or no more than eight designated areas. In some embodiments, at least one interactive DR scene has between one and five designated areas, or between one and three designated areas. In some embodiments, the interactive DR scene and designated area have a one-to-one relationship.

In some embodiments, different interactive DR scenes are accessible by a subject through one or more DR pathways, through one or more DR portal objects, or the like.

Similarly, different designated areas within an interactive DR scene or among different DR scenes are accessible by a subject through one or more DR pathways, through one or more DR portal objects, or the like.

Figure 10A:
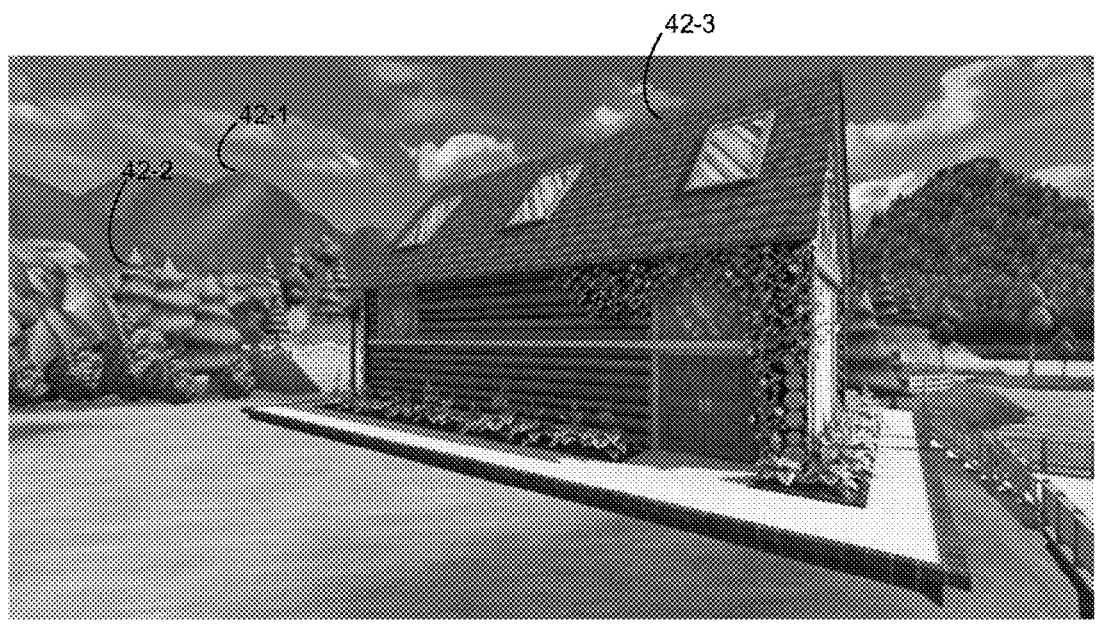
FIGS. 10A, 10B, 10C, and 10D collectively illustrate an exemplary interactive DR scene, in accordance with some embodiments of the present disclosure.
Figure 10B:
Figure 10C:
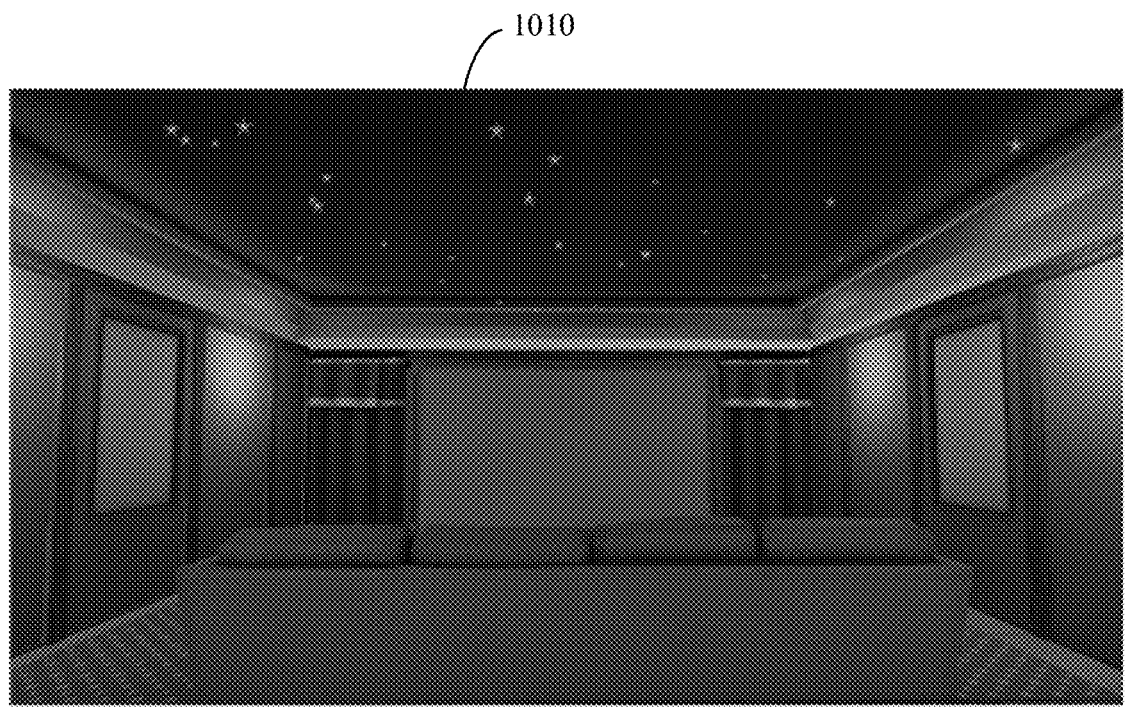

Referring to FIGS. 10A-10D, there is depicted one or more exemplary interactive DR scenes 1000 in accordance with some embodiments of the present disclosure. As a non-limiting example, in some embodiments, the interactive DR scene 1000 is illustrated to simulate a home environment, such as a lake house. Specifically, FIG. 10A illustrates an interactive DR scene 1000 that includes a first object 42-1 providing terrain for the interactive DR scene, a second object 42-1 providing a landscape (e.g., tree) feature, and a third object 42-3 providing an exterior (or a portion of it) of the lake house, and FIG. 10B illustrates the interior (or a portion of it) of the lake house. In some embodiments, the interactive DR scene 1000 includes one or more designated areas. For instance, as a non-limiting example, in some embodiments, the interactive DR scene 1000 includes a designated area 1010 (e.g., designated area 1010 of FIG. 10C). In some embodiments, the designation area 1010 simulates a home theater, and is referred to herein as an education room or a theater room, which provides a comfortable interactive DR scene for engaging with a video of the present disclosure. In some embodiments, the designated area 1010 simulates a home study, and is referred to herein as a study room.

While the Interactive DR scene 1000 is illustrated to simulate a home environment, it should be noted that this is by way of example and is non-limiting. In some embodiments, the interactive DR scene 1000 is configured to simulate any suitable indoor or outdoor, real or nonreal environment, including but not limited to schools, offices, museums, lakes, mountains, or the like. Moreover, while the interactive DR scene 1000 is illustrated to have one or two designated areas, it should be noted that the Interactive DR scene 1000 can have more than two designated areas. For instance, in some embodiments, the Interactive DR scene 1000 includes three, four, five, six, seven, eight, nine, ten, or more than ten designated areas. Further, while the designated area 1010 are illustrated to be interior areas, in some embodiments, a designated area of the interactive DR scene 1000 is also an exterior area, such as a lawn, a shade under a tree, or the like. However, the present disclosure is not limited thereto. In some embodiments, the designated area 1010 simulates an island, a waterfall, a winter landscape, an aurora, or the like.

Figure 14:
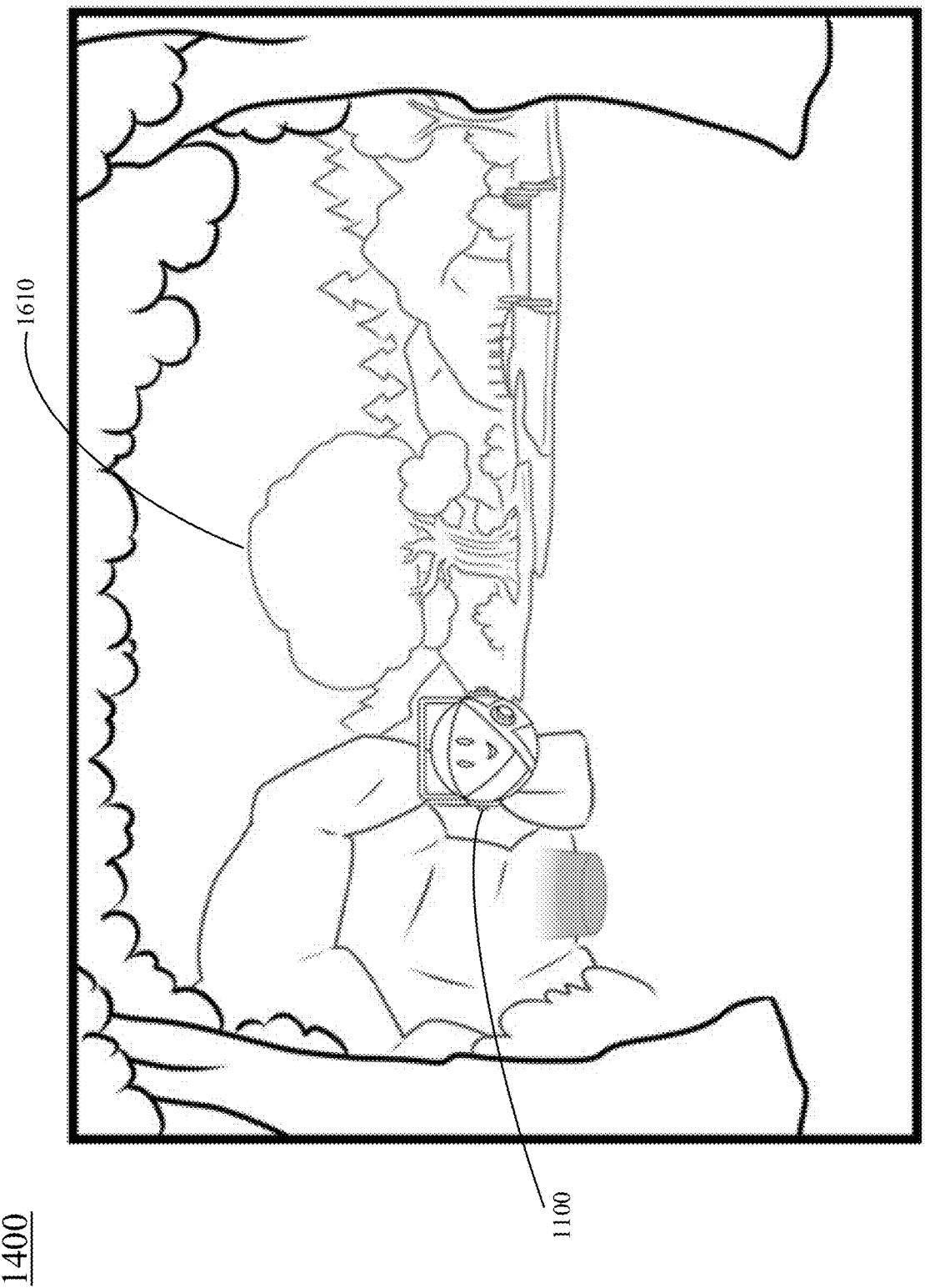
FIG. 14 illustrates another exemplary interactive DR scene, in accordance with an embodiment of the present disclosure.
Figure 19A:

Referring to FIG. 14, there is depicted an exemplary interactive DR scene 1400 in accordance with some embodiments of the present disclosure. In the illustrated embodiment, the interactive DR scene 1400 simulates a wooded environment, which is known as a woods of wisdom herein. In some embodiments, the interactive DR scene 1400 includes one or more designated areas that is accessible from within the interactive DR scene 1400 (e.g., the engine 322 dynamically renders each designated area on the display of the client device 300 as the subject traverses through the interactive DR scene). For instance, as a non-limiting example, in some embodiments, the interactive DR scene 1100 includes the designated area 1010 illustrated in FIG. 19A, or any combination thereof.

In some embodiments, the designated area 1010 is configured to host or allow for a subject to perform a respective interactive DR activity, such as learning how to associate one or more emotions and/or one or more behaviors with anxious thoughts or triggering events, such as anxious thoughts in the form of statements exhibited by the subject when interacting with the systems, methods, and devices of the present disclosure. In some embodiments, the designated area 1010 is configured to display a ledger associated one or more interactive DR activities (e.g., a scene object 42 configured as a DR wellbeing object), that reflects a characteristic of the subject, such as a progression through one or more interactive DR activity of the present disclosure, a status of the psychiatric or mental condition exhibited by the subject, or the like. In some embodiments, the ledger is configured to dynamically update its appearance in accordance with a determination of a change in the characteristic of the subject, such as in accordance with the determination of a positive change in the characteristic of the subject (e.g., an increase in value, such as a higher score value), or when the subject is deemed to satisfy a threshold condition associated with the respective interactive DR activity. In some embodiments, the designated area 1010 is configured for a subject to practice a first interactive DR activity for a first CBT technique, such as a "gather evidence" CBT technique activity (e.g., interactive activity 650-5 of FIG. 10). In some embodiments, the designated area 1010 is configured for a subject to practice a second interactive DR activity, such as a "usefulness and core belief" CBT technique activity or a first assessment activity. In some embodiments, the designated area is configured for a subject to practice a third interactive DR CBT technique activity, such as a creating space CBT defusion technique activity or a second assessment activity.

In some embodiments, the interactive DR scene 1400 is configured to simulate any suitable indoor or outdoor, real or nonreal environment, including but not limited to homes, schools, offices, museums, lakes, mountains, or the like, which provides for an immersion experience for the subject when interacting with a respective interactive DR activity. In some embodiments, each designated area associated with an interactive DR scene includes a common theme, such as the home theme, the school theme, a woods theme, the lake theme, the mountain theme, a winter theme, a desert theme, a space theme, a party theme, the office theme, the museum theme, an abstract theme, or the like. However, the present disclosure is not limited thereto. For instance, the interactive DR scene 1000 can have six, seven, eight, nine, ten, or more than ten designated areas 1010, and the additional designated areas can be used for additional interactive DR CBT technique activities or other educational/therapeutical activities such as mindfulness practices. In some embodiments, there are a number of various designated areas, which can be within the interactive DR scene 1010, in the interactive DR scene 1000 or other interactive DR scenes, for practicing a mindfulness activity, and a subject is allowed to choose which site the subject prefers. In this way, the interactive DR scene provides access to the plurality of interactive DR activities that collectively provide tools to improve the psychiatric or mental condition exhibited by the subject.

2.2. Exemplary Digital Reality Objects

The present disclosure provides various DR objects (e.g., objects 42 of FIG. 2B), such as a DR assistant object, a DR journey object, a number of different DR recordable objects (e.g., DR-evidence recoding object, DR belief-recording object, DR third-person-recording object, DR word-recording object), a DR vessel object, a DR wellbeing object, a DR moving object, a DR belief object, a DR thought-indicative object, or a combination thereof. Some of DR objects, such as the DR assistant and the DR vessel object that can be used in different reframing activities, are described in this section. Others are described elsewhere, for instance, in next sections along with more detailed description of the methods.

Exemplary DR Assistant Object.

Referring to FIG. 11, there is depicted an exemplary DR assistant 1100 in accordance with some embodiments of the present disclosure. In some embodiments, the DR assistant serves as a virtual guide to assist a subject, such as to aid during a DR experience presented to the subject in order to improve the ability of the subject to manage a psychiatric or mental condition. In some embodiments, the DR assistant is present in any interactive DR scene and in any designated areas within an interactive DR scene unless the subject or a healthcare professional associated with the subject explicitly asks not to have the presence of the DR assistant. In various embodiments, the DR assistant is one who greets the subject when the subject enters the interactive DR scene (e.g., interactive DR scene 1000, interactive DR scene 1400, etc.). In some embodiments, the DR assistant is present during one or more interactive DR technique activities taking place in the interactive DR scene 1400 simulating the woods of wisdom. In some embodiments, the DR assistant is present during each and every DR technique activity. In some embodiments, the DR assistant is portrayed as one who also struggles with a psychiatric or mental issue (e.g., social anxiety disorder), such as the psychiatric or mental issue exhibited by the subject. However, the present disclosure is not limited thereto.

While FIG. 11 illustrates the DR assistant as a cute and friendly robot NPC, it should be noted that this is by way of example and it is non-limiting. In some embodiments, the DR assistant is rendered in any suitable shapes, sizes, colors, textures, or the like. The DR assistant can also be configured to portrayed any real or nonreal, existent or non-existent, fictional, or non-fictional, mythical, or non-mythical characters. In some embodiment, more than one DR assistants are provided and a subject is allowed to choose or switch a single DR assistant to interactive with when desired. In addition, while the DR assistant is sometimes referred to as "Ari," it should be noted that the DR assistant can have any suitable names.

Exemplary DR Journey Object.

Figure 10D:
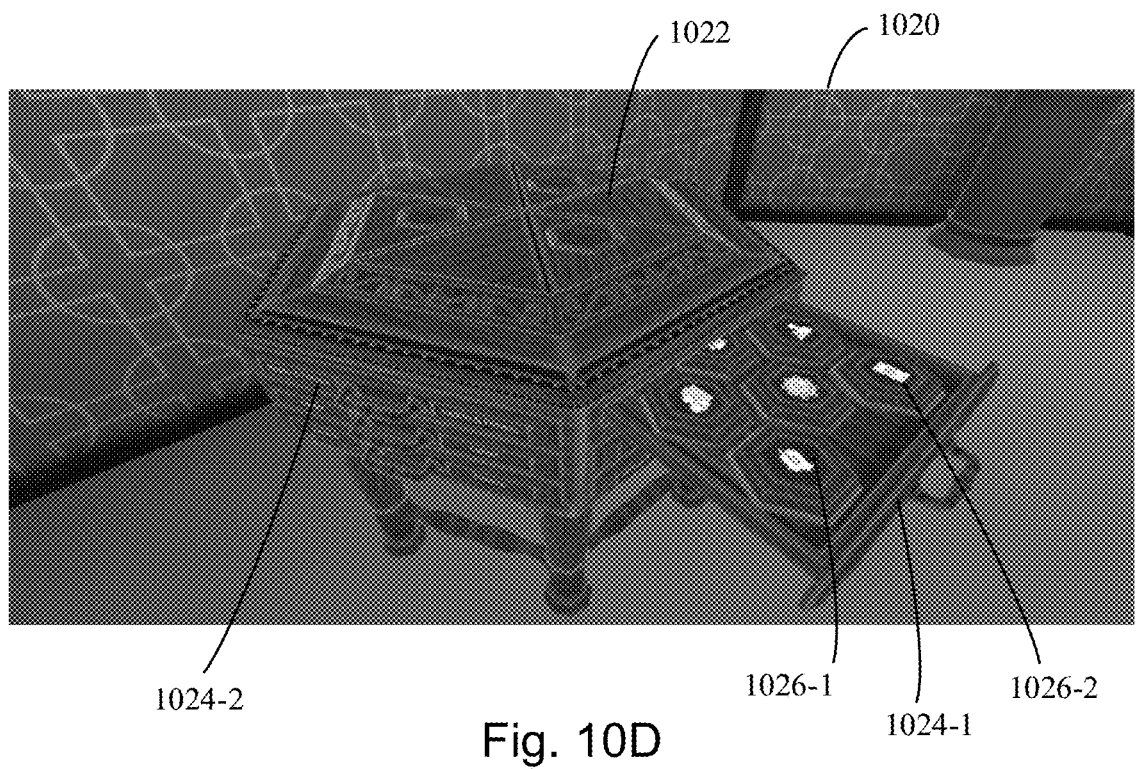

Referring to FIG. 10D, there is depicted an exemplary DR journey object 1022 in accordance with some embodiments of the present disclosure.

In some embodiments, the DR journey object is a navigational and progress tracking tool to visualize progression through an experience by a subject. In some embodiments, the DR journey object is permanently, or exclusively, located in the interactive DR scene 1000 (e.g., the lake house), for instance, in the designated area 1020 (e.g., the study room) within the interactive DR scene 1000.

In some embodiments, the DR journey object is used to set and/or review goals, such as long-term and/or short-term goals for some activities (e.g., CBT technique activities) taken place in the interactive DR scene 1400 (e.g., the woods of wisdom). For instance, as a non-limiting example, FIG. 10D illustrates the DR journey object 1022 simulating a game table or the like. The table includes various drawers, e.g., a drawer 1024-1 and a drawer 1024-2. One or more drawers are configured to house long-term goal constructs that represent one or more long term goals provided by the subject (e.g., through an assessment presented to the subject through the display of the client device and/or at the DR journey object within the interactive DR scene) and/or associated with the subject (e.g., by a medical practitioner and/or by a model, etc.). For instance, by way of example, the drawer 1024-1 is illustrated to house a plurality of long-term goal constructs, such as a long-term goal construct 1026-1 and a long-term goal construct 1026-2, each simulating a grabbable tile, a game piece, or the like in order to associate the long-term goal with a DR interactable object 42. In some embodiments, to set a long-term goal, a subject is allowed to find a long-term goal construct (e.g., a first long long-term goal construct in a plurality of long-term goal constructs) representing the long-term goal of the subject in a drawer and place it on top of the table to lock it in. In some embodiments, a subject sets one or more long-term goals, two or more long-term goals, three or more long-term goals, four or more long-term goals, or five or more long-term goals. In some embodiments, a subject sets at least one long-term goals, at least two long-term goals, at least three long-term goals, at least four long-term goals, or at least five long-term goals. In some embodiments, a subject is allowed or required to set one long-term goal, two long-term goals, or three long-term goals. In some embodiments, a long-term goal includes a plurality of short-term goals that collectively accomplish the long-term goal. However, the present disclosure is not limited thereto.

While FIG. 10D illustrates the DR journey object 1022 simulating a game table, it should be noted that this is by way of example and it is non-limiting. The DR journey object 1022 can simulate any suitable real or nonreal, existent or non-existent object, and can be rendered in any suitable shapes, sizes, colors, textures or the like. For instance, the DR journey object can be rendered the same as or similar to those disclosed in U.S. Provisional Patent Application No. 63/223,871 filed Jul. 20, 2021, U.S. Provisional Patent Application No. 63/284,862 filed Dec. 1, 2021, and U.S. patent application Ser. No. 17/869,670 filed Jul. 20, 2022, each of which is hereby incorporated by reference in its entirety for all purposes.

Exemplary DR Recordable Objects.

In some embodiments, a DR mechanism in the systems, methods, and devices of the present disclosure involve recording audio uttered by a subject (e.g., uttered towards an input device 362 of FIG. 3), such as by having the subject provide a statement into an object within an interactive DR scene. In some embodiments, the recording of the statement or utterance by the subject results in a speech-to-text display (e.g., dynamically rendering as an object) within the interactive DR scene. A DR recordable object can be rendered in any suitable shapes, sizes, colors, textures, or the like. A DR recordable object can also be configured to simulate any real or nonreal, existent or non-existent articles, items, devices, gadgets, plants, fruits, images, texts, symbols, cartoons, or the like. In some embodiments, DR recordable objects are identifiable by a unique material and/or indicator that distinguishes them from other DR interactable objects. Accordingly, by allowing the subject to provide a statement that is then utilized to interactive with the interactive DR scene, the systems, methods, and devices of the present disclosure improve interactive with the DR technique activities of the present disclosure and, therefore, improve the ability of the subject to manage the mental or psychiatric condition exhibited by the subject.

The present disclosure provides a number of different DR recordable objects. For instance, as non-limiting example, FIG. 12A illustrates a DR recordable object 1210 simulating a candle, FIG. 12B illustrating a DR recordable object 1220 simulating a torch, FIG. 12C illustrates a DR recordable object 1230 simulating an apple, and FIG. 12D illustrates a DR recordable object 1240 simulating a pear. A recordable object can simulate other objects such as a headlight, a kindling, a bucket, or the like, which will be described later along with some DR activities configured for the subject to practice some cognitive reframing techniques. One of skill in the art will appreciate that other ornamental appearances of the recordable object are applicable to the systems, methods, and devices of the present disclosure.

In some embodiments, audio recording starts when a subject (e.g., avatar of the subject) grabs a DR recordable object within an interactive DR scene and holds the DR recordable object closer to a body of the subject, such as by moving a glove input device 310 towards a HUD of the client device 300. In some embodiments, this triggers an ornamental change for the DR recordable object, such as a material property change, and/or a user interface element to appear (e.g., a sign element 1211 signaling the recording as illustrated in FIG. 12A). In some embodiments, the subject speaks into the DR recordable object and/or the recording ends when the subject (e.g., avatar of the subject) pulls the DR recordable object away. However, it should be noted that the present disclosure is not limited thereto. For instance, audio recording can start or end in response to any suitable action, selection, command, or the like by the subject, such as any suitable action, selection, command, or the like by the subject provided through input 310 and/or input 364 of FIG. 3. For instance, as a non-limiting example, audio recording can start or end in response to an audio command from the subject, a specific gesture from the subject, a selection or a push of a button, or the like. In various embodiments, the recording can be redone as many times as needed.

In some embodiments, the recorded audio is automatically converted to a text and/or the text is automatically displayed within the interactive DR scene, for instance, at or adjacent to the DR recordable object, such as to allow the subject to visualize and critically think about the recorded statement provided by the subject. In some embodiments, the text is displayed after an epoch, such as after a gate criterion has been satisfied or the text is approved by a model and/or a medical practitioner associated with the subject. In some embodiments, the recorded audio is converted to a text and/or the text is displayed in response to an action, a selection, or a command of the subject. For instance, in some embodiments, the audio is recorded in a first interactive DR scene and displayed in a second interactive DR scene different than the first interactive DR scene. In some embodiments, the text converted from a recorded audio can include one or more words, one or more phrases, one or more sentences, or any combination thereof. The text converted from the recorded audio can be a full text, e.g., including each and every words converted from the recorded audio. The text converted from the recorded audio can also be an abridged text, e.g., a text from a portion of the recorded radio or distilled from the full text or the like. As non-limiting examples, each of FIGS. 12B, 12C and 12D illustrates a text (e.g., the text 1224, the text 1234 and the text 1244) converted from a recorded radio and displayed adjacent to each respective recordable object within an in.

In some embodiments, a DR recordable object, such as the DR recordable object 1210 (e.g., DR candle object 42), the DR recordable object 1220 (e.g., DR torch object), or the like, is used by the subject to log a first thought or statement and/or reframe the first thought or statement, such as by providing a second thought or statement. In some embodiments, when a subject speaks into the DR recordable object, an indicative feature 1222 appears, alone or in addition to the text, to indicate a type of the thought. As a non-limiting example, FIG. 12B illustrates the indicative feature 1222 simulating a frame in color. In some embodiments, different types of thoughts (e.g., anxious thoughts, reframed thoughts, or positive thoughts or affirmations) are presented in different colors. For instance, an anxious thought is indicated by a flame in a first color (e.g., red), a reframed thought is indicated by a flame in a second color (e.g., yellow), and/or a positive thought is indicated by a flame in a third color (e.g., green). However, the present disclosure is not limited thereto.

In some embodiments, when logging anxious thoughts, the DR recordable object is also used to record a triggering event associated with the anxious thought, such as an event that causes the subject to have the anxious thought. In some embodiments, the trigger event appears as a dull red glow at the end of the DR recordable object, with embers floating up from the DR recordable object. However, the present disclosure is not limited thereto.

Exemplary DR Vessel Object.

Referring to FIGS. 13A-13G, there is depicted an exemplary DR vessel object 1300 in accordance with some embodiments of the present disclosure. In some embodiments, the DR vessel object includes the functionality of the DR recording object. However, the present disclosure is not limited thereto. In some embodiments, the DR vessel object 1300 is illustrated to simulate a lantern or the like. The DR vessel object 1300 is a DR object 42 that a subject interacts with during some interactive DR experiences (e.g., within an interactive DR scene). For instance, in some embodiments, the DR vessel object 1300 is a vessel for a subject to interact with during DR cognitive reframing technique activities in the interactive DR scene 1400, e.g., for a subject to associate thought(s) or statement(s) representing thought(s) with the DR vessel object, to carry around thought(s) or statement(s) representing thought(s) using the DR vessel object, or the like.

In some embodiments, the DR vessel object 1300 includes one or more features (e.g., attributes, functions and/or components). Non-limiting examples of features include, but are not limited to, a feature 1310, a feature 1320, a feature 1330, a feature 1340, and/or a feature 1350.

The feature 1310 is configured to allow a subject to select whether the subject wants to record an anxious or a positive thought. In some embodiments, the feature 1310 is configured to allow the subject to select whether the subject wants to record an anxious, a positive thought, or one or more other types of thoughts (e.g., a reframed thought). The feature 1310 can simulate one or more DR flippers, one or more DR switches, one or more DR buttons, one or more DR arrows, one or more DR wheels, one or more DR lenses, one or more locks, one or more DR knobs, or the like, or any combination thereof. As a non-limiting example, the feature 1310 is illustrated to simulate a switch. In some embodiments, the feature in a first state, such as flipping it in one direction, signals that an anxious thought is about to be recorded. In some embodiments, the feature in a second state, such as flipping it the other way, signals that either an affirmation or reframed thought is about to be recorded.

In some embodiments, once the subjected has selected the type of thoughts that the subject is about to record, the subject (e.g., avatar of the subject) is allowed to grab the DR recordable object 1210 or the DR recordable object 1220 and record a statement representing the thought of the subject into the DR recordable object 1210 or the DR recordable object 1220. The DR recordable object 1210 or the DR recordable object 1220 can then be used to associate the DR vessel object 1300 with the recorded thought. For instance, in embodiments where the DR recordable object 1210 simulates a candle or the DR recordable object 1220 simulates a torch, the indicative feature 1222 simulating a frame appears when a subject speaks into it. The subject is then allowed to light the DR vessel object 1300 (e.g., the lantern's wick) with the flame, and/or close the door to finalize associating the DR vessel object 1300 with the recorded thought. In some embodiments, whichever way the switch is flipped determines the color of the flame produced when the subject makes a recording. However, the present disclosure is not limited thereto.

In some embodiments, the feature 1320 is rendered in the DR vessel object to represent a thought. By way of example, the feature 1320 is illustrated to simulate a flame, a light, a lighted interior, a colored wall, or the like. A DR vessel object can be used to contain (e.g., be associated with or linked to) any type of thoughts, e.g., anxious thoughts, reframed thoughts, positive thoughts, or affirmations. In some embodiments, the feature 1320 is rendered to indicate the type of a thought with a color scheme. For instance, as a non-limiting example, the feature 1320 is rendered in a first color (e.g., red) to indicate an anxious thought, rendered in a second color (e.g., yellow) to indicate a reframed thought, and/or rendered in a third color (e.g., green) to indicate a positive thought or an affirmation. In some embodiments, the feature 1320 uses the same or substantially the same color scheme as the indicative feature 1222 of the DR recordable object 1210 or the DR recordable object 1220 (e.g., the color of the candle or torch flame). In some embodiments, other color schemes or different types of schemes (e.g., using labels, symbols, pictures, audios, or the like) are available.

In some embodiments, the feature 1330 is configured for rating a level of impact a thought has on a subject. As a non-limiting example, the feature 1330 is illustrated to simulate a knob serving as a dimmer or the like. Adjusting the feature 1330, e.g., turning the dimmer in either direction, changes the intensity of the light glowing inside of the DR vessel object 1300, thereby indicating the level of impact the thought has on the subject. In some embodiments, the stronger the impact the thought has on the subject, the brighter the light becomes. In some embodiments, the feature 1330 can be adjusted continuously. In some embodiments, the feature 1330 can be adjusted discontinuously, e.g., can be held at any one of a plurality of positions. In some embodiments, there are two different positions for assigning two different levels of impact. In some embodiments, there are at least three, at least four, at least five, at least six, at least seven, at least eight, at least nine, at least ten, or at least 11 positions for assigning at least three, at least four, at least five, at least six, at least seven, at least eight, at least nine, at least ten, or at least 11 different levels of impact. In some embodiments, there are at most three, at most four, at most five, at most six, at most seven, at most eight, at most nine, at most ten, or at most 11 positions for assigning at most three, at most four, at most five, at most six, at most seven, at most eight, at most nine, at most ten, or at most 11 different levels of impact. In some embodiments, when the feature 1330 is held on a position, a text will be presented on the display at or adjacent to the DR vessel object 1300, and/or an audio will be played to inform the subject what the current level of impact is. Examples of such texts or audios include, but are not limited to, "first level," "second level," "third level," "Minimal," "Moderate," "Strong," or the like.

In some embodiments, a DR vessel object 1300 includes additional, optional, or alternative features. For instance, as a non-limiting example, FIGS. 13D and 13E illustrate a DR vessel object 1300 having additional feature 1340 and additional feature 1350.

The additional feature 1340 is configured to indicate the total number of statements contained in (e.g., associated with or linked to) the DR vessel object 1300. Usually, a statement (representing a thought) contained in a DR vessel object 1300 is generated by a subject recording into a DR recordable object such as the DR recordable object 1210, the DR recordable object 1220, or the like. In certain embodiments, a statement contained in a DR vessel object 1300 is a prestored statement representing a common anxious thought or a thought of others that is not recorded by the subject.

A DR vessel object 1300 can contain any suitable number of prestored statements representing common anxious thoughts or thoughts of others, any suitable number of statements each representing a thought generated by a subject recording into a DR recordable object, or both. For instance, as a non-limiting example, in some embodiments, a DR vessel object 1300 is used to contain at least one, at least two, at least three, or at least four statements each representing a thought generated by a subject without any prestored statements. In some embodiments, the DR vessel object 1300 is used to contain at most one, at most two, at most three, or at most four statements each representing a thought generated by a subject without any prestored statements. As another non-limiting example, in some embodiments, a DR vessel object 1300 is configured to contain only prestored statements representing common anxious thoughts or thoughts from others (e.g., thoughts from a different subject, thoughts from a medical practitioner associated by a medical practitioner associated with the subject, one or more predetermined thoughts generated by a model of the present disclosure, etc.). As a further non-limiting example, in some embodiments, a DR vessel object 1300 is configured to contain at least one prestored statement representing a common anxious thought and at least one statement representing a thought generated by a subject. In some embodiments, the at least one prestored statement representing the common anxious thought and the at least one statement representing the thought generated by a subject allows the subject to compare the common anxious thought against the thought generated by a subject, such as to determine an adequacy of the thought generated by the subject.

In some embodiments, the additional feature 1350 is configured for the subject to browse through the statements contained in the DR vessel object, which includes prestored statements representing common anxious thoughts, statements recorded by the subject, or the like. In some embodiments, the additional feature 1350 is also configured for the subject to select a statement representing a thought for reframing or other actions (e.g., when the subject stops browsing or pressing the additional feature 1350). As a non-limiting example, the additional feature 1350 is illustrated to simulate an arrow button or arrow buttons.

In some embodiments, the additional feature 1340 is also configured to indicate the order of the instant statement among all the statements (e.g., 1 of 8, 2 of 8, 6 of 8, or the like) while the subject browses through the statements. In some embodiments, the text of the instant statement is presented at the DR vessel object while the subject browses through the statements.

In some embodiments, for instance, when a DR vessel object 1300 is used for education or training technique activity purposes (e.g., when guiding the subject to learn how to interactive with an interactive DR technique activity, such as how to associate the one or more emotions and/or one or more behaviors with the anxious thought or the triggering event, how to label anxious thoughts, or the like), the DR vessel object is also referred to herein as a DR educational-vessel object. It should be noted that a DR educational-vessel object can, but do not necessarily have to, include a plurality of presented statements.

While FIGS. 13A-13G illustrate the DR vessel object 1300 simulating a lantern or the like, it should be noted that this is by way of example and is non-limiting. A DR vessel object can be rendered in any suitable shapes, sizes, colors, textures or the like. A DR vessel object can also be configured to simulate any real or nonreal, existent or non-existent articles, items, devices, gadgets, cartoons, or the like. For instance, as a non-limiting example, a DR vessel object can be configured to simulate a lamp, a basket, a pumpkin, or the like. In additional, two DR vessel objects (e.g., one for a first activity and one for a second activity) can be, but do not have to, identical. For instance, they can differ in shape, size, color, texture, character, or the like.

Referring to FIGS. 15A-15D, in some embodiments, a DR vessel object is used in an interactive DR technique activity for a subject to learn how to link emotions and behaviors to a thought. In some embodiments, during the interactive DR technique activity, the DR vessel object is used to illuminate words (e.g., a single word, a group of words that makes a phrase or a sentence or the like), such as a word or phrase 1520-1 and a word or phrase 1520-2, glowing on a DR structure object 1510 (e.g., a wall, a hill, a palisade, or the like). In some embodiments, the words on the DR structure object describe one or more feelings and/or sensations that is associated with an anxious thought, such as the thought selected by the subject. In some embodiments, the words are generated by a model of the present disclosure and/or a medical practitioner associated with the subject, such as by having a first model generate a plurality of words and then the medical practitioner curating a set of words from the plurality of words, which is then illustrated on the DR structure object in the interactive DR scene implementing the interactive DR technique activity. In some embodiments, the closer the DR vessel object is to a word(s), the brighter the word(s) glows. In some embodiments, a subject is allowed to select the word(s) by touching them (e.g., by having the avatar of the subject touching them). In some embodiments, touching the words causes the words to stay illuminated, even after the lantern has been moved away. In some embodiments, after finalizing the selection by setting the DR vessel object down, the selected words float off the DR structure object and/or transform appearance, such as by transforming into tiny bugs 1530, which buzz around the DR vessel object. In some embodiments, the bugs are rendered in a color (e.g., red) indicative of the type of the thought (e.g., anxious thought). However, the present disclosure is not limited thereto.

Referring to FIG. 16B, in some embodiments, after a thought is reframed, the subject is allowed to place the DR vessel object with the reframed thought on a DR stream object 1630. In some embodiments, the DR stream object is located in a vicinity of a DR wellbeing object 1610 or will carry the DR vessel object with the reframed thought to the vicinity of the DR wellbeing object 1610. In certain embodiments, once a DR vessel object is placed on the DR stream object, it is no longer interactive, and/or takes on the appearance of a water lantern. In various embodiments, the number of the DR vessel objects with reframed thoughts will affect the health (e.g., appearance) of the DR wellbeing object that reflects the mental and emotional wellbeing of the subject.

A DR vessel object can include any combination of the feature 1310, the feature 1320, the feature 1330, the feature 1340, and the feature 1350. For instance, in embodiments where a DR vessel object is intended to hold only one thought at a time, the DR vessel object can, but do not necessarily have to, have either the additional feature 1340 and/or the additional feature 1350. The DR vessel object can also include other additional, optional, or alternative features. For instance, the DR vessel object can include a feature to allow a subject (an avatar of the subject) to put the DR vessel object on a belt of an avatar associated with the subject rather than carrying the DR vessel object around within the interactive DR scene. The DR vessel object can also include a label that indicates what type of distortion the thought is.

Exemplary DR Wellbeing Object.

Referring to FIGS. 16A-16C, there is depicted an exemplary DR wellbeing object 1610 in accordance with some embodiments of the present disclosure. As a non-limiting example, the DR wellbeing object 1610 is rendered within the interactive DR scene 1400, and is illustrated to simulate a tree, which is generally referred to herein as a wisdom tree. The health (e.g., appearance such as size, shape, color, ornament, or the like) of the wisdom tree is configured to reflect the mental and/or emotional wellbeing of a subject.

In some embodiments, an appearance of the DR wellbeing object, such as an appearance the health of the wisdom tree improves over the course as a subject progresses through each level of cognitive reframing activities. For instance, in some embodiments, a subject is allowed to exercise identifying, challenging, and ultimately restructuring anxious thoughts (e.g., practice a technique of the present disclosure). After a thought is reframed, the DR vessel object with the reframed thought is carried, by the subject, by the DR stream object, or the like, to a vicinity of the DR wellbeing object 1610. In some embodiments, the DR vessel object with the reframed thought nourishes the DR wellbeing object 1610 and improves the health of the DR wellbeing object 1610, which provides a visualization of the subject of the improvement in the ability to manage the mental or psychiatric condition exhibited by the subject through the use of the systems, methods, and devices of the present disclosure. Accordingly, in some embodiments, as the health of the DR wellbeing object 1610 improves, the appearance of the DR wellbeing object 1610 on the display changes, for instance, growing taller, becoming bigger, changing colors, with more decorations, or the like. As a non-limiting example, FIG. 16C illustrates a DR decorative object 1620 indicative of the improvement of the health of the DR wellbeing object 1610.

While FIGS. 16A-16C illustrate the DR wellbeing object 1610 to simulate a tree, it should be noted that this is by way of example and is non-limiting. A DR wellbeing object can be rendered in any suitable shapes, sizes, colors, textures or the like. A DR wellbeing object can also be configured to simulate any real or nonreal, existent or non-existent, fictional or non-fictional, mythical or non-mythical characters, symbol, cartoons, or the like. For instance, as a non-limiting example, a DR wellbeing object can be configured to simulate a trophy, a flower, a gift, a star, a grove, or the like.

2.3. Overview of the Method

Figure 4A:
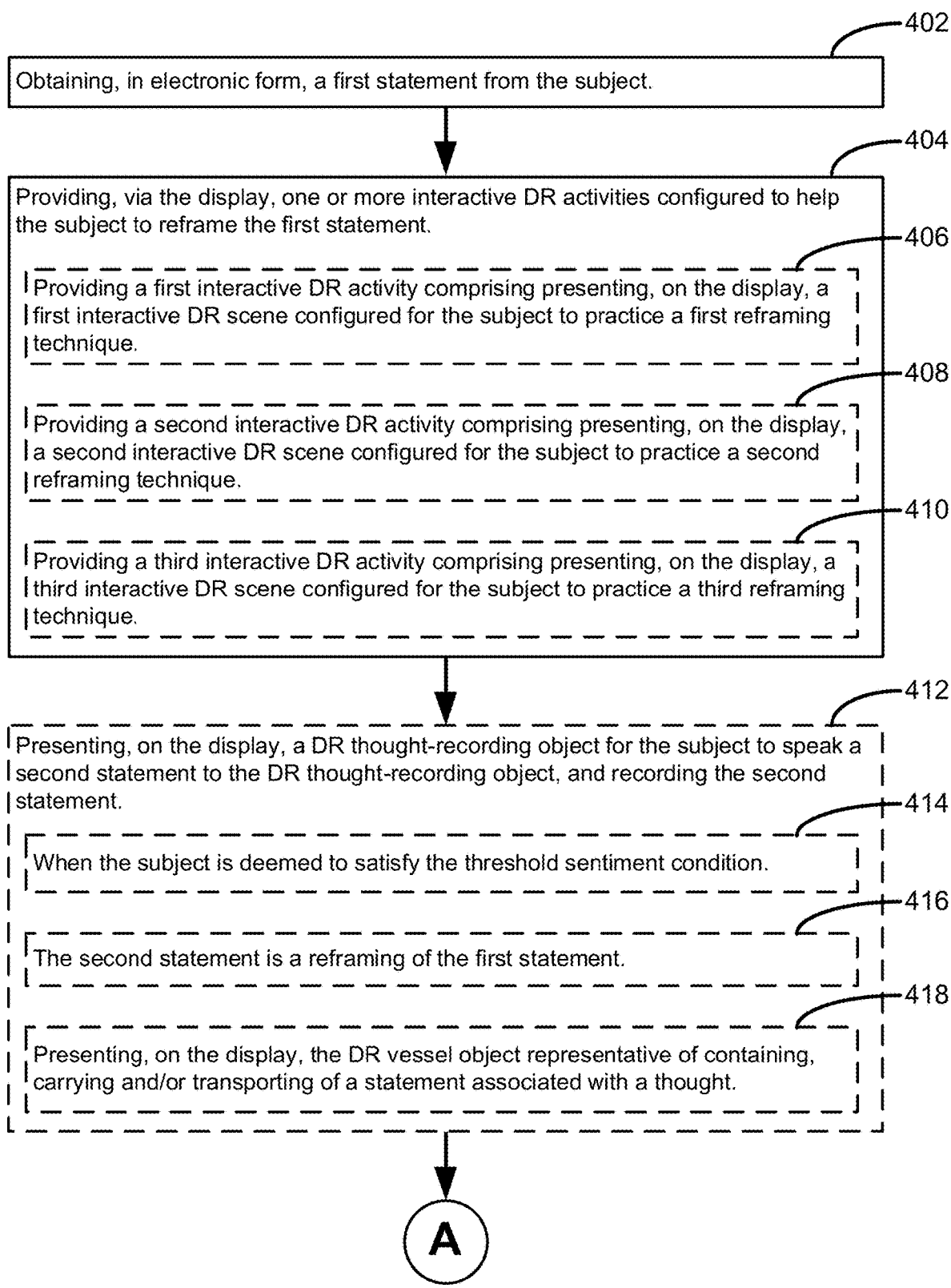
FIGS. 4A and 4B collectively illustrate exemplary methods for implementing one or more cognitive behavioral therapy (CBT) techniques to improve an ability of a subject to manage a psychiatric or mental condition of the subject, in which optional embodiments are indicated by dashed boxes, in accordance with some embodiments of the present disclosure.
Figure 4B:
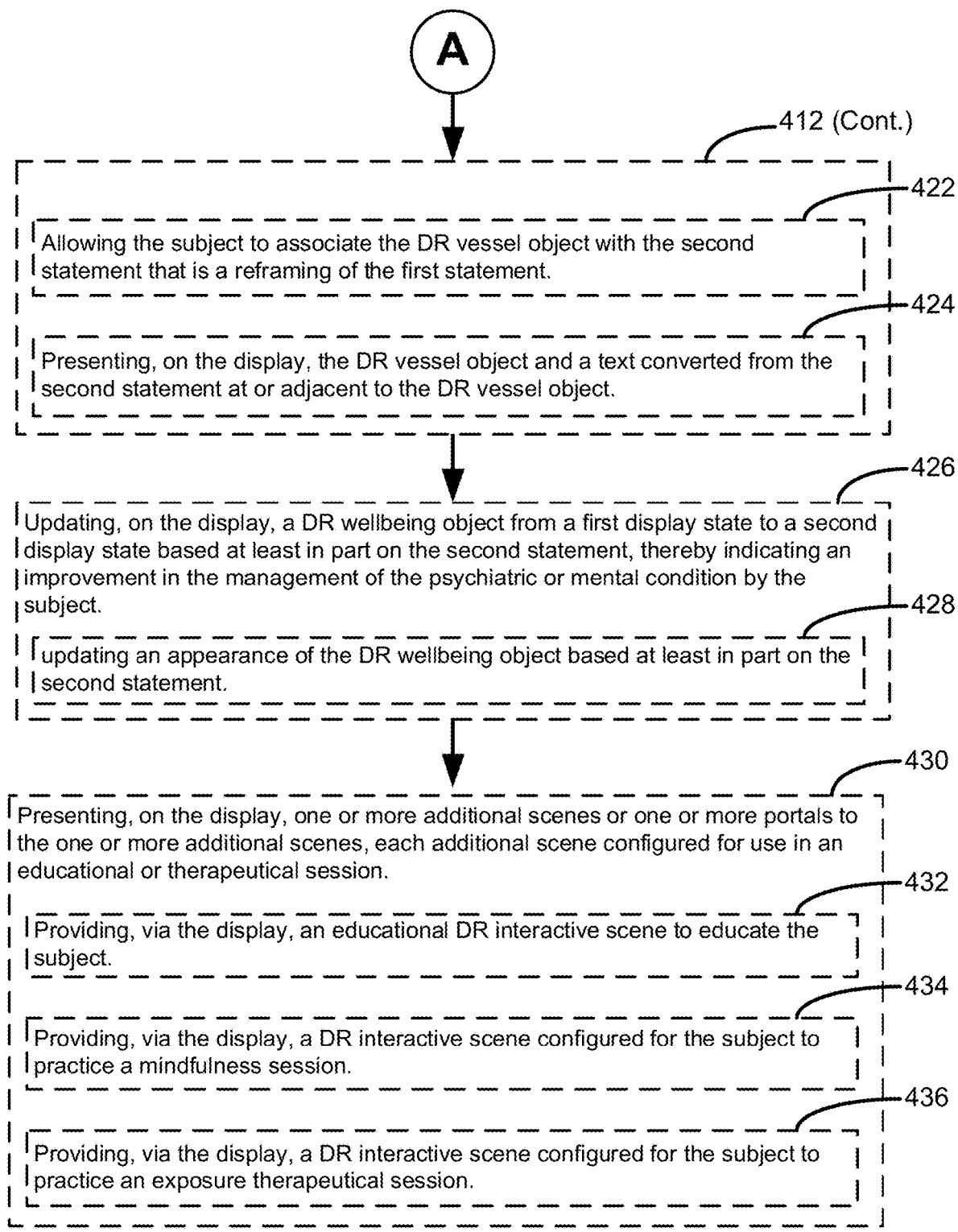

Referring now to FIGS. 4A and 4B, there is depicted a flowchart illustrating an exemplary method 400 in accordance with some embodiments of the present disclosure. In the flowchart, the preferred parts of the method are shown in solid line boxes, whereas additional, optional, or alterative parts of the method are shown in dashed line boxes. The method is configured to improve the ability of a subject to manage a psychiatric or mental condition exhibited by the subject, such as by having the subject interact with a plurality of interactive DR activities presenting within an interactive DR scene. More specifically, in some embodiments, the method 400 is configured to improve the ability of a subject to manage their psychiatric or mental condition by implementing an interactive DR activity for a cognitive restructuring technique, such as an evidence gathering technique, within the interactive DR scene, for example, by having a subject self-identify a feature (e.g., harmful or negative evidence) associated with an utterance (e.g., thought or statement) spoken by the subject, evaluating if the self-identified feature (e.g., evidence) is sufficient to reframe the utterance, conducting one or more assessments by the subject, reframing the utterance by the subject, or a combination thereof, through the plurality of interactive DR activities, in order to improve the psychiatric or mental condition of the subject. In some embodiments, this procedure improves the psychiatric or mental condition of the subject by modulating harm expectancy and/or a perception of control for the subject based on engagement with the subject and the interactive DR scene.

Accordingly, in some embodiments, the method 400 provides a plurality of self-applied interactive DR cognitive reframing activities for the subject within the interactive DR scene, which allows the subject to improve their psychiatric or mental condition by only engaging with the interactive DR scene, which is highly advantageous. In some embodiments, the method 400 of the present disclosure allows for the subject to identify negative thoughts or statements. In some embodiments, the method 400 further allows the subject to disrupt a native cognitive pattern associated with the formation of the negative thought or statement by the subject with a new cognitive pattern associated with the formation of a positive or adaptive thought or statement through the plurality of interactive DR activities performed by the subject. Moreover, in some embodiments, the method 400 further allows the subject to disrupt the native cognitive pattern associated with the formation of the negative thought or statement by the subject with the new cognitive pattern associated with the formation of a positive or adaptive thought or statement by persistently, concurrently, simultaneously, or a combination thereof, displaying information associated with the performance of the subject during the plurality of interactive DR activities, which is advantageous by reinforcing particular information associated with the subject when the subject is performing a respective interactive DR activity in the plurality of interactive DR activities.

Accordingly, the method is performed at a computer system associated with the subject, such as system 100, digital reality system 200, client device 300, or a combination thereof disclosed herein. In this way, the method 400 utilizes one or more determinations, one or more evaluations, one or more calculations, or the like needed to improve the ability of a subject to manage the psychiatric or mental condition exhibited by the subject by implementing an interactive DR activity because it cannot be mentally performed.

Block 402. Referring to block 402, the method 400 includes obtaining, in electronic form, a first statement from the subject. In some embodiments, the first statement represents a thought of the subject, such as an anxious thought of the subject that was triggered by a situation or an event. The first statement can be obtained in a variety of ways. For instance, the first statement can be recorded using an audio recorder of the computer system (e.g., input 364 of client device 300 FIG. 3), selected from a plurality of prestored statements, inputted through a web or a mobile application such as the client application 2100 disclosed herein, through an interactive DR object (e.g., interactive DR recording object, interactive DR thought-recording object, etc.). Accordingly, by obtaining the first statement from the subject in electronic form, the method 400 is capable of performing a variety of determinations and/or evaluations on the first statement, such as evaluating a wave-form of the first statement and/or one or more syntaxes associated with the first statement, which is advantageous. Moreover, the computer system facilitates those users that experience difficulty providing statements in oral form to live subjects because such users are not dissuaded from providing the first statement since they are providing it to the computer system, as opposed to another subject. However, the present disclosure is not limited thereto.

Alternatively, in some embodiments, the first statement is selected by the method (e.g., a computational model of the method), a healthcare professional (e.g., a clinician) associated with the subject, or a combination thereof. The first statement selected by the method and/or the healthcare professional can represent a thought of the subject, a common thought, or a thought of other subjects with similar conditions as the subject (e.g., the same condition as the mental or psychiatric condition exhibited by the subject). However, the present disclosure is not limited thereto.

Blocks 404-410. Referring to block 404 through block 410, the method also includes providing, via a display of the computer system, one or more interactive digital reality (DR) activities through an interactive DR scene. The one or more interactive DR activities are configured to help the subject to reframe the first statement, e.g., helping the subject to reconstruct the thought represented by the first statement into a second statement, which is considered more beneficial in comparison against the first statement. In some embodiments, each interactive DR activities helps the subject reframe the first statement. In some embodiments, the one or more interactive DR activities collectively help the subject reframe the first statement. For instance, in some embodiments, the method helps the subject to reframe the first statement into a second statement representing a more positive thought than the thought represented by the first statement (e.g., in accordance with a determination by a sentiment evaluation provided by a first model and/or a medical practitioner associated with the subject).

In some embodiments, the method helps the subject to reframe a first cognitive pattern associated with a formation of the first statement by the subject into a second cognitive pattern associated with a formation of the second statement. Accordingly, by helping the subject reframe into second cognitive pattern, such as by disrupting the native first cognitive pattern with the new second cognitive pattern associated, the method 400 improves management of the psychiatric or mental condition for the subject when the subject interacts with the interactive DR activities within the interactive DR scene.

The method can provide any suitable number of interactive DR activities, e.g., one, two, three, four, five, six, or more than six interactive DR activities, that are configured to help the subject to improve an approach to forming the first statement, such as through one or more CBT techniques realized in the form of an interactive DR activity (e.g., interactive DR technique activity). For instance, in some embodiments, the method provides one interactive DR activity, such as a first interactive DR activity, a second interactive DR activity, or a third interactive activity, to help the subject to reframe the first statement. In another embodiment, the method provides two interactive DR activities, such as any two of the first, second and third interactive DR activities, to help the subject to reframe the first statement. In a further embodiment, the method provides three interactive DR activities, such as the first, second and third interactive DR activities, to help the subject to reframe the first statement. In a still further embodiment, the method provides more than three interactive DR activities. In some embodiments, the method provides at least one interactive DR activity, at least two interactive DR activities, at least three interactive DR activities, at least four interactive DR activities, at least five interactive DR activities, at least six interactive DR activities, at least seven interactive DR activities, at least eight interactive DR activities, at least nine interactive DR activities, or at least ten interactive DR activities. In some embodiments, the method provides at most one interactive DR activity, at most two interactive DR activities, at most three interactive DR activities, at most four interactive DR activities, at most five interactive DR activities, at most six interactive DR activities, at most seven interactive DR activities, at most eight interactive DR activities, at most nine interactive DR activities, or at most ten interactive DR activities.

In some embodiments, the first interactive DR activity is configured for the subject to practice a first CBT technique. The second interactive DR activity is configured for the subject to practice a second CBT technique. The third interactive DR activity is configured for the subject to practice a third CBT technique. For instance, in some embodiments, the first interactive DR activity is configured for the subject to practice a "gather evidence" CBT technique. The second interactive DR activity is configured for the subject to practice a "usefulness and core beliefs" CBT technique. The third interactive DR activity is configured for the subject to practice a "create space" CBT technique. However, the present disclosure is not limited thereto.

Different interactive DR activities can be performed independently and/or separately from each other. For instance, the first interactive DR activity can be performed alone or with one or more additional activities. Similarly, the second interactive DR activity can be performed alone or with one or more additional activities. The third interactive DR activity can be performed alone or with one or more additional activities. Moreover, while ordinal numbers (e.g., first, second, third) are used to name different activities, these ordinal numbers do not necessarily imply the order of the activities to take place. For instance, the first interactive DR activity can be performed before or after the second or third interactive DR activity. Similarly, the second interactive DR activity can be performed before or after the first or third interactive DR activity. The third interactive DR activity can be performed before or after the first or second interactive DR activity. Further, in embodiments where multiple activities are provided, activities can be but do not have to be conducted in a sequential order. For instance, in embodiments where the first and second interactive DR activities are provided, the subject may be required to perform the activities in an order when the subject is a first-time user, e.g., performing the first and then second activities, or performing the second and then first activities as preset by the method or as prescribed by a healthcare professional associated with the subject. In some embodiments, once the subject has performed an interactive DR activity (e.g., either the first or second interactive DR activity), the subject is allowed to go back and have access to that interactive DR activity anytime the subject chooses.

In some embodiments, each interactive DR activity is associated with (e.g., interacted with by the subject through) a corresponding interactive DR scene. In some embodiments, each interactive DR activity is associated a first interactive DR scene.

In various embodiments, a CBT activity (e.g., providing one or more interactive DR activities configured to help the subject to reframe a statement representing a thought) configured is to have the subject provide a higher number of reframed thoughts and positive affirmations compared to unresolved anxious thoughts, such as in comparison to an initial session interacting with the interactive DR activity. For instance, in some embodiments, the method 400 improves the management of the mental or psychiatric condition by having a subject improve a skill of recognizing and challenging anxious thoughts as the anxious thoughts are formed by the subject (e.g., as the thought occurs) through interactions with the interactive DR activity, rather than letting the thought overwhelm the subject, which can cause the subject to exhibit an anxiety condition. In some embodiments, there is no limit to how many thoughts a subject can reframe, and there is no final level to beat, since the CBT techniques disclosed herein are intended to be practiced again and again. However, the present disclosure is not limited thereto. In some embodiments, a subject is rewarded by the method 400 for reframing thoughts by receiving various items throughout the interactive DR activity and/or by seeing the DR wellbeing object (e.g., the wisdom tree) thrive the more the subject returns, which helps improve management of the psychiatric or mental condition by the subject. In some embodiments, the ultimate goal of cognitive restructuring is to change any damaging core beliefs at the root of automatic thoughts. In some embodiments, there is not always a binary win or lose outcome when the subject interacts with an interactive DR activity because having the subject lose does not aid in the management of the psychiatric or mental condition. Rather, in some such embodiments, the interactive DR technique activity is considered successful if a subject is subsequently able to reframe an anxious thought, such as in the interactive DR scene or in a physical environment remote from the interactive DR scene. In some embodiments, the medical practitioner associated with the subject is present at the physical environment remote from the interactive DR scene and determines if the interactive DR technique activity is considered successful for the subject. However, the present disclosure is not limited thereto.

Blocks 412-416. Referring to block 412 through block 416, in some embodiments, additionally or optionally, the method includes presenting, on the display, a DR recording object for the subject to speak a second statement to the DR recording object and recording the second statement. For instance, in some embodiments, the method presents the DR recordable object 1210 (e.g., candle), the DR recordable object 1220 (e.g., torch), or the like for the subject to speak a second statement and record the second statement. In some embodiments, the second statement in is a reframing of the first statement (e.g., the second statement representing a reframed thought of the subject).

In some embodiments, a recording of a respective statement by the subject is transitorily stored by the computer system system. In some embodiments, the recording of the respective statement by the subject is persistently stored by the computer system, such as within a user profile associated with the subject. Accordingly, by storing the respective statements obtained from the subject when interacting with the one or more interactive DR activities, the method 400 creates a historical record of statements obtained from the subject, which is advantageous for future determinations and/or evaluations associated with the subject. However, the present disclosure is not limited thereto.

In some embodiments, the presenting of the DR recording object is performed when the subject is deemed to satisfy a threshold condition, such as a threshold sentiment condition. Determination of whether the subject is deemed to satisfy a threshold condition can be self-administered, oversighted by a healthcare professional associated with the subject, based on one or more physiological measurements, determined by the method, or any combination thereof, which is advantageous because the progression of the subject through the plurality of interactive DR activities is modifiable and/or configurable through the threshold conditions. For instance, as a non-limiting example, the subject is deemed to satisfy a threshold sentiment condition, (i) when the subject is, indicates or feels ready to reframe the thought, (ii) when the subject completes the required session as programed by the method or prescribed by the healthcare professional associated with the subject, (iii) when the one or more physiological measurements (e.g., heart beats, body temperature) indicates that the subject is ready to reframe the thought, (iv) when a healthcare professional associated with the subject determines that the subject is ready to reframe the thought, (v) when the method determines that the subject is ready to reframe the thought, or (vi) any combination thereof. In some embodiments, in determining whether the subject is ready to reframe the though, the method (e.g., one or more computational models) or the healthcare professional associated with the subject takes into consideration of the one or more physiological measurements, and/or an improvement measured by an established assessment scale such as a severity of anxiety and depression improvement measured by one of the scales disclosed in U.S. Provisional Patent Application No. 63/223,871, filed Jul. 20, 2021, U.S. Provisional Patent Application No. 63/284,862, filed Dec. 1, 2021, and U.S. patent application Ser. No. 17/869,670, filed Jul. 20, 2022, each of which is hereby incorporated by reference in its entirety for all purposes.

In some embodiments, whether the subject is deemed to satisfy a threshold condition is determined, or partly determined, by the method using one or more models and/or a medical practitioner associated with the subject. The one or more models include, but are not limited to, a logistic regression model, a neural network model, a support vector machine model, a Naive Bayes model, a nearest neighbor model, a random forest model, a decision tree model, a boosted trees model, a multinomial logistic regression model, a linear model, a linear regression model, a Gradient Boosting model, a mixture model, a hidden Markov model, a Gaussian model, a linear discriminant model, or any combinations thereof. In some embodiments, the linear regression model is a concordance-index, which gives a higher score to a subject who experienced an activity (e.g., a psychiatric or mental condition exhibited by the subject) than a subject who had not experienced the activity.

In some embodiments, the threshold condition includes one or more physiological markers, such as a skin conductance (SC), a heart rate (HR), a blood volume pulse (BVP). In some embodiments, the threshold condition includes a deactivation of the parasympathetic nervous system (PNS), an activation of the sympathetic nervous system (SNS), or both.

Blocks 418-422. Referring to block 418 and block 422, in some embodiments, additionally or optionally, the method includes presenting, on the display, the DR object representative of containing, carrying, transporting, or a combination thereof of a statement associated with a thought, and allowing the subject to associate the DR object with the second statement that is a reframing of the first statement. For instance, in some embodiments, the method presents, on the display, a DR object 1300, which can be a new DR object (e.g., does not containing the first statement), or the DR object that contains (e.g., associated with or linked to) the first statement. The DR object 1300 can be presented when or after the DR recordable object 1210 (e.g., candle), the DR recordable object 1220 (e.g., torch), or the like is presented for the subject to speak and record the second statement.

In some embodiments, the DR object 1300 can be associated with the second statement in a similar fashion as disclosed herein with respect to FIGS. 13A-13F. In some embodiments, because the second statement is a reframing of the first statement and represents a reframed thought, the feature 1320 of the DR object 1300 containing the second statement is rendered in a different color than the feature 1320 of the DR object 1300 containing the first statement. For instance, in some embodiments, while the feature 1320 of the DR object 1300 containing the first statement is rendered in a first color (e.g., red), the feature 1320 of the DR object 1300 containing the second statement will be rendered in a second color (e.g., yellow).

Block 424. Referring to block 424, in some embodiments, additionally or optionally, the method includes presenting, on the display, the DR object and a text converted from the second statement at or adjacent to the DR object. For instance, in some embodiments, the method presents, on the display, the DR object associated with the second statement, and a text converted from the second statement at or adjacent to the DR object in a similar fashion as disclosed herein with respect to FIGS. 13A-13F.

Blocks 426-428. Referring to block 426 and block 428, in some embodiments, additionally or optionally, the method includes updating, on the display, a DR object, such a ledger associated with a second affordance region 650-2, from a first display state to a second display state based at least in part on the second statement. For instance, as a non-limiting example, in some embodiments, the health of a tree DR object reflects the mental and/or emotional wellbeing of a subject, e.g., damaging thoughts will weigh the tree down while reframed thoughts will help the tree grow. Over the course, as the subject progresses through each level of cognitive reframing activities, the health of the tree (e.g., appearance of tree, such as size, shape, color, ornament, or the like) improves. By way of example, in some embodiments, the DR object in a first display state includes no DR decorative objects indicating no thought has been reframed, and the DR object in a second display state with the DR decorative object indicates some thought(s) have been reframed.

Blocks 430-436. Referring to block 430 through block 436, in some embodiments, additionally or optionally, the method includes presenting, on the display, one or more additional DR scenes or one or more portals to the one or more additional scenes, each additional scene configured for use in an educational or therapeutical session, such as one or more interactive DR activities that provide the educational or therapeutical session. The method can present any suitable number of additional DR scenes or portals to the additional DR scenes. For instance, in some embodiments, the method presents a single additional scene or a portal to a single additional scene. In some embodiments, the method presents more than one, more than two, more than three, more than four, more than five, more than ten, more than fifteen, or more than twenty additional DR scenes or portals to the additional DR scenes. In some embodiments, the method presents at most one, at most two, at most three, at most four, at most five, at most ten, at most fifteen, or at most twenty additional DR scenes or portals to the additional DR scenes.

Examples of additional DR scenes include, but are not limited to, an educational DR interactive scene to educate the subject (e.g., providing education on cognitive behavioral therapy, mindfulness therapy, exposure therapy, reframing techniques, linking emotions and behaviors, and/or goal settings), a DR interactive scene configured for the subject to practice a mindfulness session, a DR interactive scene configured for the subject to practice an exposure therapeutical session, or the like.

In some embodiments, an additional interactive DR activity can be presented before, after, or intermittently with an interactive DR scene (e.g., the first, second or third interactive DR activity). For instance, in some embodiments, as a non-limiting example, an educational DR interactive activity on cognitive behavioral therapy in a first interactive DR scene is presented before any interactive DR activity configured to help the subject to reframe the first statement in is presented if the subject is a first time user. In some embodiments, the first interactive DR activity is accessible to the subject anytime the subject chooses. As another non-limiting example, a DR interactive scene for a mindfulness DR activity is accessible to the subject anytime the subject chooses if the subject has practiced the mindfulness activity at least once. As a further non-limiting example, a DR interactive scene for an exposure activity can be presented before an interactive DR activity for CBT activity and then be accessible to the subject after completion of the interactive DR activity. In some embodiments, the method allows the subject to go back and access any educational or therapeutical activities that the subject has completed at least once.

2.4. Obtaining a First Statement

Figure 5A:
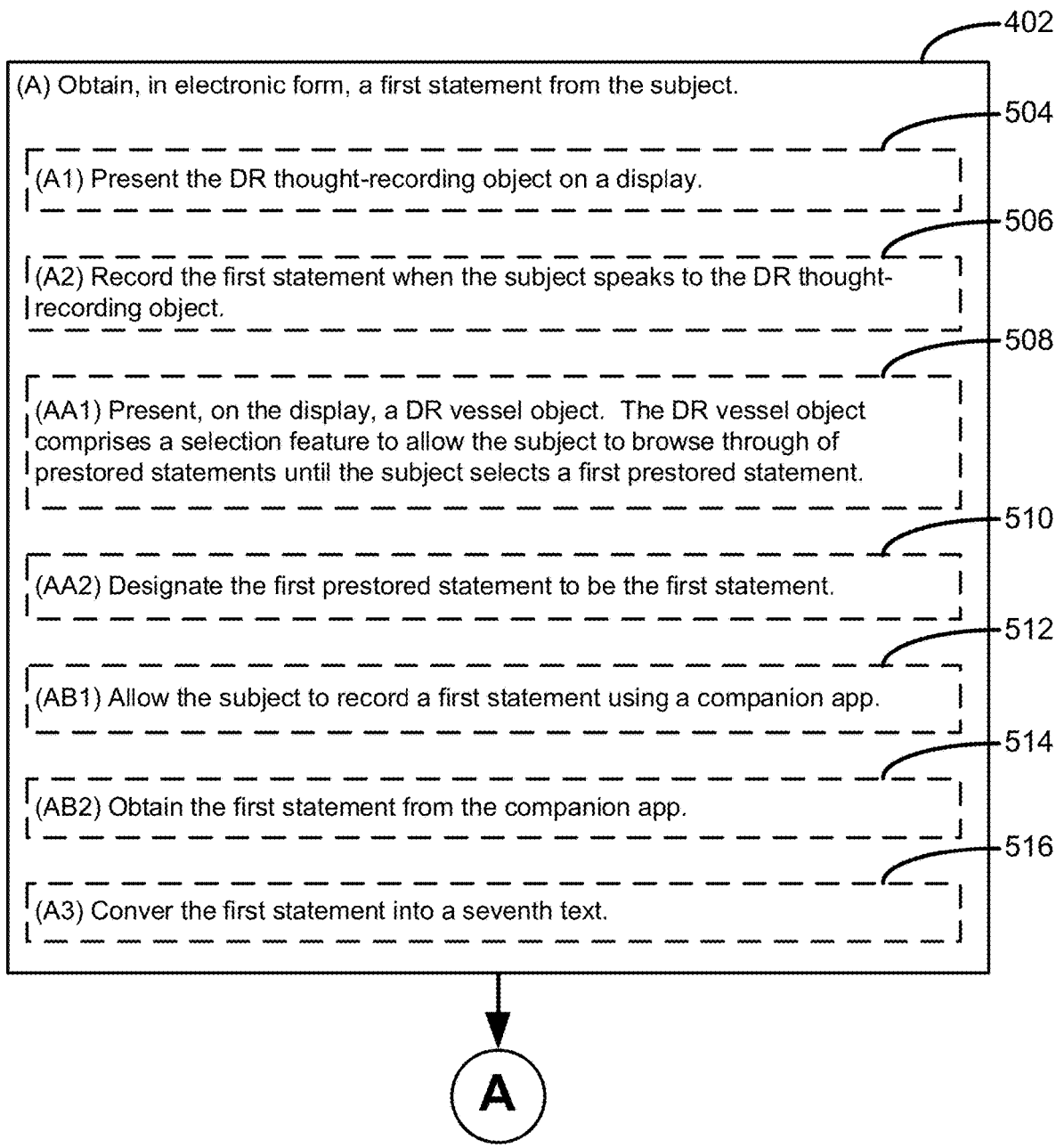
FIGS. 5A and 5B collectively illustrate exemplary methods for obtaining a statement (e.g., a statement representing a thought) from a subject, in which optional embodiments are indicated by dashed boxes, in accordance with some embodiments of the present disclosure.
Figure 5B:
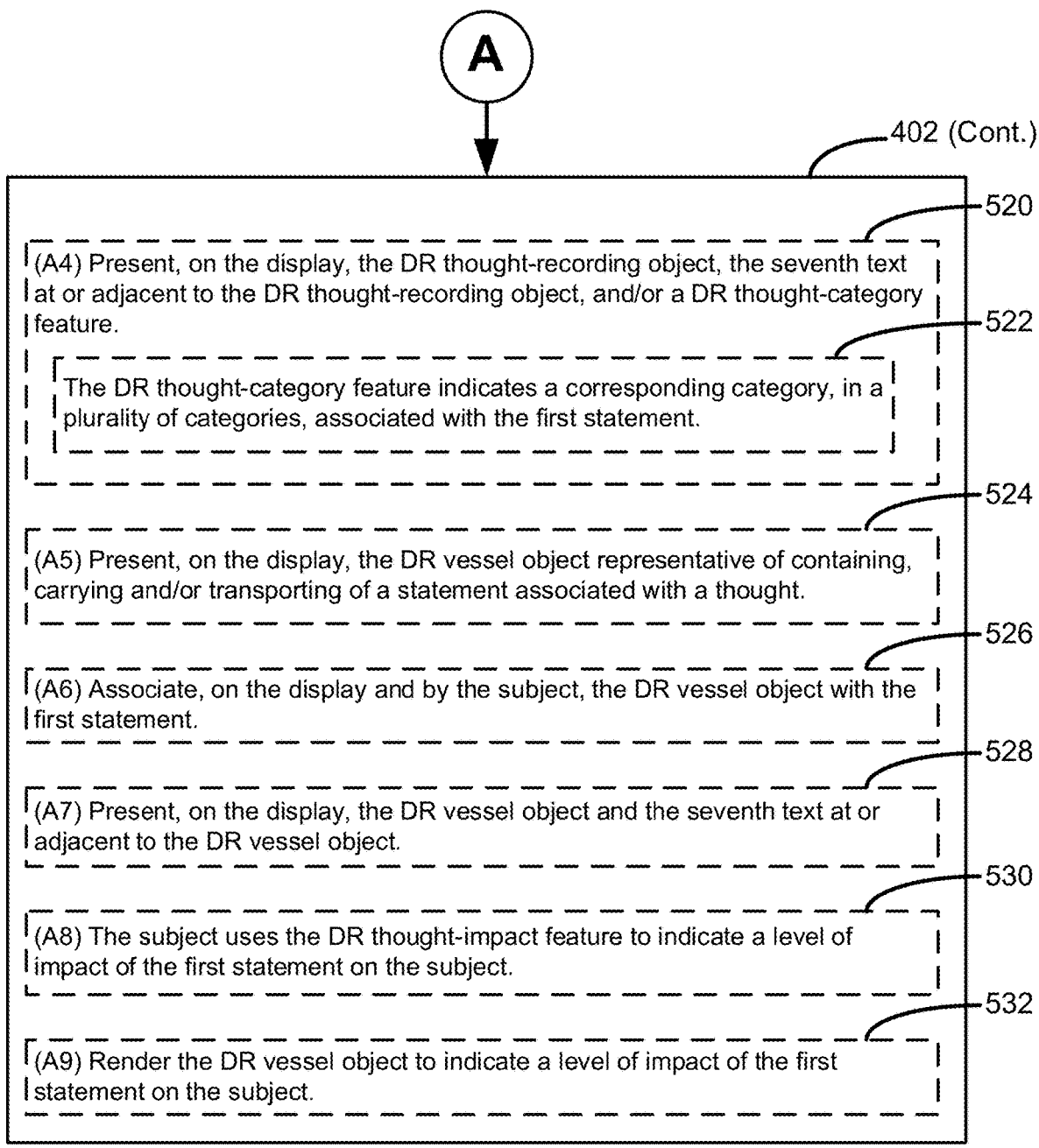

Referring to FIGS. 5A and 5B, there is depicted a flowchart illustrating exemplary methods for obtaining a statement from the subject in accordance with some embodiments of the present disclosure. A statement, such as a first statement representing a thought of a subject, can be obtained in a number of ways. For instance, as a non-limiting example, a first statement can be obtained using a DR thought-recording object, such as the DR recordable object 1210 (e.g., candle), the DR recordable object 1220 (e.g., torch), or the like. As another non-limiting example, a first statement can be obtained through a DR object, such as the vessel object 1300 (e.g., lantern) that contains one or more prestored statements. As a further non-limiting example, a first statement can be obtained through a client application, such as the client application 2100 illustrated in FIGS. 21A-21C. In some embodiments, a statement can also be selected by the method (e.g., one or more computational models) and/or the healthcare professional, and can represent a thought of the subject, a common thought, or a thought of others with similar conditions as the subject.

Blocks 504-506. Referring to block 504 and block 506, in some embodiments, in obtaining a first statement from the subject, the method includes presenting, on the display, a DR thought-recording object, and recording the first statement when the subject speaks to the DR thought-recording object. Examples of a DR thought-recording object include, but are not limited to the DR recordable object 1310 (e.g., candle), the DR recordable object 1320 (e.g., torch) or the like. For instance, FIG. 12A illustrates presenting and using the DR recordable object 1210 (e.g., candle) to record a first statement, and FIG. 12B illustrates presenting and using the DR recordable object 1220 (e.g., torch) to record a first statement. In some embodiments, the recording of the first statement is triggered by an action of the subject. For instance, in some embodiments, the recording of the first statement starts when the subject (e.g., avatar of the subject) places the DR thought-recording object adjacent to the mouth of the subject (e.g., avatar of the subject) and stops when the subject (e.g., avatar of the subject) puts the DR thought-recording object away from the mouth of the subject (e.g., avatar of the subject).

Figure 13G:
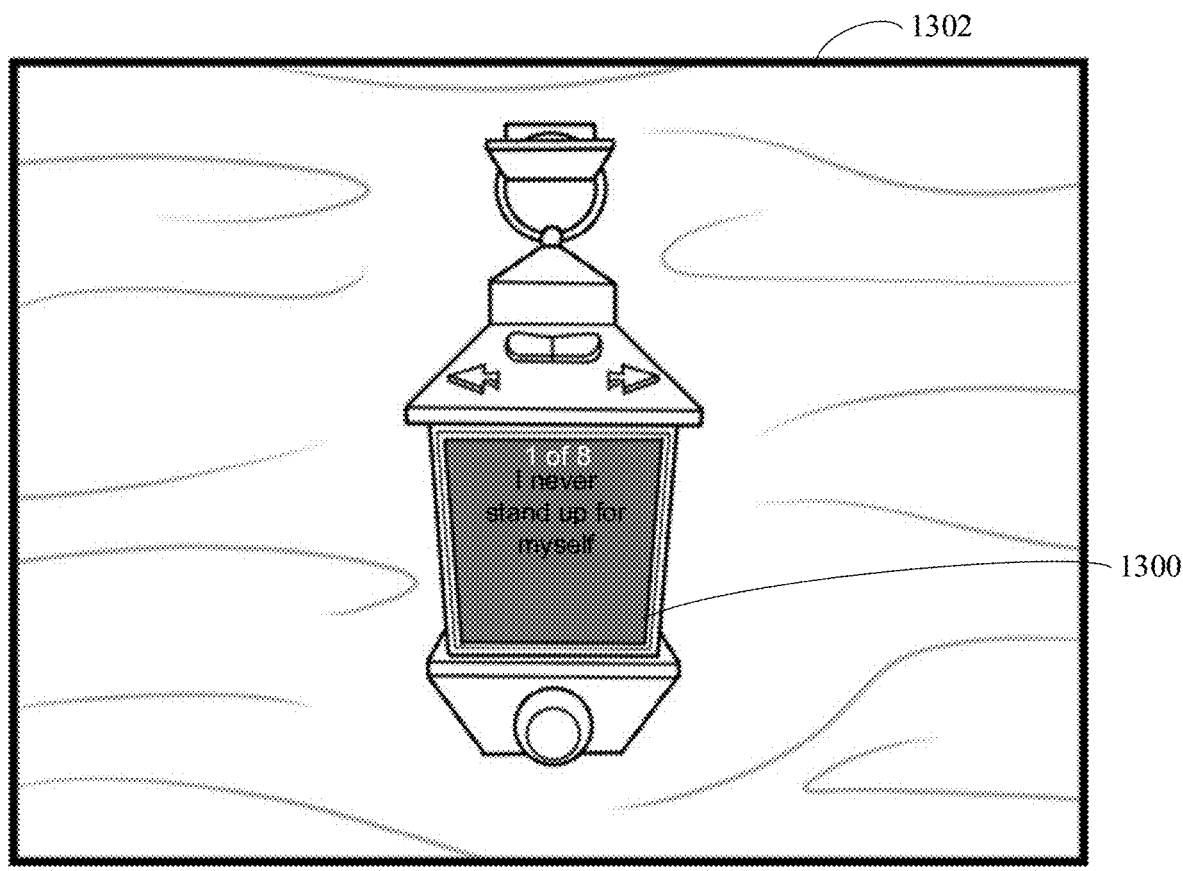

Blocks 508-510. Referring to block 508 and block 510, in some embodiments, to obtain a first statement from the subject, the method includes presenting, on the display, a DR object, such as the DR object 1300 illustrated in FIGS. 13D-13G that includes, or contains, a plurality of prestored statements. In some embodiments, the DR object includes a selection feature, such as the feature 1350, to allow the subject to browse through the plurality of prestored statements until the subject selects a prestored statement. The selection feature can simulate one or more DR flippers, one or more DR switches, one or more DR buttons, one or more DR arrows, one or more DR wheels, one or more DR lenses, one or more locks, one or more DR knobs, or the like, or any combination thereof. In some embodiments, the DR object includes, or contains, at least one, at least two, at least three, at least four, at least five, at least six, at least seven, at least eight, at least nine, at least ten, at least fifteen, or at least twenty prestored statements. In some embodiments, the DR object includes, or contains, at most one, at most two, at most three, at most four, at most five, at most six, at most seven, at most eight, at most nine, at most ten, at most fifteen, or at most twenty prestored statements. By way of example, FIGS. 13D, 13E and 13G illustrate that there are eight prestored statements representing eight common anxious thoughts in the DR object. In some embodiments, once the subject selects a prestored statement, the method designates the prestored statement selected by the subject to be the first statement.

Blocks 512-514. Referring to block 512 and block 514, in some embodiments, to obtain a first statement from the subject, the method includes allowing the subject to record (e.g., enter) a first statement using a client application, such as the client application 2100 illustrated in FIGS. 21A-21C. The client application can be installed and run on a computer, tablet, smartphone and/or other electronic devices. In some embodiments, the client application is a web-based app, a mobile app, or the like. In some embodiments, the client application is rendered (e.g., presented) within an interactive DR scene. In some embodiments, the client application allows the subject to record one or more statements, each representing a thought (e.g., a cognitive distortion). In some embodiments, in addition to recording one or more statements, the client application allows the subject to record their triggers. In some embodiments, after the subject records a first statement representing a thought in the client application of the client device associated with the subject, the method obtains the first statement from the client application.

Blocks 516-522. Referring to block 516 through block 522, in some embodiments, additionally or optionally, the method includes converting the first statement into a text, and/or presenting, on the display, the DR thought-recording object, the text at or adjacent to the DR thought-recording object. The text converted from the first statement can include one or more words, one or more phrases, one or more sentences, or any combination thereof. The text converted from the first statement can be a full text, e.g., including each and every words converted from the first statement. The text converted from the first statement can also be an abridged text, e.g., a text from a portion of the first statement or distilled from the full text or the like. By way of example, FIG. 12B illustrates the DR thought-recording object (e.g., the DR recordable object 1220) and a text 1224 converted from the first statement displayed adjacent to the DR thought-recording object.

In some embodiments, additionally or optionally, the method includes presenting, on the display, the DR thought-recording object with a DR thought-category feature to indicate a corresponding category, in a plurality of categories, associated with the first statement. For instance, by way of example, FIG. 12B illustrates the DR thought-recording object (e.g., the DR recordable object 1220) with the feature 1222 rendered in color to indicate the type of the thought represented by the first statement. In some embodiments, the feature 1222 is rendered in a first color (e.g., red) if the first statement represents an anxious thought, in a second color if the first statement represents a positive thought, and/or in a third color (e.g., yellow) if the first statement represents a reframed thought.

Blocks 524-528. Referring to block 524 through block 528, in some embodiments, additionally or optionally, the method includes presenting, on the display, a DR object representative of containing, carrying and/or transporting of a statement associated with a thought, and associating, on the display and by the subject, the DR vessel object with the first statement. For instance, by way of example, FIG. 13A illustrates the DR object 1300 (e.g., lantern) presented on the display, where the subject is allowed to associate the DR object 1300 with the first statement by lighting the DR object 1300 with the feature 1222 (e.g., flame) of the DR thought-recording object.

In some embodiments, additionally or optionally, the method includes presenting, on the display, the DR object and the text converted from the first statement at or adjacent to the DR object. For instance, by way of example, FIG. 13B illustrates the DR object with the text converted from the first statement shown at the DR object, e.g., the text being shown or printed on a front side of the DR object (e.g., on the front of the lantern or visible thought the front of the lantern).

In some embodiments, at least a portion of the DR object is rendered in a color indicative of a corresponding category, in a plurality of categories, associated with the first statement. For instance, by way of example, FIG. 13B illustrates the feature 1320 of the DR object (e.g., an interior of the lantern) rendered in a color (e.g., red), indicating that the type of the thought represented by the first statement is an anxious thought. In some embodiments, the feature 1320 is rendered to simulate a flame inside of the DR object.

Blocks 530-532. Referring to block 530 and block 532, in some embodiments, additionally or optionally, the method includes using, by the subject, a DR thought-impact feature to assign a level of impact of the first statement on the subject. In some embodiments, the method includes rendering the DR object to indicate a level of impact of the first statement on the subject. For instance, as a non-limiting example, FIG. 13C illustrates the DR object 1300 includes a DR thought-impact feature, such as the feature 1330 (e.g., dimmer). The feature 1330 allows the subject to assign a level of impact of the first statement (the thought represented by the first statement) on the subject. In some embodiments, the subject is asked (e.g., by the DR assistant, a healthcare professional or the like) to think how much the thought represented by the first statement impacts the subject. In some such embodiments, once asked, the subject is then allowed to use the feature 1330 (e.g., dimmer) to assign the level of impact. In some embodiments, the stronger the impact the thought represented by the first statement has on the subject, the brighter the light in the DR object 1300 (e.g., lantern) becomes.

While block 516 through block 532 are placed within block 402, it should be noted that this is by way of illustration and is non-limiting. Additional or optional steps exemplified by any of block 516 through block 532 can be performed, but do not necessarily have to be performed, immediately after the first statement is obtained. For instance, as a non-limiting example, a mindfulness activity may be conducted after the first statement is obtained but before a DR object exemplified by block 524 is presented.

2.5. Providing a First Interactive DR Activity

Figure 6A:
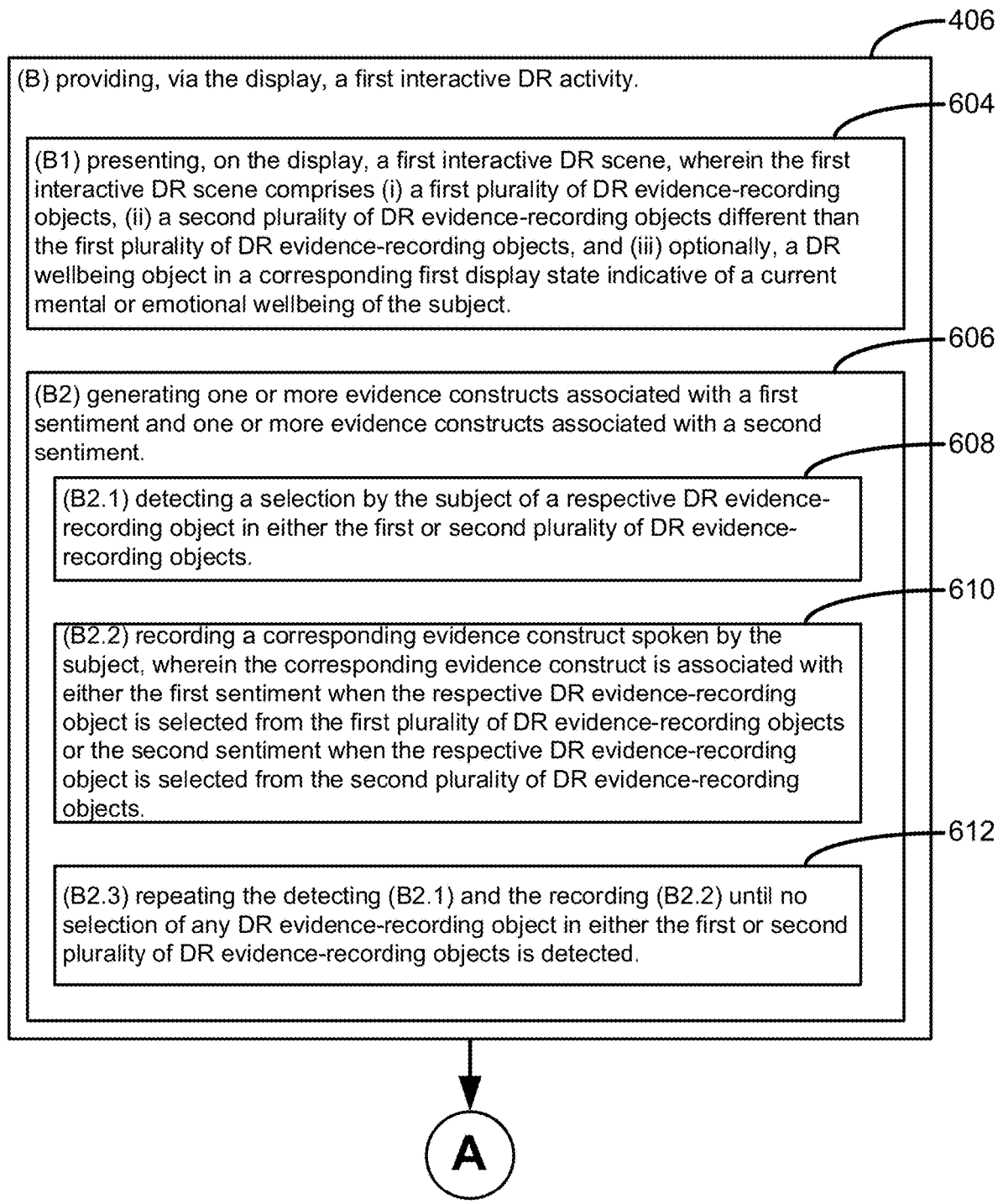
FIGS. 6A, 6B, and 6C collectively illustrate exemplary methods for providing an interactive DR activity configured for a subject to practice a gather evidence CBT technique, in which optional embodiments are indicated by dashed boxes, in accordance with some embodiments of the present disclosure.
Figure 6B:
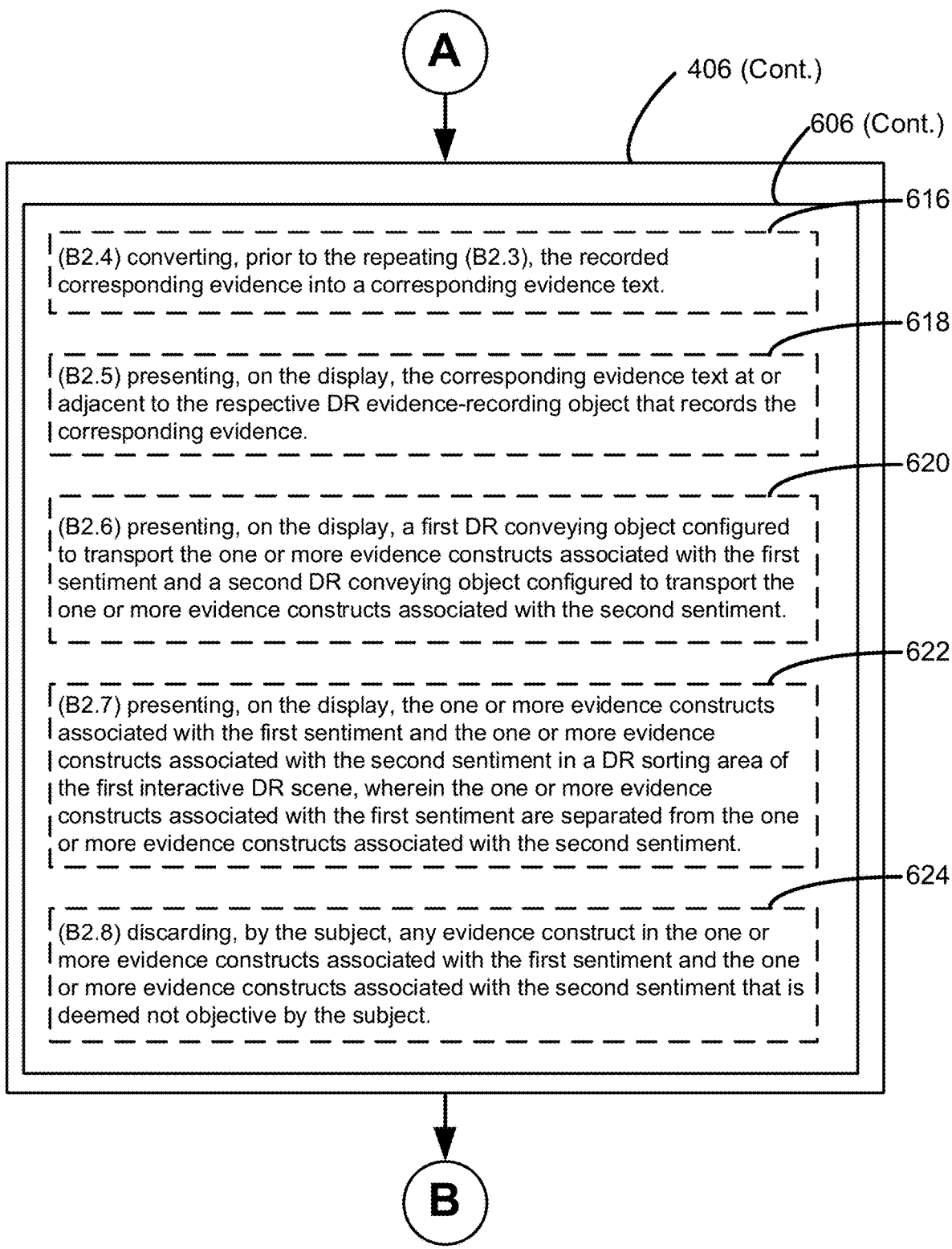
Figure 6C:
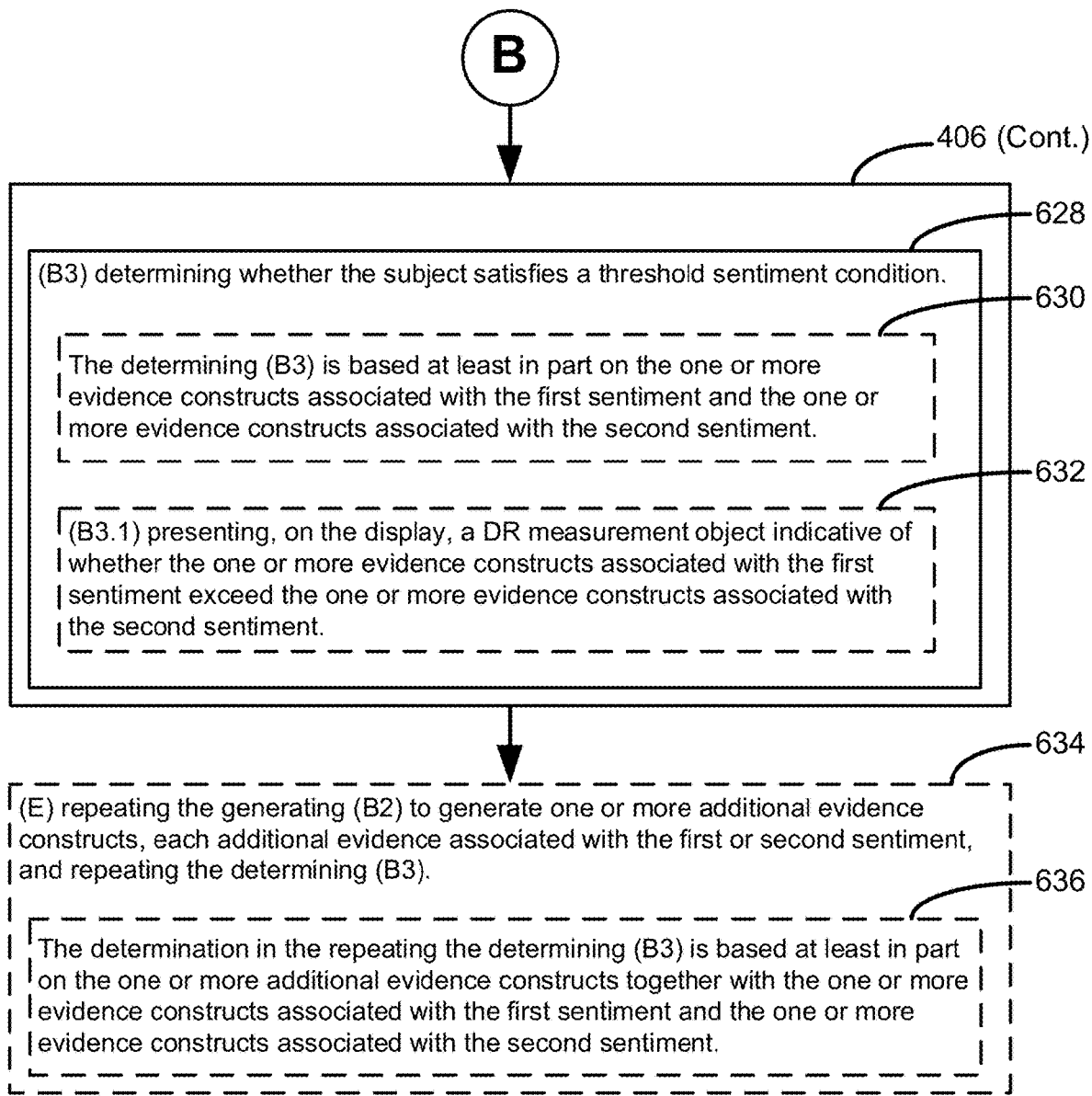

Referring to FIGS. 6A-6C, there is depicted a flowchart illustrating exemplary methods for providing a first interactive DR activity in accordance with some embodiments of the present disclosure. In some embodiments, the first interactive DR activity is configured to allow a subject to gather evidence for and against a thought, e.g., the thought represented by the first statement. Specifically, a plurality of DR recordable objects is provided for the subject to record evidence supporting the thought and evidence against the thought. In some embodiments, the plurality of DR recordable objects includes a first plurality of DR recordable objects and a second plurality of DR recordable objects that is different (e.g., different in type, shape, size, color, appearance, or the like) than the first plurality of DR recordable objects. In some embodiments, an evaluation is then made (e.g., by one or more models and/or a medical practitioner associated with the subject) to determine whether the evidence supporting the thought gathered by the subject outweighs the evidence against the thought gathered by the subject or verse versa. In some embodiments, before the evaluation, the subject is allowed to sort through the evidence, e.g., throwing away any evidence that the subject considers weak.

In various embodiments, this first interactive DR activity is configured so that the subject does not necessarily to win by finding more evidence on either side in a binary win or lose outcome for the first interactive DR activity, but rather to encourage the subject to challenge anxious thoughts of the subject by considering other perspectives.

Block 604. Referring to block 604, to provide a first interactive DR activity, the method includes presenting, on the display, a first interactive DR scene. In some embodiments, the first interactive DR scene includes a first plurality of DR recording objects, a second plurality of DR recording objects different than the first plurality of DR recording objects, a DR wellbeing object in a corresponding first display state indicative of a current mental or emotional wellbeing of the subject, or a combination thereof.

Figure 17A:
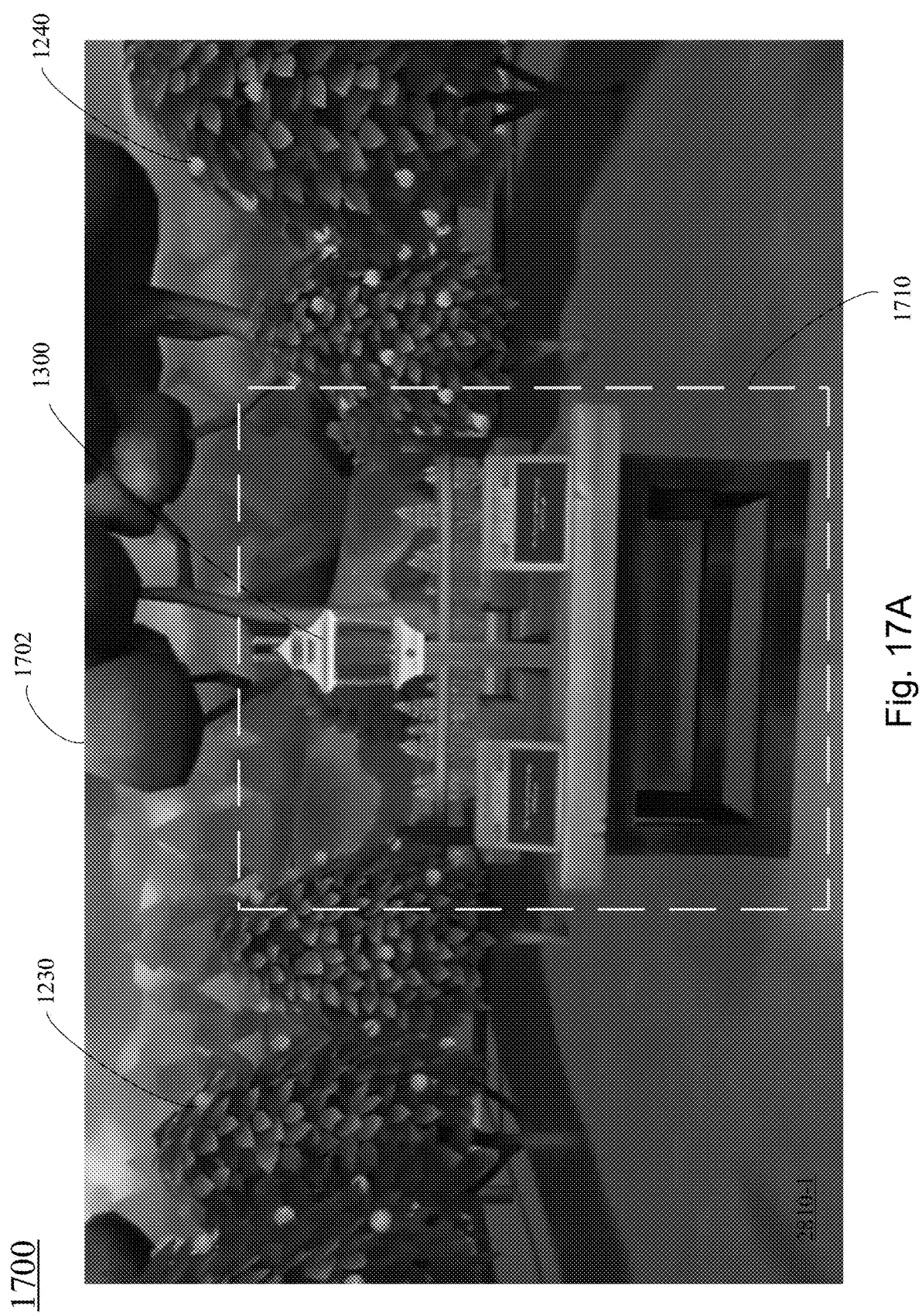
FIGS. 17A, 17B, 17C, 17D, 17E, and 17F illustrate a first exemplary DR activity configured for a subject to practice a CBT technique, in accordance with some embodiments of the present disclosure.
Figure 18A:
FIGS. 18A, 18B, 18C, 18D, 18E, 18F, and 18G illustrate a second exemplary DR activity configured for a subject to practice another CBT technique, in accordance with some embodiments of the present disclosure.
Figure 18B:
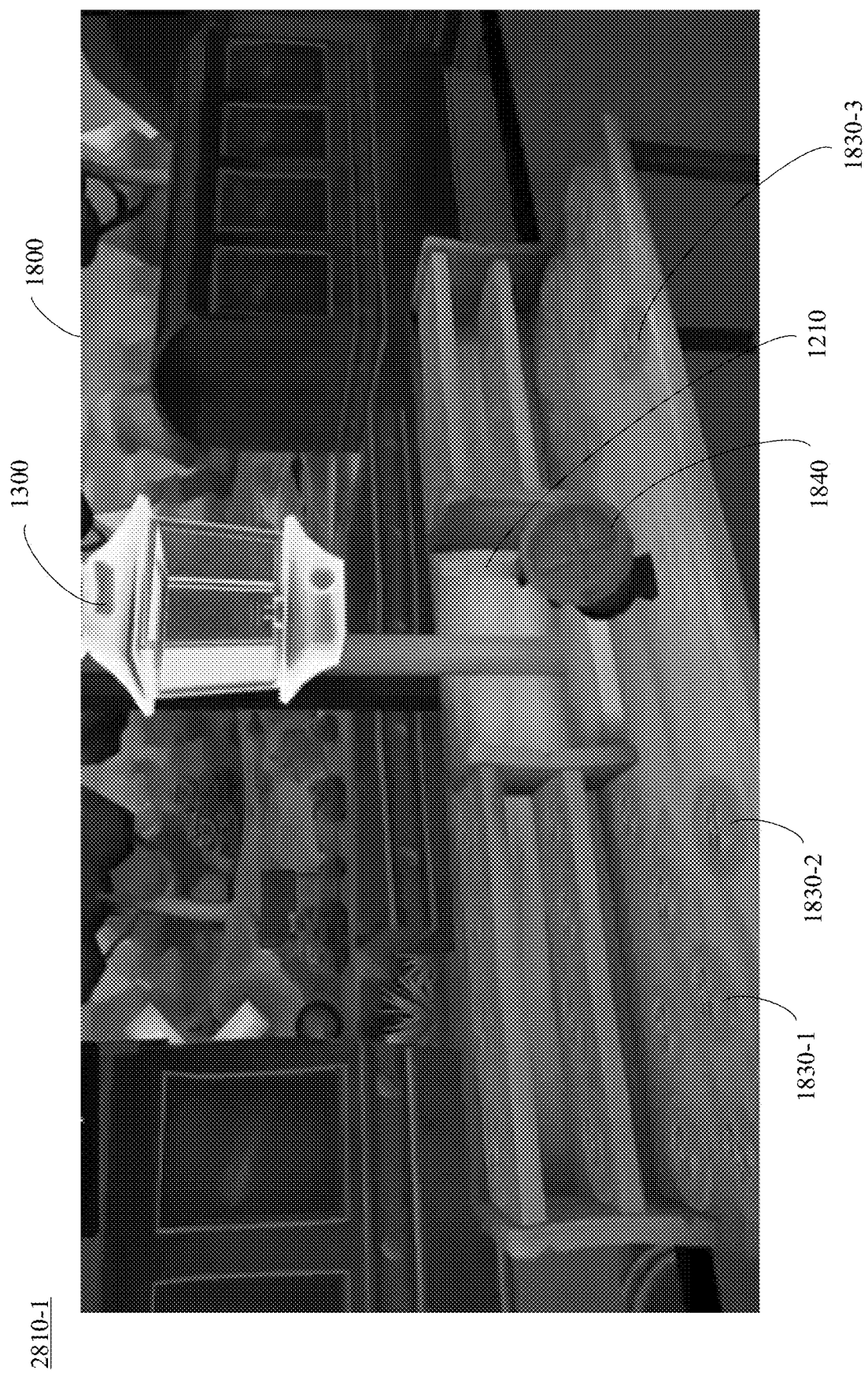
Figure 18C:
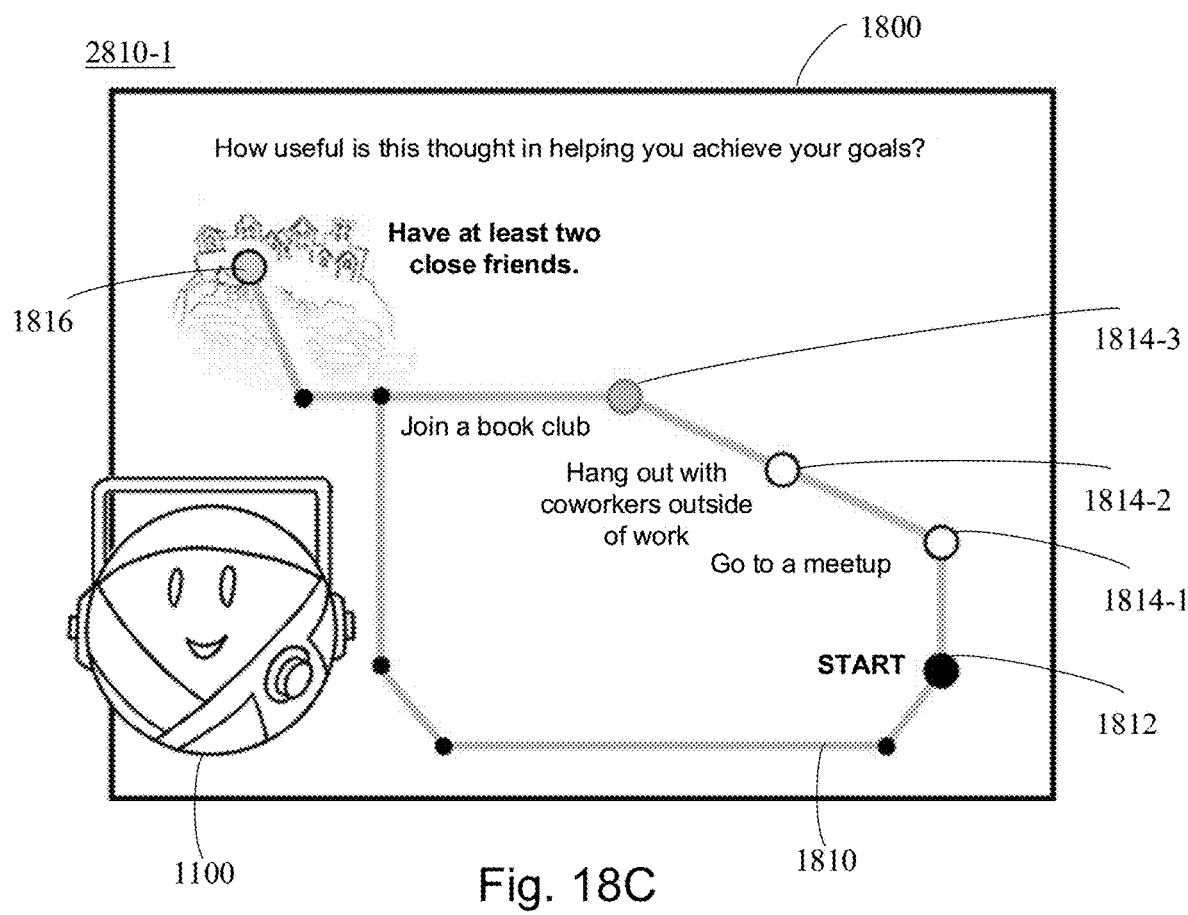
Figure 18D:
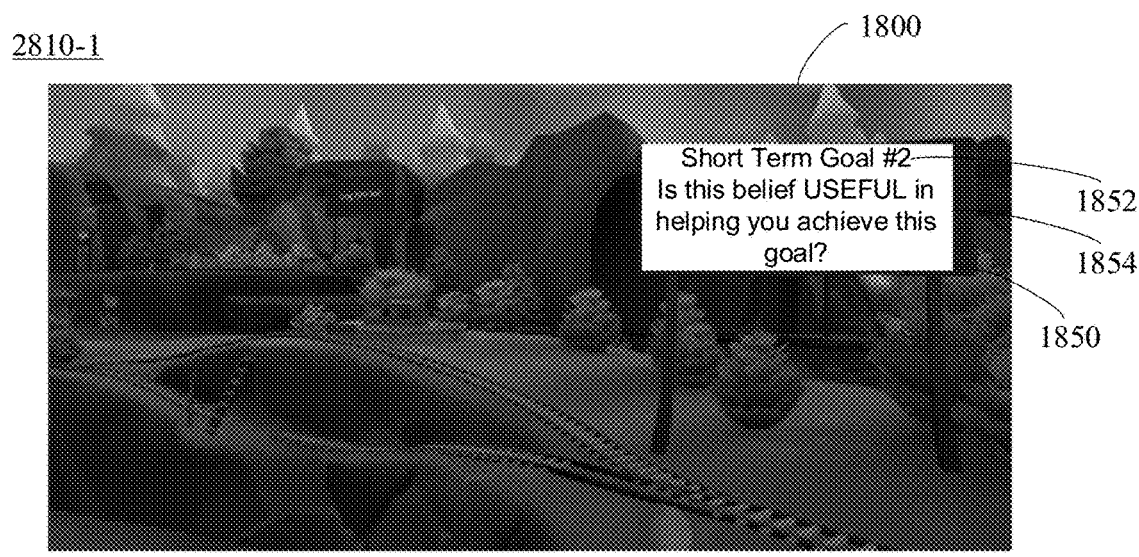

For instance, as a non-limiting example, FIG. 17A illustrates a first interactive DR scene 1700 simulating an orchard. The first interactive DR scene includes a first plurality of DR recording objects and a second plurality of DR recording objects, such as such as the DR recordable object 1230 simulating an apple and the DR recordable object 1240 simulating a pear. The DR recordable object 1230 (e.g., apple) can be either the first or second plurality of DR recording objects. Similarly, the DR recordable object 1240 (e.g., pear) can be either the first or second plurality of DR recording objects.

While FIG. 17A illustrates the apple trees and pear trees located in close proximity, such as within a first DR designated area, it should be noted that the apple and pear trees can be, but do not necessarily have to be, located in close proximity. For instance, as a non-limiting example, an orchard can be fenced with a first entrance to a first portion of the DR orchard (e.g., the portion with apple trees in a first DR designated area of the first interactive DR scene) and a second entrance to a second portion of the DR orchard (e.g., the portion with pear trees in a second DR designated area of the first interactive DR scene).

Moreover, while FIG. 17A illustrates the first interactive DR scene simulates an orchard, it should also be noted that the first interactive DR scene can simulate any suitable scene, including but not limited to real or nonreal, fictional or non-fictional scenes. Similarly, the first and second pluralities of recording objects can simulate any suitable objects. For instance, as a non-limiting example, the first interactive DR scene can simulate an orchard with the first or second plurality of recording objects simulates a fruit (e.g., mango, orange, banana, kiwi, or the like) other than apple or pear. As another non-limiting example, the first interactive DR scene can simulate a garden with the first or second plurality of recording objects simulates a flower (e.g., rose, lotus, jasmine, sunflower, daisy, tulip, *magnolia*, lavender or the like) or a leaf of a plant (e.g., roses, maple trees, bamboo, or the like). As a further non-limiting example, the first interactive DR scene can simulate a ping pang room with the first and second pluralities of recording objects simulate ping pang balls in different color.

In some embodiments, each of the first plurality of DR recording objects is a first type of plant or food and each of the second plurality of DR recording objects is a second type of plant or food. In some embodiments, the first or second type of plant or food is a vegetation selected from the group consisting of leaves, needles, stalks, stems, flowers, fruits, seeds, roots, tubers, and rhizomes. In some embodiments, the first or second type of plant or food is a fruit selected from the group consisting of apples, pears, oranges, grapefruits, mandarins, limes, nectarines, apricots, peaches, plums, bananas, mangoes, strawberries, and kiwifruits. In some embodiments, one of the first and second types of fruits is apple and the other of the first and second types of fruits is pear.

In some embodiments, the first interactive DR scene includes (e.g., associated with or connected to) a DR wellbeing object, such as the DR wellbeing object 1610 illustrated in FIGS. 16A-16C. In some embodiments, the DR wellbeing object is in a state indicative of a current mental or emotional wellbeing of the subject. In some embodiments, the DR wellbeing object is accessible from the first interactive DR scene, for instance, by one or more pathways, through one or more portals, or the like.

In some embodiments, the first interactive DR scene includes, additionally or optionally, other DR objects. For instance, in some embodiments, the subject is accompanied by the DR assistant 1100. In some embodiments, the DR object is carried by the subject to the first interactive DR scene or presented to the subject when the subject enters the first interactive DR scene.

Blocks 606-612. Referring to block 606 through block 612, in some embodiments, the method includes generating one or more evidence constructs associated with a first sentiment and one or more evidence constructs associated with a second sentiment. In some embodiments, one of the first and second sentiments is a positive sentiment and the other of the first and second sentiments is a negative sentiment. In some embodiments, one of the first and second sentiments is an arousing sentiment and the other of the first and second sentiments is a negative or neutral sentiment.

In some embodiments, an evidence construct is a recording (e.g., a data element) of an utterance provided by the subject (e.g., obtained through input 364 of client device 300 of FIG. 3) that is associated with a prior statement associated with the subject, such as a first statement provided by the subject or a second predetermined statement generated by a model and/or a medical practitioner associated with the subject.

In some embodiments, an evidence construct associated with the first sentiment is an evidence gathered by the subject that supports the thought, while an evidence construct associated with the second sentiment is an evidence gathered by the subject that opposes the thought. In some embodiments, an evidence construct associated with the first sentiment is an evidence gathered by the subject that opposes the thought while an evidence construct associated with the second sentiment is an evidence gathered by the subject that supports the thought.

In some embodiments, to generate an evidence construct, the method includes detecting a selection by the subject of a respective DR recording object in either the first or second plurality of DR recording objects, and recording a corresponding evidence construct spoken by the subject. In some embodiments, the corresponding evidence construct is associated with the first sentiment when the respective DR recording object is selected from the first plurality of DR recording objects or is associated with the second sentiment when the respective DR recording object is selected from the second plurality of DR recording objects.

Figure 17B:
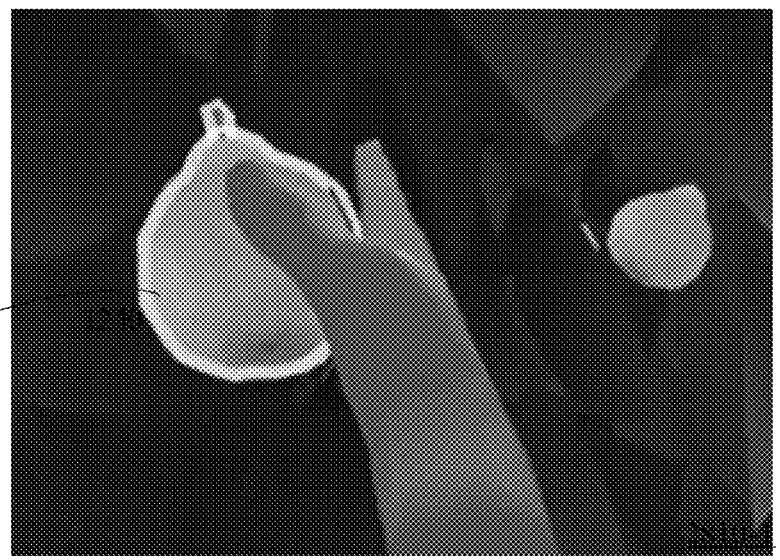
Figure 17C:
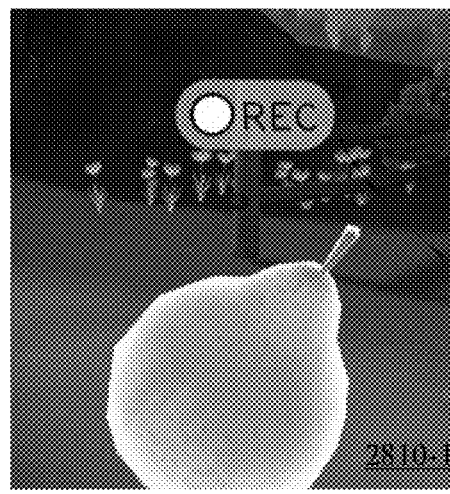

For instance, by way of example, FIGS. 17B-17C collectively illustrate an exemplary process for generating an evidence construct using the DR recordable object 1240 (e.g., pear). In some embodiments, the DR recordable object 1240 (e.g., pear) is configured to record evidence against the thought, such that when the subject picks the DR recordable object and records into the DR recordable object evidence that opposes the thought (e.g., provides a second statement through the input 364 and/or the input 310 of the client device), the method associates the recorded evidence with a sentiment against the thought. This generates an evidence construct 1740, represented by the DR recordable object 1240 (e.g., pear) with the recording that opposes the thought. In some embodiments, that the DR recordable object 1230 (e.g., apple) is configured to record evidence supporting the thought, such that when the subject picks an apple and record into the DR recordable object evidence that supports the thought, the method associates the recorded evidence with a sentiment supporting the thought. This generates an evidence construct 1730, represented by the DR recordable object 1230 (e.g., apple) with the recording that supports the thought.

In some embodiments, the method associated the recorded evidence with a sentiment based on an evaluation of the recorded evidence by one or more models of the present disclosure (e.g., a first sentiment analysis model).

In some embodiments, to generate multiple evidence constructs associated with the first sentiment and/or second sentiment, the method includes repeating the detecting and recording steps until no selection of any DR recording object in either the first or second plurality of DR recording objects is detected.

In some embodiments, the one or more evidence constructs associated with the first sentiment and the one or more evidence constructs associated with the second sentiment are generated in any order the subject prefers. For instance, in some embodiments, the one or more evidence constructs associated with the first sentiment are generated prior to the one or more one or more evidence constructs associated with the second sentiment. In another embodiment, the one or more evidence constructs associated with the first sentiment are generated subsequent to the one or more one or more evidence constructs associated with the second sentiment. In a further embodiment, the one or more evidence constructs associated with the first sentiment are generated concurrently with the one or more one or more evidence constructs associated with the second sentiment, e.g., at least one evidence construct associated with the first sentiment is generated before all of the one or more evidence constructs associated with the second sentiment and at least one evidence construct associated with the second sentiment is generated before all of the one or more evidence constructs associated with the first sentiment.

In some embodiments, the one or more evidence constructs associated with the first sentiment are included in or represented by the one or more DR recording objects selected by the subject from the first plurality of DR recording objects. Similarly, the one or more evidence constructs associated with the second sentiment are included in or represented by the one or more DR recording objects selected by the subject from the second plurality of DR recording objects. For instance, in some embodiments, if a first DR recordable object (e.g., an apple or a pear) is used to record an evidence construct associated with the first sentiment, the recorded evidence construct associated with the first sentiment is included, or contained, in (e.g., associated with, linked with, or presented by) the first DR recordable object. Similarly, if a second DR recordable object is used to record an evidence construct associated with the second sentiment, the recorded evidence construct associated with the second sentiment is included in (e.g., associated with, linked with, presented by, accommodated by, contained within, etc.) the second DR recordable object.

Figure 17D:
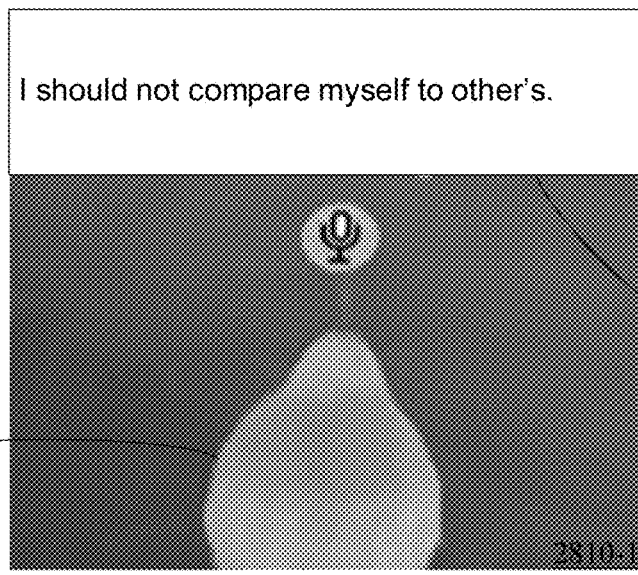

Blocks 616-618. Referring to block 616 and block 618, in some embodiments, additionally or optionally, the method includes converting the recorded corresponding evidence into a corresponding evidence text. In some embodiments, the method includes presenting, on the display, the corresponding evidence text at or adjacent to the respective DR recording object that records the corresponding evidence. Preferably, the converting of the recorded corresponding evidence into a corresponding evidence text is performed before the repeating of the detecting and recording steps, e.g., before the subject picks an apple or a pear to generate another evidence construct. As a non-limiting example, FIGS. 12D and 17D illustrates the conversion of a recorded evidence and presentation of a corresponding text using a DR recordable object 1240. As another non-limiting example, FIG. 12C illustrates the conversion of a recorded evidence and presentation of a corresponding text using a DR recordable object 1230.

Figure 17E:
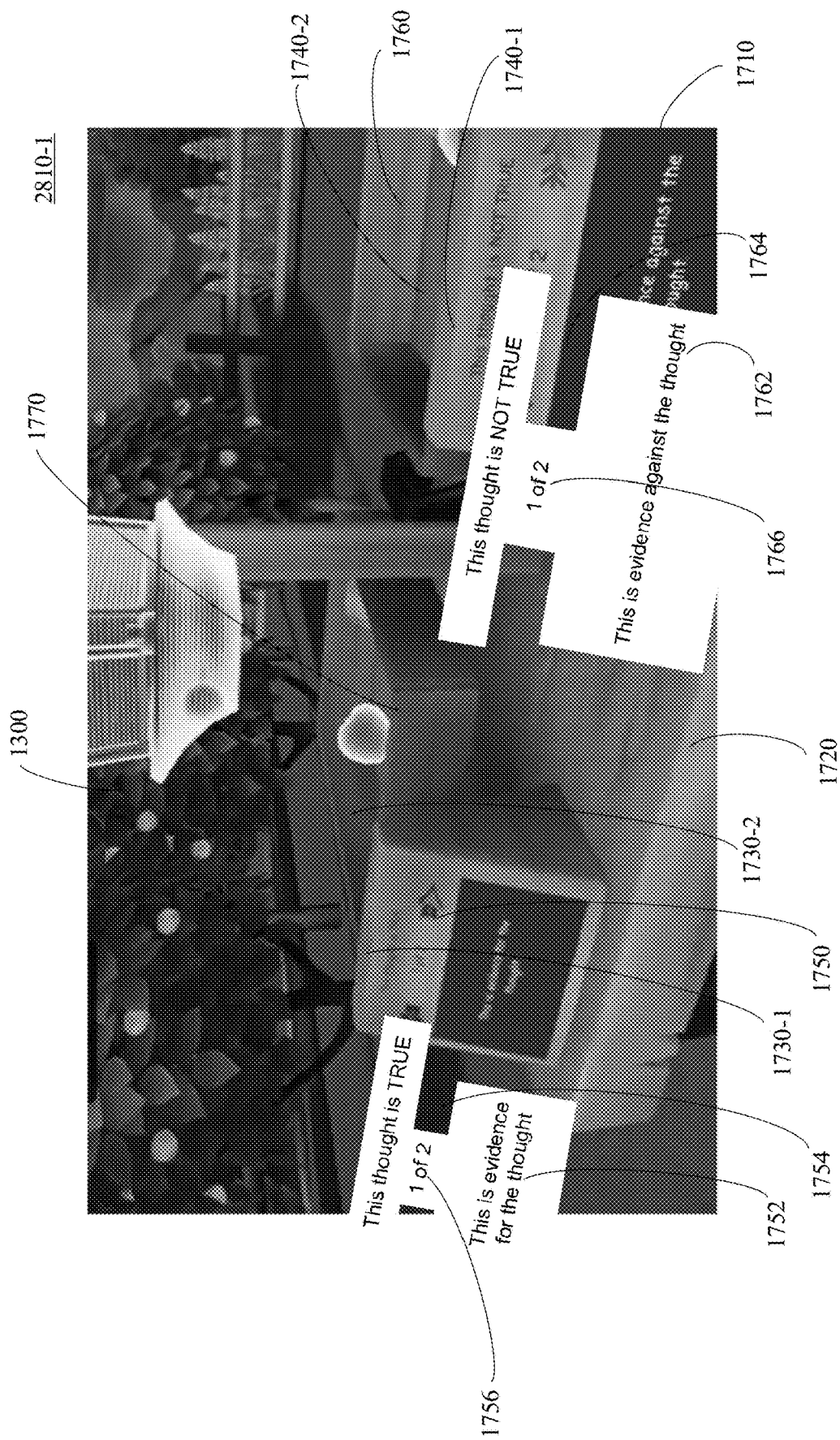
Figure 17F:
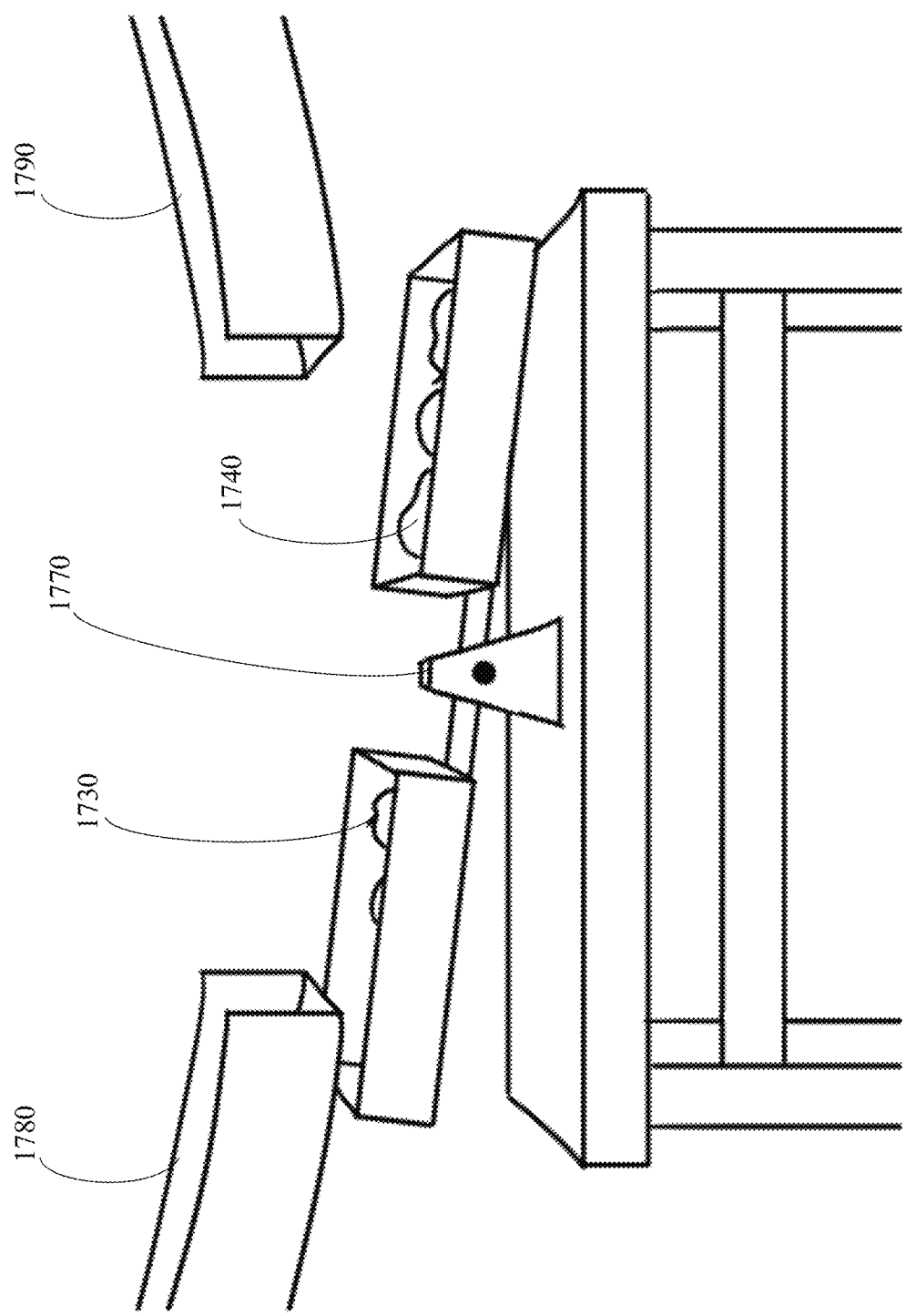

Block 620. Referring to block 620, in some embodiments, additionally or optionally, the method includes presenting, on the display, a first DR conveying object configured to transport the one or more evidence constructs associated with the first sentiment and a second DR conveying object configured to transport the one or more evidence constructs associated with the second sentiment. The first or second DR conveying object can simulate any object that is suitable for moving objects. Examples of such conveying objects include, but are not limited to, one or more channels, one or more belts, one or more carts, one or more buckets, one or more containers, one or more chutes, one or more pathways, one or more portals, or the like. As a non-limiting example, FIG. 17F illustrates a first DR conveying object 1780 configured to transport evidence constructs 1730 and a second DR conveying object 1790 configured to transport evidence constructions 1740, in which each of the first and second DR conveying objects simulating a chute.

It should be noted the first and second DR conveying objects are additional or optional DR objects, and the first interactive DR scene can, but does not necessarily have to, have the first or second DR conveying object. For instance, in some embodiments, when evidence constructs associated with the first and second sentiments are generated in close proximity, the method does not include presenting the first and/or second DR conveying objects.

Blocks 622-624. Referring to block 622 and block 624, in some embodiments, additionally or optionally, the method includes presenting, on the display, the one or more evidence constructs associated with the first sentiment and the one or more evidence constructs associated with the second sentiment in a DR sorting area of the first interactive DR scene. In some embodiments, the DR sorting area is an area (e.g., a DR designated area) at or near where the one or more evidence constructs associated with the first sentiment and the one or more evidence constructs associated with the second sentiment are recorded. The DR sorting area can also be an area in the first interactive DR scene that is specifically designated for sorting purposes, and/or away from where the one or more evidence constructs associated with the first sentiment and the one or more evidence constructs associated with the second sentiment are recorded. As a non-limiting example, FIGS. 17A and 17E illustrate a DR sorting area 1710 at or near where the one or more evidence constructs 1730 and the one or more evidence constructs 1740 are generated.

In some embodiments, a DR sorting area includes a first DR containing object for holding the one or more evidence constructs associated with the first sentiment and a second DR containing object for holding the one or more evidence constructs associated with the second sentiment. The first or second DR containing object can simulate any suitable object, such as one or more containers, one or more boxes, one or more bins, one or more trays, one or more plates, one or more drums, or a combination thereof. As a non-limiting example, it is illustrated that the DR sorting area 1710 includes a DR containing object 1750 simulating a bin for holding the one or more evidence constructs 1730 (e.g., apple with recorded evidence) and a DR containing object 1760 simulating a bin for holding the one or more evidence constructs 1740 (e.g., pear with recorded evidence).

In some embodiments, a sorting area includes additional or optional DR objects. For instance, as a non-limiting example, in some embodiments, the DR sorting area 1710 includes a DR working object 1720 for placing the DR containing object 1750 and the DR containing object 1760. By way of example, the DR working object 1720 is illustrated to simulate a workbench, a table, a stand, or the like. As another non-limited example, in some embodiments, the DR object 1300 is also placed in the DR sorting area to inform the subject the thought that the subject is working on.

In some embodiments, the one or more evidence constructs associated with the first sentiment are separated from the one or more evidence constructs associated with the second sentiment. For instance, as a non-limiting example, in some embodiments, the one or more evidence constructs 1730 (e.g., apple with recorded evidence) are placed in the DR containing object 1750, while the one or more evidence constructs 1740 (e.g., pear with recorded evidence) are placed in the DR containing object 1760. In some embodiments, when an evidence construct is dropped in a DR containing object, an audio of the recorded evidence will be replayed back. In some embodiments, a text converted from the recorded evidence will be shown at or near the DR containing object, or shown together with the replayed recorded evidence.

In some embodiments, the method is configured to prevent a subject from placing an evidence construct into a wrong DR containing object, e.g., any evidence construct 1730 is not allowed to be put into the DR containing object 1760 and any evidence construct 1740 is not allowed to be put into the DR containing object 1750. In some embodiments, additionally or optionally, a feature indicative of a purpose of a DR containing object is displayed at or near DR containing object to help the subject to place an evidence construct into the right DR containing object. For instance, as a non-limiting example, in some embodiments, a feature 1752 (e.g., a text, a label, a figure, or the like) is displayed near the DR containing object 1750 to indicate that the DR containing object 1750 is for any evidence for the thought (e.g., evidence construct 1730). Similarly, a feature 1762 (e.g., a text, a label, a figure, or the like) is displayed near the DR containing object 1760 to indicate that the DR containing object 1760 is for any evidence against the thought, e.g., evidence construct 1760.

In some embodiments, additionally or optionally, the method allows the subject to discard any evidence construct in the one or more evidence constructs associated with the first sentiment and the one or more evidence constructs associated with the second sentiment that is deemed not objective by the subject. In some embodiments, the method allows the subject to go through the evidence constructs the subject has gathered before throwing away any evidence construct. In some embodiments, the subject throws away an evidence construct by removing the evidence construct from the DR containing object, such as by grabbing the DR containing object in the interactive DR scene and/or by input 310 of the client device 300 associated with the subject (e.g., instructing a DR assistant to remove the evidence from the DR containing object).

For instance, in some embodiments, the method allows the subject to visualize (e.g., read) the one or more evidence constructs associated with the first sentiment and the one or more evidence constructs associated with the second sentiment by presenting a corresponding evidence text converted from the corresponding evidence construct at or adjacent to the respective DR recording object that records the corresponding evidence construct. In some embodiments, the corresponding evidence text is presented at or adjacent to the respective DR recording object when the subject touches or picks up the respective DR recording object. Alternatively or additionally, in some embodiments, the method replays the corresponding record audio when the subject touches or picks up the respective DR recording object.

In some embodiments, additionally or optionally, a feature configured for the subject to browse through the one or more evidence constructs in a DR containing object is displayed at or near DR containing object. In some embodiments, additionally or optionally, a feature indicative of the total number of evidence constructs in a DR containing object and/or which evidence construct the subject is considering at the moment (e.g., 1 of 2) is displayed at or near DR containing object. For instance, as a non-limiting example, a feature 1754 (e.g., an arrow or the like) and a feature 1756 (e.g., a text or the like) are displayed near the DR containing object 1750. In some embodiments, the feature 1754 allows the subject to browse through the evidence constructs 1730 in the DR containing object 1750. In some embodiments, the feature 1756 shows the total number (e.g., "2") of evidence constructs 1730 in the DR containing object 1750 and/or the instant evidence construct (e.g., "1") that the subject is considering at the moment. Similarly, a feature 1764 (e.g., an arrow or the like) and a feature 1766 (e.g., a text or the like) are displayed near the DR containing object 1760. In some embodiments, the feature 1764 allows the subject to browse through the evidence constructs 1740 in the DR containing object 1760. In some embodiments, the feature 1766 shows the total number (e.g., "2") of evidence constructs 1740 in the DR containing object 1760 and/or the instant evidence construct (e.g., "1") that the subject is considering at the moment.

In some embodiments, additionally or optionally, an evidence construct glows, changes color, or the like when the subject is considering it, to further indicate which evidence construct is being considered by the subject at the moment. For instance, as a non-limiting example, FIG. 17E illustrates that the evidence construct 1730-1 and the evidence construct 1740-1 changed colors (e.g., from an original color of an apple or pear to blue or the like), indicating that they are being considered by a subject at the moment.

In some embodiments, the subject determines if any evidence construct is "weak," e.g., rooted in subjective emotion or assumptions rather than objective fact. In some embodiments, the DR assistant 1100 and/or a healthcare professional associated with the subject provide guidance to the subject in determining whether or not an evidence construct is weak. In some embodiments, the subject is allowed to throw away any evidence construct that the subject, the DR assistant 1100 (e.g., an output provided by a model and realized through interactions with the DR assistant), the healthcare professional, or a combination thereof considers weak.

Blocks 628-630. Referring to block 628 and block 630, in some embodiments, the method includes determining whether the subject satisfies a threshold sentiment condition. Determination of whether the subject is deemed to satisfy a threshold sentiment condition can be self-administered, oversighted by a healthcare professional associated with the subject, based on one or more physiological measurements, determined by the method (e.g., by one or more models disclosed herein), or any combination thereof.

In some embodiments, the determining of whether the subject satisfies a threshold sentiment condition is based at least in part on the one or more evidence constructs associated with the first sentiment and the one or more evidence constructs associated with the second sentiment. For instance, as a non-limiting example, in some embodiments, the subject, a healthcare professional associated with the subject and/or the method evaluate the one or more evidence constructs associated with the first sentiment and the one or more evidence constructs associated with the second sentiment, and then determine whether the subject satisfies a threshold sentiment condition based on the evaluation. Examples of evaluation include, but not limited to, the quality of each evidence construct (e.g., whether it is rooted in emotion, assumptions, or objective facts), physiological measurement(s) taken while the subject records the one or more evidence constructs associated with the first sentiment, physiological measurement(s) taken while the subject records the one or more evidence constructs associated with the second sentiment, the number of the one or more evidence constructs associated with the first sentiment, the number of the one or more evidence constructs associated with the second sentiment, or any combination thereof.

In some embodiment, the one or more evidence constructs associated with the first sentiment are considered to exceed the one or more evidence constructs associated with the second sentiment when a quality of the one or more evidence constructs associated with the first sentiment exceeds a quality of the one or more evidence constructs associated with the second sentiment, regardless of the quality (e.g., the number) of the one or more evidence constructs associated with the first or second sentiment, and vice versa. In some embodiments, the one or more evidence constructs associated with the first sentiment are considered to exceed the one or more evidence constructs associated with the second sentiment when a quantity (e.g., the number) of the one or more evidence constructs associated with the first sentiment exceeds a quantity of the one or more evidence constructs associated with the second sentiment, and vice versa. In some embodiments, the one or more evidence constructs associated with the first sentiment are considered to exceed the one or more evidence constructs associated with the second sentiment when both the quality and quality of the one or more evidence constructs associated with the first sentiment exceed the quality and quantity of the one or more evidence constructs associated with the second sentiment, and vice versa.

In some embodiments, the subject satisfies a threshold sentiment condition when the one or more evidence constructs associated with the positive sentiment (e.g., evidence against an anxious thought or evidence supporting a positive thought) exceed the one or more evidence constructs associated with the negative sentiment (e.g., evidence supporting an anxious thought or evidence against a positive thought).

Block 632. Referring to block 632, in some embodiments, additionally or optionally, the method includes presenting, on the display, a DR measurement object. In some embodiments, the DR measurement object is indicative of whether the one or more evidence constructs associated with the first sentiment exceed the one or more evidence constructs associated with the second sentiment. In some embodiments, the DR measurement object can be rendered to simulate any suitable measurement tool in any suitable shape, size, color, or the like. As a non-limiting example, FIGS. 17E and 17F illustrate a DR measurement object 1770 simulating a balance scale. In some embodiments, the area where a DR measurement object is located is also referred to as a DR weighting area of the first interactive DR scene.

While a balance scale is shown, it should be noted that whether the one or more evidence constructs associated with the first sentiment exceed the one or more evidence constructs associated with the second sentiment can be, but do not necessarily have to be, based on the weights or the numbers of the evidence constructs, as disclosed above with reference to blocks 628-630.

Blocks 634-636. Referring to block 634 and block 636, in some embodiments, additionally or optionally, the method includes repeating the generating step as exemplified by at least block 606 to generate one or more additional evidence constructs. In some embodiments, each additional evidence is associated with the first or second sentiment. The method also includes repeating the determining step as exemplified by at least block 628 to determine whether the subject satisfies a threshold sentiment condition after generating the one or more additional evidence constructs.

In some embodiments, the determining of whether the subject satisfies a threshold sentiment condition after generating the one or more additional evidence constructs is based at least in part on the one or more additional evidence constructs together with the one or more evidence constructs associated with the first sentiment and the one or more evidence constructs associated with the second sentiment. For instance, as a non-limiting example, in some embodiments, the subject, a healthcare professional associated with the subject, a computational model, or a combination thereof evaluate the one or more additional evidence constructs together with the one or more evidence constructs associated with the first sentiment and the one or more evidence constructs associated with the second sentiment, and then determine whether the subject satisfies a threshold sentiment condition based on the evaluation.

2.6. Providing a Second Interactive DR Activity

Figure 7A:
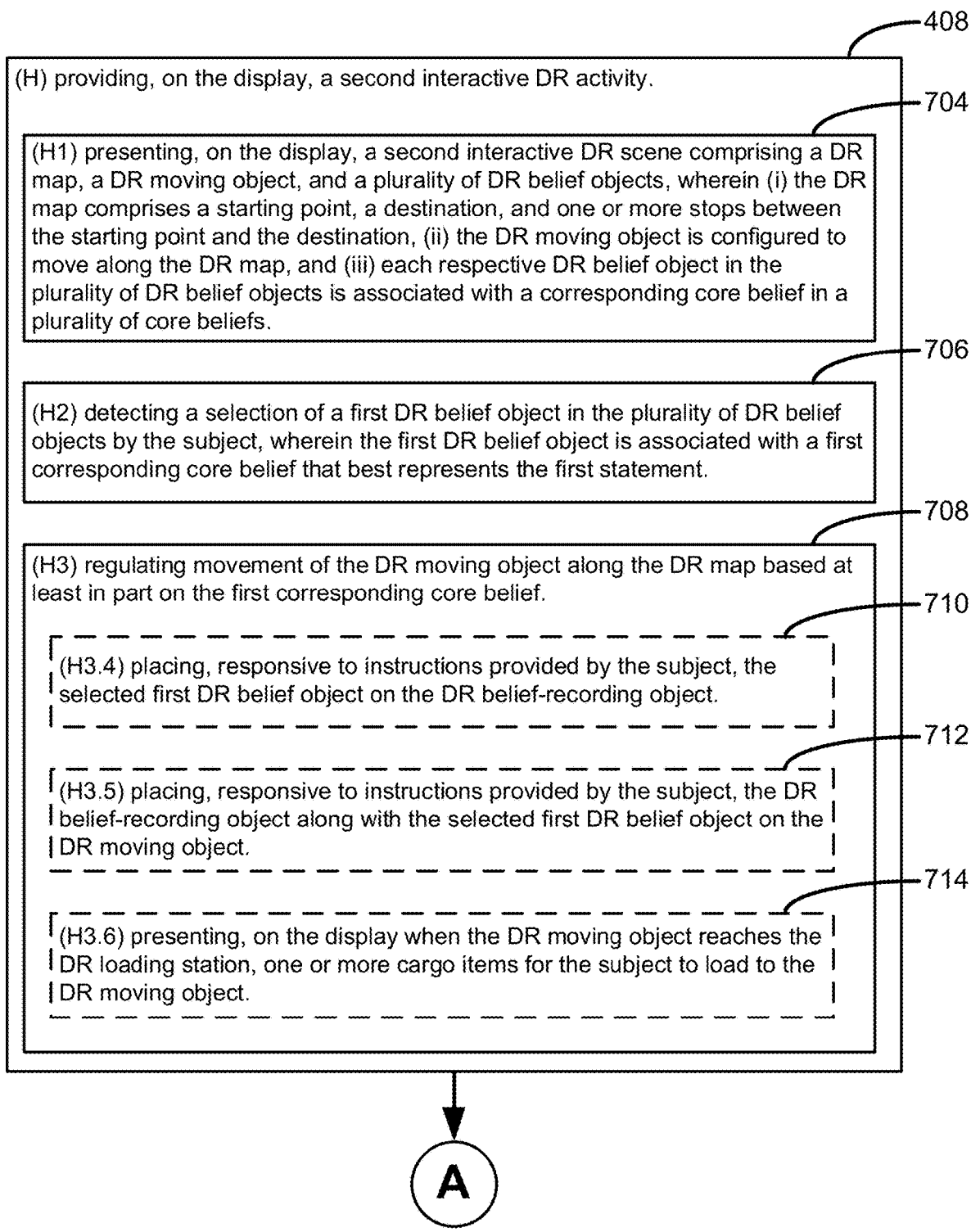
FIGS. 7A, 7B, and 7C collectively illustrate exemplary methods for providing an interactive DR activity configured for the subject to practice a usefulness and core beliefs CBT technique, in which optional embodiments are indicated by dashed boxes, in accordance with some embodiments of the present disclosure.
Figure 7B:
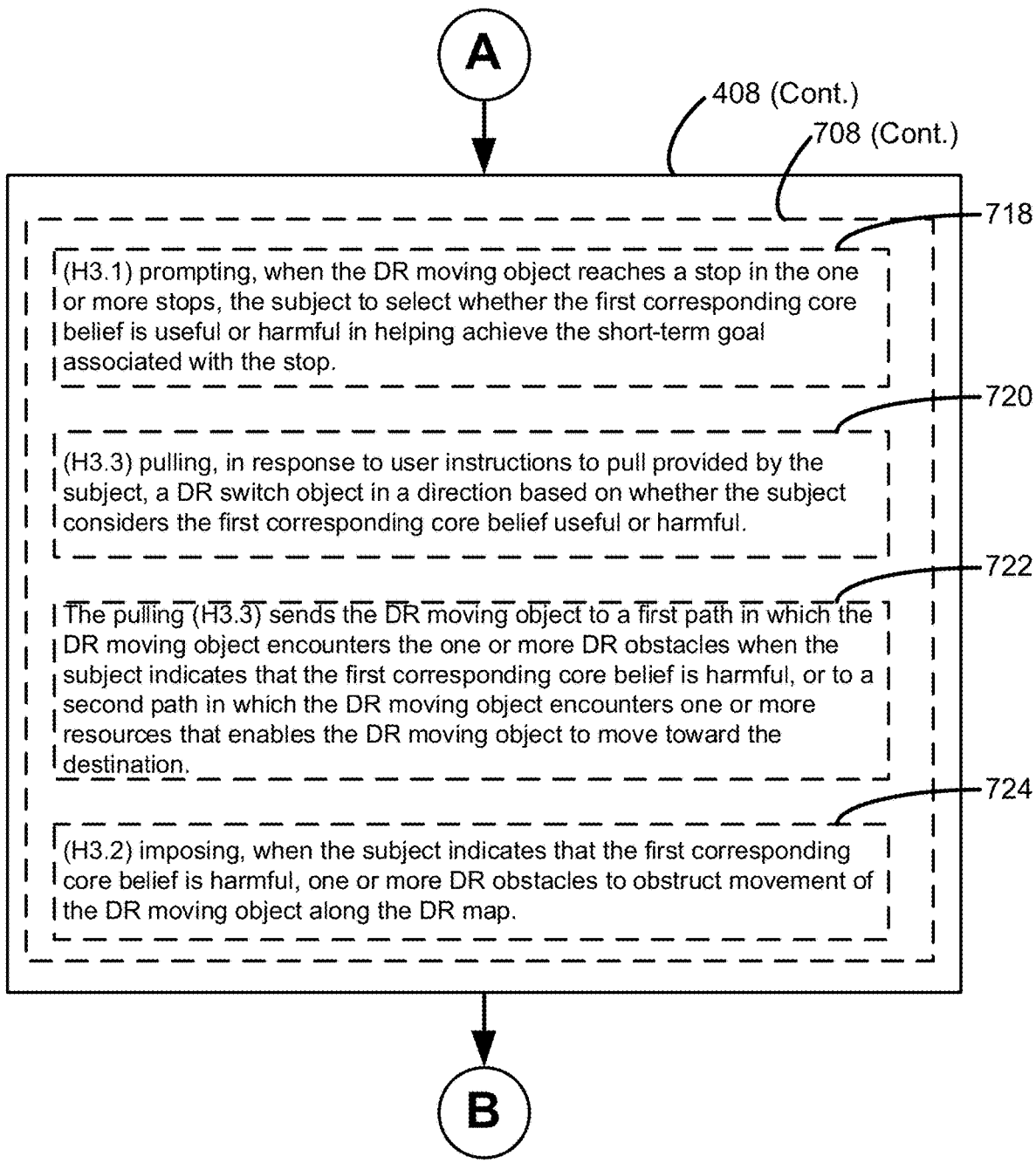
Figure 7C:
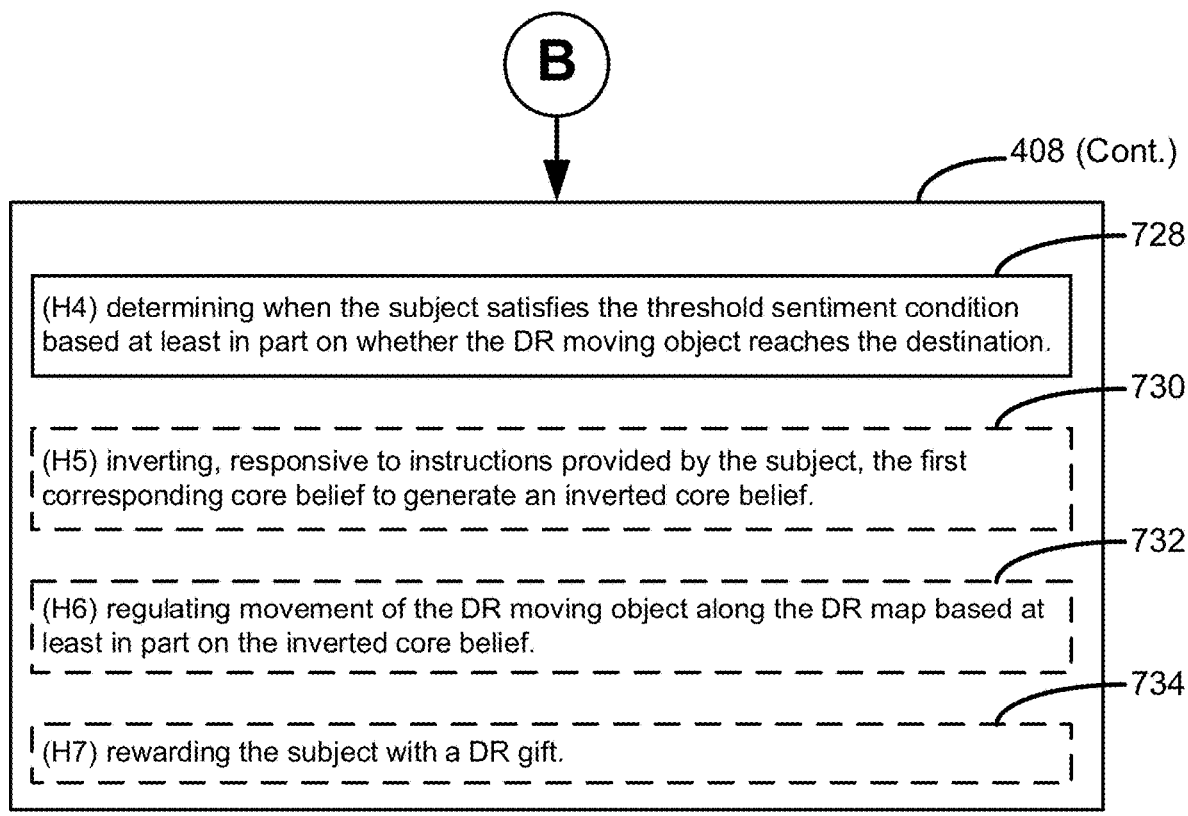
Figure 8A:
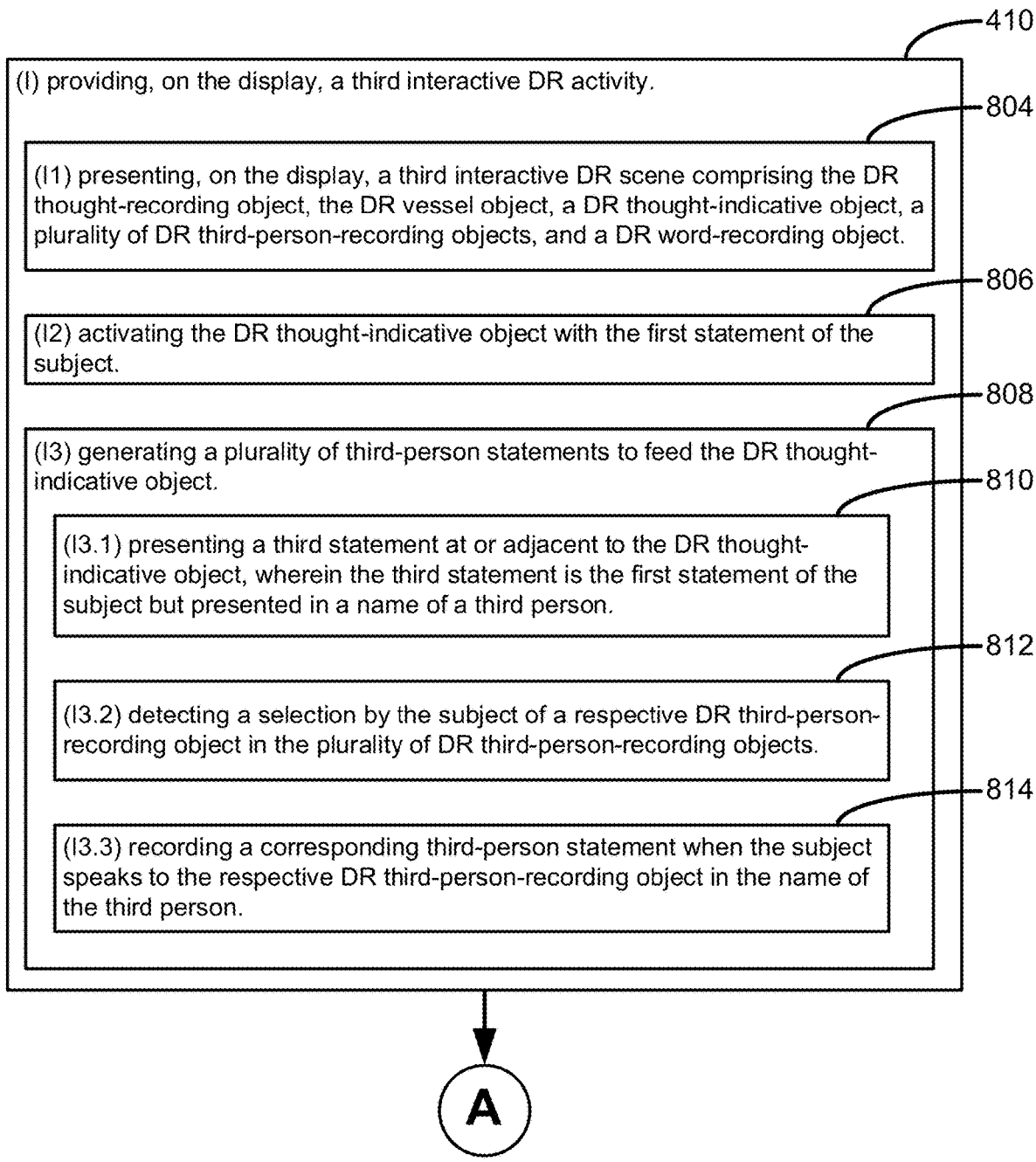
FIGS. 8A, 8B, 8C, 8D, and 8E collectively illustrate exemplary methods for providing an interactive DR activity configured for the subject to practice a create space CBT technique, in which optional embodiments are indicated by dashed boxes, in accordance with some embodiments of the present disclosure.
Figure 8B:
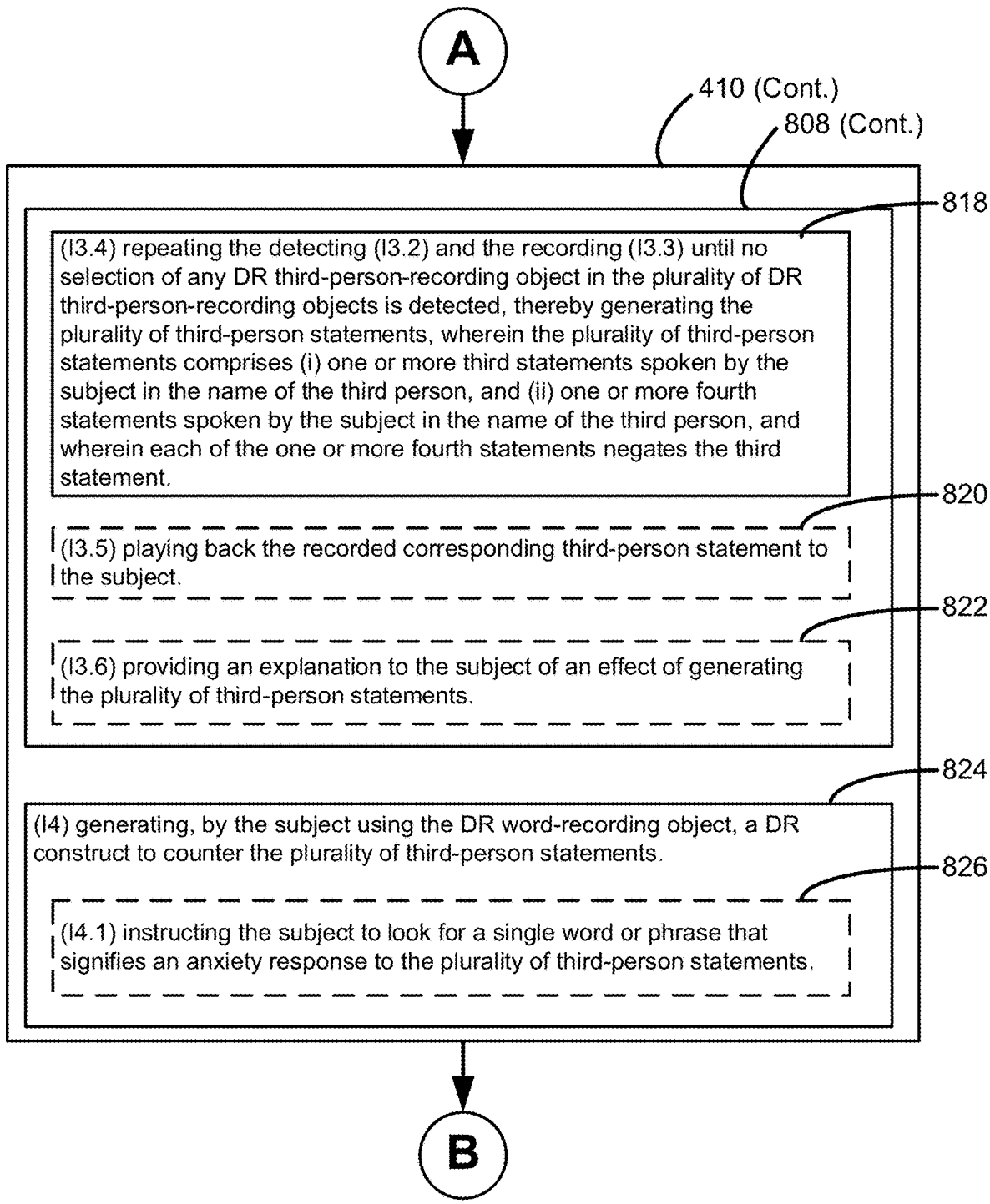
Figure 8C:
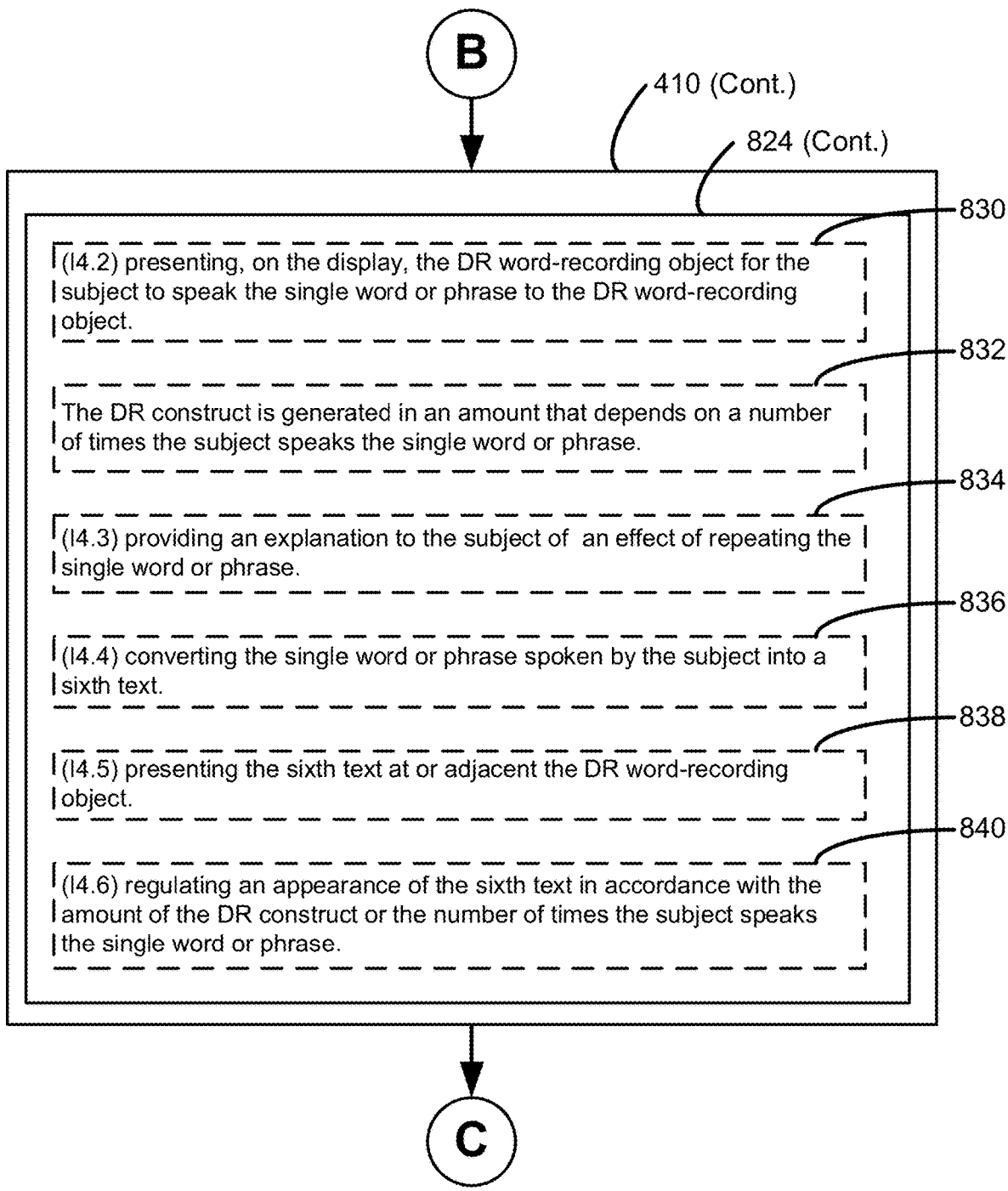
Figure 8D:
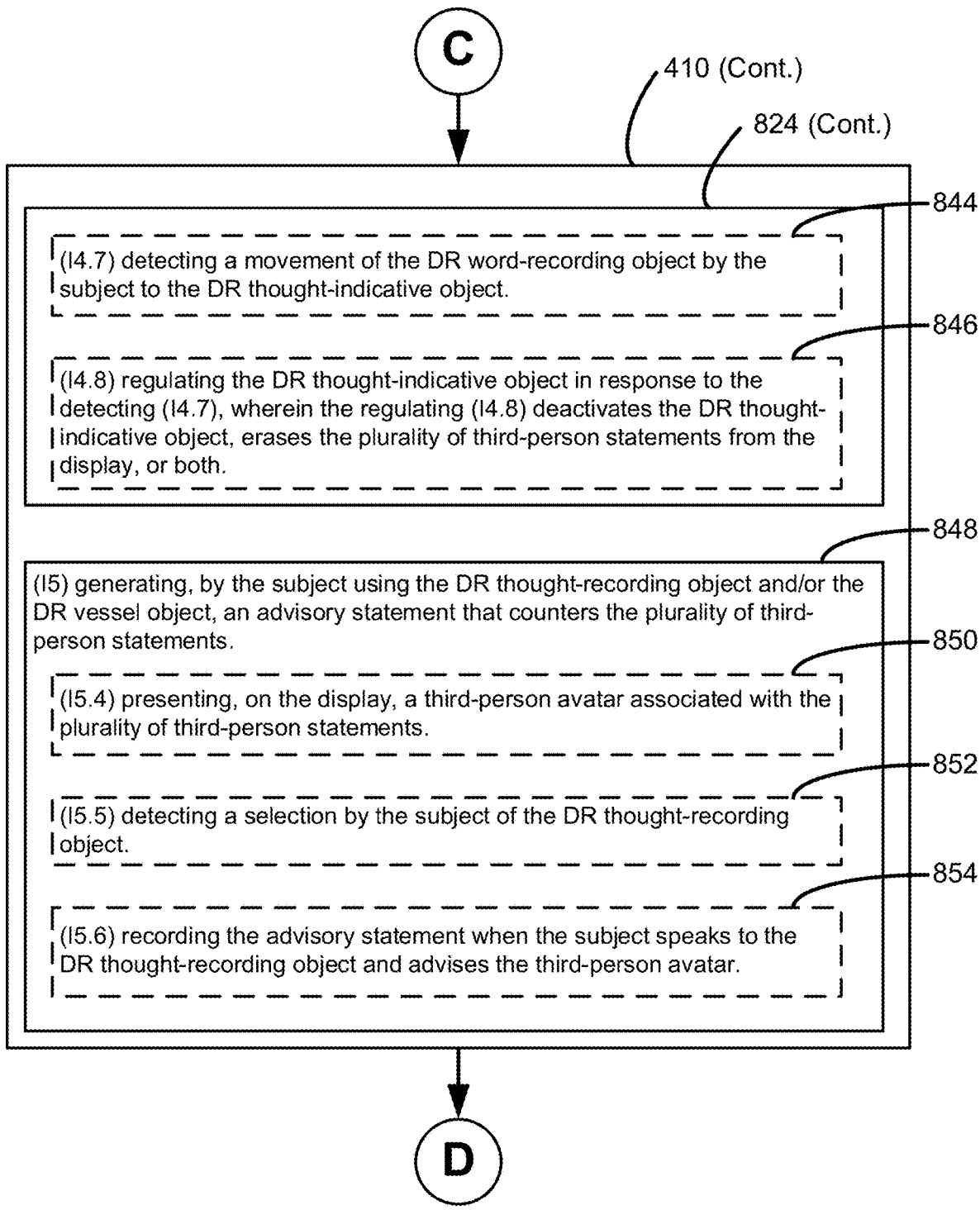
Figure 8E:
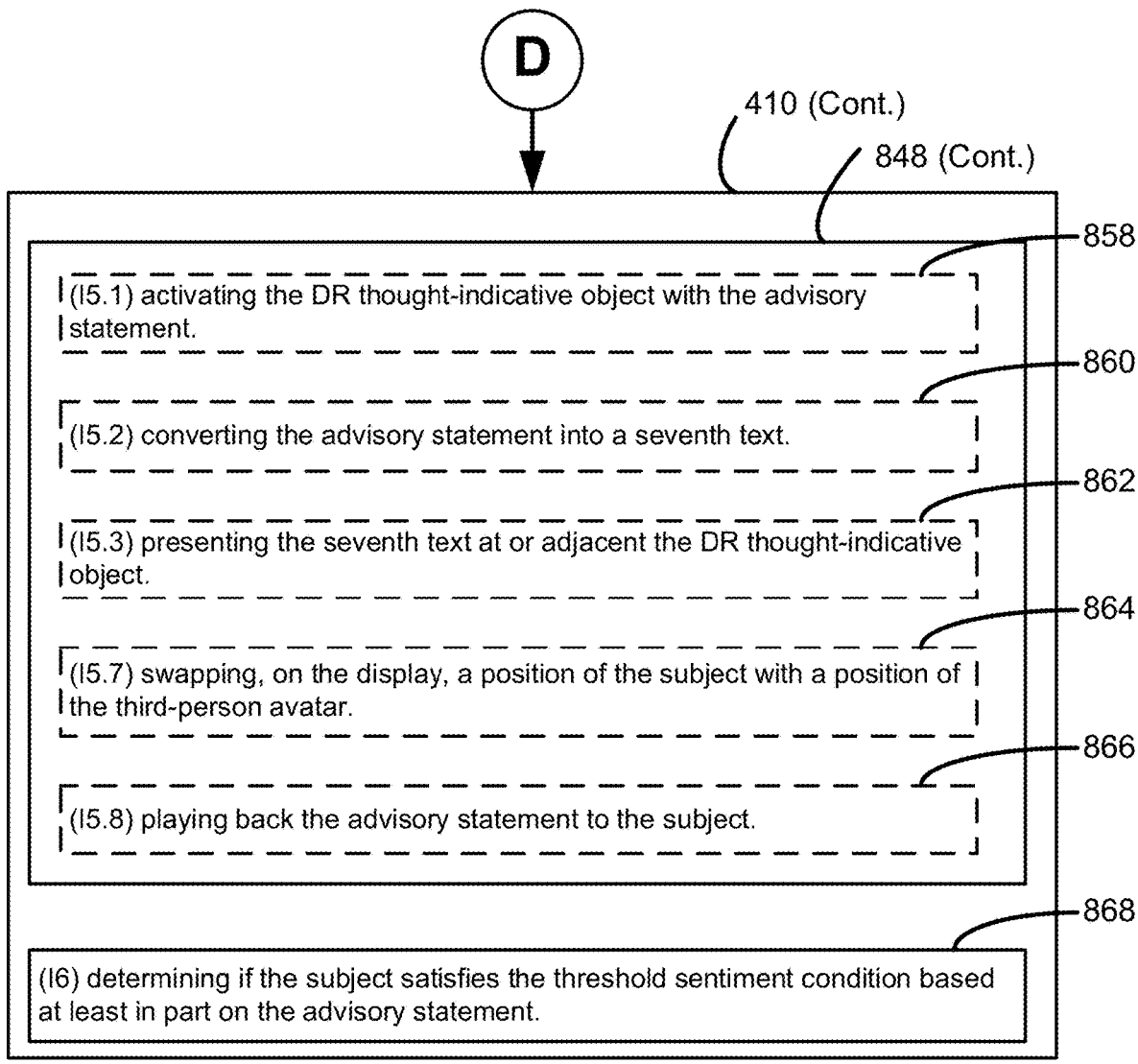
Figure 9A:
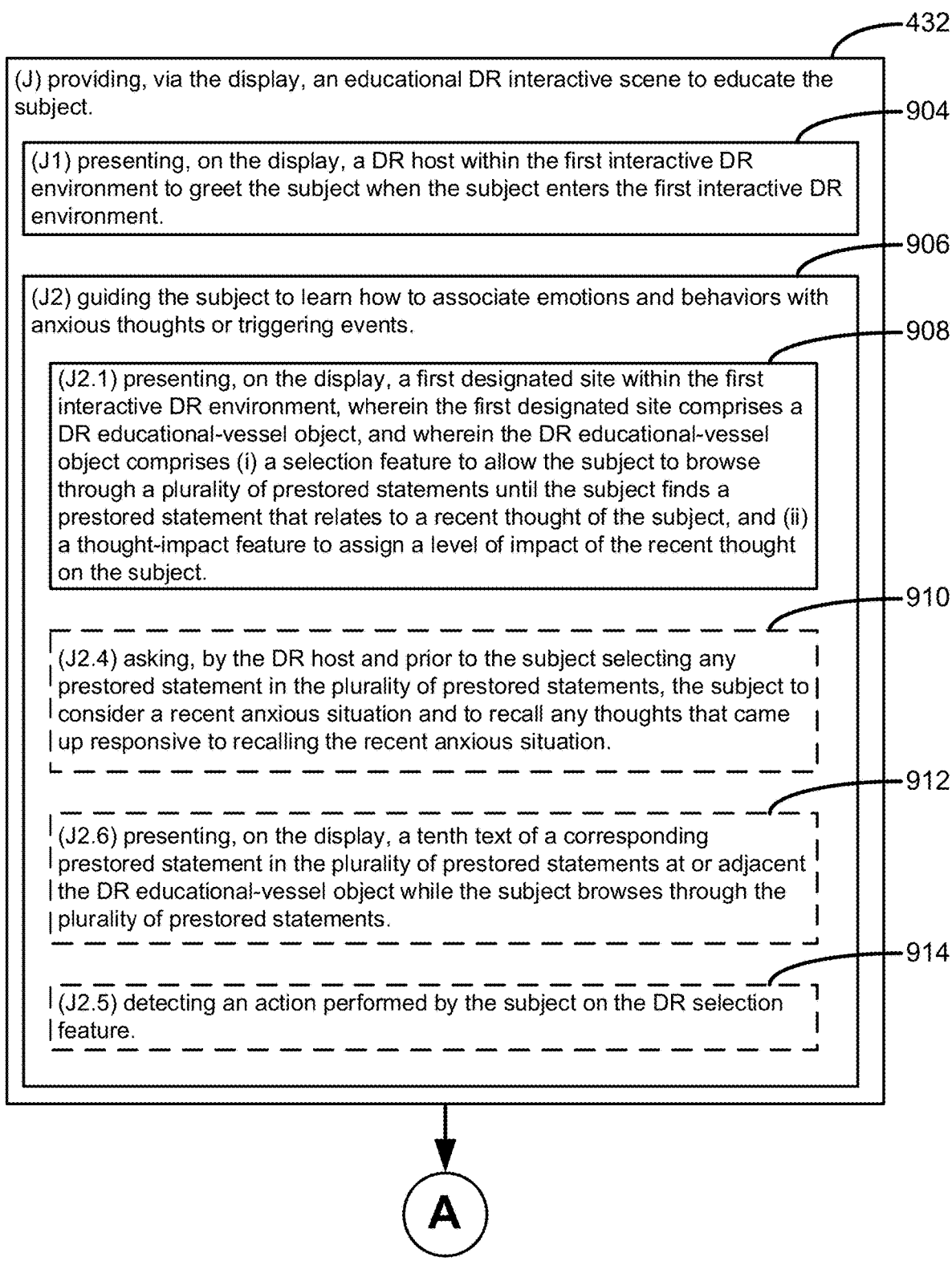
FIGS. 9A, 9B, 9C, 9D, 9E, and 9F collectively illustrate exemplary methods for providing an educational DR interactive scene to educate the subject, in which optional embodiments are indicated by dashed boxes, in accordance with some embodiments of the present disclosure.
Figure 9B:
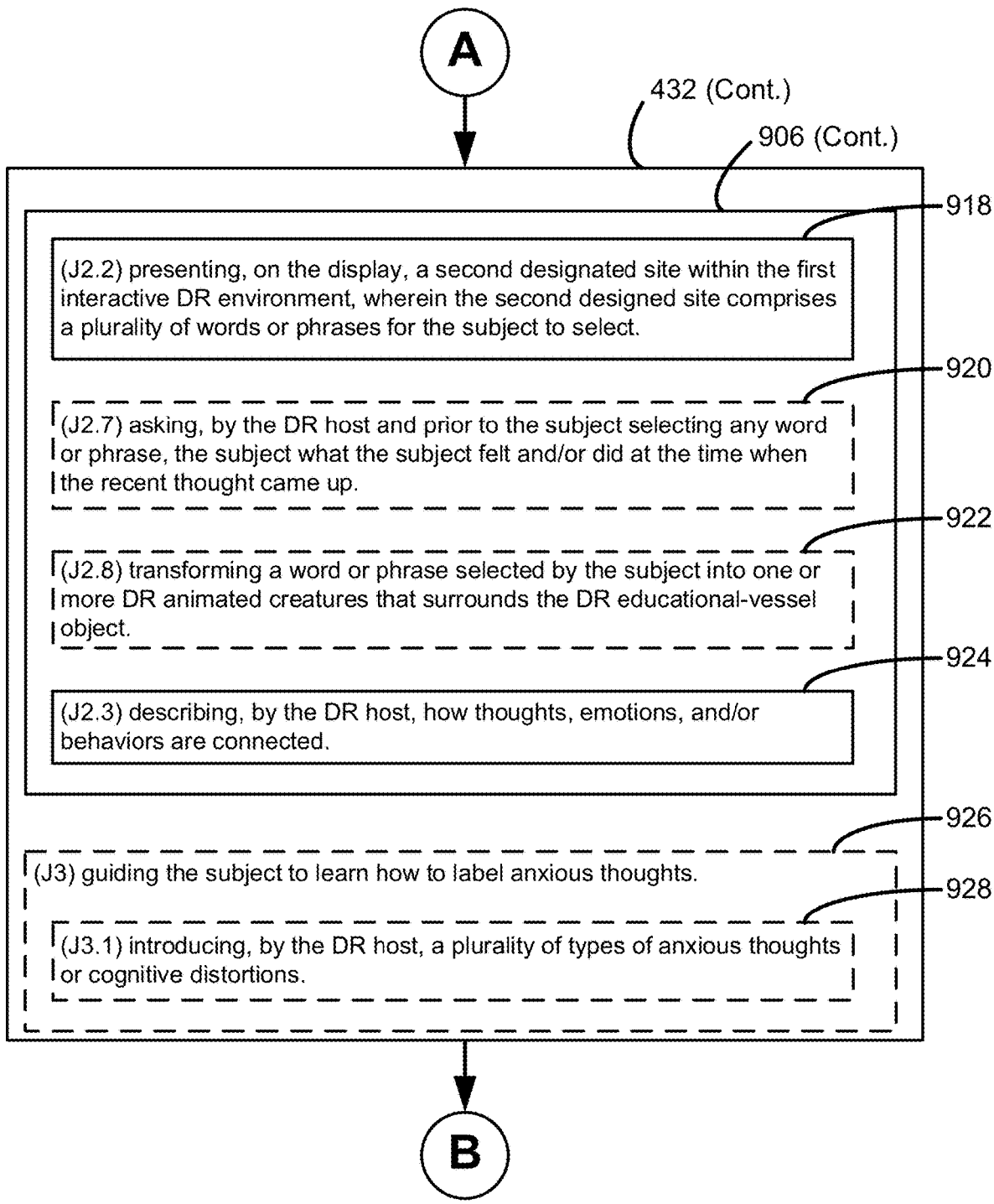
Figure 9C:
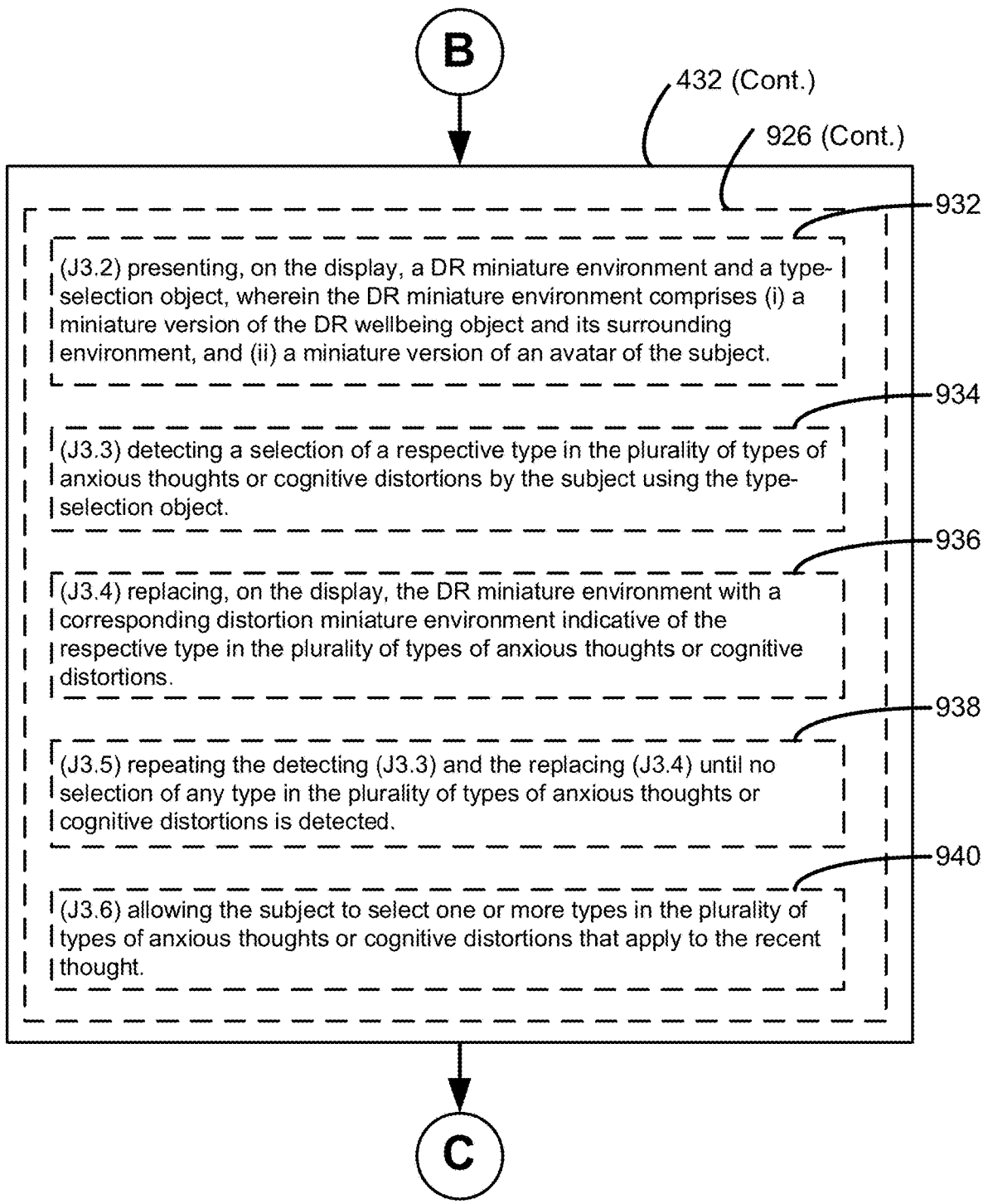
Figure 9D:
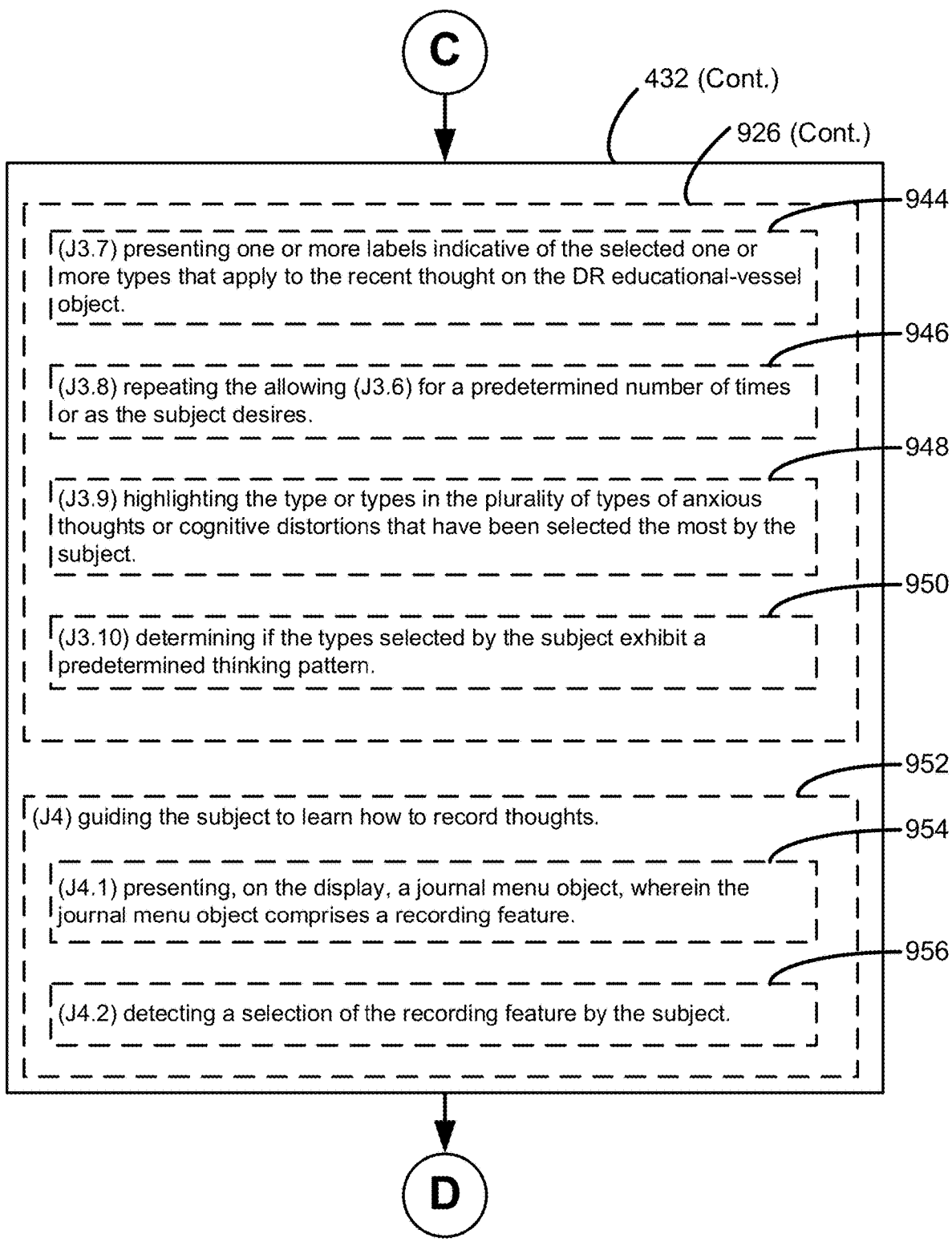
Figure 9E:
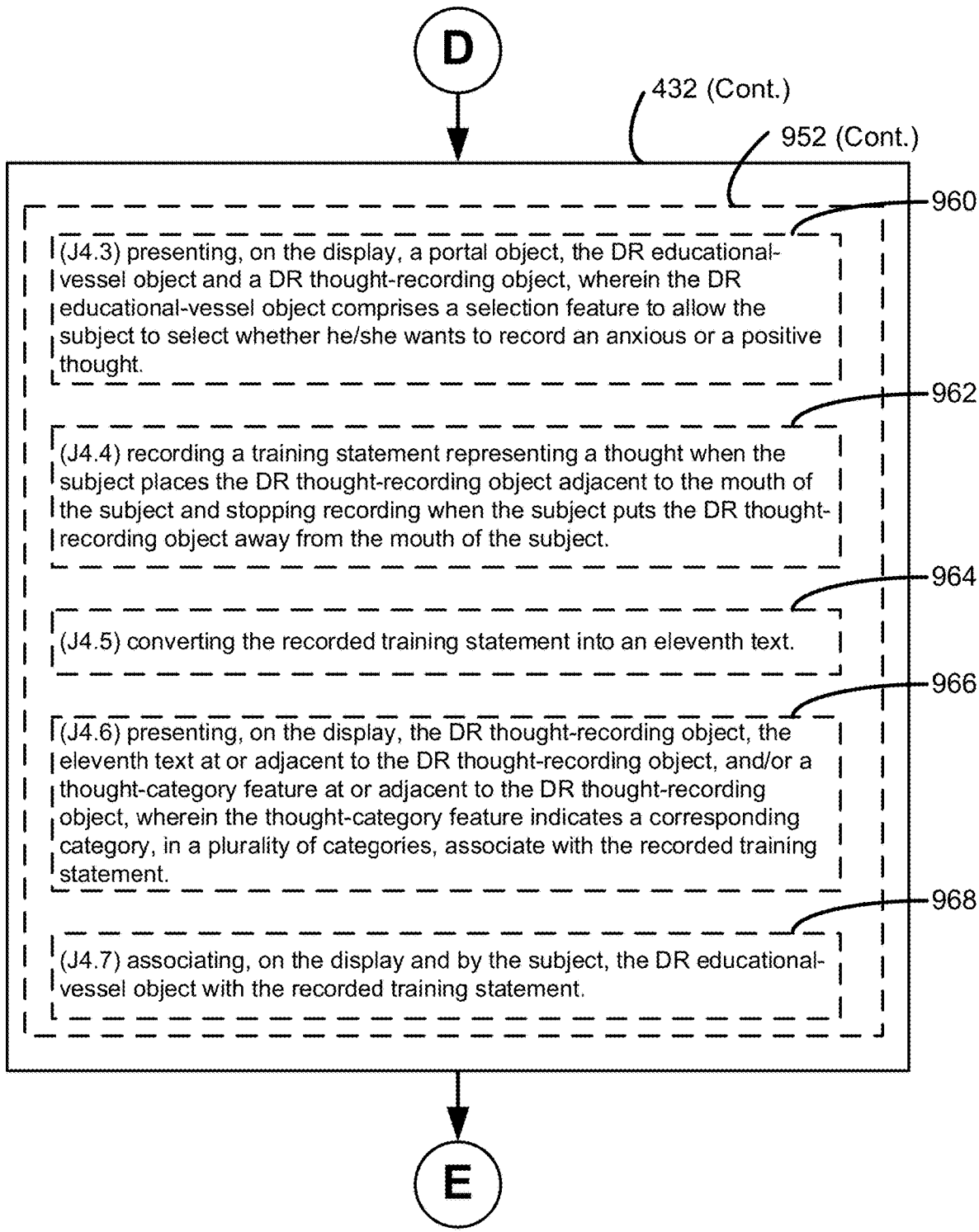
Figure 9F:
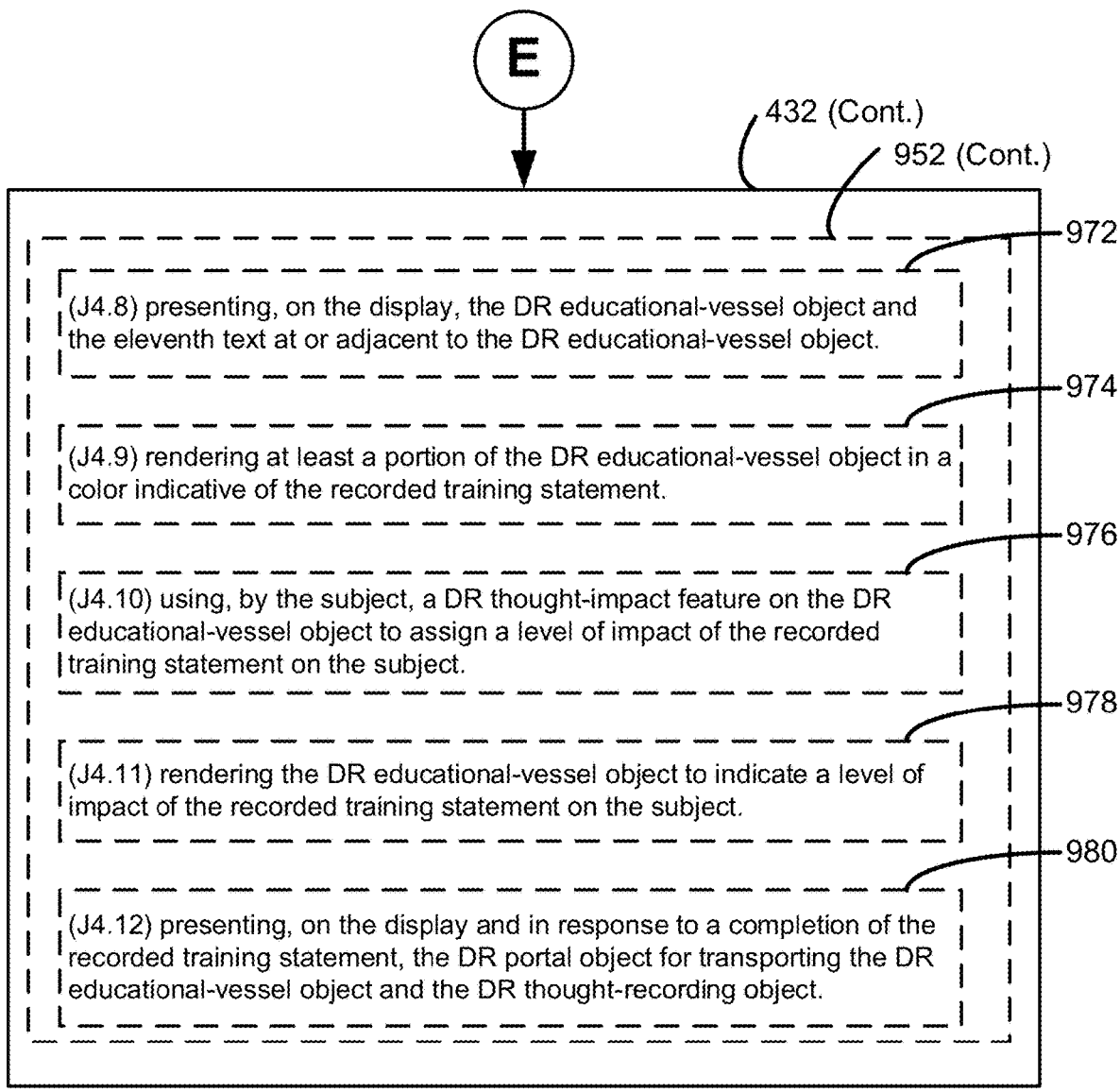

Referring to FIGS. 7A-7C, there is depicted a flowchart illustrating exemplary methods for providing a second interactive DR activity in accordance with some embodiments of the present disclosure. In some embodiments, the second interactive DR activity is associated with a second CBT technique different than a first CBT technique of the first interactive DR activity. For instance, in some embodiments, the second interactive DR activity is a usefulness and core belief CBT technique, which is configured to help a subject to identify a core belief at the root of an anxious thought (e.g., the thought represented by the first statement) and to determine how useful or harmful the core belief is towards one or more short-term and/or one or more long-term goals of the subject. Specifically, in some such embodiments, the second interactive DR activity allows a subject to help move a DR moving object through one or more stops to a destination, which represents progress of the subject in identify the core belief at the root of the anxious thought and, therefore, improving management of the psychiatric or mental condition exhibited by the subject. In some embodiments, the destination represents a long-term goal, which can be a goal set by the subject or a goal for training purposes. In some embodiments, each of the one or more stops represents a short-term goal related to the long-term goal. Accordingly, the DR moving object further represents the progress of the subject in achieving far-reaching long-term goals by accomplishing a series of short-term goals, such as milestones set along that path to the achievement of the long-term goal. Accordingly, the second interactive DR activity helps the subject improve the ability to manage the psychiatric or mental condition exhibited by segmenting the long-term goals into smaller, short-term goals. However, the present disclosure is not limited thereto.

In some embodiments, a short-term goal can be preset (e.g., predetermined by a model and/or a medical practitioner associated with the subject), set during the process, and/or revised during the process. How useful or harmful the core belief is toward helping the subject achieve these goals directly impacts how efficiently the DR moving object operates and whether or not it reaches the destination. In some embodiment, a submenu of the DR journey object 1022 is used during this second interactive DR activity so that the subject can update the short-term goals. In some embodiments, this submenu resembles a DR map 1810, showing each of the stops along the path of the DR moving object.

In some embodiments, this second interactive DR activity is configured for a subject to get the DR moving object to arrive (e.g., traverse a path towards) the destination. In some embodiments, this is achieved by the subject identifying the destructiveness of the core beliefs associated with the subject through a series of interactions with the second interactive DR activity. In some embodiments, the movement of the DR moving object is achieved by practicing the act of verbally inverting the core belief into a more constructive thought or belief.

Block 704. Referring to block 704, to provide a second interactive DR activity, the method includes presenting, on the display, a second interactive DR scene. In some embodiments, the second interactive DR scene includes a DR map, a DR moving object, and a plurality of DR belief objects. In some embodiments, the DR map includes a starting point (e.g., a first terminal point), a destination (e.g., a second terminal point), and one or more stops between the starting point and the destination (e.g., one or more intermediate points interconnecting the first terminal point and the second terminal point). The DR moving object is configured to move along the DR map. In some embodiments, each respective DR belief object in the plurality of DR belief objects is associated with a corresponding core belief in a plurality of core beliefs.

For instance, as a non-limiting example, FIGS. 18A-18G collectively illustrate a second interactive DR scene 1800 simulating a railway environment. The second interactive DR scene 1800 includes a DR map 1810 simulating a railway. The DR map 1810 includes a starting point 1812, a destination 1816, and one or more stops, such as a stop 1814-1, a stop 1814-2 and/or a stop 1814-3, between the starting point and the destination. While three stops are illustrated, it should be noted that the DR map can have less or more than three stops. For instance, in some embodiments, the DR map includes at least one, at least two, at least three, at least four, at least five, at least six, at least eight, or at least ten stops. In some embodiments, the DR map includes at most one, at most two, at most three, at most four, at most five, at most six, at most eight, or at most ten stops.

In some embodiments, the second interactive DR scene 1800 also includes a DR moving object 1820 simulating a train. The DR moving object 1820 is configured to move along the DR map 1810. In various embodiments, a subject does not directly interact with the DR moving object often, but actions of the subject have an effect on how the DR moving object operates (e.g., how the train runs, which route the train takes, or the like), and/or whether or not the DR moving object arrives to the destination. In some embodiments, the DR moving object can be rendered in one of two states: large and miniature. In some embodiments, the DR moving object includes a feature indicating how well the DR moving object is moving and/or if it is moving at all. For instance, in some embodiments, when the DR moving object simulates an engine device, such as a train, the exhaust (e.g., steam of the train) has various states (e.g., black, gray, white, or transparent) depending on how well the engine is running, or if it is running at all. In some embodiments, the body (e.g., shape, size, or the like) of the DR moving object also undergoes one or more changes depending on the events (e.g., some events may cause damage to the DR moving object).

In some embodiments, the second interactive DR scene 1800 further includes a plurality of DR belief objects, e.g., a DR belief object 1830-1, a DR belief object 1830-2, and/or a DR belief object 1830-3, that simulate a plurality of lenses or the like. Each respective DR belief object in the plurality of DR belief objects is associated with a corresponding core belief in a plurality of core beliefs. For instance, a first DR belief object 1830-1 is associated with a first core belief (e.g., having no influence) and a second DR belief object 1830-2 is associated with a second core belief (e.g., not good enough). In some embodiments, the text of a corresponding core belief is shown (e.g., printed) on a respective DR belief object.

In some embodiments, the second interactive DR scene includes, additionally or optionally, other DR objects. For instance, in some embodiments, the subject is accompanied by the DR assistant 1100. In some embodiments, the DR object 1300 is carried by the subject to the second interactive DR scene or presented to the subject when the subject enters the second interactive DR scene. In some embodiments, a DR thought-recording object, such as the recordable object 1210 or the recordable object 1220, is also carried by the subject to the second interactive DR scene or presented to the subject when the subject enters the second interactive DR scene.

In some embodiments, the second interactive DR scene includes a DR belief-recording object, such as a DR belief-recording object 1840 simulating a headlight. In some embodiments, the DR belief-recording object is a recordable object or becomes a recordable object during the second DR activity.

While FIGS. 18A-18G illustrates the second interactive DR scene simulating a railway environment, it should be noted that the second interactive DR scene can simulate any suitable scene, including but not limited to real or nonreal, fictional or non-fictional scenes. Similarly, the DR map, the DR moving object, the plurality of DR belief objects and the DR belief-recording object can simulate any suitable objects. For instance, as a non-limiting example, the second interactive DR scene can simulate a country road environment with the DR moving object simulating a car, a truck, a bicycle, or the like. As another non-limiting example, the second interactive DR scene can simulate a mountain trail environment with the subject represented as the DR moving object.

Block 706. Referring to block 706, the method also includes detecting a selection of a first DR belief object in the plurality of DR belief objects by the subject. In some embodiments, the first DR belief object is associated with a first corresponding core belief that best represents the first statement. In some embodiments, the DR assistant gives the subject a refresher (e.g., a lesson, a guide, etc.) on core beliefs. In some embodiments, the DR assistant asks the subject to identify a core belief that is at the root of the anxious thought of the subject. In some embodiments, the subject browses through the plurality of DR belief objects until the subject selects one that best represents the first statement, e.g., the thought contained in the DR object.

Block 708. Referring to block 708, in some embodiments, the method includes regulating movement of the DR moving object along the DR map based at least in part on the first corresponding core belief. For instance, in some embodiments, at each of the one or more stops, the subject has to determine how "useful" or "harmful" the first corresponding core belief is in helping the subject achieve the short-term goals associated with the subject. If it is determined that the first corresponding core belief is harmful, the DR moving object will encounter one or more problems that retard or arrest the DR moving object, such as one or more delays, damage, difficult routes, lack of supplies, or the like. If it is determined that the first corresponding core belief is useful, the DR moving object will receive maintenance, supplies or the like, and/or the DR moving object will move/run more efficiently. In various embodiments, if the first statement represents an anxious thought, the DR moving object would not reach the destination with the first corresponding core belief that best represents the first statement. In such embodiments, the method allows the subject to invert the first corresponding core belief and regulate movement of the DR moving object along the DR map based at least in part on the inverted core belief.

Block 710. Referring to block 710, in some embodiments, additionally or optionally, the method includes placing, responsive to instructions provided by the subject, the selected first DR belief object on the DR belief-recording object. For instance, in some embodiments, when the plurality of DR belief objects 1830 simulates lenses and the DR belief-recording object 1840 simulates a headlight, the method allows the subject to pick up a lens that best represents the first statement after the subject looks through the plurality of lenses (e.g., go through the core beliefs associated with the lenses. In some embodiments, the method then allows the subject to place the selected lens in the headlight.

Block 712. Referring to block 712, in some embodiments, additionally or optionally, the method includes placing, responsive to instructions provided by the subject, the DR belief-recording object along with the selected first DR belief object on the DR moving object. For instance, in embodiments where the DR moving object simulates a train, the method allows the subject to place the headlight along with the selected lens (e.g., a headlight assembly) on the front of the train.

Figure 18E:
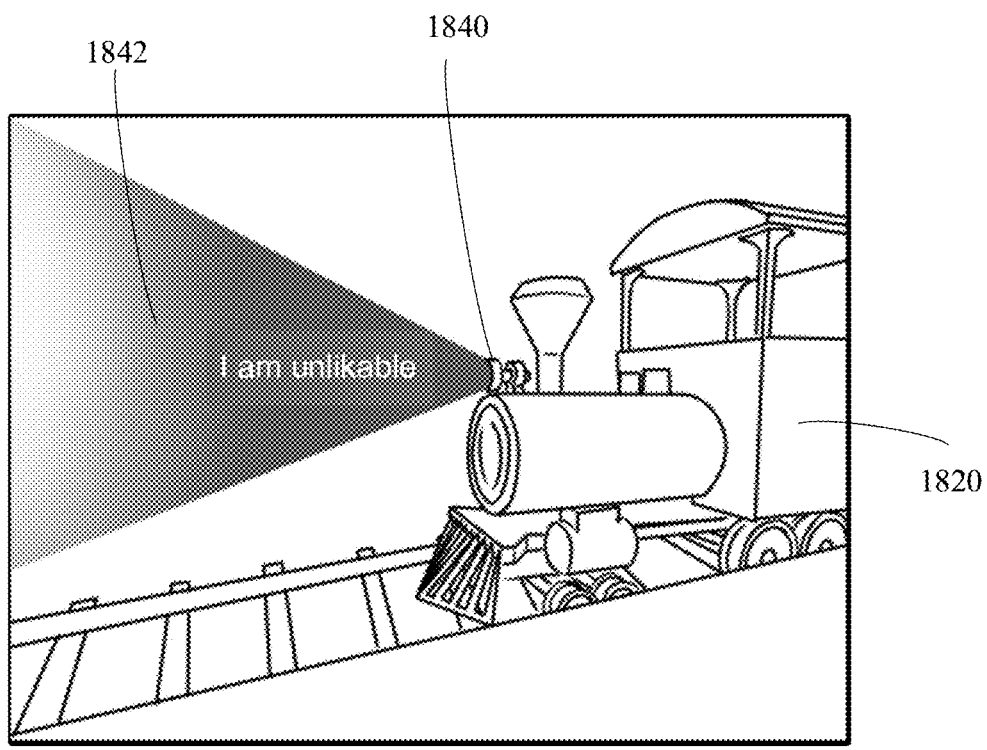
Figure 18F:
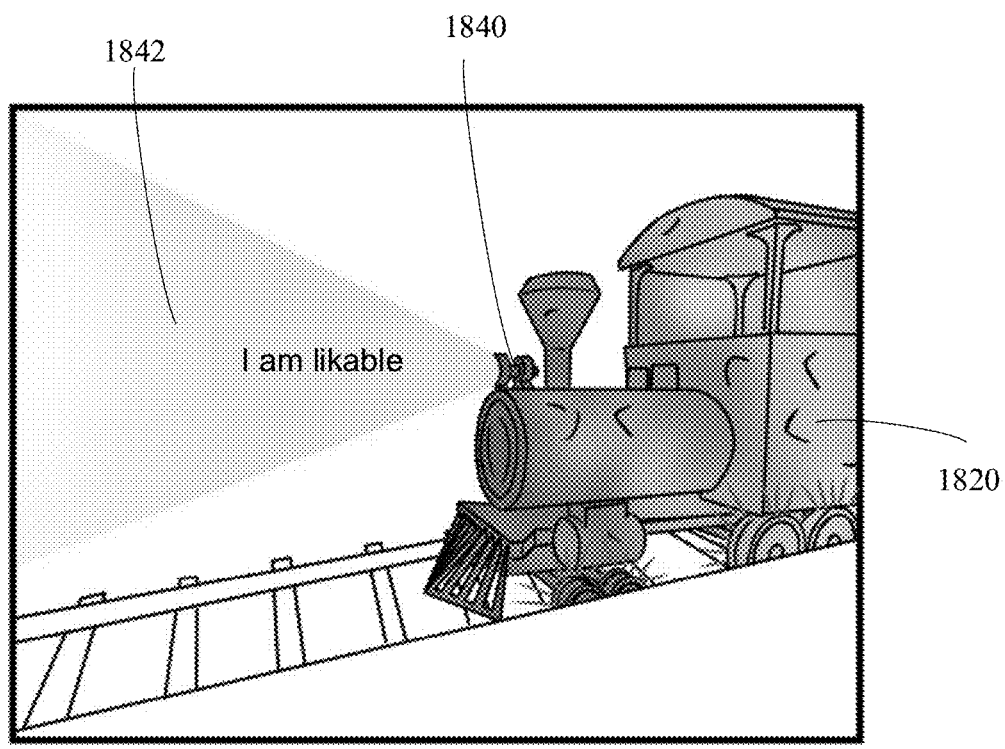

In some embodiments, once the DR belief-recording object along with the selected first DR belief object is placed on the DR moving object, the DR moving object is presented with a belief-type feature configured to indicate a type of the first corresponding core belief. For instance, as a non-limiting example, FIGS. 18E and 18F illustrate a belief-type feature 1842 simulating a light projected from the headlight. In some embodiments, the belief-type feature 1842 glows in a color, indicating whether the first corresponding core belief is a core belief that needs to be worked on or a core belief that has been worked on (e.g., an inverted core belief). For instance, in some embodiments, the light appears initially in a first color (e.g., red) to indicate a core belief that needs to be worked on and in a second color (e.g., yellow) to indicate a core belief that has been worked on. In some embodiments, the text of the first corresponding core belief is visible in the glow of the belief-type feature 1842.

In some embodiments, placing the headlight along with the selected lens on the front of the train causes the light to turn on. In some embodiments, the light appears initially in a first color (e.g., red) with the text of the first corresponding core belief showing in the glow of the light. Later, the headlight becomes a recordable object, and is used to invert the first corresponding core belief. With the inverted core belief, the light shining from the headlight changes from the first color to a second color (e.g., from red to yellow).

In some embodiments, the DR moving object starts to move along the DR map responsive to instructions provided by the subject, or once the DR belief-recording object along with the selected first DR belief object is placed on the DR moving object. In some embodiments, the DR moving object heads off through a tunnel and/or emerges on the other side of the tunnel at a miniature scale. In some embodiments, a version of the subject's avatar is the conductor of the DR moving object.

Block 714. Referring to block 714, in some embodiments, additionally or optionally, the method includes presenting, on the display when the DR moving object reaches a DR loading station, one or more cargo items for the subject to load to the DR moving object. In some embodiments, the DR moving object reaches the DR loading station before reaching any one of the one or more stops. In some embodiments, the DR moving object reaches the DR loading station at least before reaching the destination.

For instance, in embodiments where the DR moving object simulates a train, the train arrives at a loading station that includes one or more cargo items (e.g., one or more DR objects simulating shipping containers, agriculture and energy products, consumer goods or the like). In some embodiments, the subject is asked to place at least one of the one or more cargo items onto the train and help the train to get to the destination. For instance, in some embodiments, the DR assistant or a healthcare professional explains to the subject that the train must get the cargo item(s) to the destination.

Figure 18G:
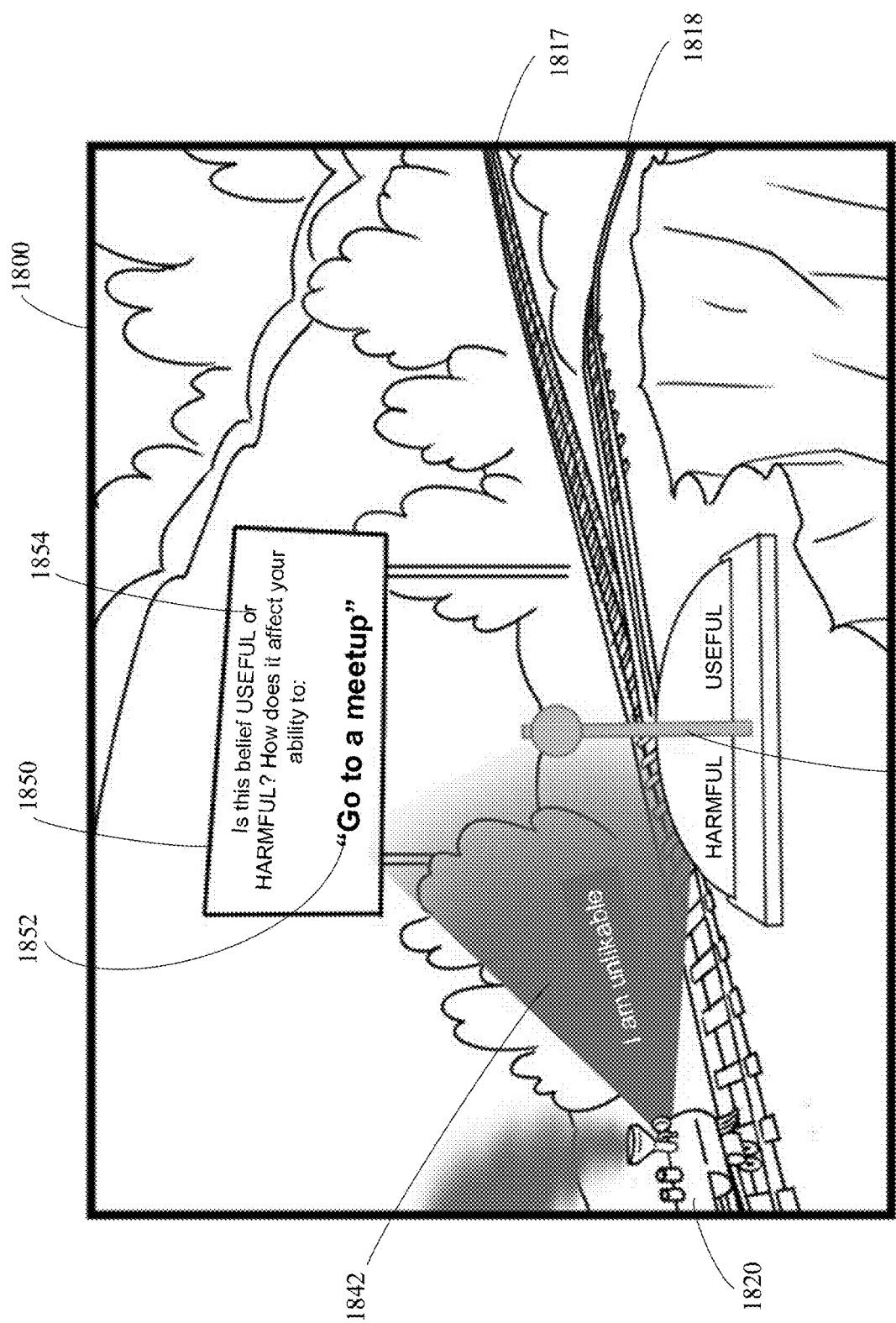

Block 718. Referring to block 718, in some embodiments, the method includes prompting, when the DR moving object reaches a stop in the one or more stops, the subject to select whether the first corresponding core belief is useful or harmful in helping achieve the short-term goal associated with the stop. In some embodiments, the prompting can be done by audio, visual, or the like. As a non-limiting example, FIG. 18G illustrates a stop 1814, with a DR object 1850 simulating a railway board or the like. Shown on the board are a feature 1852 (e.g., a text or the like) indicating the short-term goal associated with the stop and a feature 1854 (e.g., a text or the like) that askes the subject to determine whether the first corresponding core belief is useful or harmful in helping achieve the short-term goal associated with the stop.

Block 720-722. Referring to block 720 and block 722, in some embodiments, additionally or optionally, the method includes pulling, in response to user instructions to pull provided by the subject, a DR switch object in a direction based on whether the subject considers the first corresponding core belief useful or harmful. For instance, as a non-limiting example, FIG. 18G illustrates a DR switching object 1860 simulating a switch, a lever or the like. In some embodiments, the DR switching object 1860 includes options, e.g., "useful" or "harmful," for the subject to pull in either direction upon the determination of whether the first corresponding core belief is useful or harmful in helping achieve the short-term goal associated with the stop.

In some embodiments, the DR switching object 1860 simulates a track switch that determines the path of the DR moving object. For instance, in some embodiments, if the subject pulls the switch to the "harmful" side, the DR moving object will be sent to a route different than that if the subjects pulls the switch to the "useful" side. In some embodiments, when the subject indicates that the first corresponding core belief is harmful, the pulling of the DR switch object sends the DR moving object to a first path, e.g., a path 1817, in which the DR moving object encounters the one or more DR obstacles. When the subject indicates that the first corresponding core belief is useful, the pulling of the DR switch object sends the DR moving object to a second path, e.g., a path 1818, in which the DR moving object encounters one or more resources that enables the DR moving object to move toward the destination.

Alternatively, in some embodiments, the DR switching object 1860 does not simulate a track switch and pulling the DR switching object to either side will not change the path of the DR moving object. In some embodiments, the DR switching object will take substantially the same path. However, the DR moving object will encounter one or more DR obstacles if the subject pulls the switch to the "harmful" side, and will encounter one or more resources that enables the DR moving object to move toward the destination if the subject pulls the switch to the "useful" side.

Examples of the one or more DR obstacles include, but are not limited to, DR blocking objects, damage on the DR map, damage on the DR moving object, lack of maintenance for the DR moving object, lack of supply (e.g., fuel, water), or any combination thereof. Examples of the one or more resources include, but are not limited to, DR maintenance for the DR moving object, DR part replacement for the DR moving object, DR supply for the DR moving object, or a combination thereof. In some embodiments, a purpose of having the one or more DR obstacles and/or the one or more resources in this DR activity is to make the practicing of this reframing technique more interesting.

As a non-limiting example, in some embodiments, there is a DR tower object simulating either a coal tower or a water tank at a stop or each of the one or more stops. If the DR switching object is pulled toward "useful," the DR tower object will be operatable to replenish the supply for the DR moving object (e.g., train). If the DR switching object is pulled toward "harmful," the DR tower object will be out of service, and no coal or water would come out.

As another non-limiting example, in some embodiments, at one of the one or more stops, rocks fall in the path of the DR moving object simulating a train if the DR switching object is pulled toward "harmful." In some embodiments, the subject has to move the rocks out of the way. In some embodiments, one or more rocks will hit the train and dent its engine. If the DR switching object is pulled toward "useful," the train is sent to a repair shop, and/or the train emerges with one or more new parts.

As a further non-limiting example, in some embodiment, at one of the one or more stops, the DR moving object simulating a train approaches a broken segment of the track if the DR switching object is pulled toward "harmful." In some embodiments, the subject has to put the track piece back in place and/or repair it using a welding torch or the like. In some embodiments, as the train crosses over, its wheels start to grind. If the DR switching object is pulled toward "useful," the train gets its wheels greased. In some embodiments, the subject has to grease the track pieces, allowing the train to pass over smoothly.

As a still further non-limiting example, in some embodiment, at one of the one or more stops, the DR moving object simulating a train approaches a blockage of dirt and/or debris covering the track if the DR switching object is pulled toward "harmful." In some embodiments, the subject has to brush the dirt off the track. In some embodiments, this results in a dust cloud dirtying the train. If the DR switching object is pulled toward "useful," the train is sent through a cleaning station where it emerges shiny and new.

The second interactive DR activity can be used for a subject to practice reframing a through and for tutoring the usefulness and core beliefs reframing technique. In some embodiments, when the second interactive DR activity is used for a subject to practice reframing a thought, the subject is allowed to make decisions, and can pull the switch in either direction. In some embodiments, when the second interactive DR activity is used for tutoring the usefulness and core beliefs reframing technique, the subject helps the DR assistant reframing a thought instead of reframing the anxious thought of the subject. In such embodiments, the method includes one or more safeguards to prevent the subject from answering incorrectly. For instance, in some embodiments, when going through each stop for the first time, if the subject says the core belief is "useful," the switch will not move and the DR assistant will correct the subject. In some embodiments, if the subject says the core belief is "harmful," the DR assistant will give an explanation as to why this is correct.

Block 724. Referring to block 724, in some embodiments, the method includes imposing, when the subject indicates that the first corresponding core belief is harmful, one or more DR obstacles to obstruct movement of the DR moving object along the DR map.

Examples of the one or more obstacles include, but are not limited to, DR blocking objects (rocks, dirt) on the DR map that have to be removed by the subject in order for the DR moving object to reach the destination, damage on the DR map, damage on the DR moving object, lack of maintenance for the DR moving object, lack of supply, or any combination thereof. In some embodiments, the one or more DR obstacles prevent the DR moving object from reaching the destination.

As a non-limiting example, in some embodiments, the DR moving object simulating a train encounters one or more DR obstacles at each stop or along the way, and gets damaged in different ways if the first corresponding core belief is harmful. In some embodiments, the one or more DR obstacles include, but are not limited to, (i) DR objects simulating rocks begin to fall, and the subject has to move them out of the way so the train can pass, (ii) some of the rocks end up hitting the train and damaging it, (iii) the track is broken, and the subject has to put the dislodged piece back into place, e.g., using a welding torch to fuse it with the rest of the track, (iv) as the train passes over, its wheels grind against the welded track, causing sparks to fly, (v) the track is blocked by a dirt pile, and the subject has to sweep the dirt off the track, (vi) the train gets dirty, (vii) the train tries to replenish its supply (e.g., coal and/or water), but the tower is "out of order" and nothing comes out, (viii) the speed of the train decreases, (ix) the train runs less and less efficiently, (x) the steam cloud of the train darkens as it runs less and less efficiently, (xi) the train ascends up the hill (e.g., toward its destination), (xii) the train eventually runs out of steam and begins to roll backwards, (xiii) the subject has to push the train to its starting point, or any combination thereof. In some embodiments, some DR obstacle(s) is presented at a stop, and some other DR obstacle(s) is presented in a different stop. In some embodiments, at least one obstacle is presented at each of the one or more stops.

Block 728. Referring to block 728, in some embodiments, additionally or optionally, the method includes determining when the subject satisfies the threshold sentiment condition based on whether the DR moving object reaches the destination. For instance, in various embodiments, the subject is considered not satisfying the threshold sentiment condition if the DR moving object does not reach the destination. In some embodiments, even though the DR moving object reaches the destination, the subject is considered not satisfying the threshold sentiment condition if the subject, a healthcare professional associated with the subject, the method (e.g., one or more models disclosed herein), physiological measurements, or any combination thereof indicate that that subject is not ready to reframe the thought.

Block 730. Referring to block 730, in some embodiments, additionally or optionally, the method includes inverting, responsive to instructions provided by the subject, the first corresponding core belief to generate an inverted core belief. In some embodiments, the inverting of the first corresponding core belief is performed when the DR moving object fails to reach the destination.

In some embodiments, the inverted core belief is generated by having the subject utter a statement, to the DR belief-recording object 1840 (e.g., headlight). In some embodiments, the inverted core belief is opposite of the first corresponding core belief. In some embodiments, the inverted core belief is converted into a text, which is presented at or adjacent to the first DR belief object, or at or adjacent to the DR belief-recording object.

In some embodiments, the belief-type feature 1842 (e.g., light) of the DR belief-recording object (e.g., headlight) changes when the inverted core belief is generated. For instance, in some embodiments, when the inverted core belief is generated, the light shining from the headlight changes from a first color (e.g., red) indicative of the first corresponding core belief to a second color (e.g., yellow) indicative of the inverted core belief as illustrated in FIGS. 18E and 18F.

Block 732. Referring to block 732, in some embodiments, additionally or optionally, the method includes regulating movement of the DR moving object along the DR map based at least in part on the inverted core belief In some embodiments, regulating movement of the DR moving object along the DR map based at least in part on the inverted core belief employs one or more processes the same as or similar to the prompting step exemplified at least by block 718, the pulling step exemplified at least by block 720 and/or block 722, the imposing step exemplified at least by block 724, the determining step exemplified at least by step 728, or any combination thereof.

As a non-limiting example, in some embodiments, the DR moving object simulating a train goes through the one or more stops a second time with the inverted core belief. If the inverted core belief is "useful," the train received various upgrades, maintenance, and/or repairs, including but not limited to, (i) the train receives one or more body repairs, (ii) all dents and scratches are removed, (iii) the subject greases the track before the train passes through, (iv) as the train crosses over the track, its wheels get cleaned, (v) the train is thoroughly cleaned and polished, (vi) all of the dirt and grime gets removed, (vi) the train successfully replenishes its supply (e.g., coal, water), (vii) the speed of the train increases, (viii) the train runs more efficiently, (ix) the steam cloud of the train lightens, (ix) when the train ascends toward the final stop this time, it does not slow down or run out of steam, (x) the train makes it to the top of the hill, (xi) the town representing the destination lights up, or any combination thereof. In some embodiments, some of the upgrades, maintenance, and/or repairs is presented at a stop, and some of the upgrades, maintenance, and/or repairs is presented in a different stop. In some embodiments, at least one of upgrade, maintenance or repair is presented at each of the one or more stops.

In some embodiments, the DR moving object would not reach the destination unless the subject inverts the first corresponding core belief. For instance, as a non-limiting example, in some embodiments, when going through the one or more stops the first time, the train will likely run out of steam, and not make it to the destination. In some embodiments, the subject (the avatar of the subject) has to push the train back to its starting position. In some embodiments, the subject then inverts the first corresponding core belief by recording a new one into the headlight, and placing it back on the train. In some embodiments, the light changes color (e.g., to a bright yellow), and the text updates. In some embodiments, the train runs through the one or more stops a second time with the reverted belief. If the subject responds that the inverted belief is useful at all of the one or more stops, the train makes it to its destination.

Block 734. Referring to block 734, in some embodiments, additionally or optionally, the method includes rewarding the subject with a DR gift when the DR moving object makes it to the destination. In some embodiments, the DR gift is a DR cargo item loaded by the subject to the DR moving object at the loading station on the DR map. For instance, in some embodiments, when the DR moving object makes it to the destination, a crate of a DR cargo item opens to reveal a reward for the subject.

2.7. Providing a Third Interactive DR Activity

Referring to FIGS. 8A-8E, there is depicted a flowchart illustrating exemplary methods for providing a third interactive DR activity in accordance with some embodiments of the present disclosure. In some embodiments, the third interactive DR activity is configured to implement a CBT technique, such as to help a subject to practice a defusion technique and/or learn how to create cognitive distance between the subject and the thoughts of the subject. In particular, in some embodiments, the third interactive DR activity is configured to help a subject to learn and practice third-person self-talk to create cognitive distance between the subject and the thoughts of the subject and accordingly reduce the anxiety associated with certain thoughts. In some embodiments, the subject is accompanied by the DR assistant during the third interactive DR activity. In some embodiments, the DR assistant describes how third-person self-talk creates cognitive distance between the subject and the thoughts of the subject, and how creation of cognitive distance can help to reduce the anxiety associated with certain thoughts.

Block 804. Referring to block 804, to provide a third interactive DR activity, the method includes presenting, on the display, a third interactive DR scene. In some embodiments, the third interactive DR scene includes a DR thought-recording object, a DR object, a DR thought-indicative object, a plurality of DR third-person-recording objects, and a DR word-recording object. Like the first and second interactive DR scenes, the third interactive DR scene can simulate any suitable real or nonreal, existent or non-existent scene. As a non-limiting example, FIGS. 19A-19J collectively illustrate a third interactive DR scene 1900 simulating a campsite. In some embodiments, the third interactive DR scene 1900 includes a DR thought-recording object, such as the DR recordable object 1220 (e.g., torch), and a DR object 1300 (e.g., lantern). In some embodiments, the third interactive DR scene 1900 also includes a DR thought-indicative object 1910 simulating a fire pit. In some embodiments, the third interactive DR scene 1900 further includes a plurality of DR third-person-recording objects, such as a DR recordable object 1920-1, a DR recordable object 1920-2, and/or a DR recordable object 1920-3. Each of the DR recordable objects 1920 simulates a kindling or the like. In some embodiments, the third interactive DR scene includes a DR word-recording object, such as a DR recordable object 1930 simulating a bucket.

In some embodiments, the third interactive DR scene includes, additionally or optionally, other DR objects. For instance, in some embodiments, the subject is accompanied by the DR assistant 1100. In some embodiments, the DR object 1300, the DR recordable object 1210 (e.g., candle) and/or the DR recordable object 1220 (e.g., torch) are carried by the subject to the third interactive DR scene or presented to the subject when the subject enters the second interactive DR scene.

Figure 19B:
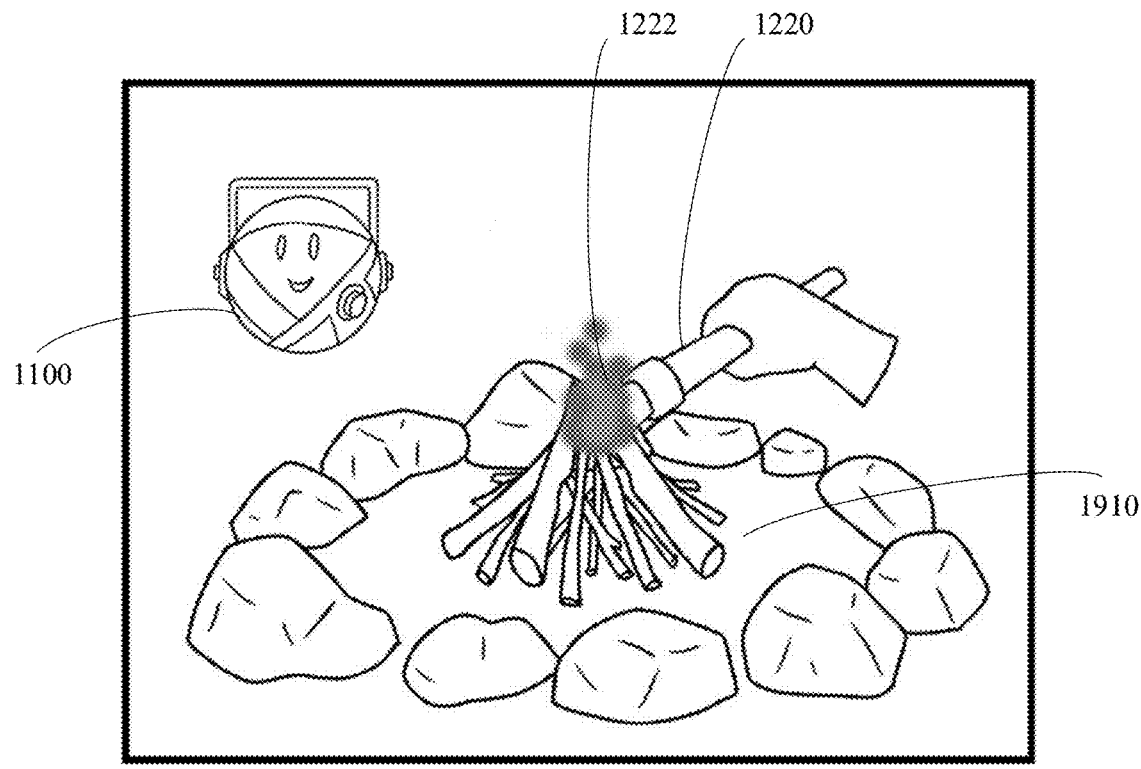
Figure 19C:
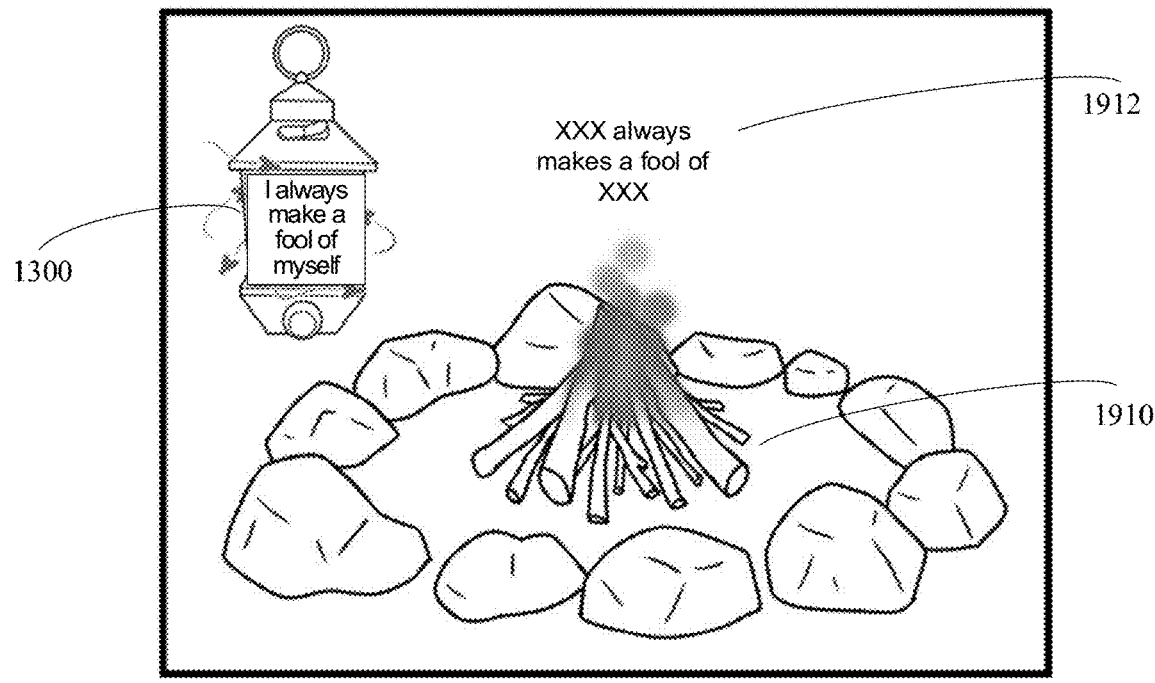

Block 806. Referring to block 806, in some embodiments, the method includes activating the DR thought-indicative object with the first statement of the subject. For instance, as a non-limiting example, FIGS. 19B and 19C illustrates that the subject is allowed to pick up the first statement representing the thought in the DR object (e.g., lantern) using the DR thought-recording object (e.g., torch) and light the DR thought-indicative object (e.g., fire pit) with it. In some embodiments, the activating of the DR thought-indicative object with the first statement of the subject is in response to a movement of the DR thought-recording object (e.g., torch) by the subject from the DR object (e.g., lantern) to the DR thought-indicative object (e.g., fire pit).

Blocks 808-818. Referring to block 808 through block 818, in some embodiments, the method includes generating a plurality of third-person statements to feed the DR thought-indicative object. To do so, in some embodiments, the method includes presenting a third statement at or adjacent to the DR thought-indicative object. In some embodiments, the third statement is the first statement of the subject but presented in a name of a third person. For instance, as a non-limiting example, FIG. 19C illustrates a text 1912, representing the third statement, above the fire. In contrast to the text printed on the DR object (e.g., the text converted from the first statement that represents the thought of the subject), the text that appears over the fire is written in a name of a third-person.

In some embodiments, to generate a plurality of third-person statements to feed the DR thought-indicative object, the method includes (a) detecting a selection by the subject of a respective DR third-person-recording object (e.g., a kindling) in the plurality of DR third-person-recording objects, (b) recording a corresponding third-person statement when the subject speaks to the respective DR third-person-recording object in the name of the third person, and (c) repeating the detecting (a) and the recording (b) until no selection of any DR third-person-recording object in the plurality of DR third-person-recording objects is detected, thereby generating the plurality of third-person statements. In some embodiments, the plurality of third-person statements includes one or more third statements spoken by the subject in the name of the third person. In some embodiments, the plurality of third-person statements also includes one or more fourth statements spoken by the subject in the name of the third person, and each of the one or more fourth statements negate the third statement.

Figure 19D:
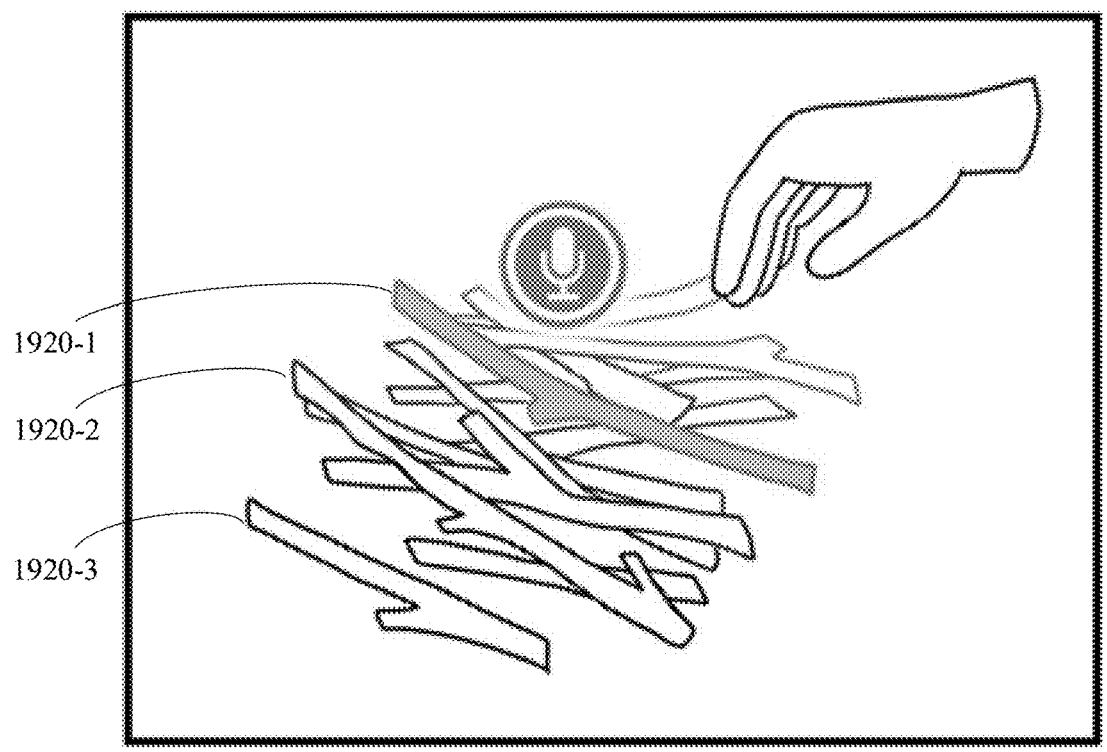
Figure 19E:
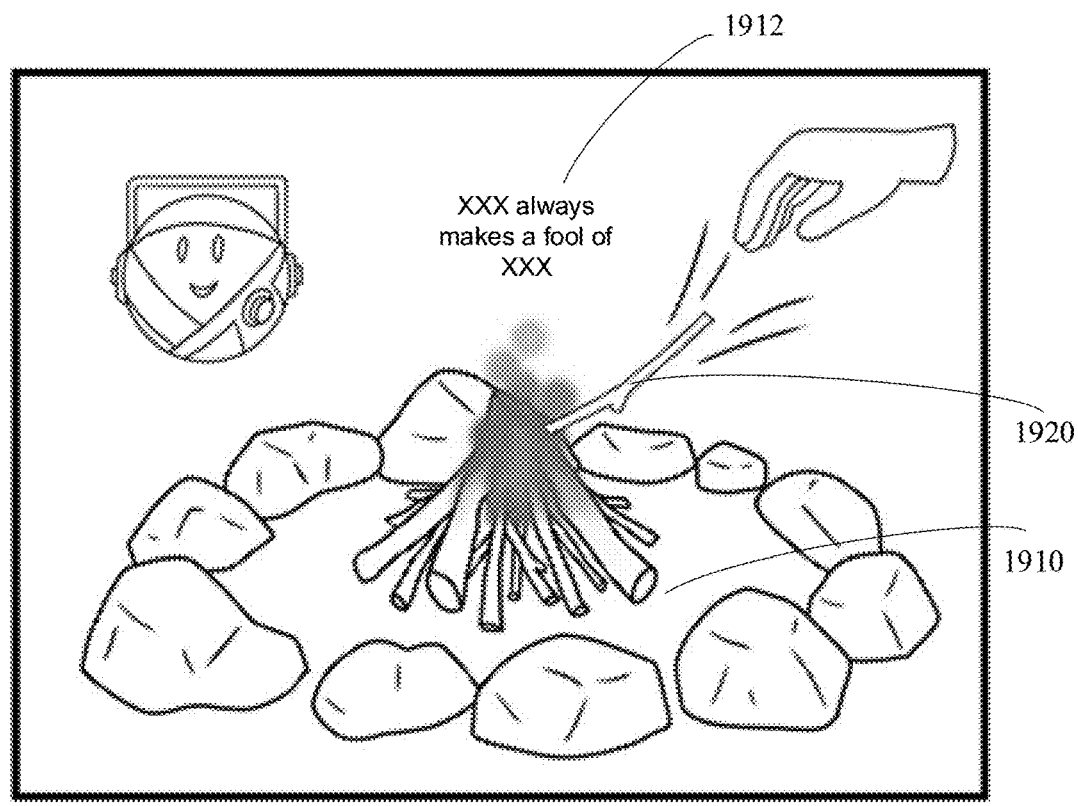

For instance, as a non-limiting example, FIGS. 19D and 19E illustrate that the subject is allowed to reach for a kindling, repeat the thought into it while speaking in the name of the third-person, and throws it into the fire. That is, in some embodiments, instead of using the first-person pronouns, the subject talks about the subject in the name of the third-person. In addition, in some embodiments, the subject is encouraged to get out any other negative thoughts and fears that come up in relation to this thought.

Block 820. Referring to block 820, in some embodiments, additionally or optionally, the method includes playing back the recorded corresponding third-person statement to the subject. In some embodiments, once the subject makes a recording, the recorded audio is played back to the subject. In some embodiments, the playing back is in response to a placement of the respective DR third-person-recording object by the subject at the DR thought-indicative object. For instance, in some embodiments, the recorded audio is played back to the subject when the subject throw the kindling to the first. In some embodiments, each time when the subject makes a recording and/or throws the kindling into the fire, the recorded audio is played back to the subject.

Block 822. Referring to block 822, in some embodiments, additionally or optionally, the method includes providing an explanation to the subject of an effect of generating the plurality of third-person statements. For instance, as a non-limiting example, in some embodiments, the DR assistant or a healthcare professional explains how third-person self-talk creates cognitive distance between the subject and the thoughts of the subject, how creation of cognitive distance can help to reduce the anxiety associated with certain thoughts, how the purpose of this third interactive DR activity is to separate the subject from the thoughts of the subject so that they do not overwhelm the subject, or the like.

Blocks 824-832. Referring to block 824 through block 832, in some embodiments, the method includes generating, by the subject using the DR word-recording object, a DR construct to counter the plurality of third-person statements. To do so, in some embodiments, the method includes instructing the subject to identify (e.g., look for) a single word or phrase that signifies an anxiety response to the plurality of third-person statements. For instance, as a non-limiting example, in some embodiments, after the subject has gotten out any thoughts that the subject needs to, the subject is asked (e.g., by the DR assistant or a healthcare professional, or the like) to identify (e.g., look for) a single word or phrase that evokes the strongest anxious response.

Figure 19F:
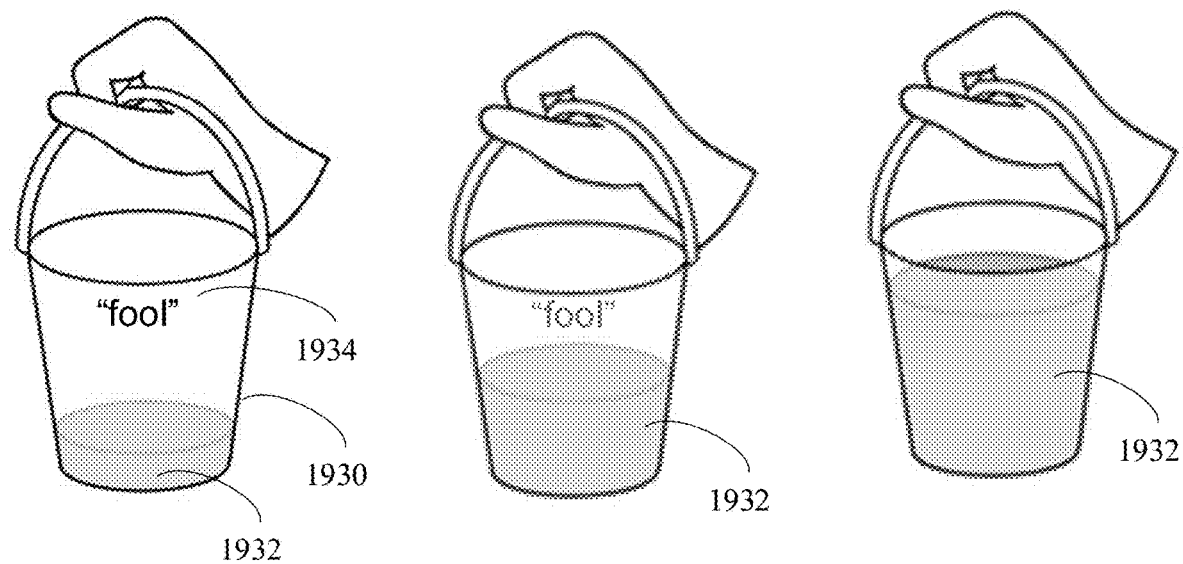
Figure 19G:
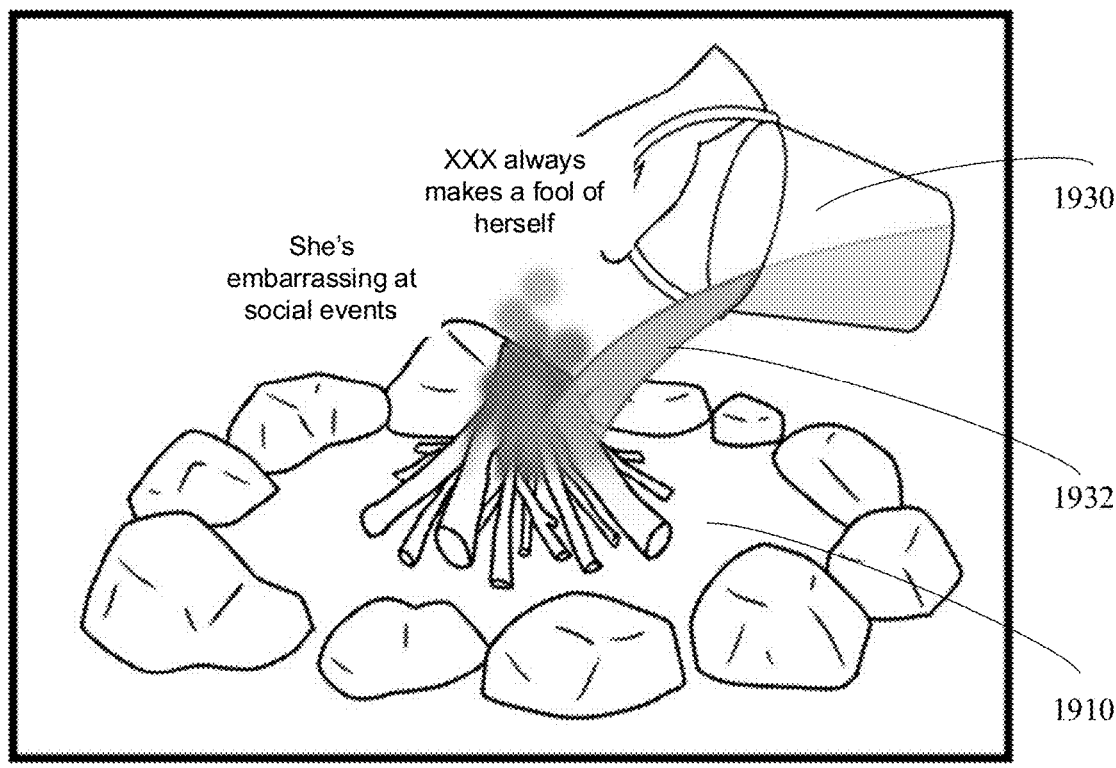

The method also includes presenting, on the display, the DR word-recording object 1930 for the subject to speak the single word or phrase to the DR word-recording object. For instance, as a non-limiting example, FIG. 19F illustrates the DR word-recording object 1930 simulating a bucket being used for the subject to speak the single word or phrase.

In some embodiments, the DR construct is generated in an amount that depends on a number of times the subject speaks the single word or phrase. For instance, in the illustrated embodiment, as the subject speaks the single word or phrase, the DR construct 1932 simulating a liquid (e.g., water) fills the bucket. In some embodiments, the amount of the liquid filling the bucket depends on a number of times the subject speaks the single word or phrase.

Block 834. Referring to block 834, in some embodiments, additionally or optionally, the method includes providing an explanation to the subject of an effect of repeating the single word or phrase. For instance, as a non-limiting example, in some embodiments, the DR assistant or a healthcare professional explains how this activity is a form of "defusion," e.g., when the subject repeats anxiety-inducing words until they lose their intensity, the subject lessens the hold they have on the subject.

Blocks 836-838. Referring to block 836 and block 838, in some embodiments, additionally or optionally, the method includes converting the single word or phrase spoken by the subject into a text and presenting the text at or adjacent the DR word-recording object. For instance, as a non-limiting example, FIG. 19F illustrates that the single word or phrase spoken by the subject is converted into a text 1934 (e.g., "fool") and the text is presented at the bucket.

Block 840. Referring to block 840, in some embodiments, additionally or optionally, the method includes regulating an appearance of the text in accordance with the amount of the DR construct or the number of times the subject speaks the single word or phrase, or any combination thereof. For instance, as a non-limiting example, FIG. 19F illustrates that the subject repeats the single word or phrase into the bucket. In some embodiments, as the number of times the subject speaks the single word or phrase increases, the amount of the DR construct (e.g., water) increases and the appearance of the text (e.g., "fool") becomes dimmer. In some embodiments, when the bucket fills with the DR construct (e.g., water), and the text disappears and is no longer visible. However, the present disclosure is not limited thereto Blocks 844-846. Referring to block 844 and block 846, additionally or optionally, in some embodiments, the method includes detecting a movement of the DR word-recording object by the subject to the DR thought-indicative object. In some embodiments, the method includes regulating the DR thought-indicative object in response to the detecting of the movement of the DR word-recording object by the subject. For instance, as a non-limiting example, FIG. 19 illustrates that the subject discards (e.g., throws away, dumps, etc.) the DR construct (e.g., water) over the fire pit. In response to this detection, in some embodiments, the method extinguishes the fire in the fire pit, e.g., deactivating the DR thought-indicative object, erasing the plurality of third-person statements from the display, or both. However, the present disclosure is not limited thereto.

Blocks 848-854. Referring to block 848 through block 854, in some embodiments, the method includes generating, by the subject using the DR thought-recording object and/or the DR object, an advisory statement that counters the plurality of third-person statements. For instance, in some embodiments, to generate an advisory statement, the method presents, on the display, a third-person avatar associated with the plurality of third-person statements, e.g., presenting a scenario simulating a friend of the subject entering the campsite. In some embodiments, additionally or optionally, the subject is asked (e.g., by the DR assistant or a healthcare professional, or the like) to imagine that the friend is actually the one dealing with the anxious thought(s) and/or fear(s). In some embodiments, additionally or optionally, the subject is asked what advice the subject would give another person going through this.

The method then detects whether or not the subject selects (e.g., picks up) the DR thought-recording object, such as the recordable object 1220 (e.g., torch). In response to the selection by the subject of the DR recordable object, the method records a statement, e.g., the advisory statement, when the subject speaks to the DR recordable object. For instance, as a non-limiting example, FIGS. 19H and 19I illustrate that the subject is allowed to retrieve the recordable object 1220 (e.g., torch) and speak into it. When the subject speaks into it, the indicative feature 1222 (e.g., flame) appears at or adjacent to the recordable object 1220 in a color (e.g., yellow) indicative of the type (e.g., advisory) of the statement.

Block 858. Referring to block 858, in some embodiments, additionally or optionally, the method includes activating the DR thought-indicative object with the advisory statement. For instance, as a non-limiting example, FIGS. 19H and 19I illustrate that the subject is allowed to light the fire pit with the flame. In some embodiments, the first pit is presented with the fire in the same color (e.g., yellow) as the flame of the torch that represents the advisory statement.

Blocks 860-862. Referring to block 860 and block 862, in some embodiments, additionally or optionally, the method includes converting the advisory statement into a seventh text, and presenting the seventh text at or adjacent the DR word-recording object. For instance, as a non-limiting example, FIG. 19I illustrates that a text 1914 converted from the advisory statement appears over the fire or the fire pit.

Blocks 864-866. Referring to block 864 and block 866, in some embodiments, additionally or optionally, the method includes swapping, on the display, a position of the subject with a position of the third-person avatar, and playing back the advisory statement to the subject. For instance, in some embodiments, the subject is asked (e.g., by the DR assistant or a healthcare professional or the like) to imagine that the subject is the friend. In some embodiments, the method allows the subject to swap places with the friend, e.g., allowing the subject to sit in the position of the friend, and looks back at the avatar of the subject on the other side of the fire fit. In some embodiments, the method plays back the advisory statement to the subject, so that the subject hears their own advice repeated back to the subject.

Block 868. Referring to block 868, in some embodiments, the method includes determining if the subject satisfies the threshold sentiment condition based at least in part on the advisory statement. For instance, in some embodiments, the subject is generally considered not satisfying the threshold sentiment condition if the statement spoken to the DR thought-recording object (e.g., the recordable object 1220 simulating a torch) by the subject could not considered as an advice (either to the subject or to a third person). In some embodiments, even though an advisory statement is generated, the subject is considered not satisfying the threshold sentiment condition if the subject, a healthcare professional associated with the subject, the method, physiological measurements, or any combination thereof indicate that that subject is not ready to reframe the thought.

2.8. Providing an Educational DR Interactive Scene

Referring to FIGS. 9A-9F, there is depicted a flowchart illustrating exemplary processes for providing an educational DR interactive scene to educate the subject. In some embodiments, the educational DR interactive scene includes one or more psychoeducational videos to introduce one or more tools, concepts, mechanics, techniques, or the like to the subject. In various embodiments, the one or more tools, concepts, mechanics, techniques, or the like introduced in this educational DR interactive scene become a part of a method for reframing thoughts discussed herein.

Block 904. Referring to block 904, in some embodiments, the method includes presenting, on the display, a DR assistant within the first interactive DR scene to greet the subject when the subject enters the first interactive DR scene. For instance, as a non-limiting example, FIG. 14 illustrates that the DR assistant 1100 greets the subject when the subject enters the interactive DR scene 1400 simulating a woods of wisdom.

Figure 20A:
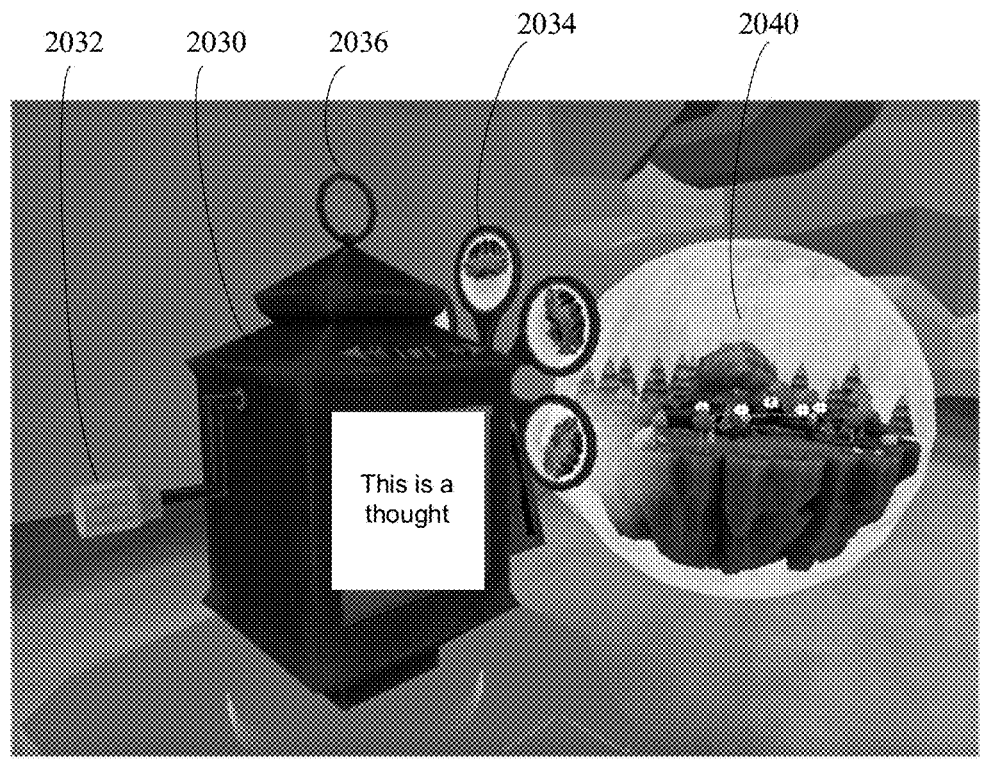
FIGS. 20A, 20B, 20C, 20D, 20E, 20F, and 20G illustrate an activity configured for a subject to learn how to label anxious thoughts, in accordance with some embodiments of the present disclosure.
Figure 20B:
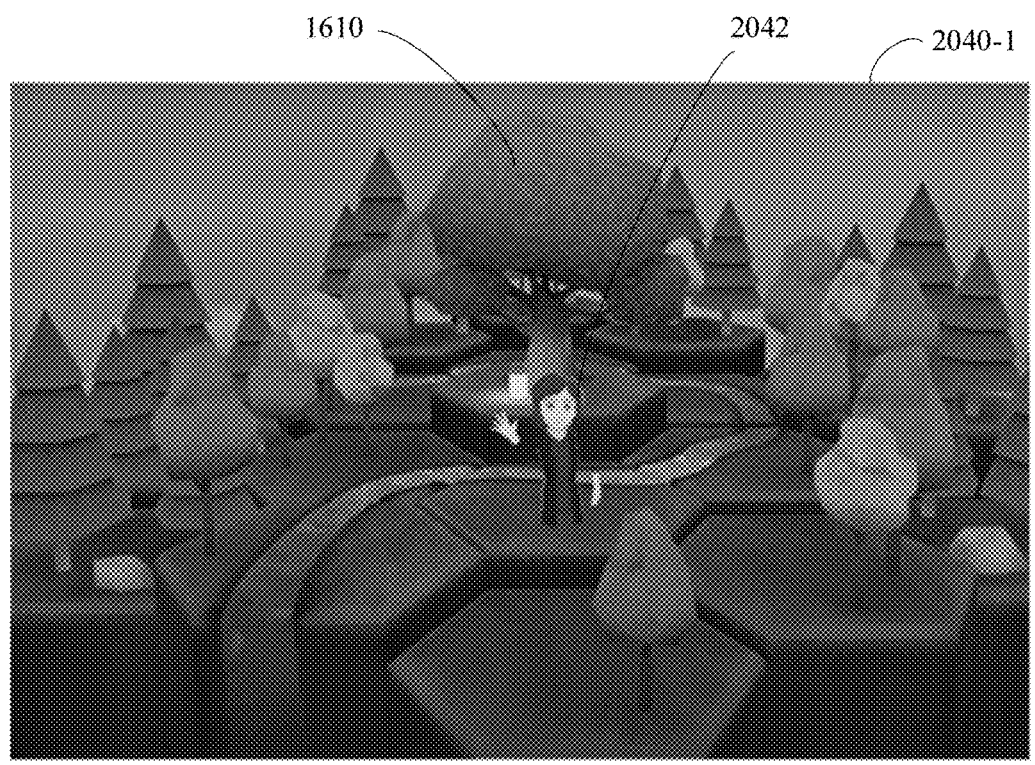
Figure 20C:
Figure 20D:
Figure 20E:
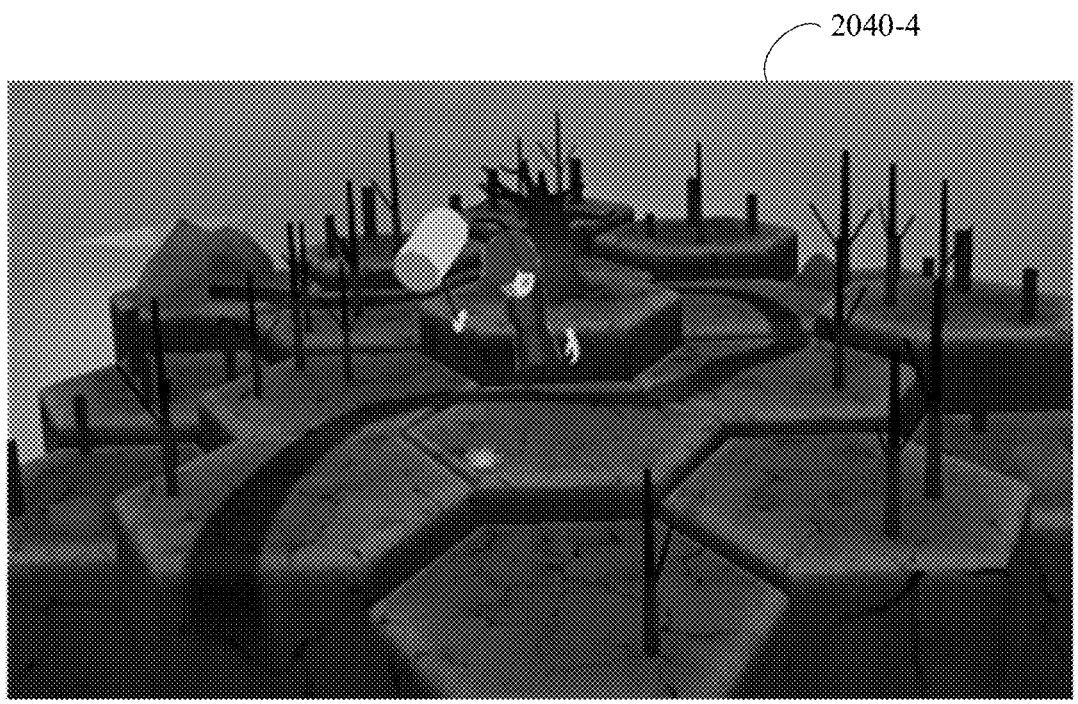
Figure 20F:
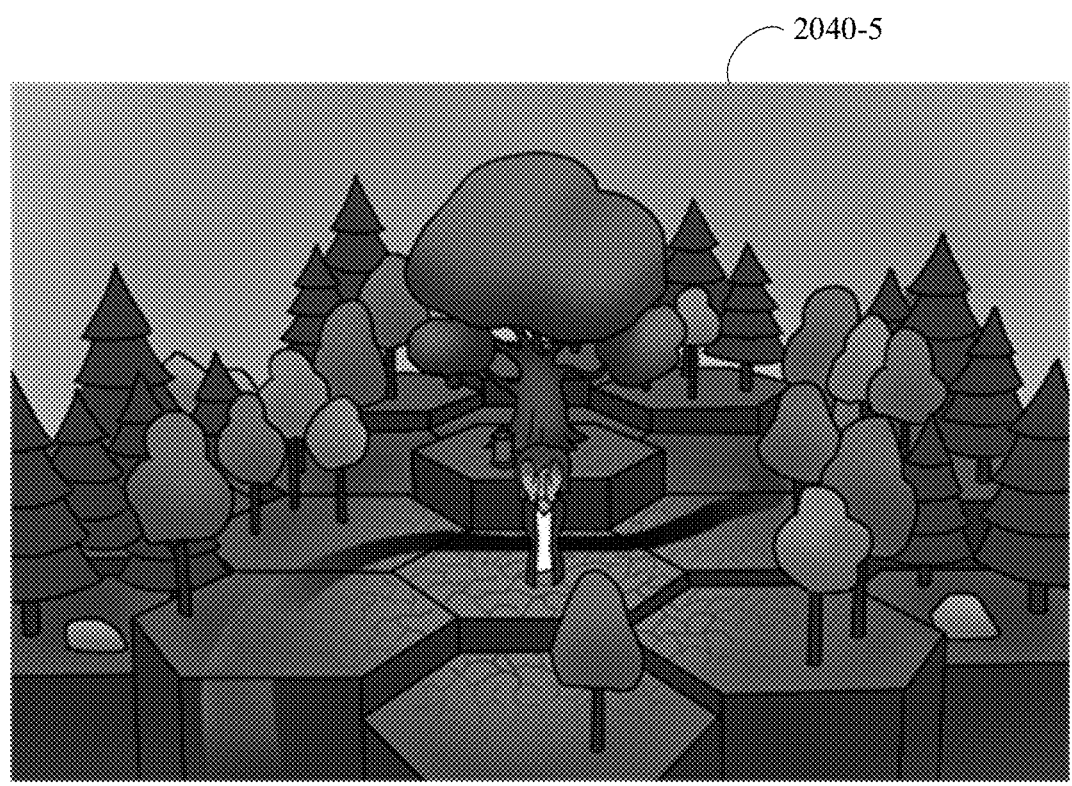
Figure 20G:
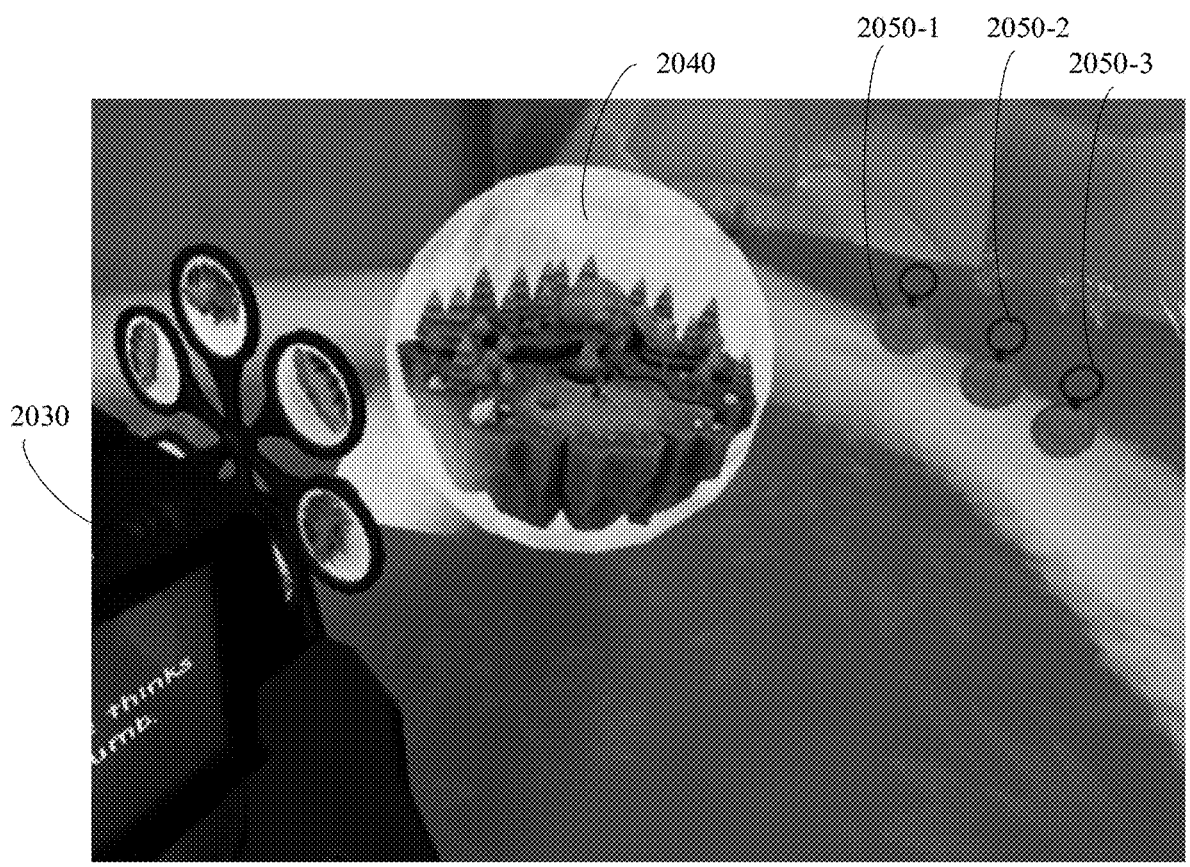

Blocks 906-908. Referring to block 906 and block 908, in some embodiments, the method includes guiding the subject to learn how to associate emotions and/or behaviors with anxious thoughts or triggering events. To do so, in some embodiments, the method presents on the display a DR educational-vessel object, e.g., a DR object 1300 with a plurality of prestored statements. In some embodiments, the DR educational-vessel object is presented in any interactive DR scene, including but not limited to the interactive DR scene 1000 or the interactive DR scene 1400. Preferably, the DR educational-vessel object is presented at a designated site within the interactive DR scene 1400. For instance, as a non-limiting example, FIG. 20G illustrates a DR educational-vessel object 1300 presented at a designated site 1302 in the interactive DR scene 1400.

Referring to FIGS. 13D-13G, in some embodiments, the DR educational-vessel object is rendered indicative of an anxious thought (e.g., with light in a color indicative of an anxious thought) when the subject arrives at the first designated site. In some embodiments, the DR educational-vessel object is rendered with a text of an anxious thought shown at or adjacent the DR educational-vessel object when the subject arrives at the first designated site (e.g., the text is printed on the front of a lantern).

In some embodiments, the DR educational-vessel object includes a selection feature, such as the feature 1350. In some embodiments, the section feature is configured to allow the subject to browse through a plurality of prestored statements until the subject finds a prestored statement that relates to a recent thought of the subject. In some embodiments, the DR educational-vessel object can contain (e.g., being linked to or associated with) any suitable number of prestored statements representing common anxious thoughts. For instance, in some embodiments, the DR educational-vessel object includes one, two, three, four, five, six, seven, eight, nine, ten, more than ten, more than fifteen, or more than twenty prestored statements. In some embodiments, the selection feature can simulate any suitable real or nonreal, existent or nonexistent feature, such as one or more DR flippers, one or more DR switches, one or more DR buttons, one or more DR arrows, one or more DR wheels, one or more DR lenses, one or more locks, one or more DR knobs, or the like, or any combination thereof. In some embodiments, the DR educational-vessel object also includes a thought-impact feature, such as the feature 1330 simulating a dimmer, to assign a level of impact of the recent thought on the subject.

Blocks 910-914. Referring to block 910 through block 914, to guide the subject to learn how to associate emotions and/or behaviors with anxious thoughts or triggering events, in some embodiments, additionally or optionally, the method includes asking, by the DR assistant and prior to the subject selecting any prestored statement in the plurality of prestored statements, the subject to consider a recent anxious situation and to recall any thoughts that came up responsive to recalling the recent anxious situation. For instance, in some embodiments, the subject is asked (e.g., by the DR assistant or a healthcare professional or the like) to think of a situation that recently made the subject anxious, and/or to recall what a thought or thoughts this event brought up. In some embodiments, the subject then is allowed to browse through different thoughts in the DR educational-vessel object using the selection feature.

In some embodiments, additionally or optionally, the method includes presenting, on the display, a tenth text of a corresponding prestored statement in the plurality of prestored statements at or adjacent the DR educational-vessel object while the subject browses through the plurality of prestored statements. For instance, as a non-limiting example, FIGS. 13D and 13E illustrate a text of the second prestored statement and a text of the sixth prestored statement, respectively, in the total eight prestored statements while the subject browses through the presented statements.

In some embodiments, additionally or optionally, the method includes detecting an action performed by the subject on the DR selection feature. For instance, as a non-limiting example, the method detects when the subject stops the action on the DR selection feature. In some embodiments, the prestored statement when the subject stops represents the thought that the subject finds related to a thought(s) of the subject. As a non-limiting example, FIG. 20E illustrates that the sixth prestored statement is what the subject finds related to the thought(s) of the subject.

In some embodiments, the subject is asked to think how much the thought impacts the subject. In some embodiments, the subject is asked through an assessment of the digital reality system 200. In some embodiments, the subject is allowed to use the feature 1330 (e.g., dimmer) to assign the level of impact. In some embodiments, the stronger the impact the thought has on the subject, the brighter the light in the DR educational-vessel object becomes. For instance, as a non-limiting example, FIG. 3F illustrates three different levels. While three different levels are illustrated, it should be noted that the number of the impact level can be two, more than three, more than four, more than five, or more than six. In some embodiments, when the feature 1330 is held on a position, a text, such as "Minimal," "Moderate," "Strong" or the like, will be presented on the display at or adjacent to the DR educational-vessel object.

Block 918. Referring to block 918, in some embodiments, to guide the subject to learn how to associate emotions and/or behaviors with anxious thoughts or triggering events, the method also includes presenting, on the display, a second designated site within the first interactive DR scene. In some embodiments, the second designed site includes a plurality of words or phrases for the subject to select. For instance, as a non-limiting example, FIGS. 15A-15D illustrates a designated site 1502 in the interactive DR scene 1400. In some embodiments, the designated site 1502 includes a plurality of words or phrases, such as a word or phrase 1520-1 and a word or phrase 1520-2.

Figure 15A:
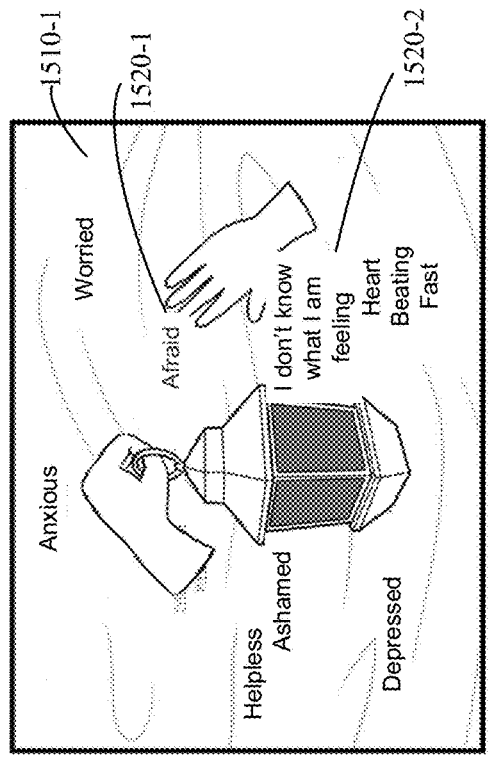
FIGS. 15A, 15B, 15C, and 15D collectively illustrate an activity configured for a subject to learn how to link one or more emotions and/or one or more behaviors to a thought, in accordance with some embodiments of the present disclosure.

In some embodiments, the method allows the subject to carry the DR educational-vessel object and follow the DR assistant to the designated site 1502. In some embodiments, the designated site 1502 can simulate any suitable real or nonreal, existent or nonexistent site. For instance, as a non-limiting example, the designated site 1502 can simulate a spacious area with one or more DR structure objects for presenting the plurality of words or phrases 1520. Examples of the one or more DR structure objects include, but are not limited to hill(s), waterfall(s), tree(s), wall(s), partition(s), palisade(s), stream(s), or the like. By way of example, FIG. 15A illustrates a DR structure object 1510.

Block 920. Referring to block 920, in some embodiments, to guide the subject to learn how to associate emotions and/or behaviors with anxious thoughts or triggering events, the method additionally or optionally includes asking, by the DR assistant and prior to the subject selecting any word or phrase, the subject what the subject felt and/or did at the time when the recent thought came up. For instance, as a non-limiting example, in some embodiments, the DR assistant asks the subject to hold up the DR educational-vessel object (e.g., lantern) to the one or more DR structure object and ask the subject when the situation occurred and the subject had this thought, how it made the subject feel. In some embodiments, the method allows the subject to use the light of the DR educational-vessel object (e.g., lantern) to illuminate the words or phrases on the one or more DR structure objects. In some embodiments, the method allows the subject to select any word(s) or phrase(s) by touching them. In some embodiments, any word(s) or phrase(s) selected by the subject stay illuminated. In some embodiments, the others fade out when the DR educational-vessel object (e.g., lantern) is no longer near them.

Figure 15B:
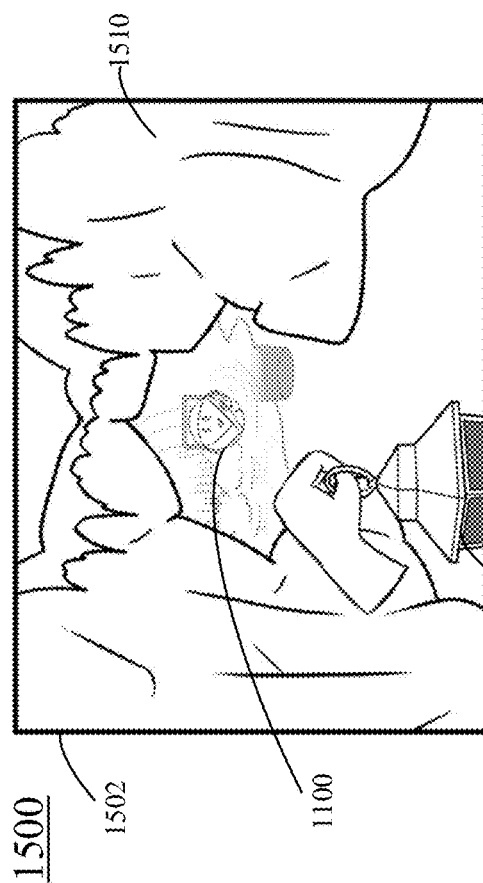
Figure 15C:
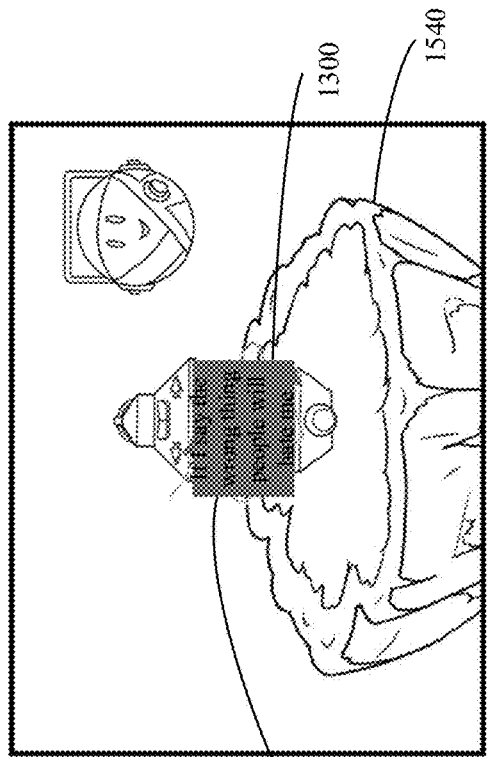
Figure 15D:
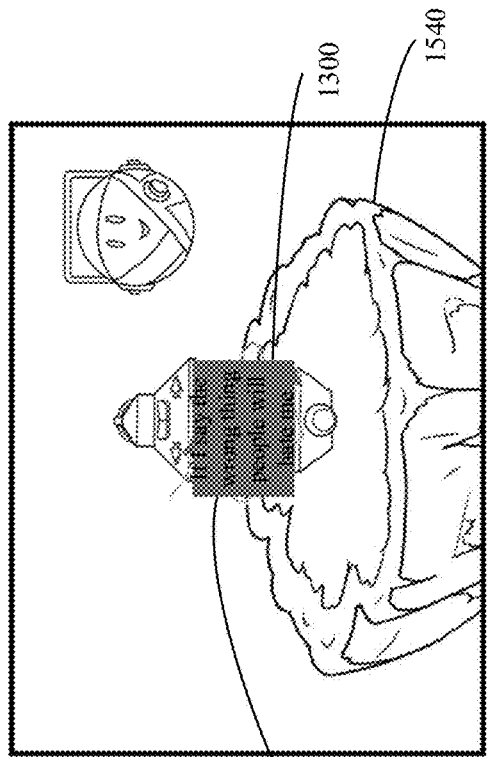

In some embodiments, additionally or optionally, the method allows the subject to follow the DR assistant to a different section of the one or more DR structure object. In some embodiments, the DR assistant asks the subject what the subject did when the situation occurred or when the subject had the thought. In some embodiments, the method allows the subject to repeat the activity and select word(s) or phrase(s) by touching them. For instance, as a non-limiting example, FIGS. 15B and 15C illustrates two different sections, e.g., a section 1510-1 and a second 1510-2, of the DR structure object 1510. In some embodiments, the subject can perform the activity in the section 1510-1 and then in the section 1510-2, or vice versa.

Block 922. Referring to block 922, in some embodiments, additionally or optionally, the method includes transforming a word or phrase selected by the subject into one or more DR animated creatures that surrounds the DR educational-vessel object. In some embodiments, the one or more DR animated creatures simulates one or more insects (e.g., bees, beetles katydids, grasshoppers, crickets, cicadas or the like) that buzz around the DR educational-vessel object. In some embodiments, the transformation of a word or phrase can occur in any suitable place within the first interactive DR scene, e.g., the interactive DR scene simulating the woods of wisdom. For instance, as a non-limiting example, in some embodiments, the second designated site includes a DR object 1540 simulating a pedestal or the like. After selection of the word(s) or phrase(s) is completed, the method allows the subject to place down the DR educational-vessel object on the DR object 1540. This causes the selected word(s) or phrase(s) float off of the one or more DR structure objects toward the subject. As the selected word(s) or phrase(s) approaches the DR educational-vessel object, the selected word(s) or phrase(s) shrinks, circles around the DR educational-vessel object, and/or turns into one or more insects.

Block 924. Referring to block 924, in some embodiments, the method includes describing, by the DR assistant, how thoughts, emotions, and/or behaviors are connected. For instance, in some embodiments, the DR assistant explains the relationship between thoughts, feelings, and behaviors (e.g., the cognitive triangle), how becoming more in tune with how thoughts, emotions, and behaviors are connected is one of the first steps to cognitive reframing, or the like. More specifically, the DR assistant explains how thoughts change the way that people feel, which subsequently changes the way that people act, which then influences people's thoughts. Without intervention, the process continues to repeat.

Blocks 926-928. Referring to block 926 and block 928, in some embodiments, the method includes guiding the subject to learn how to label anxious thoughts. Labelling activity helps the subject to start thinking about the fact that the thoughts of the subject are possibly distorted, inaccurate, or useful. Currently, the science appears to show that it is questionable if it matters how much a subject selects the perfect label for a thought. Accordingly, in some embodiments, the method allows a subject to move on even if the subject does not get the label right. However, the concept of having a number of different types of anxious thoughts or cognitive distortions to place the thoughts into helps the subject, even if the subject selects the wrong label. In some embodiments, the labelling activity helps the subject to notice the thoughts of the subject in the real world (e.g., raises awareness to the thinking patterns). If a subject does not recognize that the thoughts of the subject are untrue, it is difficult to reframe the thought.

Accordingly, in some embodiments, the method includes introducing, by the DR assistant, a plurality of types of anxious thoughts or cognitive distortions. For instance, in some embodiments, the DR assistant talks about how anxious thoughts can fall into different categories. Examples of anxious thought categories include, but are not limited to, a first catastrophizing category, a second all-or-nothing-thinking category, a third disqualifying the positive category, a fourth personalization and blame category, a fifth mind reading category, or a combination thereof. In some embodiments, catastrophizing is a way of thinking that assumes the worst for a reaction or outcome, or jumps to a conclusion. In some embodiments, all-or-nothing-thinking is a way of thinking that views everything in a binary state (e.g., black and white) with other states (e.g., no middle ground, no grey area, etc.). In some embodiments, disqualifying the positive is a way of thinking that diminishes one's accomplishments and focuses solely on the negative. In some embodiments, personalization and blame includes internalizing thoughts instead of speaking statements, and/or assigning blame entirely to oneself (e.g., to the subject) or others, regardless of other factors. In some embodiments, mind reading is a form of jumping to conclusions that involves assuming what someone else is thinking without having much evidence for the subject to base the assumption therefrom.

Block 932. Referring to block 932, in some embodiments, to guide the subject to learn how to label anxious thoughts, the method includes presenting, on the display, a DR miniature environment and a DR type-selection object. In some embodiments, the DR miniature environment includes (i) a miniature version of the DR wellbeing object and its surrounding environment, and a miniature version of an avatar of the subject. For instance, as a non-limiting example, FIGS. 20A and 20B illustrate a DR type-selection object 2030 simulating a projector and a DR miniature environment 2040 projected from the DR type-selection object 2030. Displayed initially in the DR miniature environment are a miniature version of the DR wellbeing object 1610 (e.g., the wisdom tree) and its surrounding environment.

In some embodiments, a small version of the avatar of the subject is also displayed. In some embodiments, the small version of the avatar of the subject can be displayed in any suitable places within the DR miniature environment. As a non-limiting example, FIG. 20B illustrates the small version of the avatar of the subject 2042 displayed at or near a center of the DR miniature environment. In some embodiments, the DR miniature environment is rendered with some hexagonal tiles, reminiscent of those used in the DR journey object.

It should be noted that the term "miniature," "small version" or the like is used to differentiate an object in a DR scene from the same object rendered in another DR scene, to differentiate an object in a portion of a DR scene from the same object rendered in another portion of the same DR scene, to differentiate an object from its surroundings, or the like. A miniature object or a small version of an object can be, but do not necessarily have to be, always small in size when displayed. For instance, in some embodiments, if a closer look is desirable or beneficial, the DR miniature environment or a portion of it is enlarged or even rendered over the entire display.

Blocks 934-936. Referring to block 934 and block 936, in some embodiments, the method includes detecting a selection of a respective type in the plurality of types of anxious thoughts or cognitive distortions by the subject using the DR type-selection object, and replacing, on the display, the DR miniature environment with a corresponding distortion miniature environment indicative of the respective type in the plurality of types of anxious thoughts or cognitive distortions. For instance, as a non-limiting example, FIG. 20A illustrates that the DR type-selection object 2030 includes a flywheel with a feature 2032 simulating a handle and a plurality of features 2034 each simulating a lens. In some embodiments, the subject is allowed to rotate, for instance, using the handle, the plurality of lenses and align any one of them in a DR optical path to simulate a selection of a respective type of an anxious thought or cognitive distortion. In some embodiments, a body portion of the DR type-selection object 2030 simulates or resembles a DR object.

In some embodiments, in response to an alignment of a lens simulating a selection of a respective type of an anxious thought or cognitive distortion, the DR miniature environment is replaced with a corresponding distortion miniature environment indicative of the respective type in the plurality of types of anxious thoughts or cognitive distortions. In some embodiments, animation of the miniature avatar also changes depending on the type of anxious thoughts the user is learning about.

For instance, as a non-limiting example, FIG. 20B illustrates an initial miniature environment 2040-1. In response to the selection of the catastrophizing category, the DR miniature environment changes to a fiery hellscape and in certain embodiments, with the miniature avatar running frantically. A non-limiting example of such a DR miniature environment is illustrated in FIG. 20C. As another non-limiting example, in response to the selection of the all-or-nothing-thinking category, the DR miniature environment changes a landscape split in half, with one half lush and vibrant, the other desolate and in certain embodiments, with the miniature avatar floating back and forth between the two. A non-limiting example of such a DR miniature environment is illustrated in FIG. 20D. As a further non-limiting example, in response to the selection of the disqualifying the positive category, the DR miniature environment changes to a desolate environment, and in certain embodiments, with a single flow emerges from the ground, which the miniature avatar crushes again and again. A non-limiting example of such a DR miniature environment is illustrated in FIG. 20E. As another further non-limiting example, in response to the selection of personalization and blame category, the DR miniature environment changes to an environment that is mostly normal aside from a small patch surrounding the miniature avatar, and in certain embodiments, the miniature avatar has its head in its hands. A non-limiting example of such a DR miniature environment is illustrated in FIG. 20F.

Referring to FIG. 20G, in some embodiments, additionally or optionally, the method includes presenting, on the display, a plurality of DR tag objects, e.g., a DR tag object 2050-1, a DR tag object 2050-2 and a DR tag object 2050-3, adjacent to the DR miniature environment 2040. In some embodiments, the plurality of DR tag objects represents a plurality of labels for the plurality of types of anxious thoughts or cognitive distortions. In some embodiments, the number of the plurality of DR tag objects can be the same as or different from the number of the plurality of types of anxious thoughts or cognitive distortions. In some embodiments, the number of the plurality of DR tag objects can be three, four, five, six, seven, eight, nine, ten, more than ten, or more than twenty.

In some embodiments, the subject is asked, for instance, by the DR assistant, to select a DR tag object to label a thought. In response to the selection by the subject, the DR assistant will let the subject know whether the selected DR tag object is a correct or incorrect label for the thought. In some embodiments, the subject is asked to select a DR tag object and place it on the DR type-selection object 2030, e.g., a DR hook feature 2036 of the DR type-selection object 2030. In response to the placement of the selected DR tag object by the subject, the DR assistant will let the subject know whether the selected DR tag object is a correct or incorrect label for the thought.

Figure 20H:
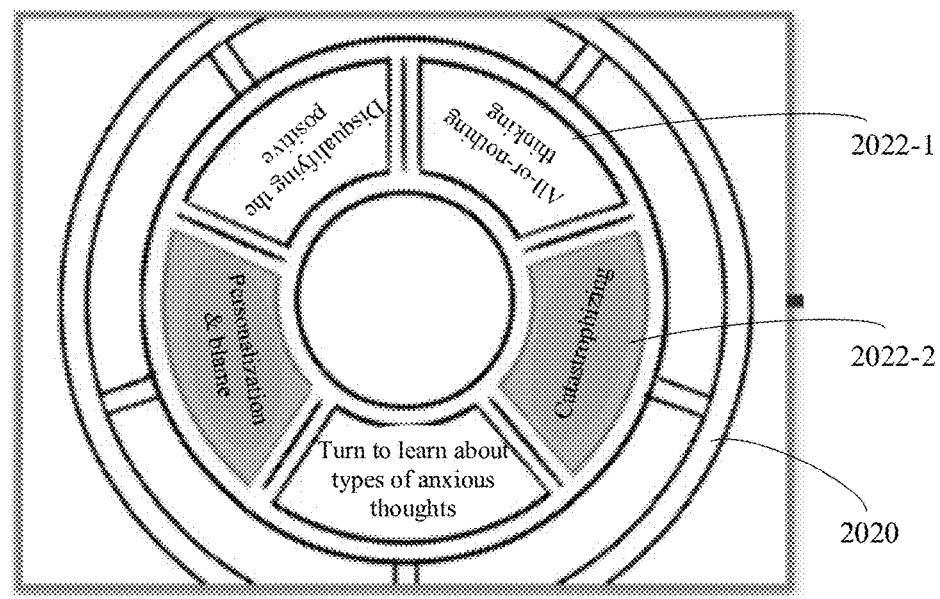

While FIG. 20A illustrates a DR type-selection object 2030 simulating a projector and a DR miniature environment 2040 projected from the DR type-selection object 2030, it should be noted that this is by way of example and is non-limiting. In some embodiments, the DR type-selection object can be rendered to simulate any suitable real or nonreal, existent or non-existent object. For instance, the DR type-selection object can be rendered to simulate a table, a pedestal, a wheel, or the like with a DR miniature environment on top of it. In some embodiments, the table, pedestal, wheel, or the like can include buttons, tiles, or the like for a subject to select and learn any type of different anxious thoughts or cognitive distortions. As a non-limiting example, in some embodiments, FIG. 20H illustrates a DR object 2020 configured for a subject to select and learn any type, e.g., a type 2022-1 or a type 2022-2, of different anxious thoughts or cognitive distortions. In some embodiments, the DR object 2020 can be used along with or without the DR type-selection object 2030 simulating a projector. For instance, the DR object 2020 can be used for a subject to select any type of anxious thoughts or cognitive distortions. In some embodiments, the selection by the subject on the DR object 2020 then causes the presentation of a corresponding distortion miniature environment on the display, directly (e.g., no need of a projector) or indirectly (e.g., through the projector).

Block 938. Referring to block 938, in some embodiments, the method also includes repeating the detecting of a selection of a respective type in the plurality of types of anxious thoughts or cognitive distortions and the replacing of the DR miniature environment with a corresponding distortion miniature environment. For instance, in some embodiments the method includes the repeating until no selection of any type in the plurality of types of anxious thoughts or cognitive distortions is detected. For instance, in some embodiments, after the subject has selected and learnt a first type (e.g., catastrophizing category) of anxious thoughts or cognitive distortions, the subject is allowed to select and learn a second type (e.g., all-or-nothing-thinking category, disqualifying the positive category, personalization and blame category, or mind reading category) of anxious thoughts or cognitive distortions. However, the present disclosure is not limited thereto. In various embodiments, the subject is allowed to select and learn different categories in any suitable orders that the subject prefers and as many times as the subject desires.

Block 940. Referring to block 940, in some embodiments, additionally or optionally, the method includes allowing the subject to select one or more types in the plurality of types of anxious thoughts or cognitive distortions that apply to the recent thought. For instance, in some embodiments, the subject is allowed to select any number (e.g., one, two, three, or more) of types in the plurality of types of anxious thoughts or cognitive distortions that the subject thinks apply to the recent thought represented by the prestored statement in the DR educational-vessel object selected by the subject.

Block 944. Referring to block 944, in some embodiments, additionally or optionally, the method includes presenting one or more labels indicative of the selected one or more types that apply to the recent thought on the DR educational-vessel object. In some embodiments, a label can be a text, a symbol, a picture, or the like. For instance, as a non-limiting example, suppose that the subject selects the catastrophizing category, a label (e.g., a text such as "Catastrophizing" or the like) indicative of the catastrophizing category will be displayed on the DR educational-vessel object (e.g., printed on the front of the DR educational-vessel object). In some embodiments, the label is displayed along with the text of the prestored statement in the DR educational-vessel object selected by the subject. In some embodiments, the label is displayed (e.g., printed) below the text of the selected prestored statement on the front of the DR educational-vessel object.

Block 946. Referring to block 946, in some embodiments, additionally or optionally, the method includes repeating the allowing of the subject to select one or more types in the plurality of types of anxious thoughts or cognitive distortions that apply to the recent thought for a predetermined number of times or as the subject desires. In some embodiments, the predetermined number of times can be set by the method, an administrator, a healthcare professional, or any combination thereof. In some embodiments, the predetermined number of times is more than one, more than two, more than three, more than four, more than five, more than six, more than seven, more than eight, more than nine, or more than ten times. In some embodiments, the predetermined number of times is at most one, at most two, at most three, at most four, at most five, at most six, at most seven, at most eight, at most nine, or at most ten times.

In some embodiments, the subject is allowed or encouraged to practice selecting one or more types in the plurality of types of anxious thoughts or cognitive distortions that apply to other thoughts represented by the prestored statements in the DR educational-vessel object. For instance, suppose that the subject has selected the sixth prestored statement, the subject is allowed or encouraged to practice selecting one or more types in the plurality of types of anxious thoughts or cognitive distortions that apply to any other (e.g., the first, second, third, or the like) prestored statement in the DR educational-vessel object.

Block 948. Referring to block 948, in some embodiments, additionally or optionally, the method includes highlighting the type or types in the plurality of types of anxious thoughts or cognitive distortions that have been selected the most by the subject. In some embodiments, this is achieved using audio and/or visual effects, or the like. For instance, as a non-limiting example, the highlighting of the type(s) selected the most by the subject is done by (i) presenting the label(s) of the type(s) selected the most by the subject on the display (e.g., on the DR educational-vessel object), (ii) highlighting the lens of the DR type-selection object 2030 simulating a projector corresponding to the type(s) selected the most by the subject, (iii) displaying the DR miniature environment(s) corresponding to the type(s) selected the most by the subject, (iv) announcing, for instance, by the DR assistant, the type(s) selected the most by the subject, (v) the label(s) of the type(s) selected the most by the subject on the DR object 2020, or (vi) any combination thereof.

Block 950. Referring to block 950, in some embodiments, additionally or optionally, the method includes determining if the types selected by the subject exhibit a predetermined thinking pattern. For instance, in some embodiments, after the subject has practiced selecting one or more types in the plurality of types of anxious thoughts or cognitive distortions that apply to the recent thought for a predetermined number of times or as the subject desires, and/or selecting one or more types in the plurality of types of anxious thoughts or cognitive distortions that apply to other thoughts represented by the prestored statements in the DR educational-vessel object, the method determines whether the types selected by the subject exhibit a predetermined thinking pattern, such as catastrophizing, all-or-nothing-thinking, disqualifying the positive, personalization and blame, mind reading, overgeneralization, mental filtering, jumping to conclusions, emotional reasoning, or the like.

Block 952. Referring to block 952, in some embodiments, the method includes guiding the subject to learn how to record thoughts (e.g., statements representing thoughts). In particular, the method guides the subject to learn how to record thoughts using a DR thought-recording object, such as the DR recordable object 1210 (e.g., candle) or the DR recordable object 1220 (e.g., torch), and a DR object 1300, which is sometimes referred to as a DR educational-vessel object due to its use for the training purpose. However, it should be noted that this DR object 1300 can contain any number of prestored statements, or do not contain any prestored statement at all. It should also be noted that a thought or thoughts can also be inputted through a client application, such as the client application 2100 illustrated in FIGS. 21A-21C.

In some embodiments, guiding the subject to learn how to record thoughts is conducted in any interactive DR scene. For instance, guiding the subject can be conducted in the interactive DR scene 1000 simulating a lake house or in the interactive DR scene 1400 simulating a woods of wisdom. In some embodiments, a subject is allowed to choose where to learn how to record thoughts. In various embodiments, the DR assistant walks the subject through the steps of recording both anxious thoughts and positive thoughts (or affirmations).

Block 954. Referring to block 954, in some embodiments, to guide the subject to learn how to record thoughts, the method includes presenting, on the display, a journal menu object. Examples of a journal menu object include, but are not limited to, the DR journey object 1022 or a part of it illustrated in FIG. 10D, the DR journey object or a part of it disclosed in U.S. Provisional Patent Application No. 63/223,871 filed Jul. 20, 2021, U.S. Provisional Patent Application No. 63/284,862 filed Dec. 1, 2021, and U.S. patent application Ser. No. 17/869,670 filed Jul. 20, 2022, each of which is hereby incorporated by reference in its entirety for all purposes. In some embodiments, the journal menu object includes a recording feature (e.g., DR recording object). In some embodiments, the recording feature can simulate a button, a switch, a knob, a key, a controller, a label (e.g., a text such as "Record a Thought"), or the like. In some embodiments, the DR assistant prompts the subject to open a journal menu and selects the recording feature.

Blocks 956-960. Referring to block 956 and block 960, in some embodiments, to guide the subject to learn how to record thoughts, the method includes detecting a selection of the recording feature by the subject, and presenting, on the display, a DR educational-vessel object and a DR thought-recording object. For instance, in some embodiments, when a selection of the recording feature by the subject is selected, the method presents on the display a DR object 1300 (with or without prestored statements) and the DR thought-recording object such as the DR recordable object 1210 (e.g., candle) or the DR recordable object 1220 (e.g., torch).

In some embodiments, the method also presents, on the display, a portal object configured to simulate bringing the DR educational-vessel object and DR thought-recording object into the display or takes the subject to where the DR educational-vessel object and DR thought-recording object are located. For instance, in some embodiments, after the subject selects the recording feature, the journal menu object closes or disappears, and the portal object appears. In some embodiments, the DR educational-vessel object and DR thought-recording object fly out of the portal object. In some embodiments, the portal object can simulate a swirl, a wind, a door, a window, a gateway, an entrance, an exit, or the like. In some embodiments, the portal object disappears once the DR educational-vessel object and DR thought-recording object has flown out of the portion object.

Blocks 962-966. Referring to block 962 through 966, in some embodiments, the method includes recording a training statement representing a thought. In some embodiments, the recording is performed when the subject places the DR thought-recording object adjacent to the mouth of the subject (the avatar of the subject) and stopping recording when the subject puts the DR thought-recording object away from the mouth of the subject.

For instance, as a non-limiting example, in some embodiments, the subject is allowed to use a selection feature, such as the feature 1310, to signal whether the subject is about to record an anxious or a positive thought. In certain embodiments, the subject is asked, for instance, by the DR assistant, to use the selection feature to signal whether the subject is about to record an anxious or a positive thought. In some embodiments, once the selection is made, the subject is allowed to grab the DR thought-recording object, such as the DR recordable object 1210 (e.g., candle) or the DR recordable object 1220 (e.g., torch), and record a statement representing the thought of the subject into it.

In some embodiments, additionally or optionally, the method includes converting the recorded training statement into an eleventh text, and presenting, on the display, the DR thought-recording object, the eleventh text at or adjacent to the DR thought-recording object, and/or a thought-category feature, such as the feature 1222 (e.g., flame), at or adjacent to the DR thought-recording object. In some embodiments, the thought-category feature indicates a corresponding category, in a plurality of categories, associate with the recorded training statement.

For instance, as a non-limiting example, in some embodiments, the thought-category feature (e.g., flame) appears over the DR thought-recording object (e.g., torch or candle) with the text converted from the recorded training statement appears above the thought-category feature (e.g., flame). In some embodiments, the thought-category feature is presented in a color indicative of the type/category of the thought. For instance, in some embodiments, if the subject selects to record an anxious thought, the thought-category feature would appear in a first color (e.g., red). If the subject selects to record a positive thought, the thought-category feature would appear in a second color (e.g., green) that is different than the first color.

Block 968. Referring to block 968, in some embodiments, the method includes associating, on the display and by the subject, the DR educational-vessel object with the recorded training statement. For instance, as a non-limiting example, in some embodiments, the subject is allowed to activate the DR educational-vessel object (e.g., lighting the wick of the lantern) with the thought-category feature (e.g., flame) of the DR thought-recording object.

Blocks 972-974. Referring to block 972 and 974, in some embodiments, additionally or optionally, the method includes presenting, on the display, the DR educational-vessel object and the eleventh text at or adjacent to the DR educational-vessel object. In some such embodiments, the method further includes rendering at least a portion of the DR educational-vessel object in a color indicative of the recorded training statement. For instance, as a non-limiting example, in some embodiments, the method presents the eleventh text (i.e., the text converted from the recorded training statement) on the front of the DR educational-vessel object and renders an interior of the DR educational-vessel object in a color indicative of the recorded training statement in a similar fashion as discussed herein with respect to the feature 1320 and/or illustrated in FIGS. 13A-13F.

Blocks 976-978. Referring to block 976 and block 978, in some embodiments, additionally or optionally, the method includes using, by the subject, a DR thought-impact feature on the DR educational-vessel object to assign a level of impact of the recorded training statement on the subject. In some such embodiments, the method further includes rendering the DR educational-vessel object to indicate a level of impact of the recorded training statement on the subject. For instance, as a non-limiting example, in some embodiments, the subject is allowed to use the DR thought-impact feature on the DR educational-vessel object to assign a level of impact of the recorded training statement on the subject, and the DR educational-vessel object is rendered to indicate a level of impact of the recorded training statement on the subject in a similar fashion as discussed with respect to the feature 1330 and/or illustrated in FIGS. 13A-13F.

Block 980. Referring to block 980, in some embodiments, additionally or optionally, the method includes presenting, on the display and in response to a completion of the recorded training statement, the DR portal object for transporting the DR educational-vessel object and the DR thought-recording object. For instance, as a non-limiting example, in some embodiments, the subject is asked (e.g., by the DR assistant, a follow-up menu object, a healthcare professional, or the like) if the subject needs to change anything. In some embodiments, once the thought is finalized, the DR portal object reappears. In some embodiments, the DR educational-vessel object and the DR thought-recording object fly off into it.

In some embodiments, if an anxious thought is recorded and prioritized, it will be available for reframing. For instance, as a non-limiting example, in some embodiments, a recorded training statement representing a prioritized anxious thought will appear (e.g., carried by the DR educational-vessel object and/or the DR thought-recording object) in the interactive DR scene 1400 simulating the woods of wisdom as a thought available to reframe.

3. Client Application

Figure 21D:
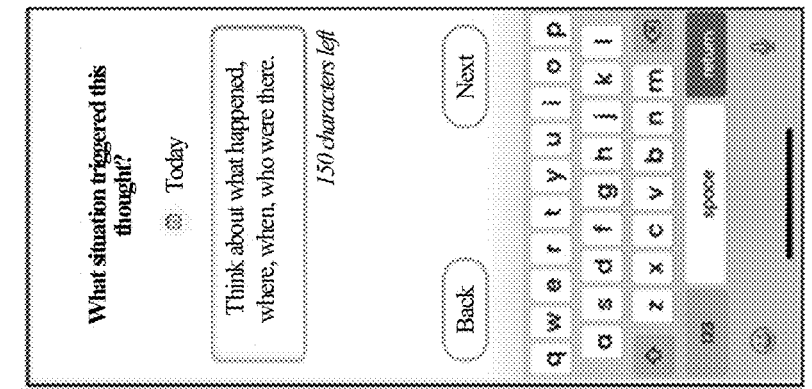
FIGS. 21A, 21B, 21C, 21D, and 21E illustrate a user interface of a client application, in accordance with some embodiments of the present disclosure.
Figure 21C:
Figure 21B:
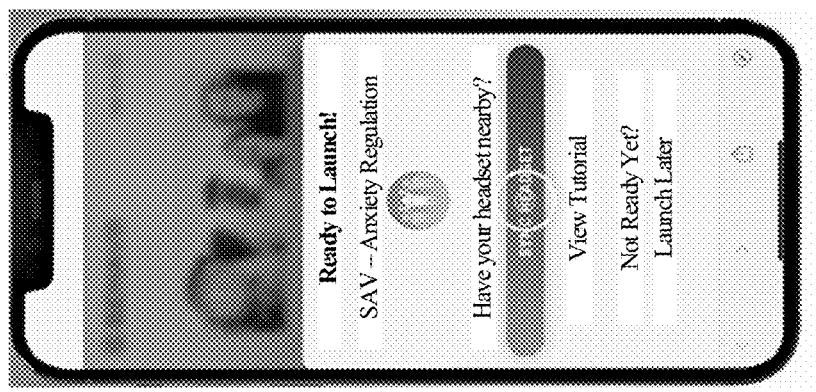
Figure 21A:
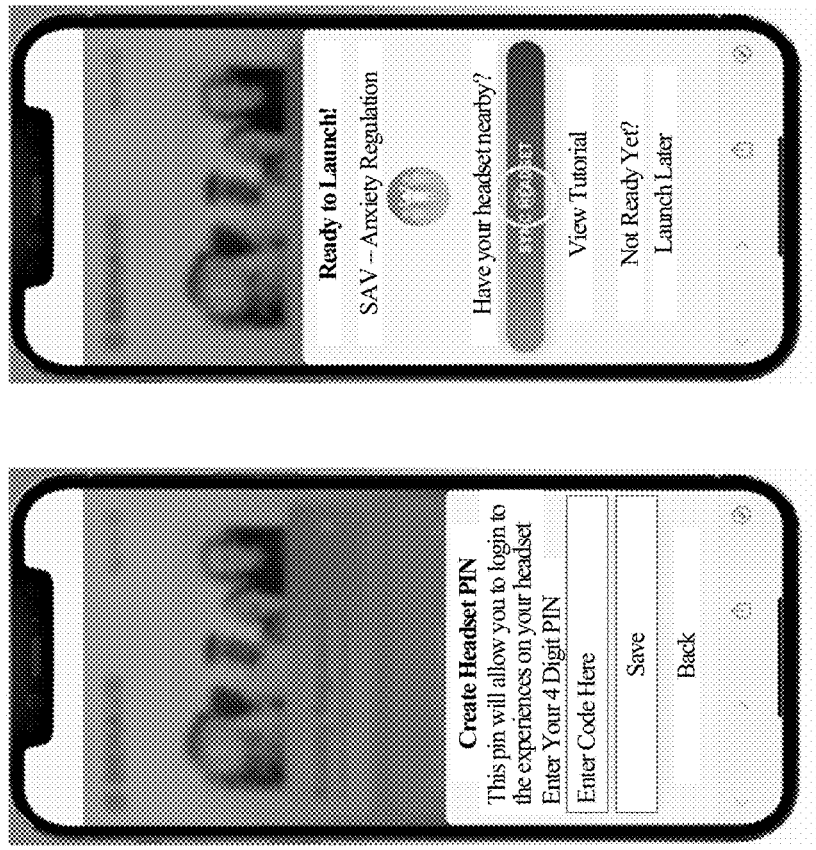
Figure 21E:
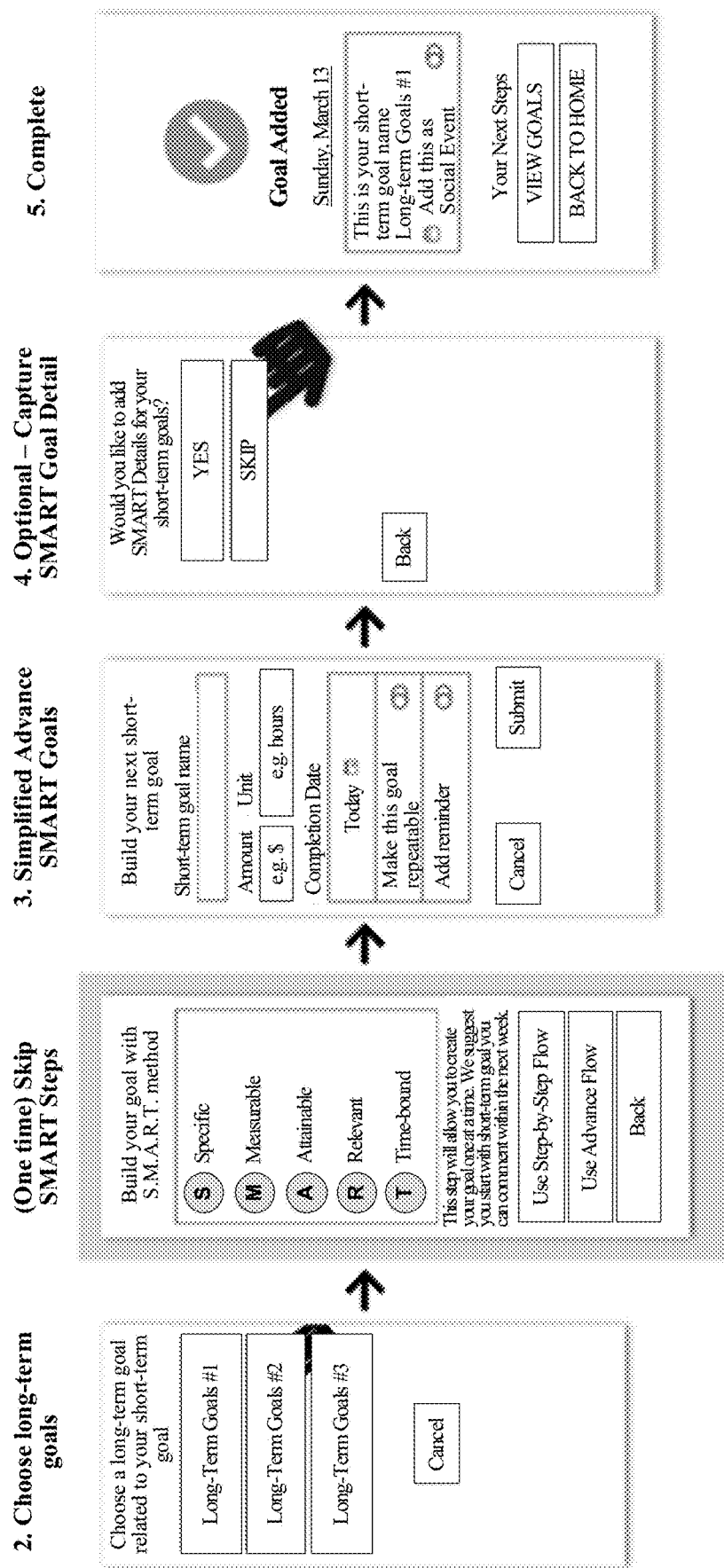

Referring to FIGS. 21A-21E, there is depicted an exemplary client application 2100 in accordance with some embodiments of the present disclosure. In some embodiments, the client application can be installed and run on a computer, tablet, smartphone and/or other electronic devices. In some embodiments, the client application is a web-based app, a mobile app, or the like. In some embodiments, the client application can be installed at or accessible by the computer system that performs the methods of the present disclosure. For instance, in some embodiments, the client application is displayed within an interactive DR scene. In some embodiments, the client application can also be installed or accessible by a device or a system that does not perform the methods of the present disclosure. As a non-limiting example, FIGS. 21A-21C illustrate the client application installed on a device, such as a client device 300, a smartphone, or the like.

Figure 21F:
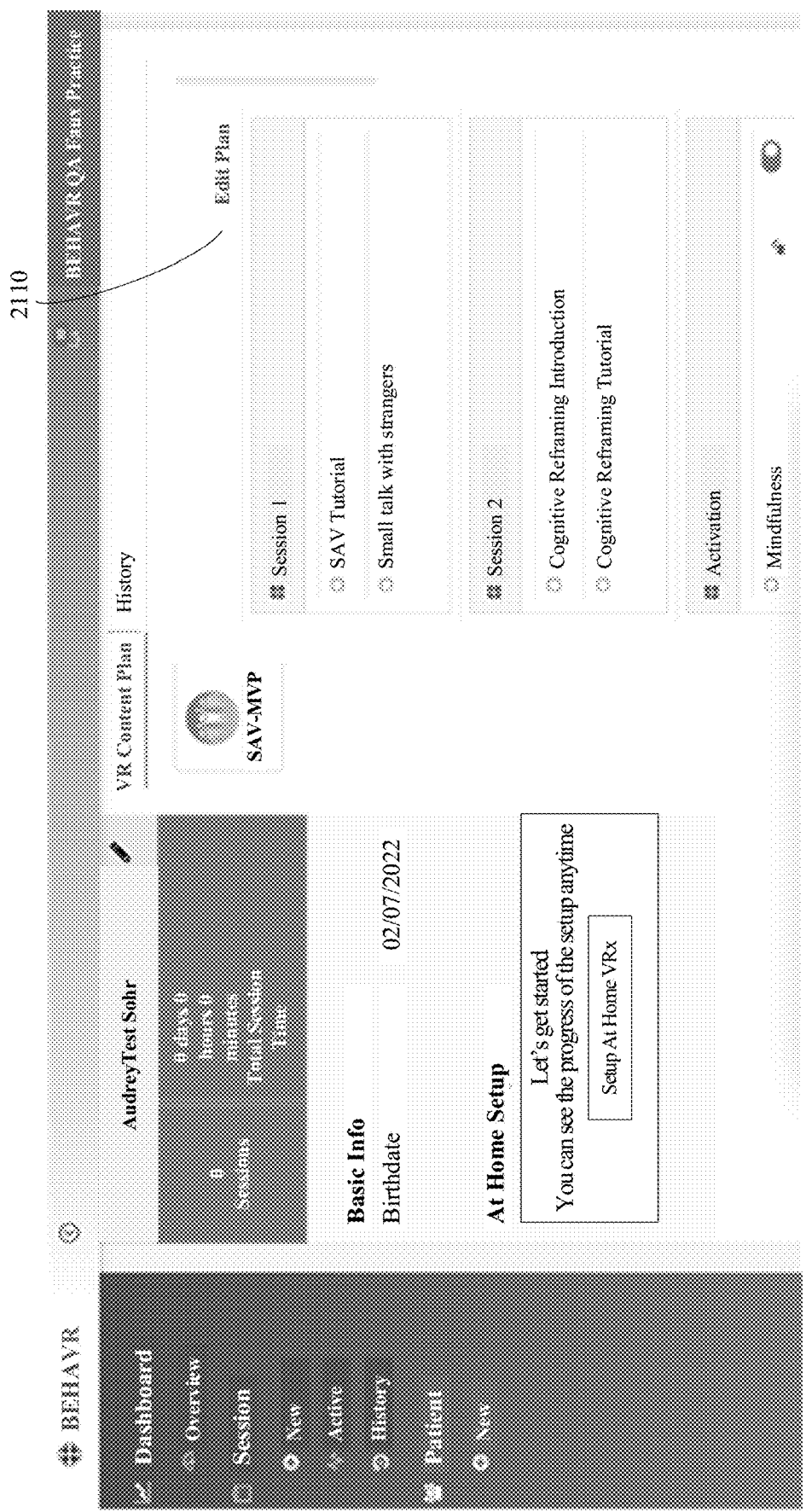
FIG. 21F illustrates a user interface of a client application, in accordance with some embodiments of the present disclosure.
Figure 24:
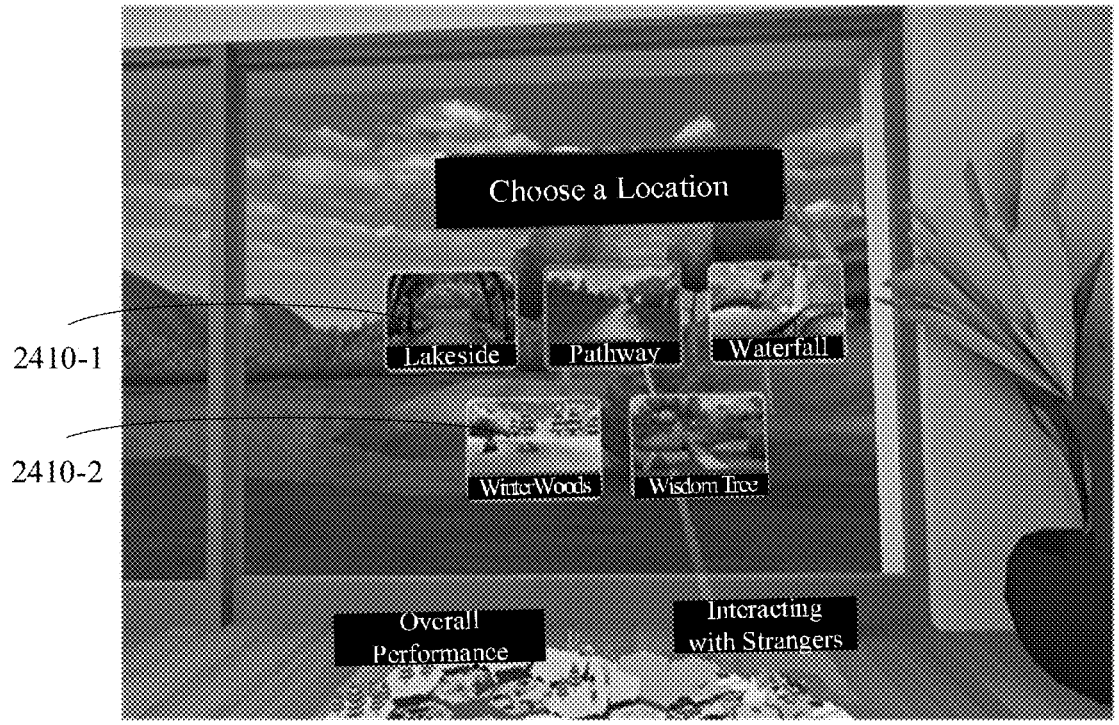
FIG. 24 illustrates an exemplary interactive DR scene configured for a subject to choose a location to practice a mindfulness technique, in accordance with some embodiments of the present disclosure.
Figure 25:
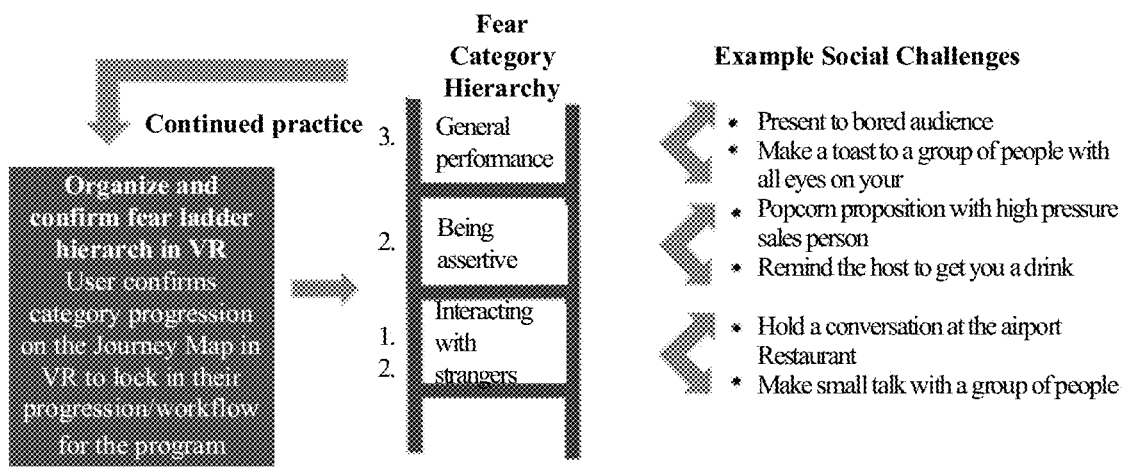
FIG. 25 illustrates an exemplary fear hierarchy of social challenges, in accordance with some embodiments of the present disclosure.

In some embodiments, the client application is an alternative, additional or optional means to facilitate subject registration/setup, regimen personalization, short-term goal setting, subject interactment, prescription, progress tracking, or the like, or any combination thereof. For instance, in some embodiments, the client application is configured to allow a healthcare professional to prescribe a regimen for a subject. In some embodiments, a healthcare professional can use a web-based client application (e.g., administrative control panel (ACP)) to create an account for a new subject and get the subject setup to register for the regimen via the client application. In some embodiments, the ACP can be a part of the client application or a portal to the client application. As a non-limiting example, FIG. 21F illustrates an ACP patient care plan page. In some embodiments, the healthcare professional can log into the ACP, add a new subject (e.g., a patient) to the ACP, and invite the new subject to register (e.g., via email, text message, or the like). In some embodiments, the subject can then register via the link in the email, text message or the like, and create username, password, or the like in the client application 2100. In some embodiments, the subject can also create a unique PIN, and syncs the headset (e.g., display 308 of client device 300 of FIG. 3) associated with the subject in the client application 2100 as illustrated in FIGS. 21A-21B. In some embodiments, once the subject is registered for the regimen, has a unique PIN, and syncs the headset associated with the subject, the subject can start the experience in digital reality as illustrated in FIG. 21C.

In some embodiments, the ACP includes an editing feature that allows the healthcare profession to track session progress of the subject and/or modify the regimen if necessary. For instance, as a non-limiting example, FIG. 21F illustrates the ACP with a "Edit Plan" feature 2110. In some embodiments, the healthcare profession can select this feature, and then manually change the categories used for social challenges, the hierarchy of the social challenge categories set by the subject, and/or other experiences prescribed for the subject.

In some embodiments, the client application 2100 is configured for a subject to set long-term and/or short-term goals. For instance, as a non-limiting example, in some embodiments, an exemplary process for setting short-term goal(s) is provided in the client application 2100. In the illustrated embodiment, a subject can select a long-term goal from a list of long-term goals and then use SMART steps, step-by-step flow, or advance flow to add one or more short-term goals that are associated with the selected long-term goal.

In some embodiments, the client application 2100 is configured for a subject to record (e.g., recording an audio, entering a text, or the like) thought(s), triggering event(s), or the like. For instance, as a non-limiting example, FIG. 21D illustrates that after a subject record a statement representing a thought, the subject is prompted to record the situation(s) that triggered the thought.

The client application 2100 can include other features or functions that are alternative, additional or optional to those in virtual/digital reality. For instance, as a non-limiting example, in some embodiments, the company app is configured for a subject or a healthcare professional to log and/or track the progression of the subject.

In some embodiments, the client application 2100 or a portal to the client application is presented in an interactive DR scene, such as the interactive DR scene 1000 or the interactive DR scene 1400, to allow a subject or a healthcare professional to access the client application.

4. Exemplary Regimens

Referring to FIG. 22, there is depicted an exemplary therapeutic regimen 2200 that utilizes the devices, systems and/or methods of the present disclosure for treatment of individuals (e.g., individuals 18 years or older) with a mental disorder. In some embodiments, the regimen 2200 can be self-administered by a subject without supervision of a health care worker (e.g., a medical practitioner) associated with the subject, or used at home by a subject (e.g., a patient) and while giving a healthcare professional (e.g., a clinician) associated with the subject the ability to asynchronously monitor and adjust the regimen (if necessary) for the subject.

In some embodiments, the therapeutic regimen 2200, cognitive reframing content is introduced in stages, e.g., over a plurality of time periods. In some embodiments, each time period can be at least a day, at least two days, at least three days, at least four days, at least five days, at least a week, at least two weeks, at least three weeks, or at least a month. In some embodiments, each time period can be at most a day, at most two days, at most three days, at most four days, at most five days, at most a week, at most two weeks, at most three weeks, or at most a month. In some embodiments, two time periods can be the same or different. In some embodiments, during a first time period, basic concepts of cognitive reframing are introduced and the subject is guided to learn how to record thoughts. In some embodiments, the basic concepts of cognitive reframing are introduced by a two-part introductory tutorial using, for example, one or more psychoeducational videos. In some embodiments, during the first period, a client application, such as the client application 2100, is also introduced.

In some embodiments, starting from the second time period, CBT techniques are unlocked one at a time. For instance, as a non-limiting example, FIG. 22 illustrates unlocking the first DR activity (e.g., gathering evidence activity) during the second time period, unlocking the second DR activity (e.g., usefulness and core beliefs activity) during the third time period, and unlocking the third DR activity (e.g., creating space activity) during the fourth time period. In some embodiments, if the subject is a first time user or if the subject prefers, the regimen demonstrates, through the DR assistant, how a technique should be used by having the subject help the DR assistant to reframe one of the DR assistant's thoughts. In some embodiments, the subject is then allowed to apply the technique to one of the thoughts of the subject during a required practice session.

In some embodiments, outside of tutorials and mandatory practice sessions, a subject is encouraged to log and reframe anxious thoughts often throughout the regimen. In some embodiments, various rewards are given each time a thought is reframed. In some embodiments, the progression of the subject is tracked in the journal menu object, which can be pulled up anywhere in the regimen. In some embodiments, the regimen is configured to allow the subject to slow down a pace if the subject chooses or if the healthcare professional associated with the subject makes that suggestion.

Referring to FIGS. 23A and 23B, there is depicted an exemplary therapeutic regimen that utilizes the devices, systems and/or methods of the present disclosure for treatment of individuals (e.g., individuals 18 years or older) with a mental health issue such as social anxiety disorder. In some embodiments, the regimen is built to be used at home by a subject (e.g., a patient) while giving a healthcare professional (e.g., a clinician) associated with the subject the ability to asynchronously monitor and adjust the regimen (if necessary) for the subject.

In some embodiments, the regimen is designed to educate the subject on long-term and short-term goal settings through a variety of psychoeducation, interactive activities, and practice. Psychoeducational interventions help individuals understand the underly biopsychosocial drivers of their mental and behavioral health. A strong foundation and understanding of psychoeducational materials support effective transdiagnostic therapies.

In some embodiments, the regimen is intended to be prescribed by a qualified healthcare professional with a dosage of one or more sessions per a time period. In some embodiments, the time period can be a day, two days, three days, four days, five days, a week, two weeks, three weeks, a month, or more than a month. A time period for a session can be the same as or different from a time period for another session. As a non-limiting example, FIGS. 23A and 23B illustrates an outline of the regimen 2300 planned over the course of eight weeks with three sessions per week. In some embodiments, the regimen includes psychoeducation, social challenge practice, mindfulness practice, cognitive reframing practice and goal settings that are allocated into 24 chapters.

In some embodiments, alternatively, additionally, or optionally, the subject is asked to perform a subjective evaluation. In some embodiments, the subjective evaluation includes a plurality of prompts, e.g., more than 2, more than 5, more than 10, more than 15, more than 20, more than 30, more than 50, more than 100, or more than 200 prompts, for the subject to answer. In some embodiments, the subjective evaluation includes a plurality of prompts, e.g., at most 2, at most 5, at most 10, at most 15, at most 20, at most 30, at most 50, at most 100, or at most 200 prompts, for the subject to answer. In some embodiments, the subjective evaluation includes about twelve prompts to about twenty-four prompts for a subject to answer. In some embodiments, the subjective evaluation is self-administered by the subject without supervision of a health care worker (e.g., a medical practitioner) associated with the subject. In some other embodiments, the subjective evaluation is performed by the subject but with supervision of a health care worker associated with the subject.

Figure 26A:
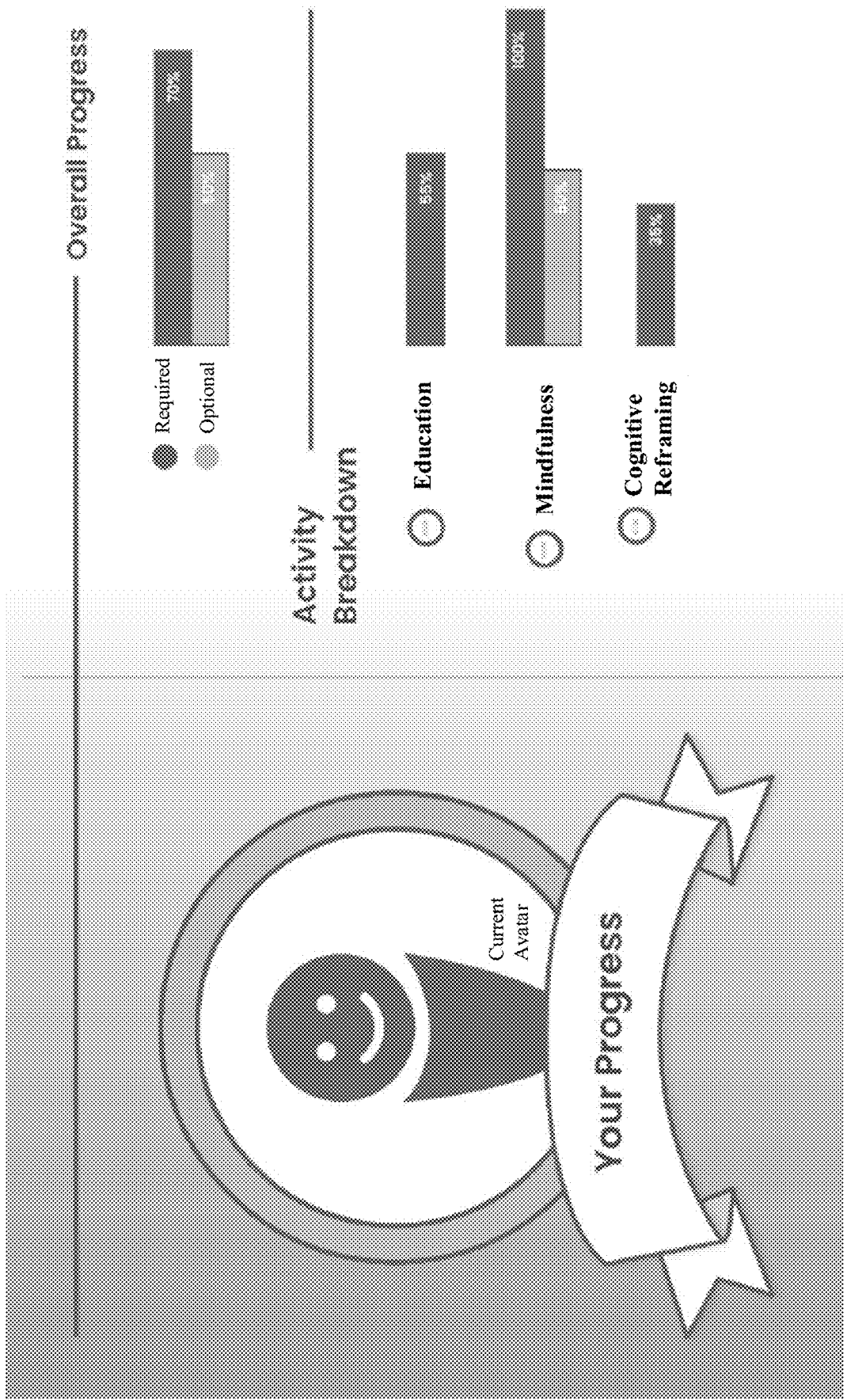
FIGS. 26A, 26B, and 26C illustrates an exemplary user interface of a DR scene or a client application configured present progress of a subject within an interactive DR activity, in accordance with some embodiments of the present disclosure.
Figure 26B:
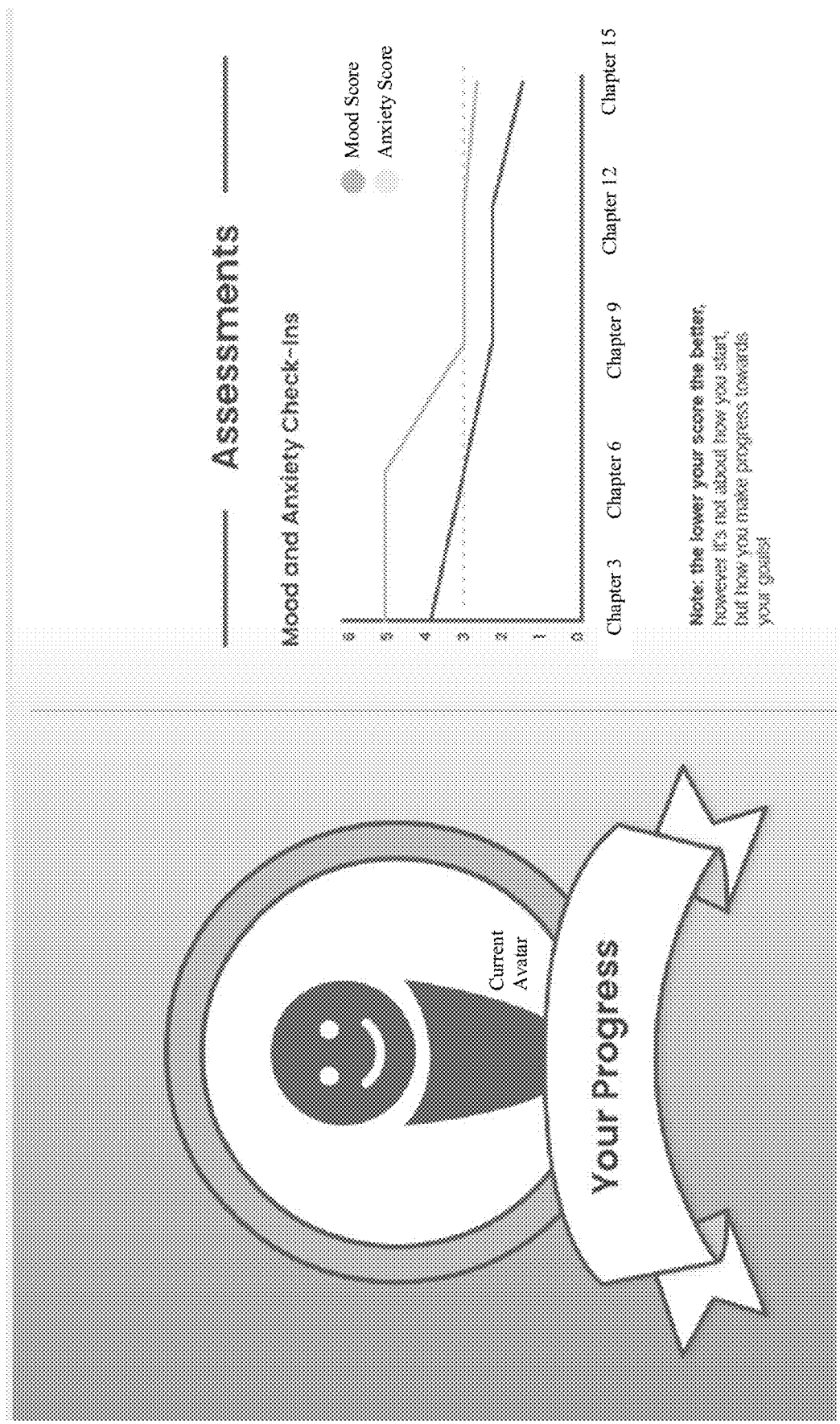
Figure 26C:
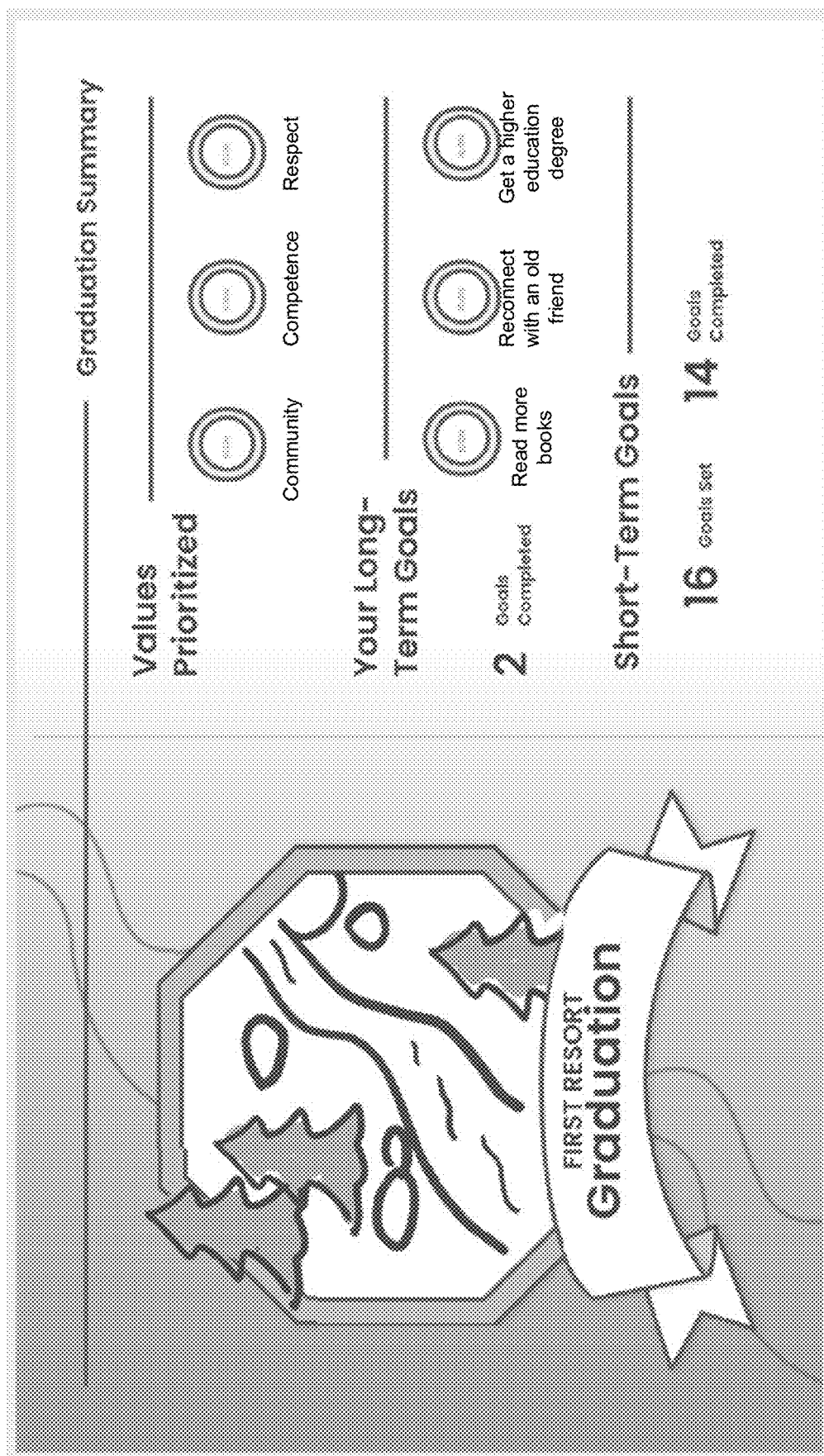

Referring to FIGS. 26A through 26C, in some embodiments, an interactive DR scene and/or a client application is configured to present a report for the subject based on a progress of the subject in an interactive DR activity. In some embodiments, the report includes a chart that illustrates a result of one or more assessments, such as one or more subjective evaluations, answered by the subject over a time period. For instance, in some embodiments, the chart includes a first axis, a respective axis, and one or more respective data plots. Each respective data plot represents a corresponding result of an assessment provided to the subject and is placed within a region defined by the first axis and the second axis. Thus, the chart provides a visualization of assessment results for the subject. In some embodiments, the chart is displayed in the report when the correspond result indicates an improved by the subject in management of the mental or psychiatric condition.

In some embodiments, the subjective evaluation is based on a Minimal Clinically Important Difference (MCID), a Clinical Global Impression Scale of Improvement (CGI), a Patient Global Impression Scale of Improvement (PGI), a Liebowitz Social Anxiety Scale (LSAS), or a combination thereof. In some embodiments, the MCID, CGI, PGI, and/or LSAS is a part of assessment module 12 of FIG. 2A.

The MCID refers to the smallest benefit of value to the subject. It captures both the magnitude of the improvement and the value the subject places on the change. In some embodiments, the MCID defines the smallest amount an outcome must change to be meaningful to the subject. Additional details and information regarding MCID assessments is found at Kaplan, R., 2005, "The Minimally Clinically Important Difference in Generic Utility-based Measures," COPD: Journal of Chronic Obstructive Pulmonary Disease, 2(1), pg. 91, which is hereby incorporated by reference in its entirety for all purposes.

The CGI evaluations a severity and/or changes in an ability of the subject to manage the psychiatric or mental condition. Additional details and information regarding CGI scale assessments is found at Perez et al., 2007, "The Clinical Global Impression Scale for Borderline Personality Disorder Patients (CHI-BPD): A Scale Sensible to Detect Changes," Actas Espanolas de Psiquiatria, 35(4), pg. 229, which is hereby incorporated by reference in its entirety for all purposes.

The PGI provides a patient rated format, as opposed to a clinician rated format of the CGI scale assessment. Additional details and information regarding the PGI assessment is found at Faith et al., 2007, "Twelve Years-Experience with the Patient Generated Index (PGI) of Quality of Life: A Graded Structured Review," Quality of Life Research, 16(4), pg. 705, which is hereby incorporated by reference in its entirety for all purposes.

The LSAS assesses social anxiety disorder in clinical research and practice. It includes a self-reported (LSAS-SR) and a clinician-administered (LSAS-CA). Additional details and information regarding an LSAS assessment is found at Rytwinski et al., 2009, "Screening for Social Anxiety Disorder with the Self-Report Version of the Liebowitz Social Anxiety Scale," Depression and Anxiety, 26(1), pg. 34, which is hereby incorporated by reference in its entirety for all purposes.

In some embodiments, there is a clinical portal where the clinician can modify the categories used for the social challenges and can track session progress of the subject. For instance, as a non-limiting example, FIG. 21F illustrates a patient care plan page where the clinician can select the "Edit Plan" feature and can manually change the hierarchy of the subject if needed.

In some embodiments, the client application also includes a feature to allow the subject to record one or more cognitive distortions and their triggers. In some embodiments, after the subject records a cognitive distortion in a client application of a client device associated with the subject, the subject has the ability to reframe the recorded cognitive distortion (e.g., a statement representing a thought) in the regimen (e.g., in the woods of wisdom of the regimen).

In some embodiments, once the subject has completed all the chapters, most importantly the subject has practiced the required social challenges, the subject will graduate from the regimen. In some embodiments, once graduated, the subject can come back in the regimen and redo any of the content (e.g., psychoeducation, tutorials, or activities) that the subject chooses.

It should be noted that the processes illustrated in the FIGS. 4A-9F are not necessarily in order. It should also be noted that the method can include the additional, optional and/or alternative processes exemplified in the flowchart in any meaningful and useful combinations. For instance, in some embodiments, the method includes generate a report for the subject and/or present the report to the subject. It should further be noted that the processes disclosed herein and exemplified in the flowchart can be, but do not have to be, executed in full. In some embodiments, the subject and/or a health care worker associated with the subject can start, terminate, resume, or restart the processes when needed or desired.

Furthermore, in some embodiments, the present disclosure is directed to providing a device (e.g., client device 300 of FIG. 3 and/or digital reality system 200 of FIGS. 2A and 2B) for implementing the CBT and/or other educational or therapeutical sessions. In some embodiments, the device is configured to improves an ability of a subject to manage a psychiatric or mental condition of the subject. Furthermore, the device includes one or more processors and a memory coupled to the one or more processors. In some embodiments, the memory includes one or more programs configured to be executed by the one or more processors. In some embodiments, the one or more programs is configured to cause the computer system to perform the methods of the present disclosure. In some embodiments, the device includes a display and/or audio circuitry (e.g., a speaker, microphone, recorder). In some embodiments, the device includes an objective lens in optical communication with a two-dimensional pixelated detector.

4.1. Presenting Interactive DR Activities for a Subject

Figure 29A:
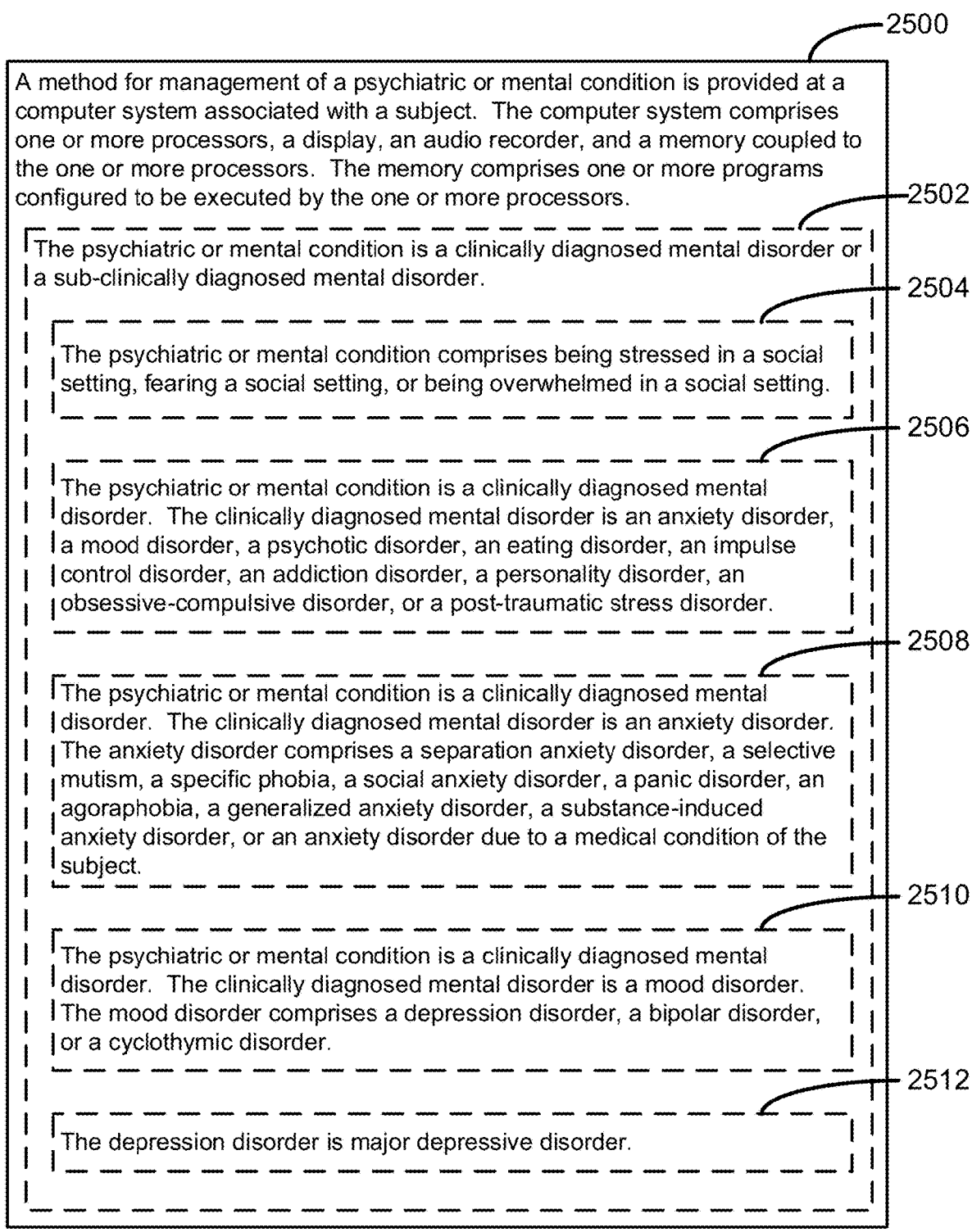
Figure 29B:
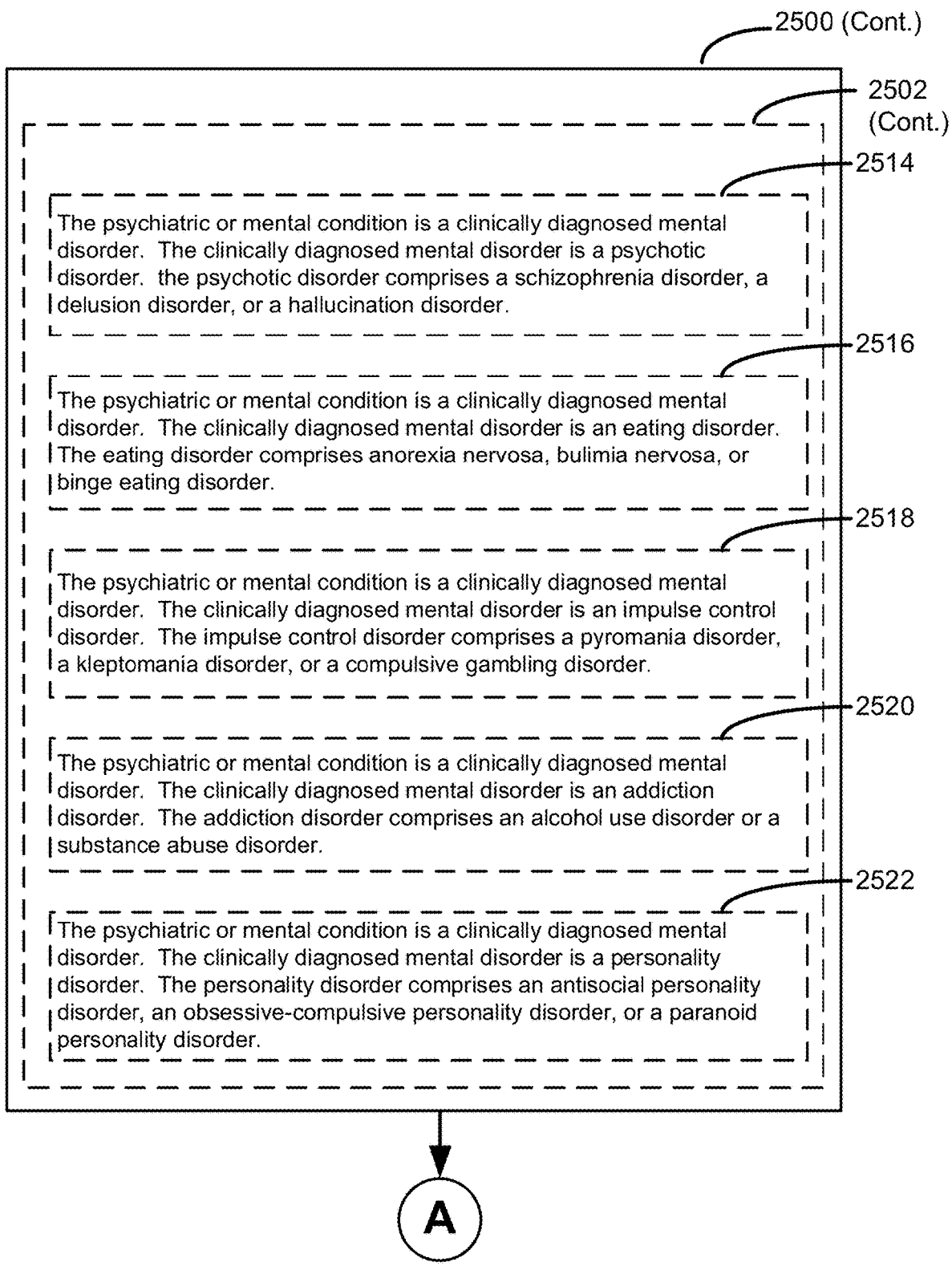
Figure 29D:
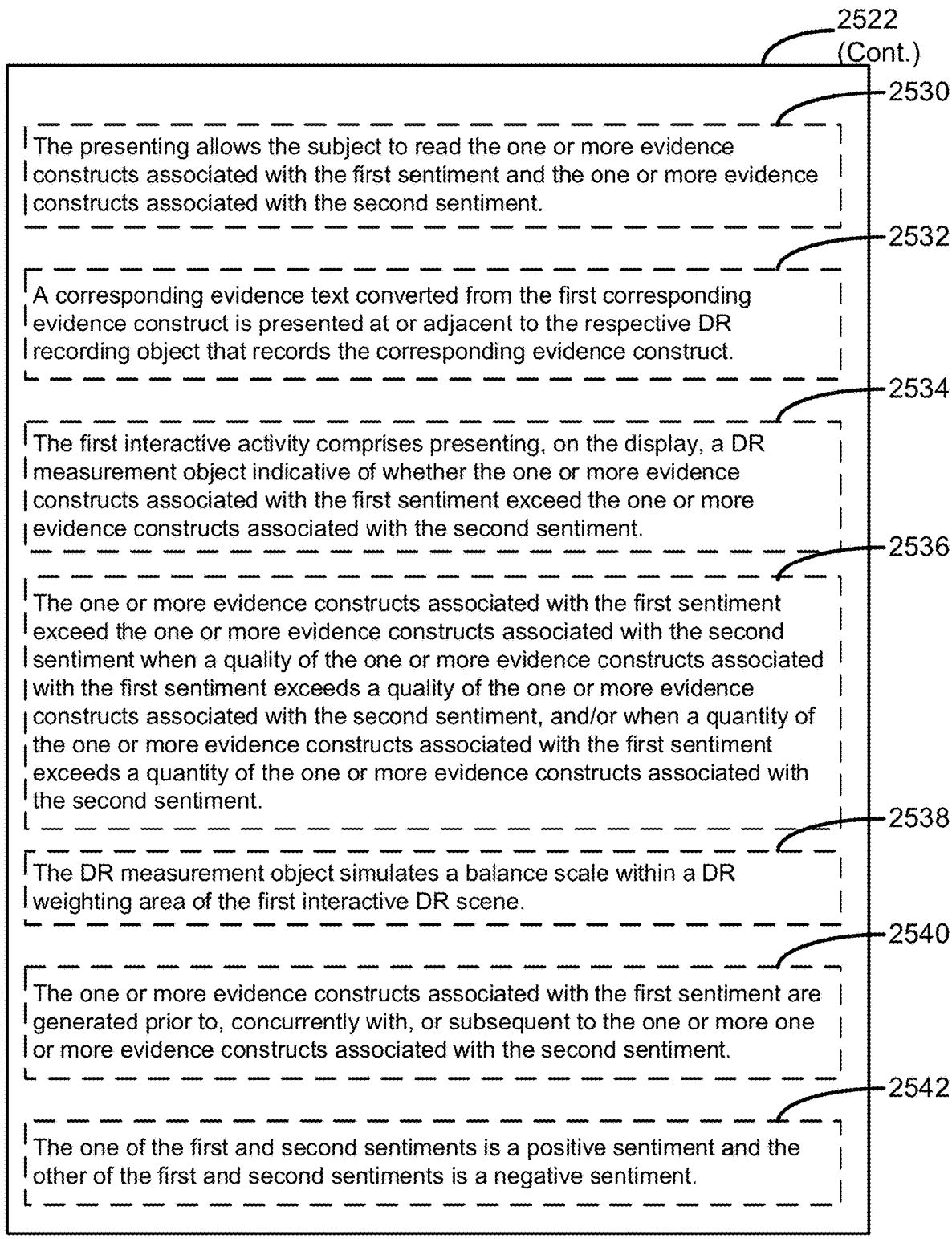
Figure 29E:
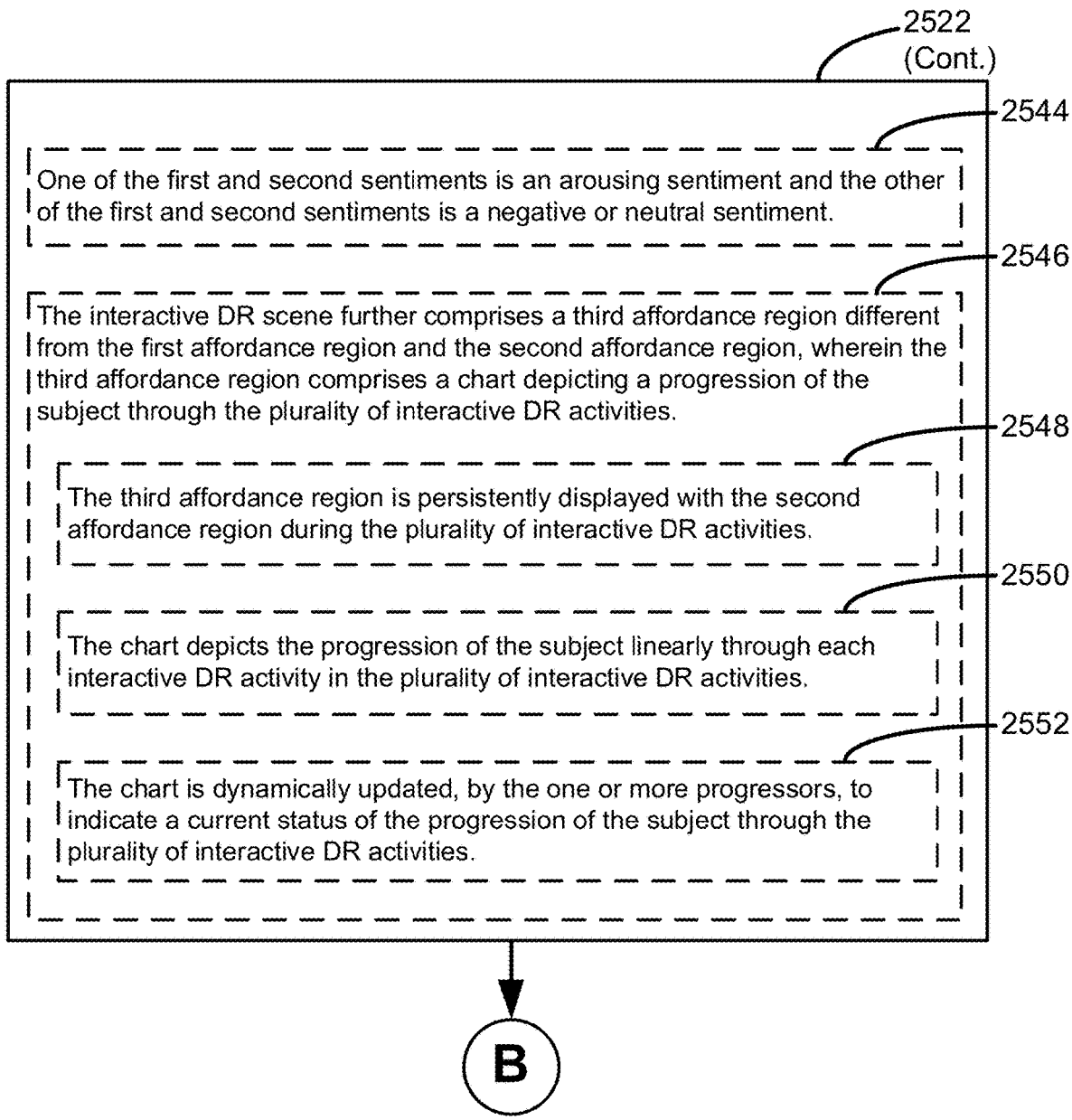
Figure 29F:
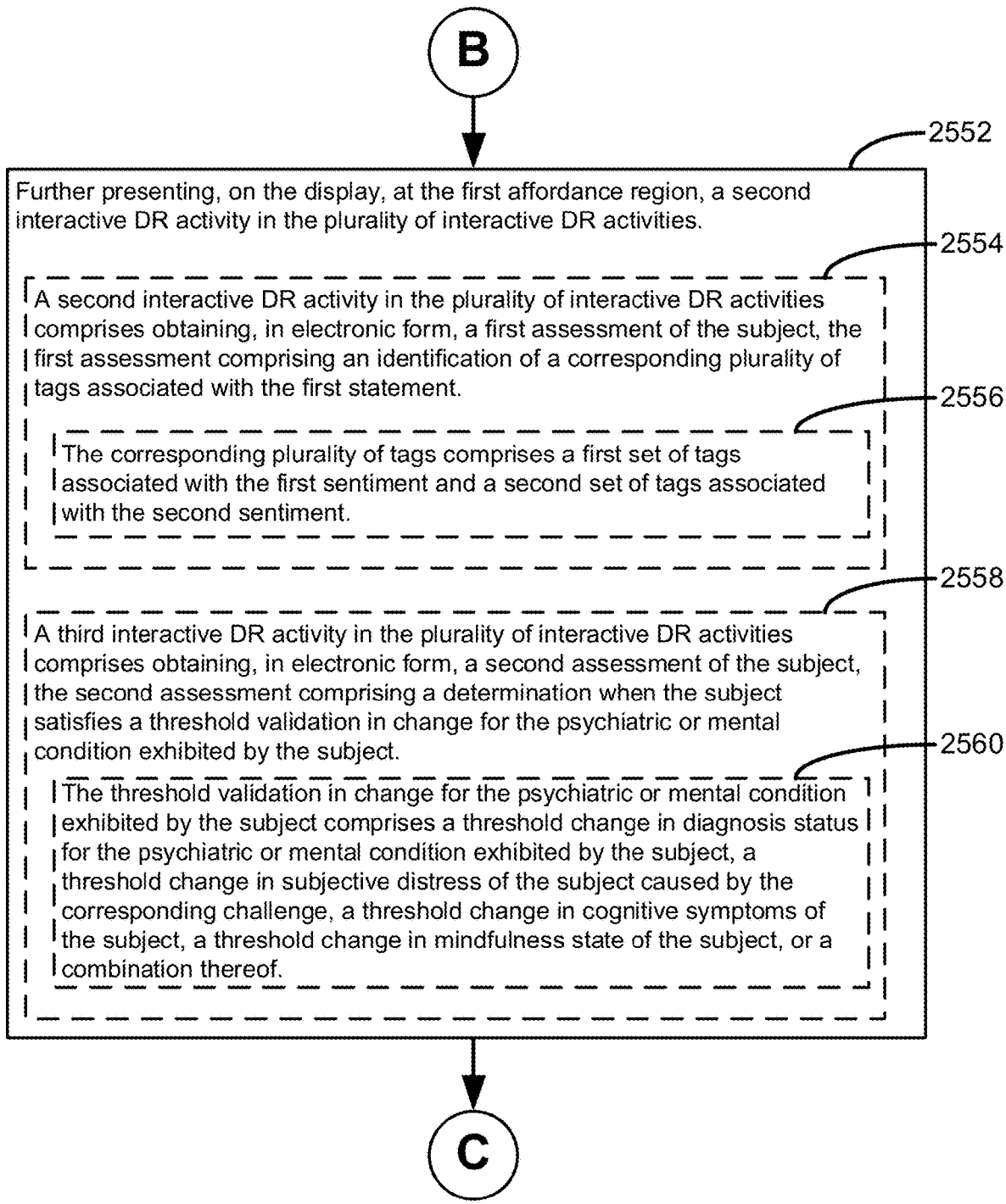
Figure 29G:
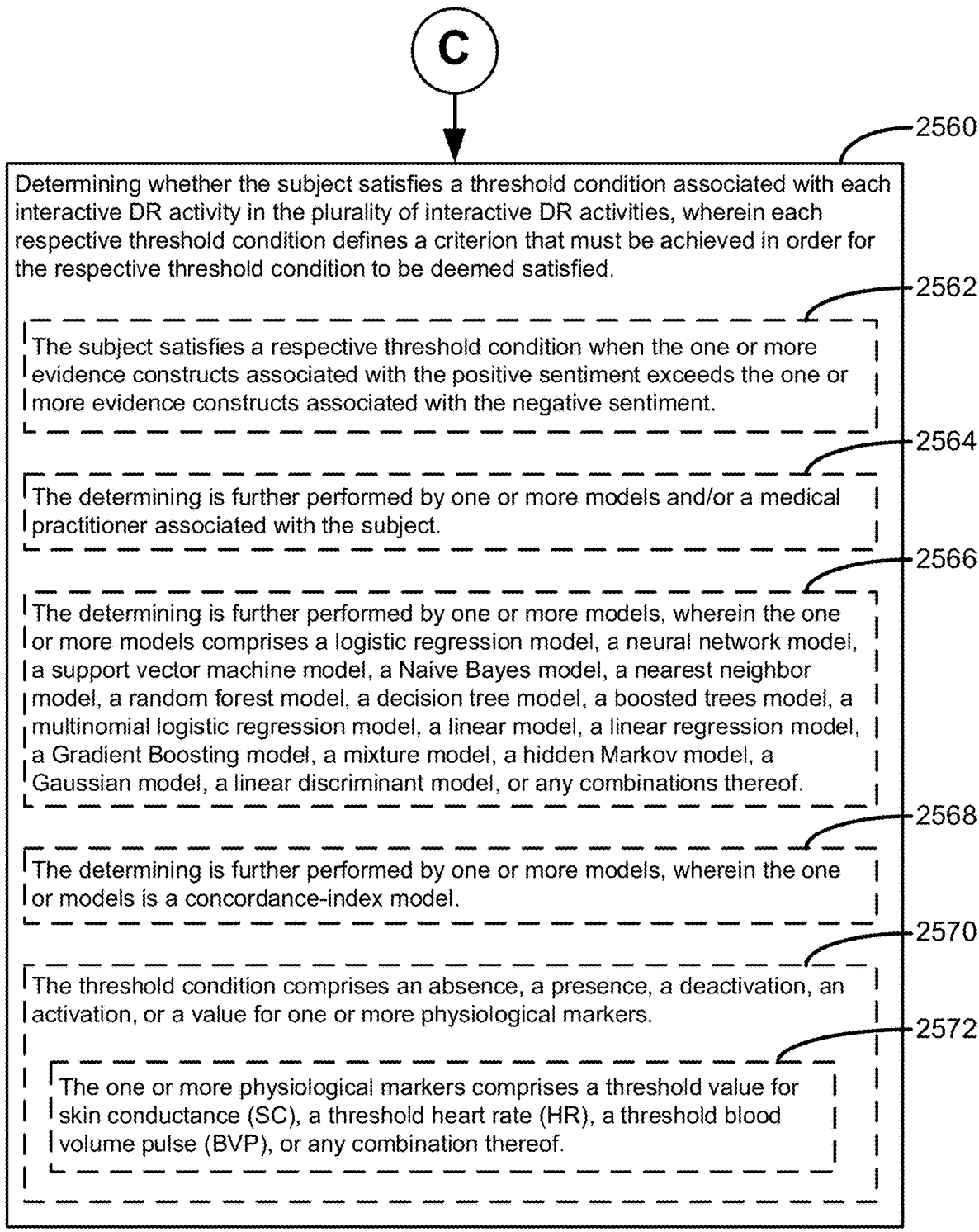
Figure 29H:
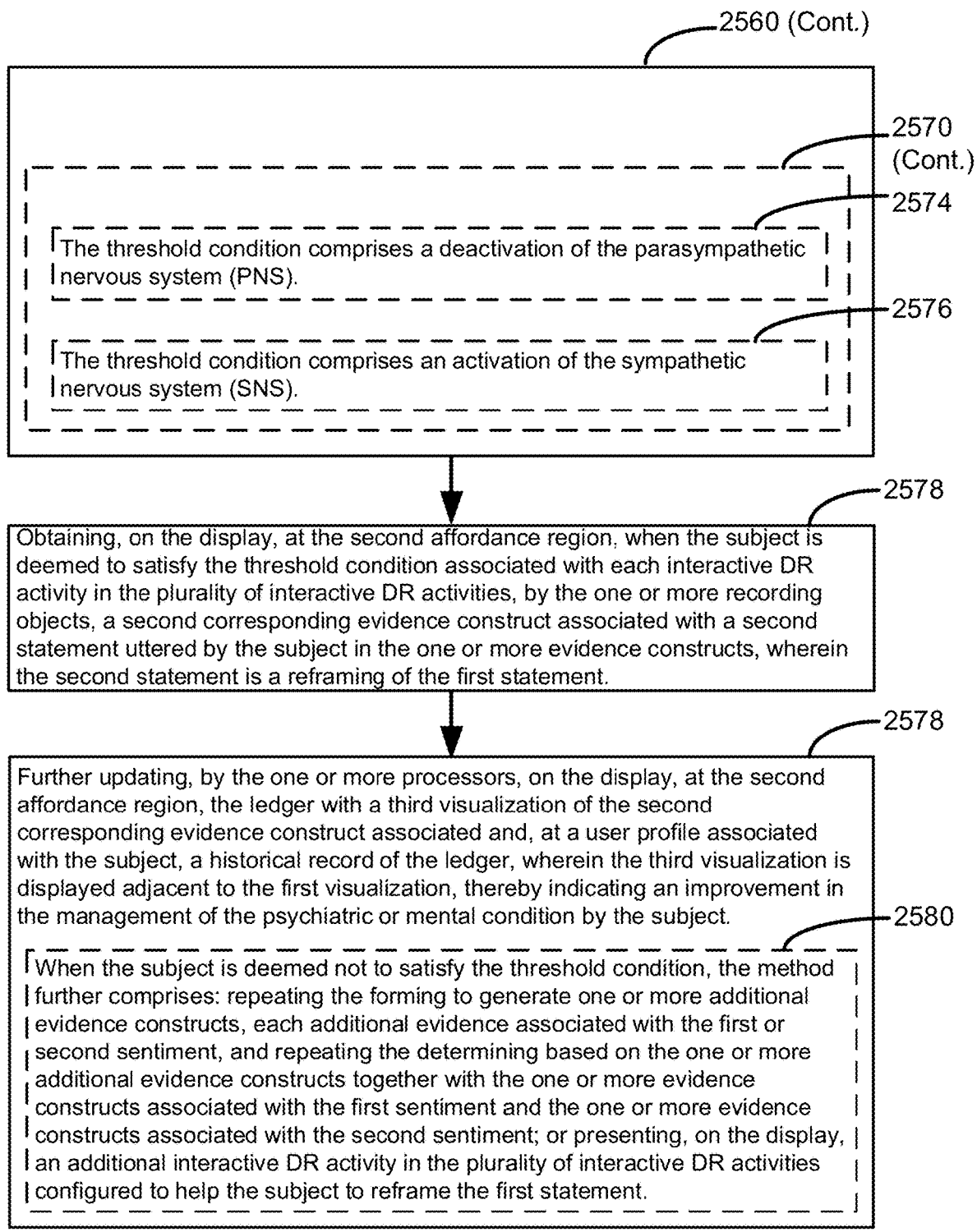

Referring to block 2500 of FIG. 29A, in some embodiments, a method for management of a psychiatric or mental condition is provided. For instance, in some embodiments, the method implements a CBT technique, such as to help a subject that exhibits the psychiatric or mental condition to practice a defusion technique and/or learn how to create cognitive distance between the subject and the thoughts of the subject and, therefore, manage the psychiatric or mental condition. Moreover, in some embodiments, the method is performed at a computer system (e.g., computer system 200 of FIG. 2A through 2B and/or client device 300 of FIG. 3) associated with a subject. For instance, in some embodiments, the computer system is utilized to receive inputs from the subject in order for the subject to interact with the computer system and, therefore, practice the defusion technique and/or learn how to create cognitive distance between the subject and the thoughts of the subject. However, the present disclosure is not limited thereto.

In some embodiments, the computer system includes one or more processors (e.g., CPU 302 of FIG. 3, CPU 202 of FIG. 2A, etc.), a display (e.g., display 308 of FIG. 3), and a memory (e.g., memory 312 of FIG. 3) coupled to the one or more processors. In some embodiments, the memory includes one or more programs configured to be executed by the one or more processors (e.g., client application 320 of FIG. 3, user profile store 14 of FIG. 2A, assessment module 12 of FIG. 2A, etc.).

Referring to block 2502, in some embodiments, the psychiatric or mental condition is a clinically diagnosed mental disorder or a sub-clinically diagnosed mental disorder.

Referring to block 2504, in some embodiments, the psychiatric or mental condition includes being stressed in a social setting, fearing a social setting, or being overwhelmed in a social setting.

Referring to block 2506, in some embodiments, the psychiatric or mental condition is a clinically diagnosed mental disorder. Moreover, in some such embodiments, the clinically diagnosed mental disorder is an anxiety disorder, a mood disorder, a psychotic disorder, an eating disorder, an impulse control disorder, an addiction disorder, a personality disorder, an obsessive-compulsive disorder, or a post-traumatic stress disorder.

Referring to block 2508, in some embodiments, the psychiatric or mental condition is a clinically diagnosed mental disorder. Moreover, in some such embodiments, the clinically diagnosed mental disorder is an anxiety disorder. In some such embodiments, the anxiety disorder includes a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

Referring to block 2510, in some embodiments, the psychiatric or mental condition is a clinically diagnosed mental disorder. In some embodiments, the clinically diagnosed mental disorder is a mood disorder. Furthermore, in some such embodiments, the mood disorder includes a depression disorder, a bipolar disorder, or a cyclothymic disorder.

Referring to block 2512, in some embodiments, the depression disorder is major depressive disorder.

Referring to block 2514, in some embodiments, the psychiatric or mental condition is a clinically diagnosed mental disorder. Moreover, in some embodiments, the clinically diagnosed mental disorder is a psychotic disorder, in which the psychotic disorder includes a schizophrenia disorder, a delusion disorder, or a hallucination disorder.

Referring to block 2516, in some embodiments, the psychiatric or mental condition is a clinically diagnosed mental disorder. Moreover, in some embodiments, the clinically diagnosed mental disorder is an eating disorder. In some such embodiments, the eating disorder includes anorexia nervosa, bulimia nervosa, or binge eating disorder.

Referring to block 2518, in some embodiments, the psychiatric or mental condition is a clinically diagnosed mental disorder. Moreover, in some such embodiments, the clinically diagnosed mental disorder is an impulse control disorder. Furthermore, in some embodiments, the impulse control disorder includes a pyromania disorder, a kleptomania disorder, or a compulsive gambling disorder.

Referring to block 2520, in some embodiments, the psychiatric or mental condition is a clinically diagnosed mental disorder. Moreover, in some embodiments, the clinically diagnosed mental disorder is an addiction disorder. For instance, in some embodiments, the addiction disorder includes an alcohol use disorder or a substance abuse disorder.

Referring to block 2522, in some embodiments, the psychiatric or mental condition is a clinically diagnosed mental disorder. Moreover, in some embodiments, the clinically diagnosed mental disorder is a personality disorder. For instance, in some such embodiments, the personality disorder includes an antisocial personality disorder, an obsessive-compulsive personality disorder, or a paranoid personality disorder.

Referring to block 2523, in some embodiments, the method includes presenting (e.g., on the display of the client device) an interactive digital reality (DR) scene.

In some embodiments, the interactive DR scene 1000 (e.g., scene 1000 of FIG. 28A) includes a plurality of affordance regions, which allow for the subject to engage with the interactive DR scene 1000 at particular DR spaces. For instance, in some embodiments, the interactive DR scene includes a first affordance region (e.g., affordance region 620-1 of FIG. 28A) and a second affordance region (e.g., affordance region 620-2 of FIG. 28A).

Figure 28A:
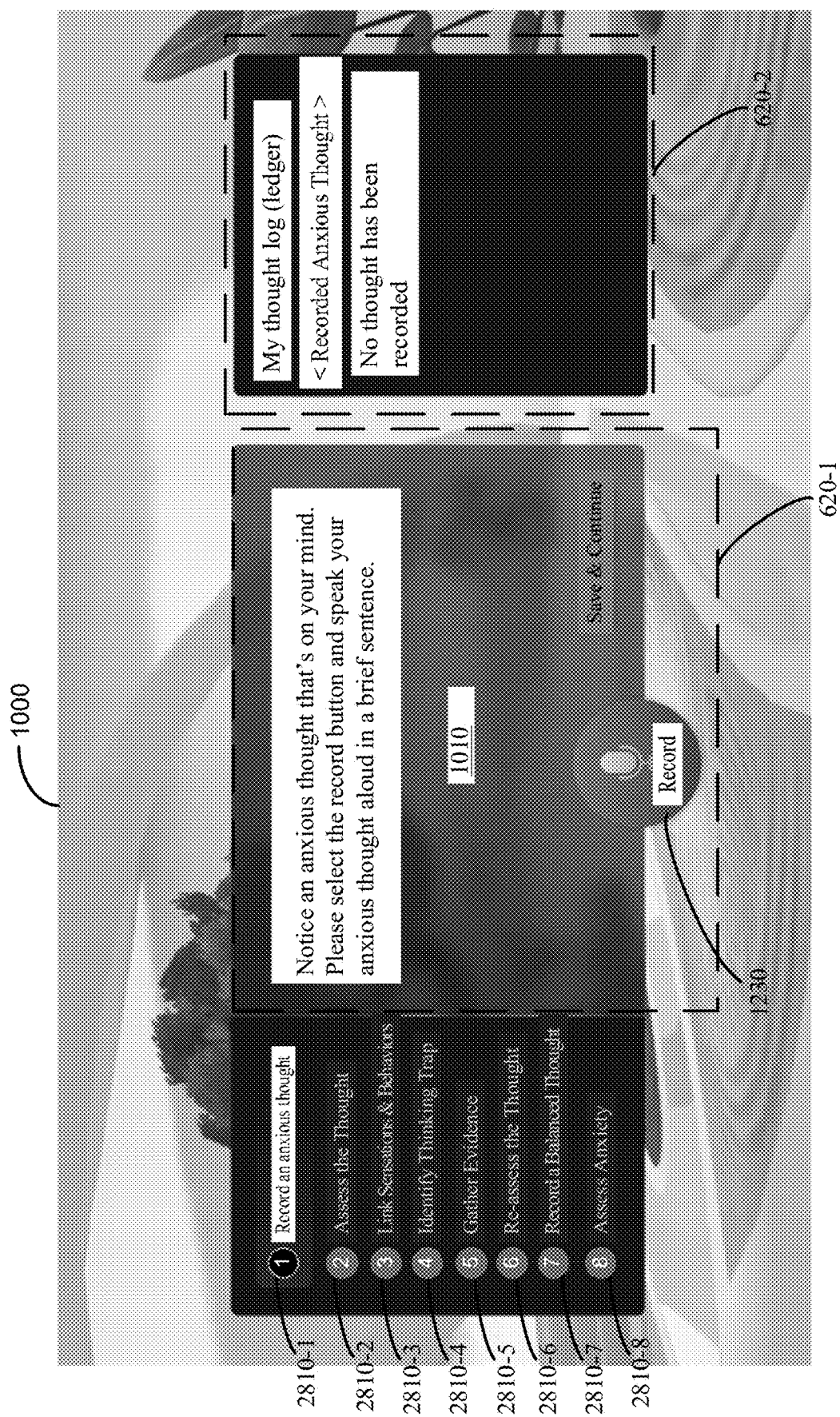
Figure 28B:
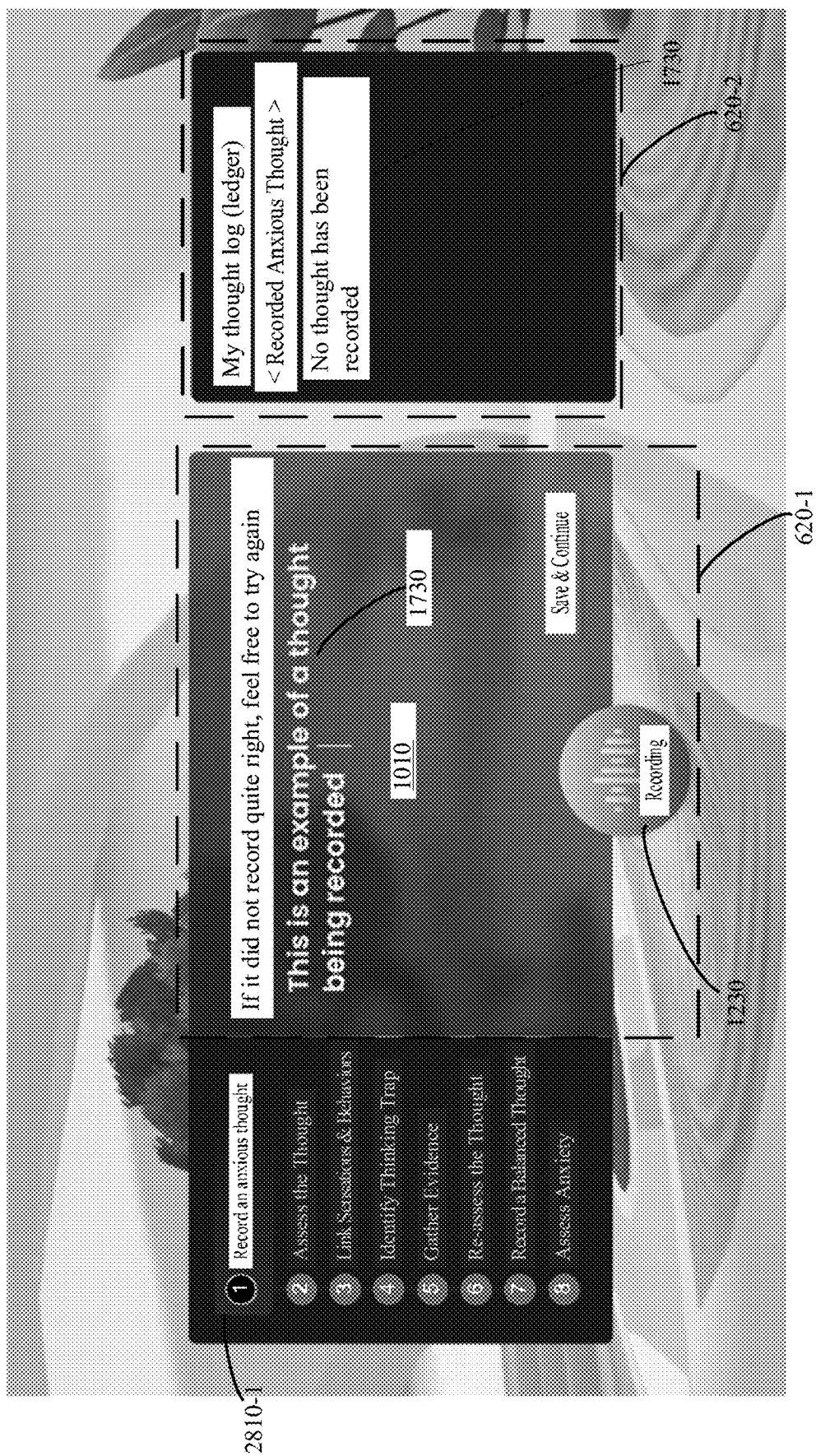
Figure 28C:
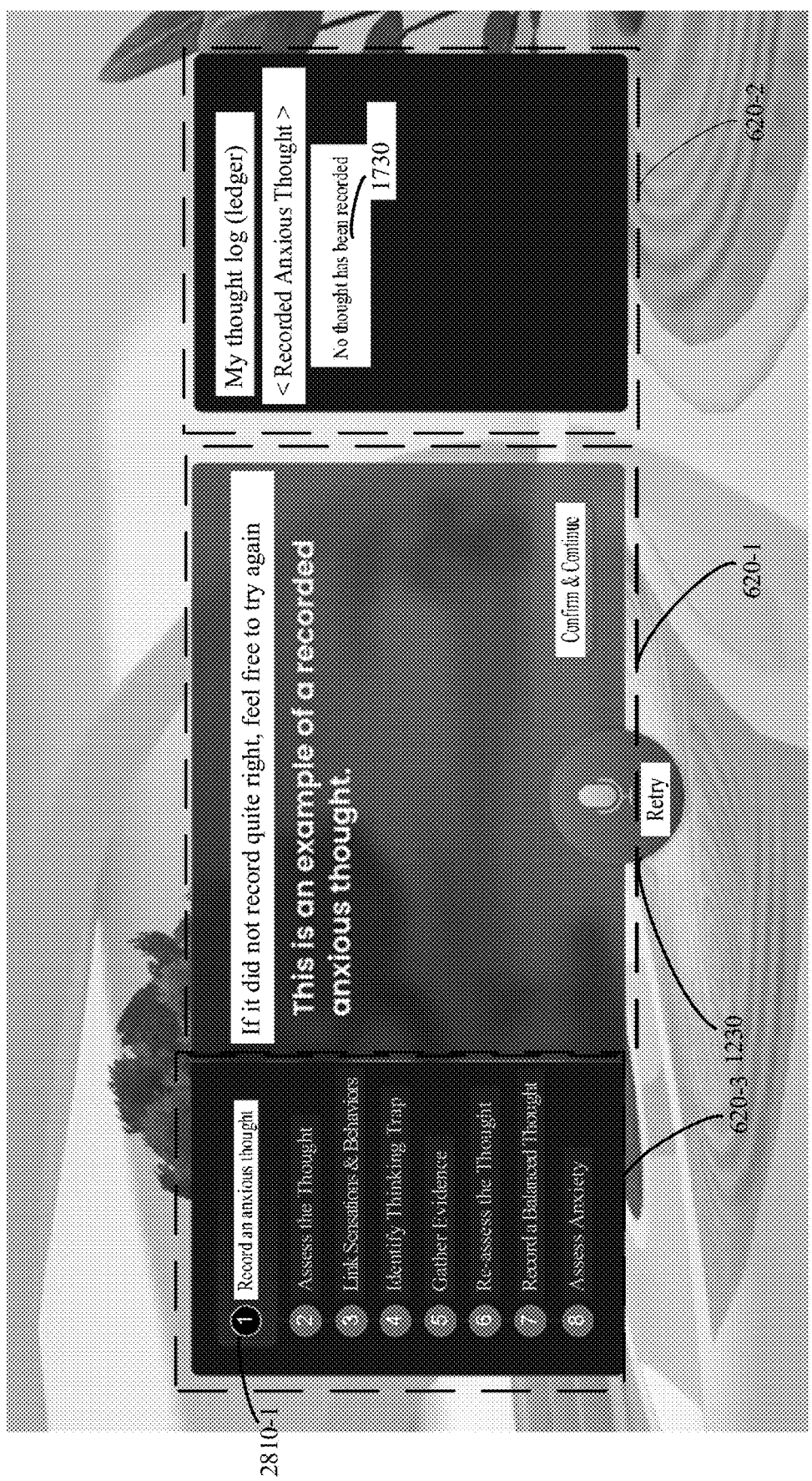
Figure 28D:
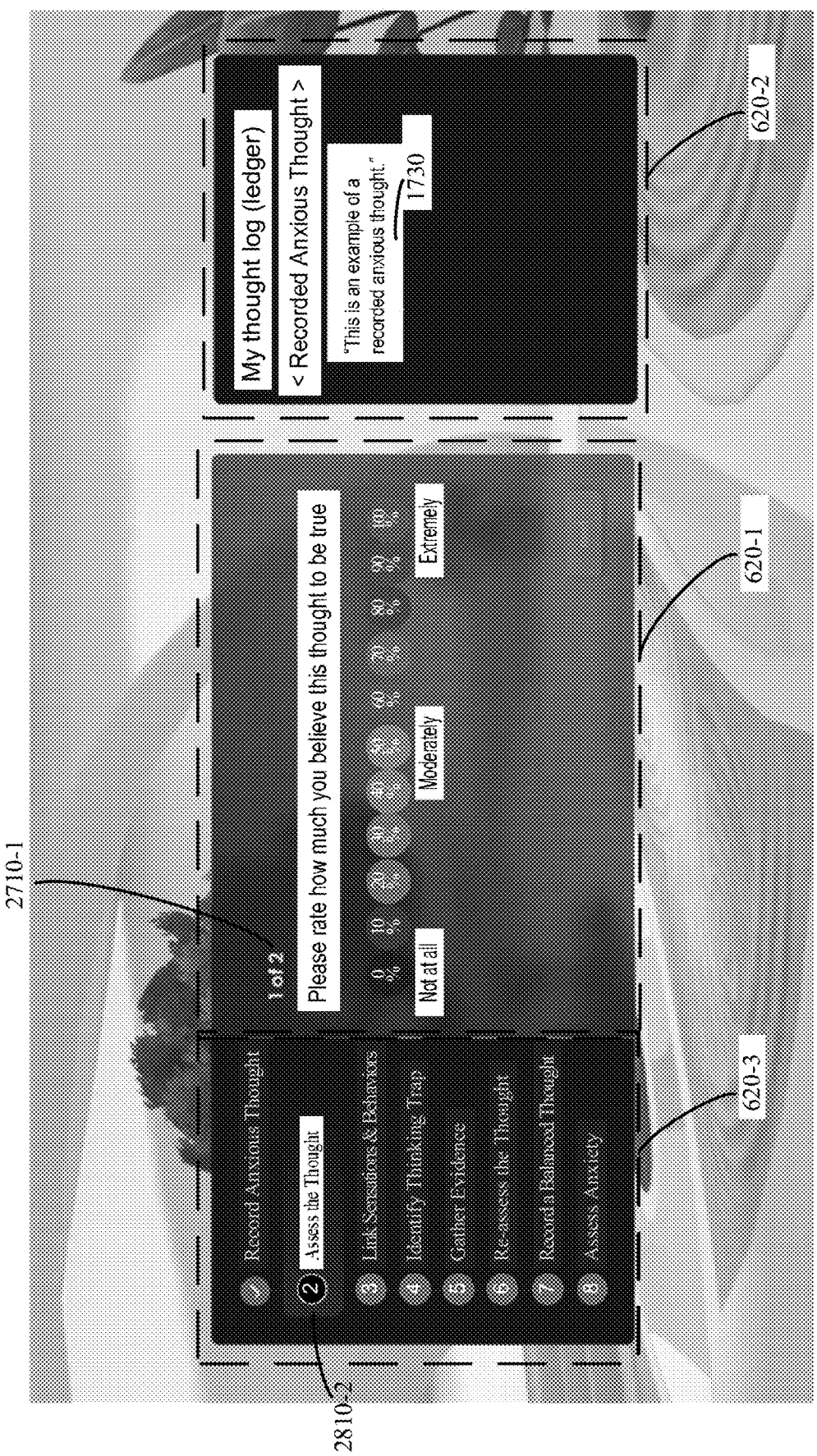
Figure 28E:
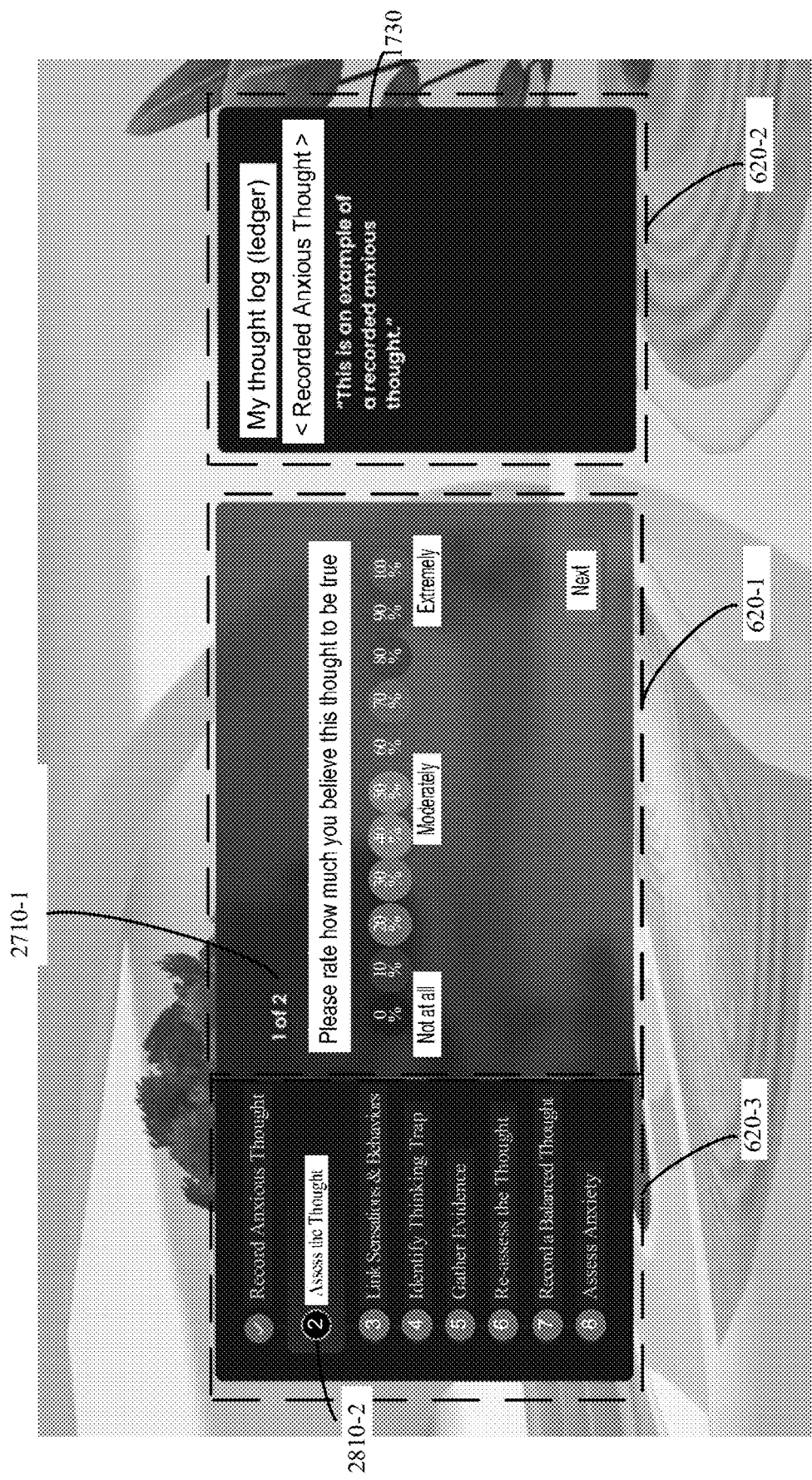
Figure 28F:
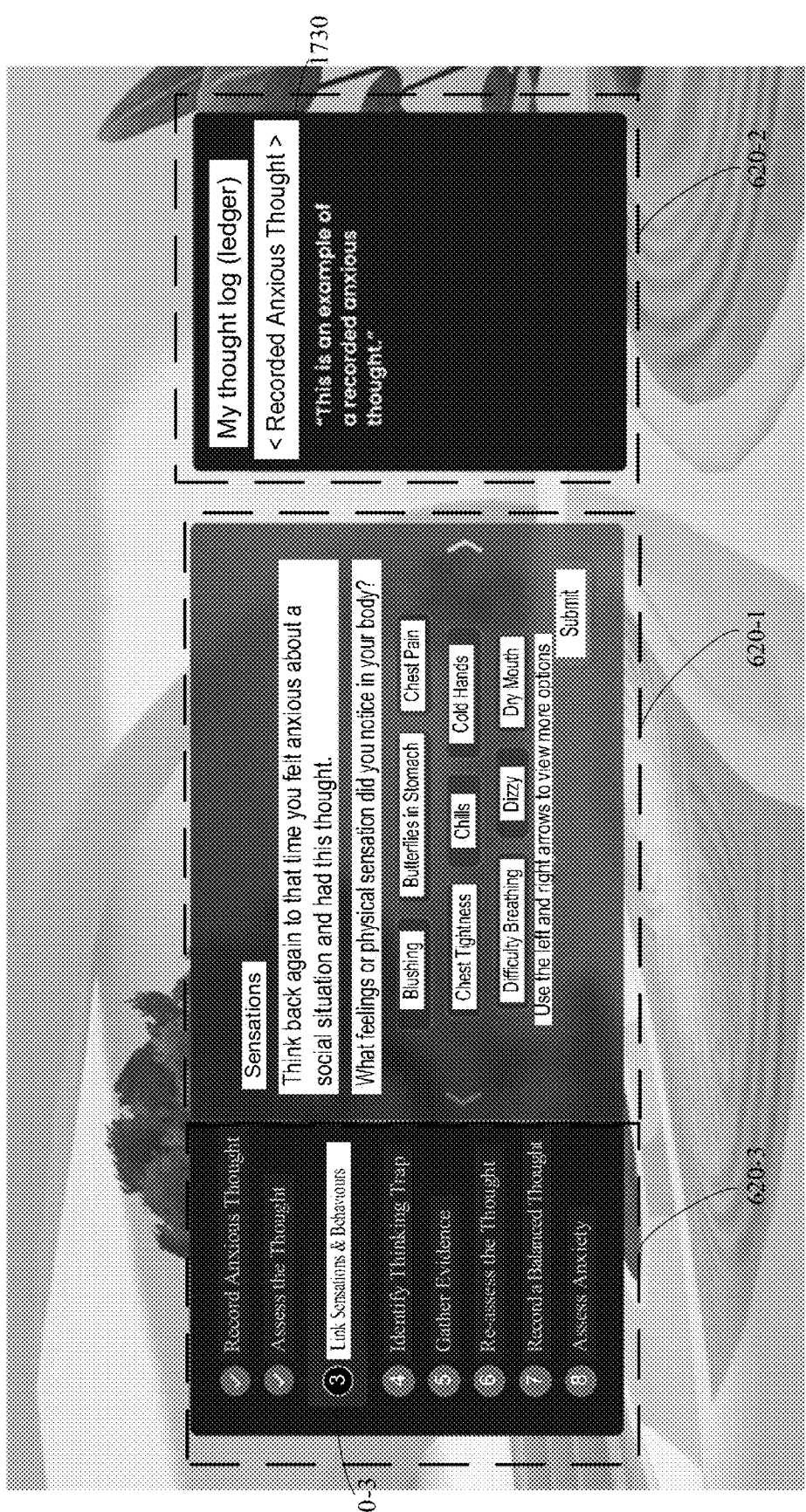
Figure 28G:
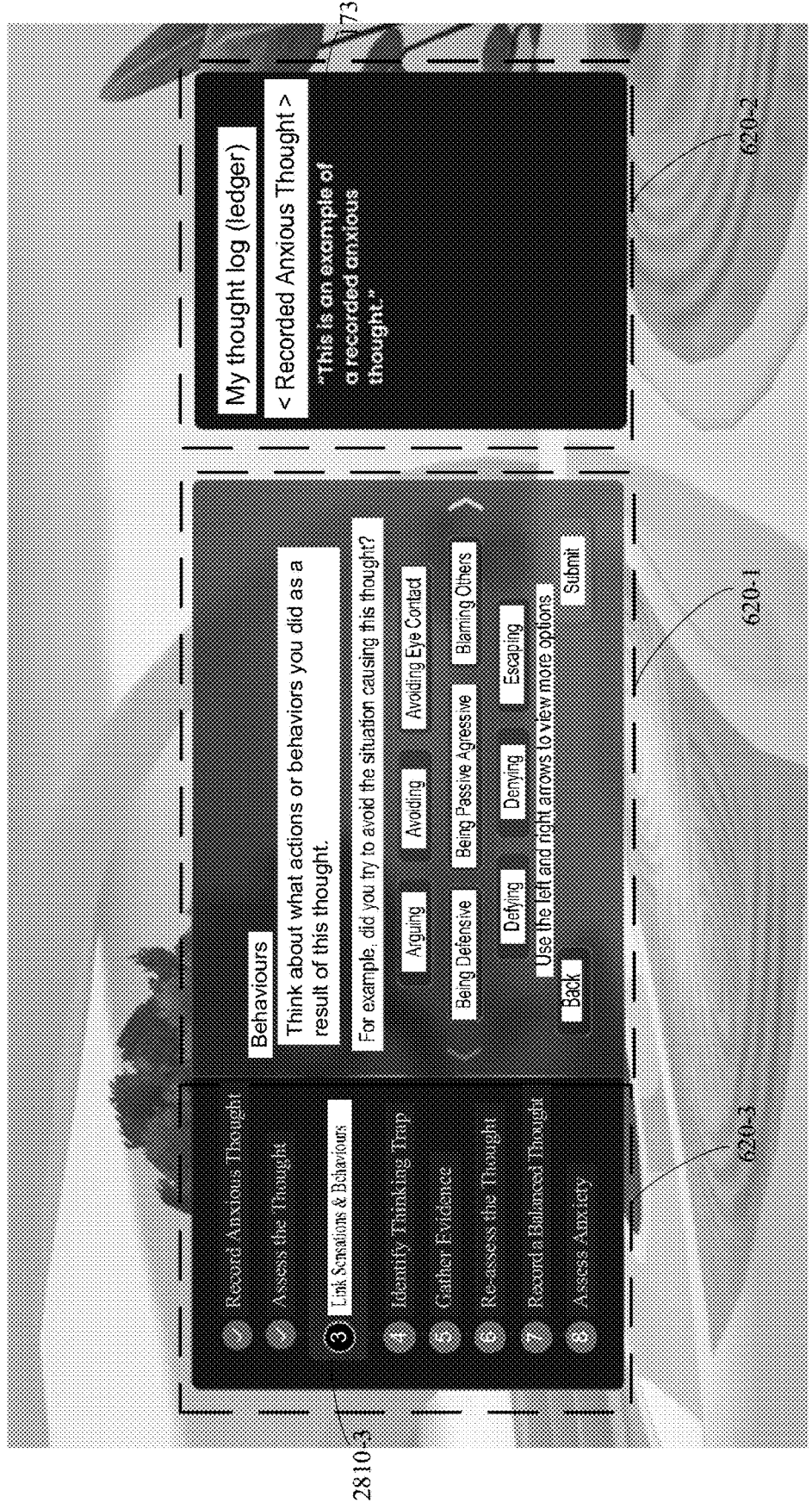
Figure 28H:
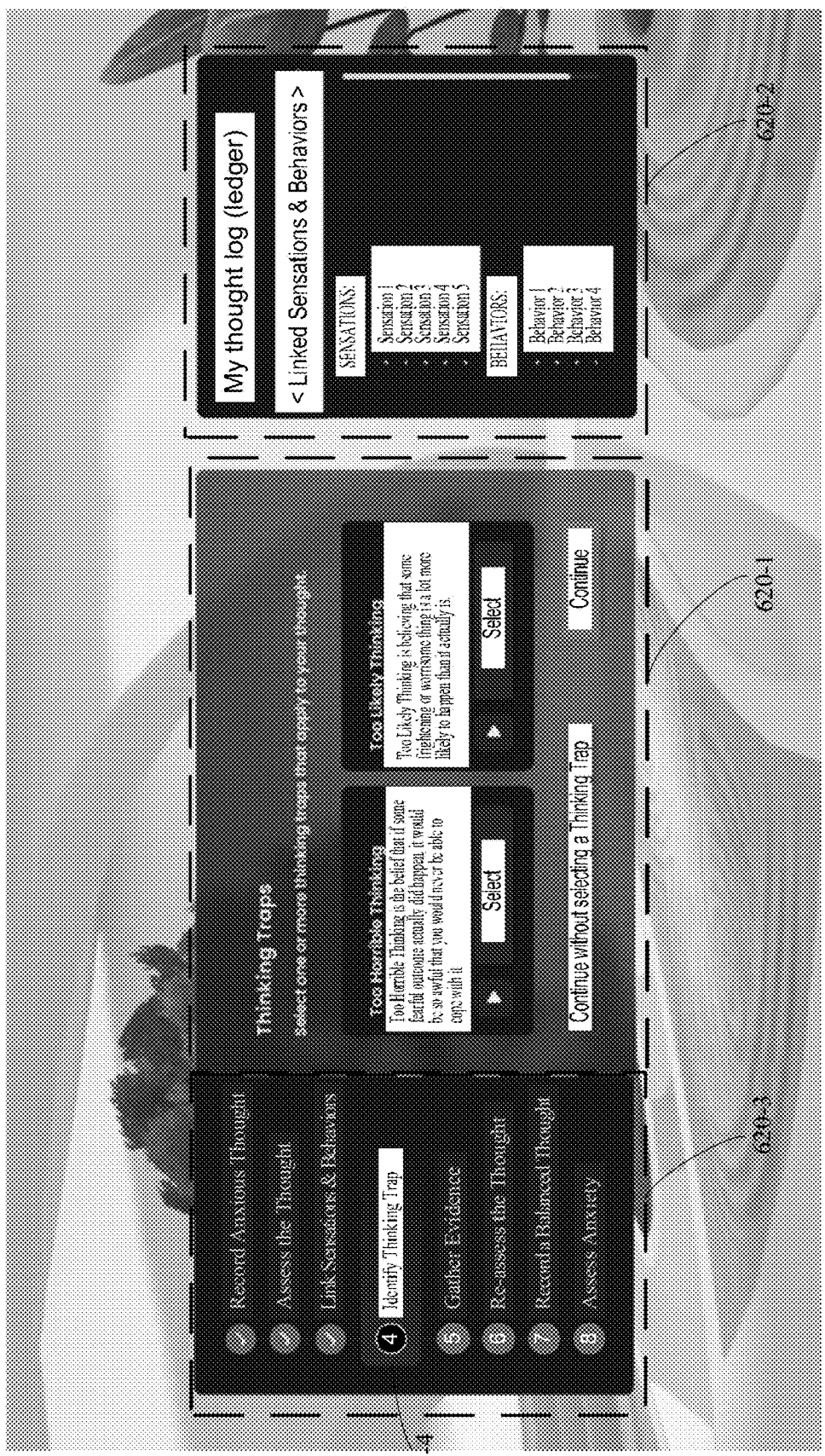
Figure 28I:
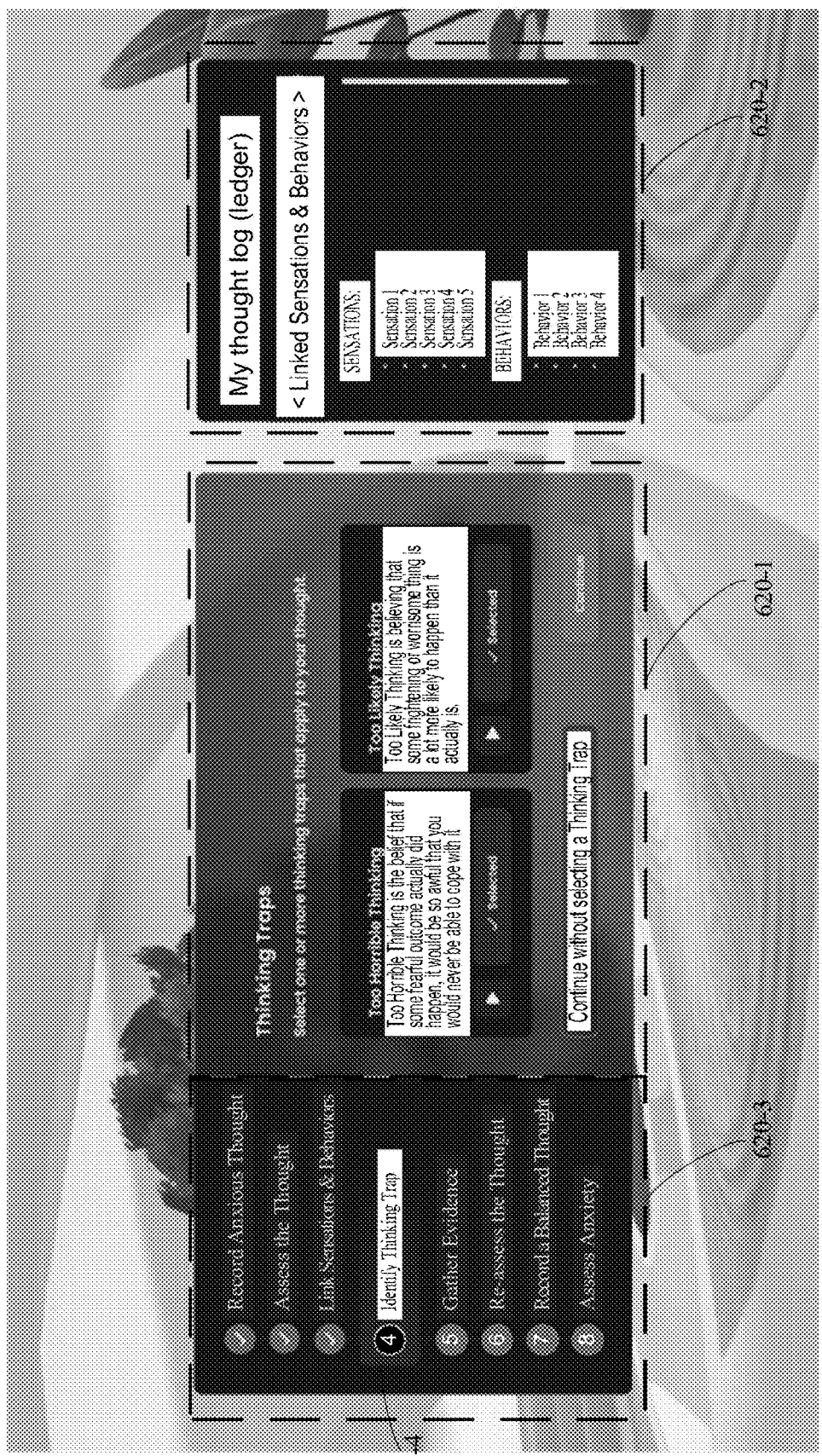
Figure 28J:
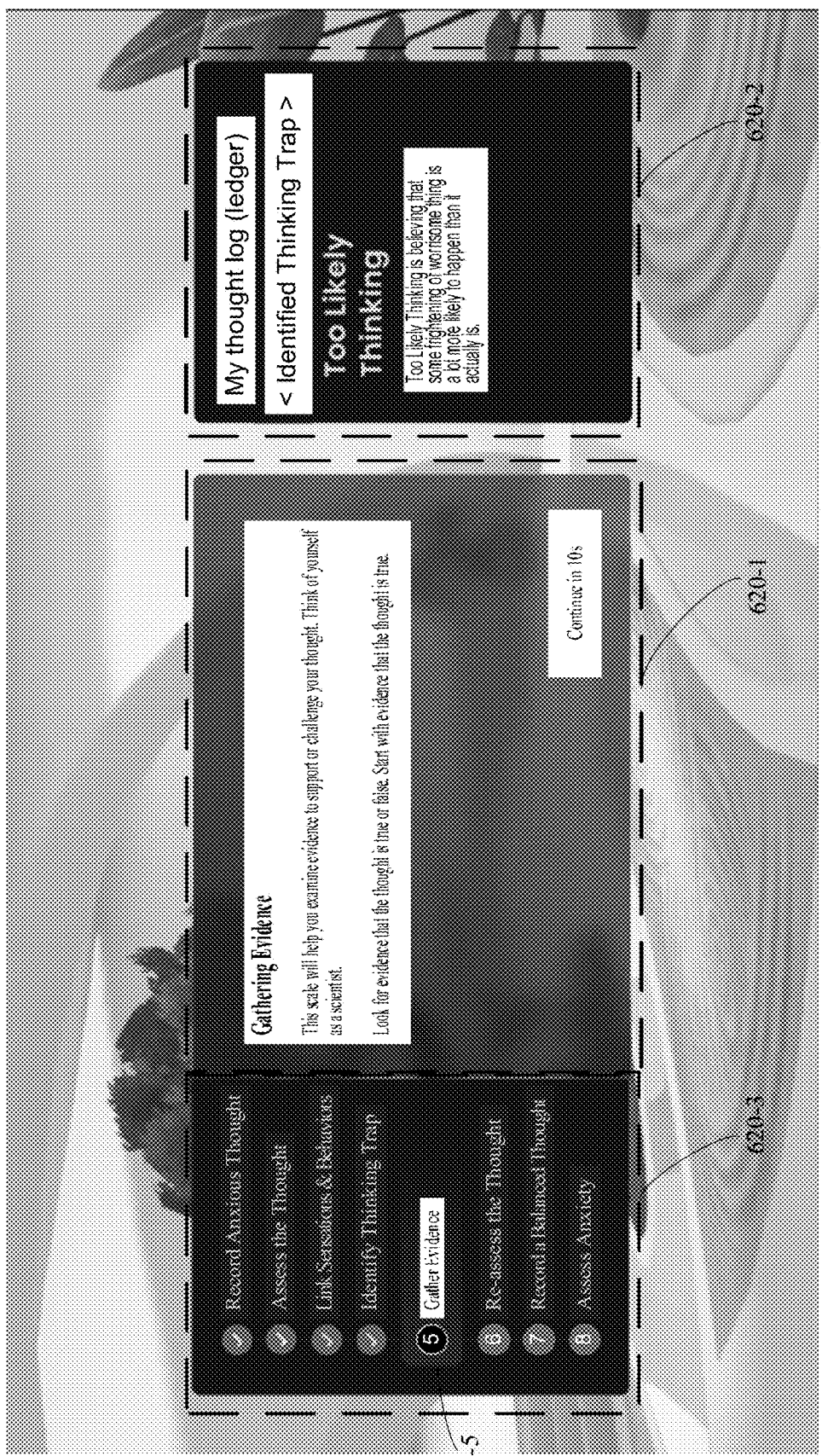
Figure 28K:
Figure 28L:
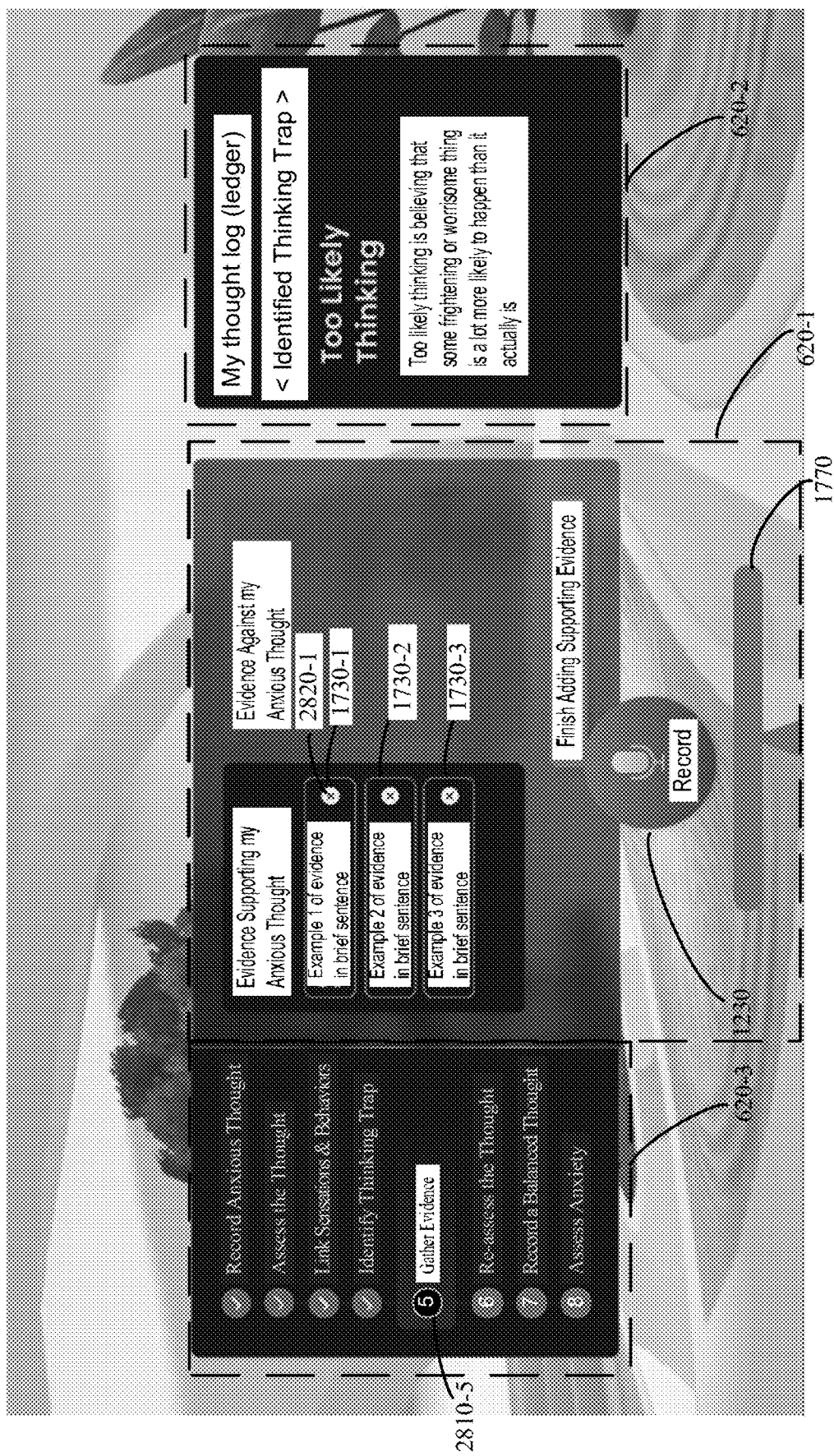
Figure 28M:
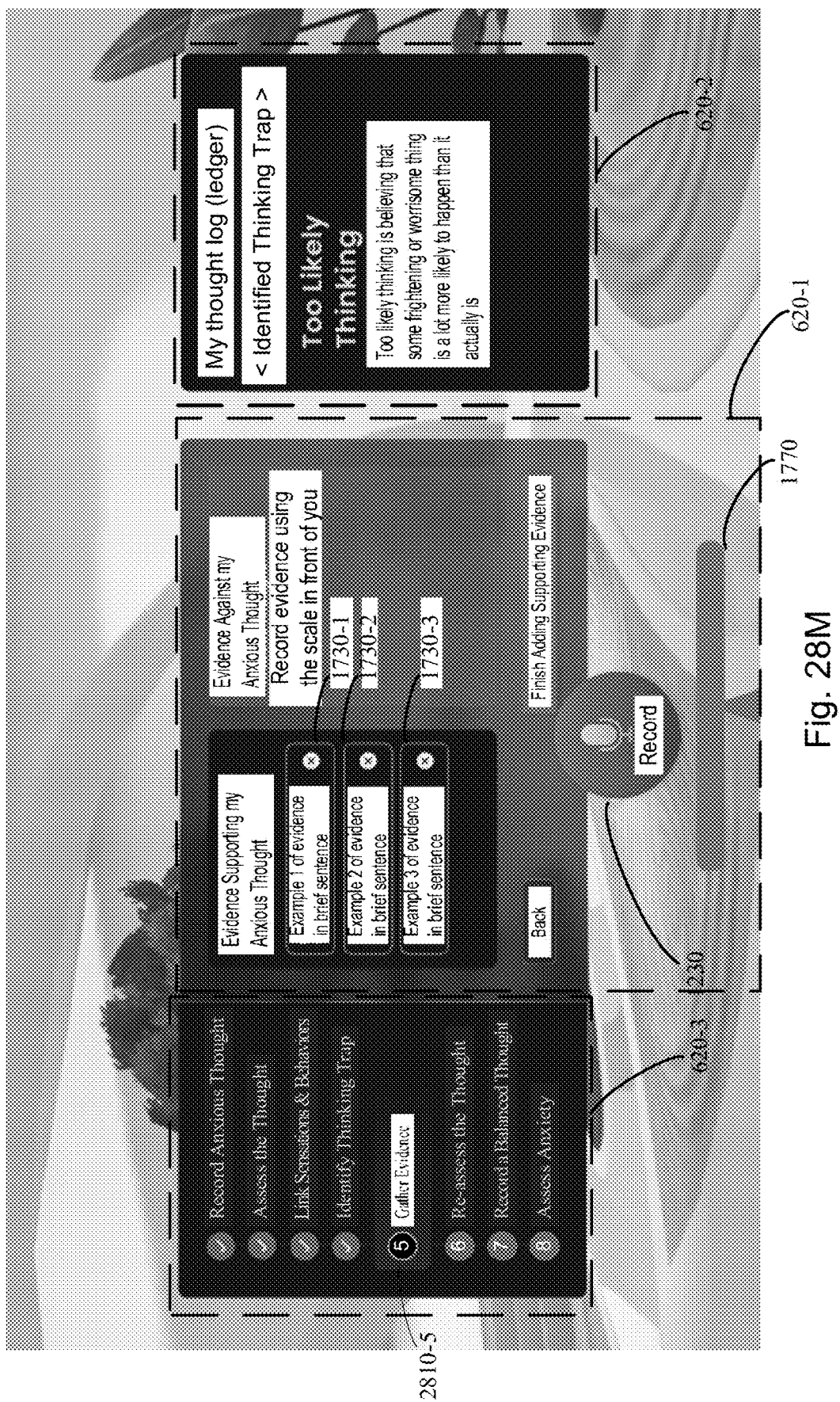
Figure 28N:
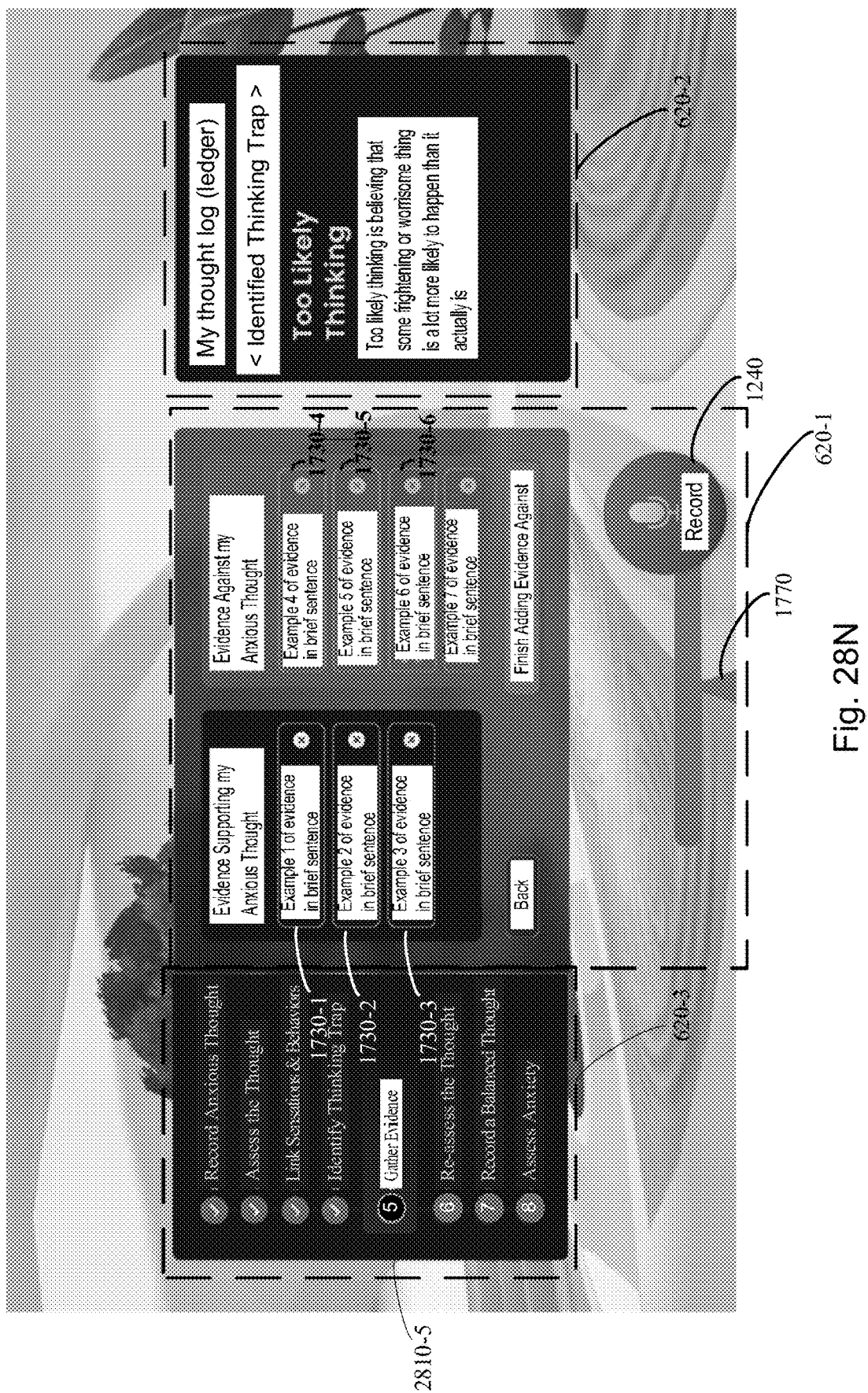
Figure 28O:
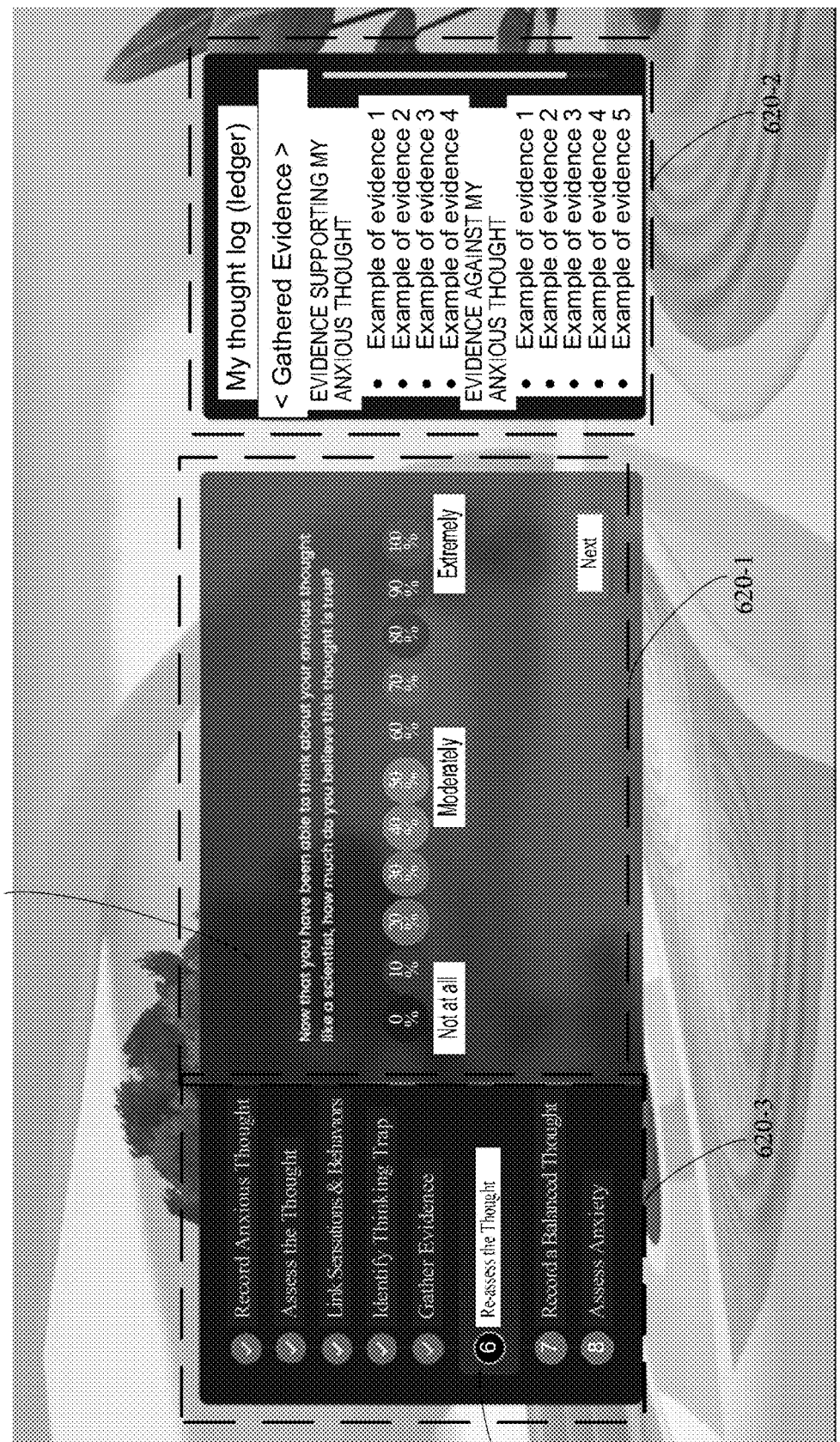
Figure 28P:
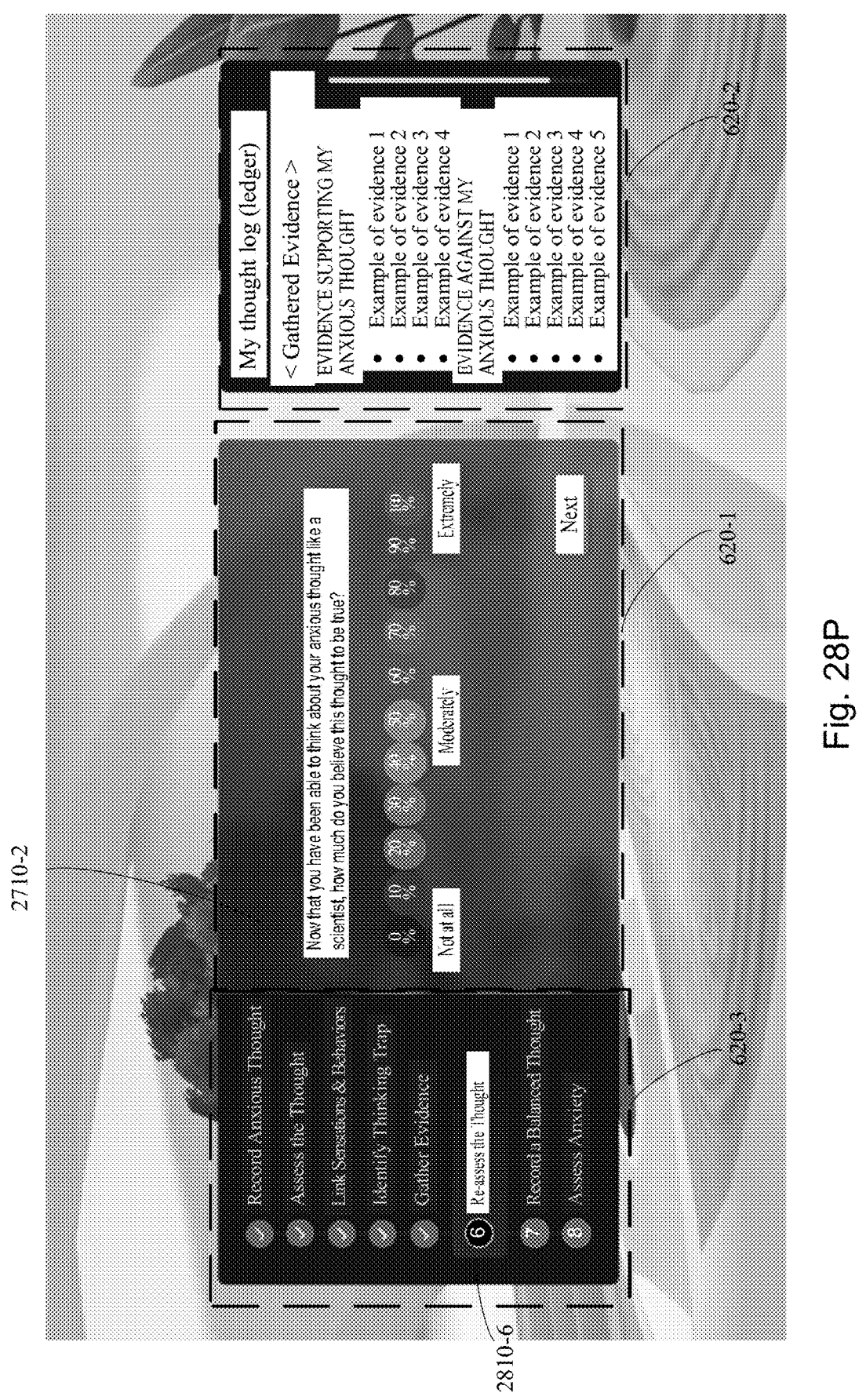
Figure 28Q:
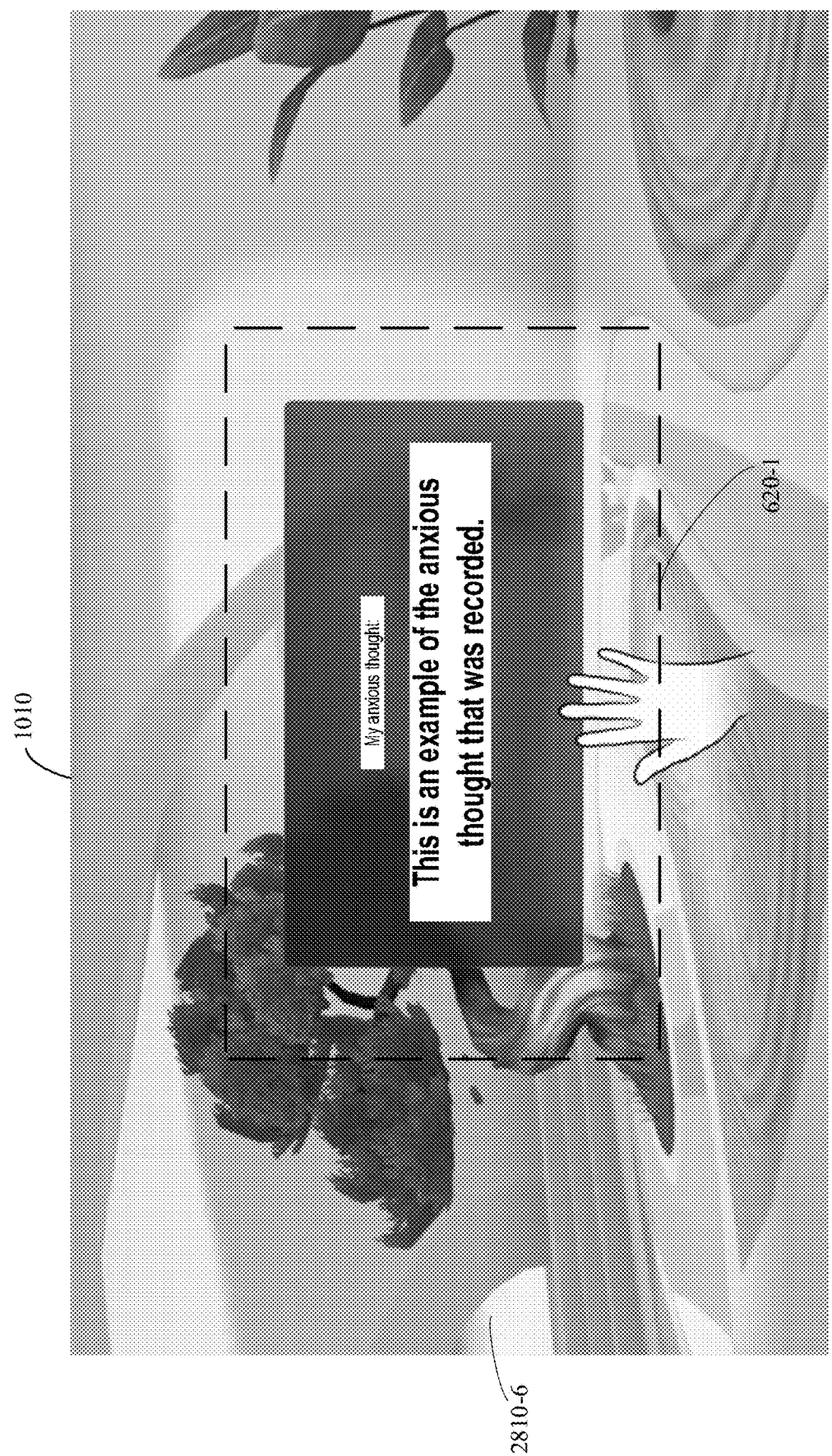
Figure 28R:
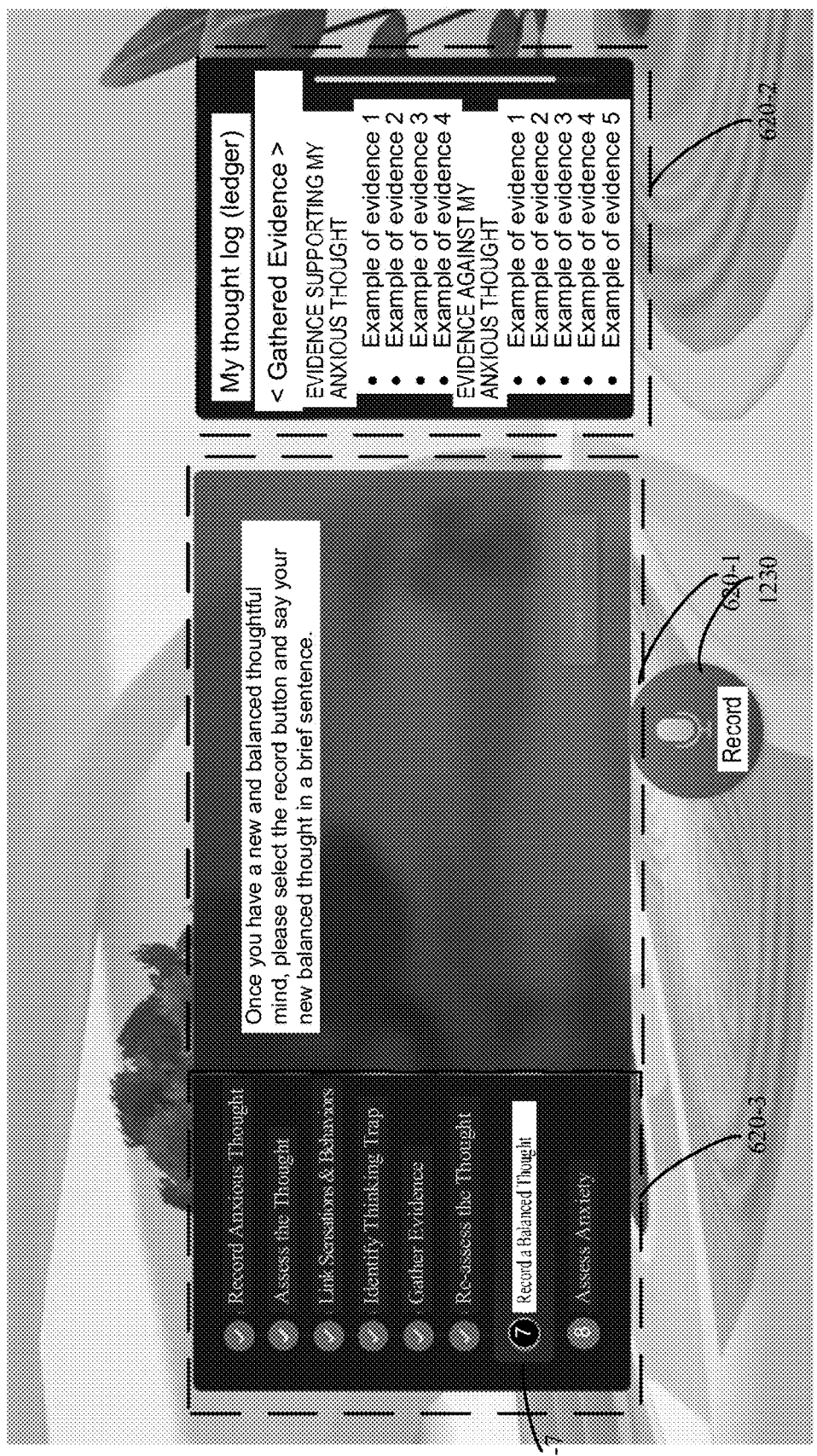
Figure 28S:
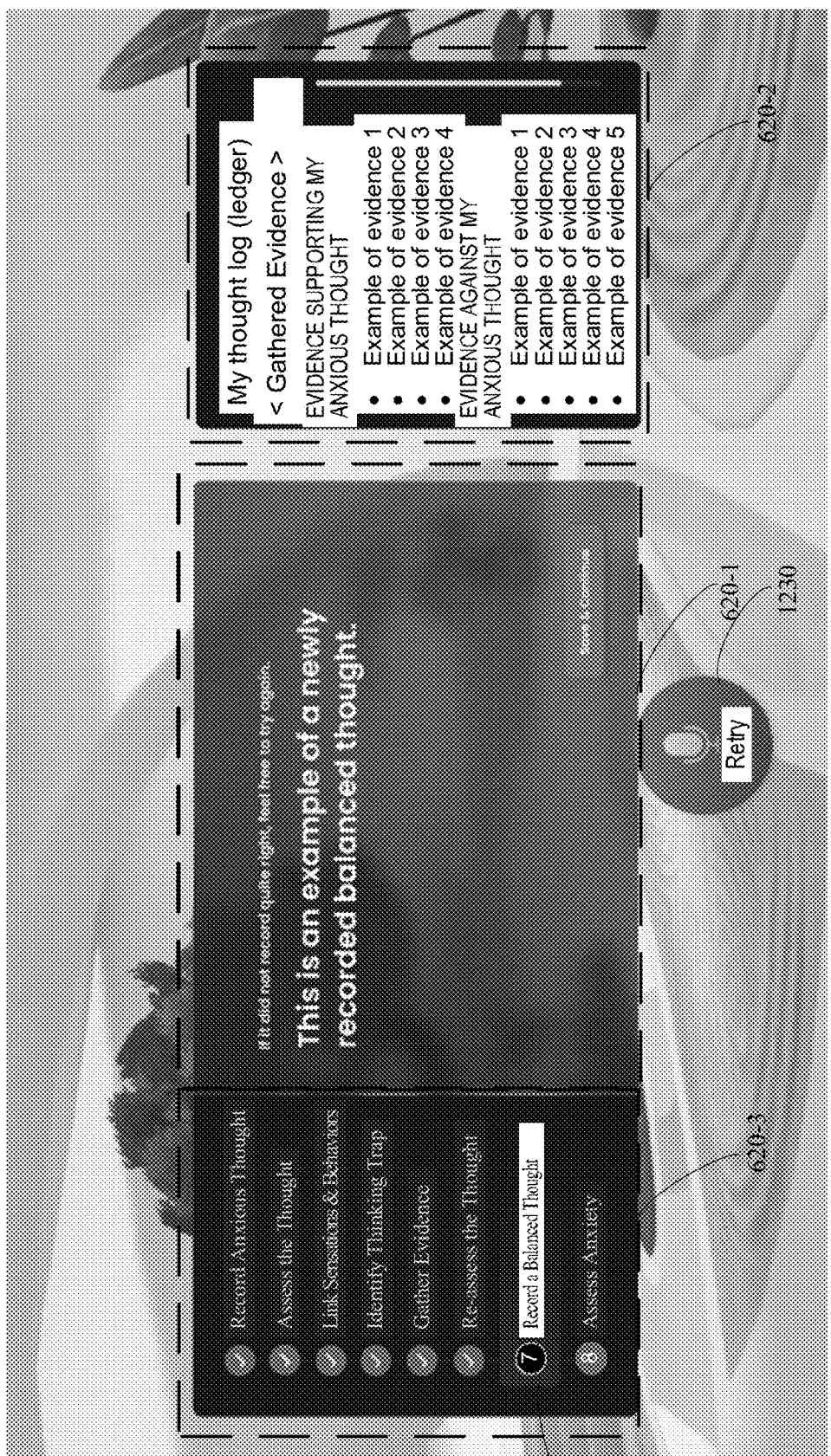
Figure 28T:
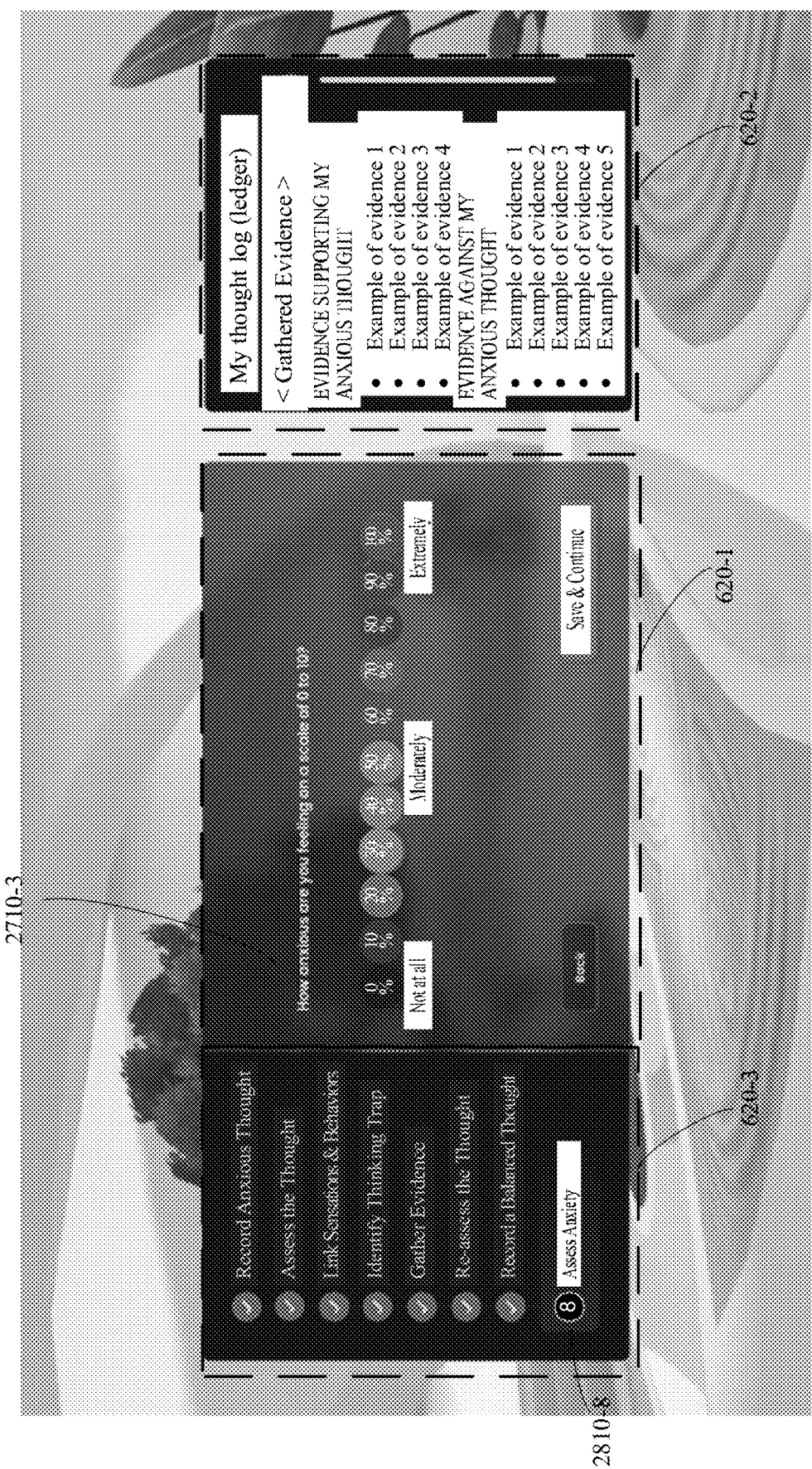

In some embodiments, the first affordance region 620-1 is associated with a plurality of interactive DR activities (e.g., first interactive activity 2810-1 of FIG. 28A, second interactive activity 2801-2 of FIG. 28E, . . . , eighth interactive activity 2810-8 of FIG. 28T, etc.). For instance, in some embodiments, the first affordance region 620-1 defines a space (e.g., designated area 1010 of FIG. 28A) within the interactive DR scene 1000 within which the subject performs a respective interactive DR activity in the plurality of interactive DR activities. For instance, referring briefly to FIG. 28A, in some embodiments, the first affordance region 620-1 provides a space 1010 within the interactive DR scene 1000 for the subject to complete a respective assessment (e.g., a second assessment generated by an assessment module 12 of a digital reality system 200 of FIG. 1, etc.). However, the present disclosure is not limited thereto.

In some embodiments, one or more affordance regions 620 are visible to the subject. For instance, in some embodiments, there is a demarcation on the display (e.g., on the graphical user interface presented through the display) that denotes one or more boundaries of an affordance region, such as a two-dimensional or three-dimensional polygon that forms the boundary of the respective affordance region. For instance, in some embodiments an affordance region 620 is bounded by a rectangular, or substantially rectangular, polygon. However, the present disclosure is not limited thereto.

In some embodiments, as illustrated in FIG. 28A, a second affordance region 620-2, which is different from the first affordance region, is associated with a ledger of activity, which is referred to herein as a "ledger." In some embodiments, the ledger of the second affordance region provides information associated with performance by the subject during one or more interactive DR activities in the plurality of interactive DR activities and/or the plurality of interactive DR activities. For instance, in some embodiments, the chart includes a first axis, a respective axis, and one or more respective data plots. Each respective data plot represents one or more evidence constructs formed during a respective interactive DR activity and is placed within the region defined by the first axis and the second axis. Thus, the ledger provides a visualization of evidence constructs formed for the subject. However, the present disclosure is not limited thereto. In some embodiments, the ledger illustrates the result of one or more assessments, such as one or more subjective evaluations, answered by the subject over a time period during the plurality of interactive DR activities. For instance, in some embodiments, the chart includes a first axis, a second axis, and one or more respective data plots. Each respective data plot represents a corresponding result of an assessment provided to the subject and is placed within the region defined by the first axis and the second axis. Thus, the ledger provides a visualization of assessment results for the subject. However, the present disclosure is not limited thereto.

In some embodiments the second affordance region 620-2 is persistently displayed during the plurality of interactive DR activities. This allows the information associated with second affordance region 620-2 to be continuously visualized and/or dynamically updated when the subject progresses through the plurality of interactive DR activities. However, the present disclosure is not limited thereto.

In some embodiments, as illustrated in FIG. 28A, the first interactive DR activity 2810-1 in the plurality of interactive DR activities includes detecting a selection by the subject of a respective recording object in one or more recording objects (e.g., recording object 1230 of FIG. 28A, recording object 1230 of FIG. 28B, recording object 1230 of FIG. 28M, etc.) at the first affordance region 620-1. Moreover, in some embodiments, the first interactive DR activity includes forming a first corresponding evidence construct (e.g., evidence construct 1730 of FIG. 28B, first evidence construct 1730-1 of FIG. 28M, etc.) associated with the subject in one or more evidence constructs. In some embodiments, the first corresponding evidence construct 1730 is associated with a first statement that is uttered by the subject during the first interactive DR activity. Then, there is presented, on the display, at the first affordance region 620-1, a first visualization of the first corresponding evidence construct, which allows the subject to read the statement previously uttered by the subject. Also, in some embodiments, the ledger at the second affordance region 620-2 is updated with a second visualization of the first corresponding evidence construct different from the first visualization of the first corresponding evidence construct.

Referring to block 2524, in some embodiments, the forming the first corresponding evidence construct further includes converting the first corresponding evidence construct into a corresponding evidence text. In some embodiments, the first visualization includes the corresponding evidence text at or adjacent to the recording object that records the corresponding evidence construct as illustrated in FIG. 28B.

Referring to block 2526, in some embodiments, each respective evidence construct 1730 is contained in or represented by the one or more recording objects 1230 selected by the subject. For instance, referring briefly to FIG. 28L, a first evidence construct 1730-1, a second evidence construct 1730-2, and a third evidence construct 1730-3 are each associated with a first recording object 1230 configured to illicit statements from the subject associated with a first sentiment (e.g., positive sentiment). Similarly, referring to FIG. 28N, a fourth evidence construct 1730-4, a fifth evidence construct 1730-5, and a sixth evidence construct 1730-6 are each associated with a second recording object 1240 configured to illicit statements from the subject associated with a second sentiment (e.g., negative sentiment). However, the present disclosure is not limited thereto.

Referring to block 2528, in some embodiments, the forming of the first corresponding evidence construct 1730 during the first interactive DR activity further includes presenting, on the display, the one or more evidence constructs 1730 associated with a first sentiment and the one or more evidence constructs 1730 associated with a second sentiment in a DR sorting area of the first affordance region. For instance, referring briefly to FIG. 28N, a fifth interactive DR activity for "Gather Evidence" displays the first evidence construct 1730-1, the second evidence construct 1730-2, and the third evidence construct 1730-3 that are each associated with the first sentiment (e.g., positive sentiment), and also displays the fourth evidence construct 1730-4, the fifth evidence construct 1730-5, and the sixth evidence construct 1730-6 that are each associated with the second sentiment (e.g., negative sentiment) in a DR sorting area that separates the one or more evidence constructs 1730 associated with the first sentiment and the one or more evidence constructs 1730 associated with the second sentiment in the DR sorting area that is depicted as a digital scale (e.g., weighing scale). However, the present disclosure is not limited thereto.

In some embodiments, the one or more evidence constructs associated with the first sentiment are separated from the one or more evidence constructs associated with the second sentiment. For instance, in some embodiments, the one or more evidence constructs associated with the first sentiment are visually separated from the one or more evidence constructs associated with the second sentiment, such as by displaying a divider or border between the tone or more evidence constructs associated with the first sentiment and the one or more evidence constructs associated with the second sentiment. In some embodiments, the one or more evidence constructs associated with the first sentiment are separated by the subject from the one or more evidence constructs associated with the second sentiment. In some embodiments, the one or more evidence constructs associated with the first sentiment are dynamically separated from the one or more evidence constructs associated with the second sentiment by the computer system (e.g., a model of the computer system).

Moreover, in some embodiments, the first interactive DR activity allows for the subject to discard any evidence construct in the one or more evidence constructs associated with the first sentiment and/or the one or more evidence constructs associated with the second sentiment that is deemed not objective by the subject. For instance, referring to FIG. 28L, each evidence construct 1730 includes a mechanism (e.g., radio button 2820) that allows the subject to discard a respective evidence construct in the one or more evidence constructs associated with the first sentiment and/or the one or more evidence constructs, enabling the user to critically think about the evidence constructs formed during the interactive DR activity and provide potentially better statements when forming other evidence constructs. However, the present disclosure is not limited thereto.

Referring to blocks 2530-2532 in some embodiments, the presenting of the one or more evidence constructs associated with the first sentiment and/or the one or more evidence constructs associated with the second sentiment allows the subject to read the one or more evidence constructs associated with the first sentiment and the one or more evidence constructs associated with the second sentiment. For instance, referring to FIG. 28N, a visualization of text associated with the utterance obtained from the subject allows the subject to reach the one or more evidence constructs associated with the first sentiment and/or the one or more evidence constructs associated with the second sentiment. As a non-limiting example, a first evidence construct 1730-1 is associated with a first statement obtained from the subject and provides a visualization of text associated with the first statement (e.g., "Example 1 of evidence in brief sentence"). Moreover, in some embodiments, a corresponding evidence text converted from the first corresponding evidence construct is presented at or adjacent to the respective DR recording object that records the corresponding evidence construct. For instance, in some embodiments, the correspondence evidence text provides a translation and/or a transcription of the utterance obtained by the subject, such as by applying the utterance obtained by the subject to a first model configured to transcript speech to text. However, the present disclosure is not limited thereto.

Referring to block 2534, in some embodiments, the first interactive activity includes presenting, on the display, a DR measurement object. In some embodiments, the DR measurement object is indicative of whether the one or more evidence constructs associated with the first sentiment exceed the one or more evidence constructs associated with the second sentiment. In some embodiments, the DR measurement object is rendered to simulate any suitable measurement tool in any suitable shape, size, color, or the like, which allows the subject to evaluate an aspect of the one or more evidence constructs associated with the first sentiment and the one or more evidence constructs associated with the second sentiment.

Referring to block 2536, in some embodiments, the one or more evidence constructs associated with the first sentiment exceed the one or more evidence constructs associated with the second sentiment when the quality of the one or more evidence constructs associated with the first sentiment exceeds the quality of the one or more evidence constructs associated with the second sentiment, and/or when the quantity of the one or more evidence constructs associated with the first sentiment exceeds the quantity of the one or more evidence constructs associated with the second sentiment. For instance, referring to FIG. 28L, the quantity of the one or more evidence constructs associated with the first sentiment of evidence supporting the statement by the subject is three, which exceeds the quantity of the one or more evidence constructs associated with the second sentiment of evidence against the statement by the subject, which is zero. As another non-limiting example, referring to FIG. 28N, the quantity of the one or more evidence constructs associated with the second sentiment of evidence against the statement by the subject is four, which exceeds the quantity of the one or more evidence constructs associated with the first sentiment of evidence supporting the statement by the subject, which is three. Accordingly, by having the one or more evidence constructs associated with the first sentiment exceed the one or more evidence constructs associated with the second sentiment when the quality of the one or more evidence constructs associated with the first sentiment exceeds the quality of the one or more evidence constructs associated with the second sentiment, and/or when the quantity of the one or more evidence constructs associated with the first sentiment exceeds the quantity of the one or more evidence constructs associated with the second sentiment, the method 2500 enables the subject to form an unbalanced quality and/or quantity of evidence constructs. However, the present disclosure is not limited thereto.

Referring to block 2538, in some embodiments, the DR measurement object simulates a balance scale within a DR weighting area of the first interactive DR scene. As a non-limiting example, FIGS. 17E and 17F and FIGS. 28K through 28N illustrate a DR measurement object 1770 simulating a balance scale. In some embodiments, the area where a DR measurement object is located is also referred to as a DR weighting area of the first interactive DR activity that is displayed within the first affordance region.

Referring to block 2540, in some embodiments, the one or more evidence constructs associated with the first sentiment are generated prior to, concurrently with, or subsequent to the one or more one or more evidence constructs associated with the second sentiment. For instance, referring to FIG. 28M, during a fifth interactive activity presented within the first affordance region, the subject is prompted to first form one or more evidence constructs that support the first statement obtained from the user prior proceeding to form one or more evidence constructs that are against the first statement. However, the present disclosure is not limited thereto.

Referring to blocks 2542-2544, in some embodiments, the one of the first and second sentiments is a positive sentiment (e.g., positive thoughts, supporting thoughts, etc.) and the other of the first and second sentiments is a negative sentiment (e.g., negative thoughts, anxious thoughts, etc.). However, the present disclosure is not limited thereto. For instance, in some embodiments, one of the first and second sentiments is an arousing sentiment and the other of the first and second sentiments is a negative or neutral sentiment. As a non-limiting example, referring briefly to FIG. 28I, the first sentiment is associated with "horrible thinking" and the second sentiment is associated with "too likely thinking." As yet another non-limiting example, referring briefly to FIGS. 28F and 28G, the first sentiment is associated with sensations of the subject and the second sentiment is behaviors of the subject.

Referring to block 2546, in some embodiments, the interactive DR scene further includes a third affordance region (e.g., third affordance region 620-3 of FIG. 28E, third affordance region 620-3 of FIG. 28F, third affordance region 620-3 of FIG. 28M, etc.). In some embodiments, the third affordance region is different from the first affordance region and the second affordance region, which allows for the third affordance region to be differentiated from the first and second affordance regions within the interactive DR scene.

In some embodiments, the third affordance region includes a chart depicting a progression of the subject through the plurality of interactive DR activities. In some embodiments, the chart illustrates a result of one or more assessments, such as one or more subjective evaluations, answered by the subject over a time period. For instance, in some embodiments, the chart includes a first axis, a respective (second) axis, and one or more respective data plots. Each respective data plot represents a corresponding result of an assessment provided to the subject and is placed within a region defined by the first axis and the second axis. Thus, the chart provides a visualization of assessment results for the subject. In some embodiments, the chart is displayed in the report when the correspond result indicates an improved by the subject in management of the mental or psychiatric condition.

Referring to block 2548, in some embodiments, the third affordance region is persistently displayed with the second affordance region during the plurality of interactive DR activities. Accordingly, by persistently displaying the third affordance region, the subject is made aware of progress and/or status of each respective interactive DR activity in the plurality of interactive DR activities, which motivates the subject to complete the threshold conditions associated with the plurality of interactive DR activities collectively.

Referring to block 2550, in some embodiments, the chart depicts the progression of the subject linearly through each interactive DR activity in the plurality of interactive DR activities. For instance, referring to FIG. 28T, the chart of the third affordance region 620-3 provides a listing of each interactive activity in the plurality of interactive activities in the order that it is to be performed by the subject within the interactive DR scene.

Referring to block 2552, in some embodiments, the chart in the affordance region 620-3 is dynamically updated, by the one or more progressors, to indicate the current status of the progression of the subject through the plurality of interactive DR activities. For instance, in some embodiments, when the subject is deemed to satisfy each respective threshold condition associated with a corresponding interactive DR activity, a visual feature of the chart is dynamically updated to indicate that the subject has completed the corresponding interactive DR activity. As a non-limiting example, referring to FIG. 28T, a check mark is placed next to a respective interactive DR activity when the subject is deemed to satisfy each respective threshold condition associated with the respective interactive DR activity.

Referring to block 2552, in some embodiments, there is further presented, on the display, at the first affordance region 620-1, a second interactive DR activity in the plurality of interactive DR activities. For instance, in some embodiments, the first affordance region is dynamically updated to present the second interactive DR activity when the subject is deemed to each respective threshold condition associated with the first interactive DR activity. In some embodiments, the second interactive DR activity is automatically presented on the display to the subject when the when the subject is deemed to each respective threshold condition associated with a corresponding interactive DR activity. In some embodiments, the subject is prompted to proceed to the second interactive DR activity upon being deemed to satisfy each respective threshold condition associated with the first interactive DR activity.

Referring to blocks 2554-2556, in some embodiments, the second interactive DR activity in the plurality of interactive DR activities includes obtaining, in electronic form, a first assessment of the subject. For instance, referring briefly to FIGS. 28D and 28E, upon being deemed to satisfy each respective threshold condition associated with the first interactive DR activity 2810-1, the subject is presented with the first assessment. In some embodiments, the first assessment includes one or more prompts. For instance, referring briefly to FIGS. 28F and 28G, in some embodiments, the first assessment includes one or more prompts that is configured to have subject to select a tag in a corresponding plurality of tags associated with the first statement that they most closely identify with. In some embodiments, the corresponding plurality of tags includes a first set of tags associated with the first sentiment and a second set of tags associated with the second sentiment. For instance, in some embodiments, the plurality of tag (e.g., tag objects of the interactive DR scene) represents a plurality of sentiments for types of anxious thoughts or cognitive distortions. In some embodiments, the number of tag is the same as or different from the number of types of anxious thoughts or cognitive distortions. However, the present disclosure is not limited thereto.

In some embodiments, the subject is asked, for instance, by the DR assistant, to select a DR tag object to label a thought. In response to the selection by the subject, the DR assistant will let the subject know whether the selected DR tag object is the correct or incorrect label for the thought. In some embodiments, the subject is asked to select a DR tag object and place it on the DR type-selection object 2030, e.g., a DR hook feature 2036 of the DR type-selection object 2030. In response to the placement of the selected DR tag object by the subject, the DR assistant will let the subject know whether the selected DR tag object is a correct or incorrect label for the thought.

Referring to blocks 2558-2560, in some embodiments, a third interactive DR activity in the plurality of interactive DR activities includes obtaining, in electronic form, a second assessment of the subject. In some embodiments, the second assessment includes a determination when the subject satisfies a threshold validation in change for the psychiatric or mental condition exhibited by the subject. In some embodiments, the threshold validation in change for the psychiatric or mental condition exhibited by the subject includes a threshold change in diagnosis status for the psychiatric or mental condition exhibited by the subject, a threshold change in subjective distress of the subject caused by the corresponding challenge, a threshold change in cognitive symptoms of the subject, a threshold change in mindfulness state of the subject, or a combination thereof. For instance, referring briefly to FIGS. 28O, 28P, and 28T, in some embodiments, the second assessment is configured to illicit one or more subjective unit of distress (SUDS) for the subject to track stress levels during the plurality of interactive DR activities. However, the present disclosure is not limited thereto.

Referring to block 2560, in some embodiments, a determination is made as to whether the subject satisfies a threshold condition associated with each interactive DR activity in the plurality of interactive DR activities. In some such embodiments, each respective threshold condition defines a criterion that must be achieved in order for the respective threshold condition to be deemed satisfied.

Referring to block 2562, in some embodiments, the subject satisfies a respective threshold condition when the one or more evidence constructs associated with the positive sentiment exceeds the one or more evidence constructs associated with the negative sentiment. For instance, in some embodiments, the one or more evidence constructs associated with the positive sentiment exceeds the one or more evidence constructs associated with the negative sentiment when a quality of the one or more evidence constructs associated with the first sentiment exceeds a quality of the one or more evidence constructs associated with the second sentiment, and/or when a quantity of the one or more evidence constructs associated with the first sentiment exceeds a quantity of the one or more evidence constructs associated with the second sentiment.

Referring to block 2564, in some embodiments, the determining is further performed by one or more models and/or a medical practitioner associated with the subject. For instance, in some embodiments, the medical practitioner defines one or more threshold conditions associated with the first interactive DR activity (e.g., a requirement that the first statement is one sentence).

In some embodiments, the one or more models receive as inputs the one or more evidence constructs associated with the first sentiment and/or the one or more evidence constructs associated with the second sentiment and evaluates at least one evidence construct in the one or more evidence constructs associated with the first sentiment and/or the one or more evidence constructs associated with the second sentiments against one or more weights and/or parameters in order to arrive at a result as to whether or not the subject is deemed to satisfy the threshold conditions.

Referring to block 2566, in some embodiments, the determining is further performed by one or more models. The one or more models includes a logistic regression model, a neural network model, a support vector machine model, a Naive Bayes model, a nearest neighbor model, a random forest model, a decision tree model, a boosted trees model, a multinomial logistic regression model, a linear model, a linear regression model, a Gradient Boosting model, a mixture model, a hidden Markov model, a Gaussian model, a linear discriminant model, or any combinations thereof.

Referring to block 2568, in some embodiments, the determining is further performed by one or more models. In some such embodiments, the one or models is a concordance-index model.

Referring to block 2570, in some embodiments, the threshold condition comprises an absence, a presence, a deactivation, an activation, or a value for one or more physiological markers.

Referring to block 2572, in some embodiments, the one or more physiological markers includes a threshold value for skin conductance (SC), a threshold heart rate (HR), a threshold blood volume pulse (BVP), or any combination thereof.

Referring to block 2574, in some embodiments, the threshold condition includes deactivation of the parasympathetic nervous system (PNS).

Referring to block 2576, in some embodiments, the threshold condition includes activation of the sympathetic nervous system (SNS).

Referring to block 2578, in some embodiments, there is obtained by the one or more recording objects, at the second affordance region on the display, a second corresponding evidence construct associated with a second statement uttered by the subject in the one or more evidence constructs, when the subject is deemed to satisfy the threshold condition associated with each interactive DR activity in the plurality of interactive DR activities. In some such embodiments the second statement is a reframing of the first statement. For instance, referring to FIGS. 28R and 28S, in some embodiments, a respective interactive DR activity is configured to record a second statement uttered by the subject in order to form the second evidence construct, in which the second statement is associated with the subject matter of the first statement of the first interactive DR activity.

Figure 28U:
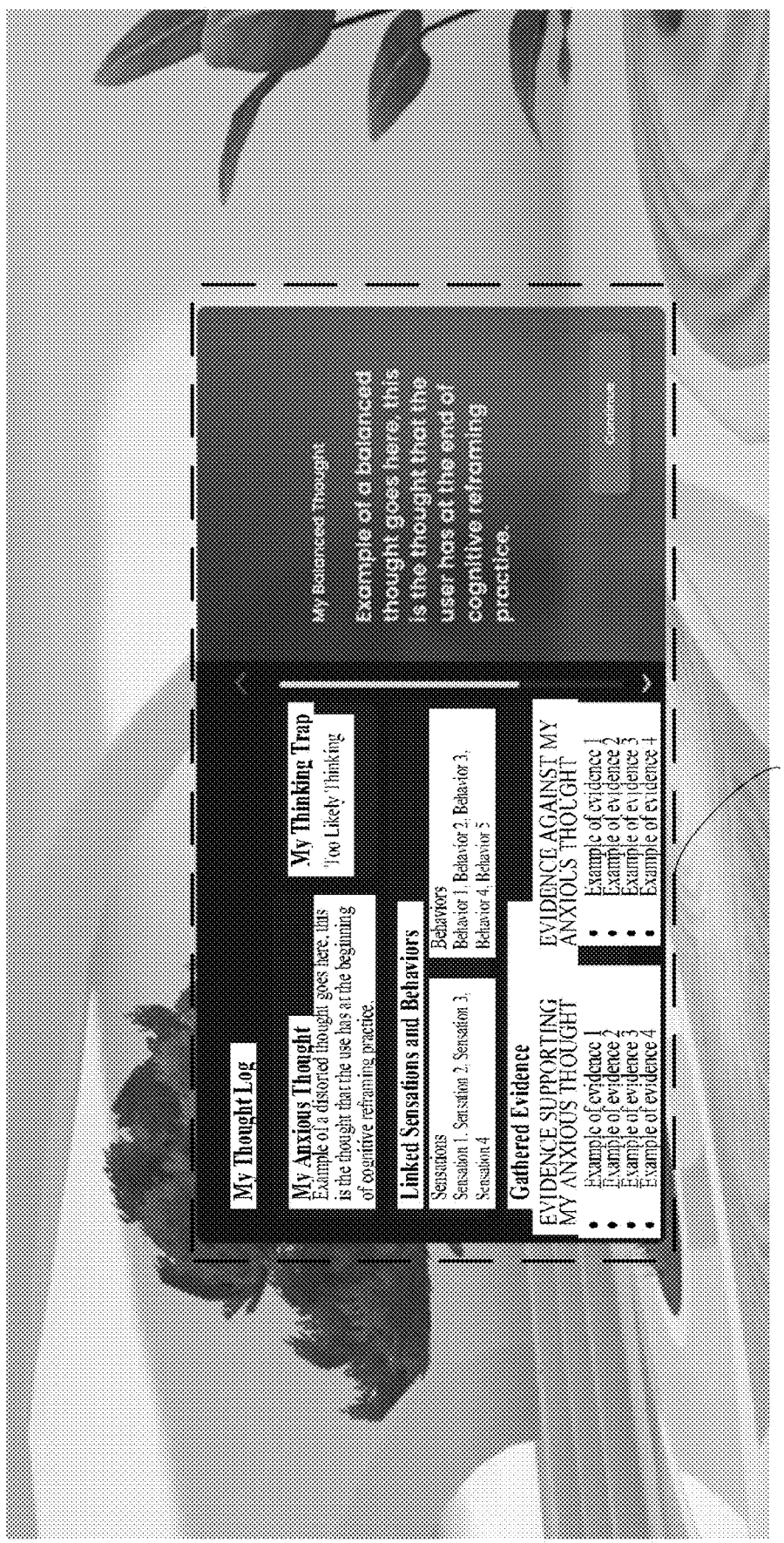
Figure 28V:
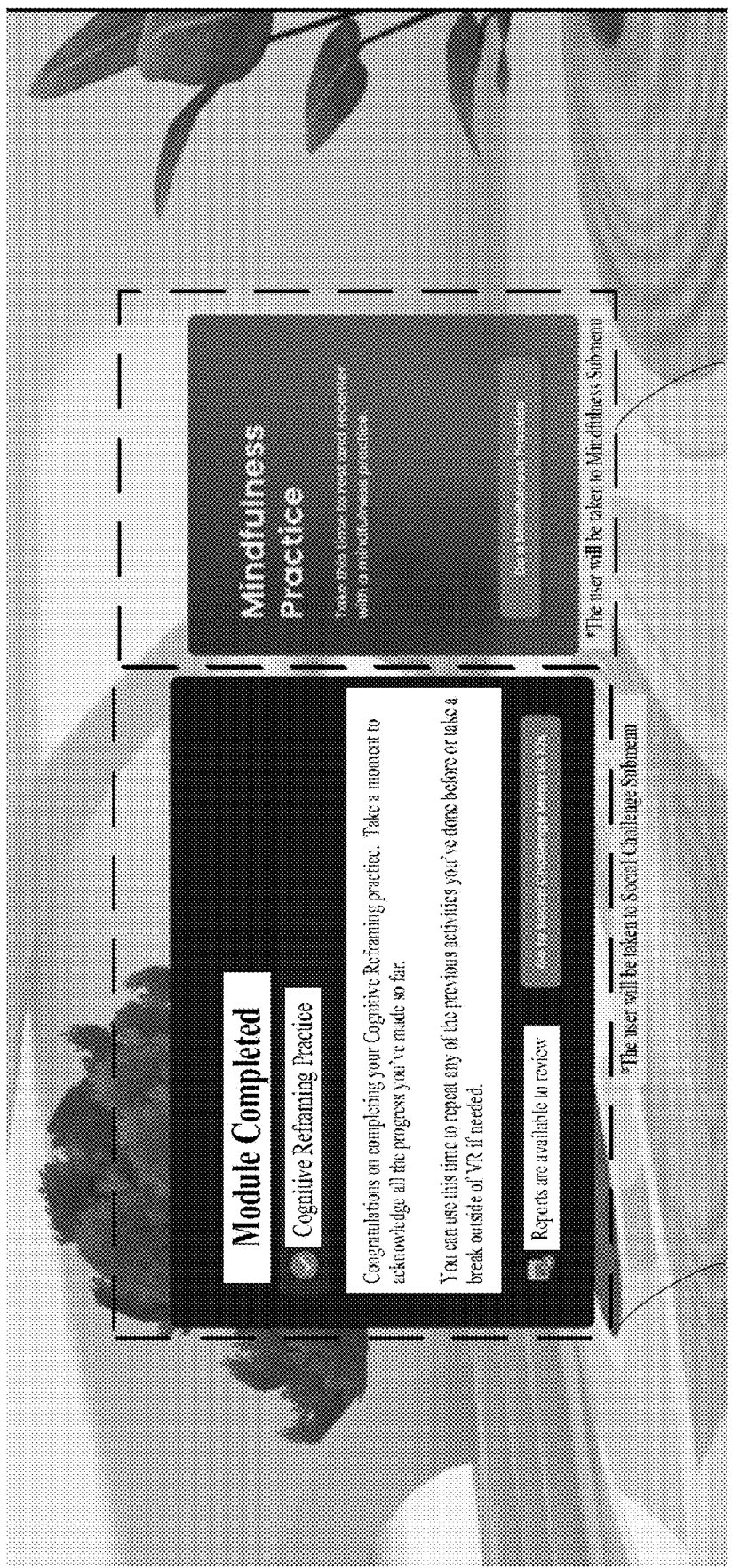

Referring to block 2578, in some embodiments, the method includes further updating the ledger at the second affordance region with a third visualization of the second corresponding evidence construct. For instance, referring to FIG. 28U, in some embodiments, second affordance region 620-2 is dynamically updated to present the third visualization of the second corresponding evidence construct instead of the second visualization of the first corresponding evidence construct. In some embodiments, the second affordance region 620-2 is dynamically updated to present both the third visualization of the second corresponding evidence construct and the second visualization of the first corresponding evidence construct.

Also, in some embodiments, a user profile (e.g., user profile 16-2 of FIG. 2A) that is associated with the subject is updated with a historical record of the ledger, such as a record of each evidence construct formed during the plurality of interactive DR activities, each assessment response obtained during the plurality of interactive DR activities, a state of each threshold condition associated with each interactive DR activities performed by the subject, or the like. In such embodiments, the third visualization is displayed adjacent to the first visualization. In so doing, an improvement in the management of the psychiatric or mental condition by the subject is indicated through both the third visualization and the first visualization.

Referring to block 2580, in some embodiments, when the subject is deemed not to satisfy the threshold condition, the method further includes repeating the forming of a corresponding evidence construct (e.g., repeating the first interactive DR activity) to generate one or more additional evidence constructs. In some embodiments, each of the additional evidence constructs is associated with the first sentiment or the second sentiment. Accordingly, by generating the one or more additional evidence constructs, the method provides for repeating the determining based on the one or more additional evidence constructs together with the one or more evidence constructs associated with the first sentiment and the one or more evidence constructs associated with the second sentiment. Moreover, in alternative embodiments, the method includes presenting, on the display, an additional interactive DR activity in the plurality of interactive DR activities configured to help the subject to reframe the first statement.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. For instance, the computer program product could contain instructions for operating the user interfaces disclosed herein. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for management of a psychiatric or mental condition, the method comprising
   at a computer system associated with a subject, the computer system comprising one or more processors, a display, an audio recorder, and a memory coupled to the one or more processors, the memory comprising one or more programs configured to be executed by the one or more processors, wherein the one or more programs comprise instructions for:
   presenting, on the display, an interactive digital reality (DR) scene comprising (i) a first affordance region associated with a plurality of interactive DR activities and (ii) a second affordance region different from the first affordance region and associated with a ledger of activity performed by the subject during the plurality of interactive DR activities and persistently displayed during the plurality of interactive DR activities, and a first interactive DR activity in the plurality of interactive DR activities comprises:

detecting, by the one or more processors, a selection by the subject of a respective recording object in one or more recording objects at the first affordance region, forming, by the one or more processors, a first corresponding evidence construct associated with the subject in one or more evidence constructs, wherein the first corresponding evidence construct is associated with a first statement uttered by the subject during the first interactive DR activity, presenting, on the display, at the first affordance region, a first visualization of the first corresponding evidence construct, and updating, on the display, at the second affordance region, the ledger with a second visualization of the first corresponding evidence construct different from the first visualization of the first corresponding evidence construct;

further presenting, on the display, at the first affordance region, a second interactive DR activity in the plurality of interactive DR activities;

determining whether the subject satisfies a threshold condition associated with each interactive DR activity in the plurality of interactive DR activities, wherein each respective threshold condition defines a criterion that must be achieved in order for the respective threshold condition to be deemed satisfied;

obtaining, on the display, at the second affordance region, when the subject is deemed to satisfy the threshold condition associated with each interactive DR activity in the plurality of interactive DR activities, by the one or more recording objects, a second corresponding evidence construct associated with a second statement uttered by the subject in the one or more evidence constructs, wherein the second statement is a reframing of the first statement; and further updating, by the one or more processors, on the display, at the second affordance region, the ledger with a third visualization of the second corresponding evidence construct associated and, at a user profile associated with the subject, a historical record of the ledger, wherein the third visualization is displayed adjacent to the first visualization, thereby indicating an improvement in the management of the psychiatric or mental condition by the subject.

2. The method of claim 1, wherein the forming the first corresponding evidence construct further comprises:

converting the first corresponding evidence construct into a corresponding evidence text; and the first visualization comprises the corresponding evidence text at or adjacent to the recording object that records the corresponding evidence construct.

3. The method of claim 1, wherein each respective evidence construct is contained in or represented by the one or more recording objects selected by the subject.

4. The method of claim 1, wherein the forming the first corresponding evidence construct further comprises presenting, on the display, the one or more evidence constructs associated with a first sentiment and the one or more evidence constructs associated with a second sentiment in a DR sorting area of the first affordance region, wherein the one or more evidence constructs associated with the first sentiment are separated from the one or more evidence constructs associated with the second sentiment; and discarding, by the subject, any evidence construct in the one or more evidence constructs associated with the first sentiment and/or the one or more evidence constructs associated with the second sentiment that is deemed not objective by the subject.

5. The method of claim 4, wherein the presenting allows the subject to read the one or more evidence constructs associated with the first sentiment and the one or more evidence constructs associated with the second sentiment.

6. The method of claim 5, wherein a corresponding evidence text converted from the first corresponding evidence construct is presented at or adjacent to the respective DR recording object that records the corresponding evidence construct.

7. The method of claim 4, wherein the first interactive activity comprises presenting, on the display, a DR measurement object indicative of whether the one or more evidence constructs associated with the first sentiment exceed the one or more evidence constructs associated with the second sentiment.

8. The method of claim 7, wherein the one or more evidence constructs associated with the first sentiment exceed the one or more evidence constructs associated with the second sentiment when a quality of the one or more evidence constructs associated with the first sentiment exceeds a quality of the one or more evidence constructs associated with the second sentiment, and/or when a quantity of the one or more evidence constructs associated with the first sentiment exceeds a quantity of the one or more evidence constructs associated with the second sentiment.

9. The method of claim 7, wherein the DR measurement object simulates a balance scale within a DR weighting area of the first interactive DR scene.

10. The method of claim 1, wherein the one or more evidence constructs associated with the first sentiment are generated prior to, concurrently with, or subsequent to the one or more one or more evidence constructs associated with the second sentiment.

11. The method of claim 4, wherein one of the first and second sentiments is a positive sentiment and the other of the first and second sentiments is a negative sentiment.

12. The method of claim 11, wherein the subject satisfies a respective threshold condition when the one or more evidence constructs associated with the positive sentiment exceeds the one or more evidence constructs associated with the negative sentiment.

13. The method of claim 1, wherein one of the first and second sentiments is an arousing sentiment and the other of the first and second sentiments is a negative or neutral sentiment.

14. The method of claim 1, wherein, when the subject is deemed not to satisfy the threshold condition, the method further comprises:

repeating the forming to generate one or more additional evidence constructs, each additional evidence associated with the first or second sentiment, and repeating the determining based on the one or more additional evidence constructs together with the one or more evidence constructs associated with the first sentiment and the one or more evidence constructs associated with the second sentiment; or presenting, on the display, an additional interactive DR activity in the plurality of interactive DR activities configured to help the subject to reframe the first statement.

15. The method of claim 1, wherein the interactive DR scene further comprises a third affordance region different from the first affordance region and the second affordance region, wherein the third affordance region comprises a chart depicting a progression of the subject through the plurality of interactive DR activities.

16. The method of claim 15, wherein the third affordance region is persistently displayed with the second affordance region during the plurality of interactive DR activities.

17. The method of claim 15, wherein the chart depicts the progression of the subject linearly through each interactive DR activity in the plurality of interactive DR activities.

18. The method of claim 15, wherein the chart is dynamically updated, by the one or more progressors, to indicate a current status of the progression of the subject through the plurality of interactive DR activities.

19. The method of claim 1, wherein a second interactive DR activity in the plurality of interactive DR activities comprises obtaining, in electronic form, a first assessment of the subject, the first assessment comprising an identification of a corresponding plurality of tags associated with the first statement.

20. The method of claim 18, wherein the corresponding plurality of tags comprises a first set of tags associated with the first sentiment and a second set of tags associated with the second sentiment.

21. The method of claim 1, wherein a third interactive DR activity in the plurality of interactive DR activities comprises obtaining, in electronic form, a second assessment of the subject, the second assessment comprising a determination when the subject satisfies a threshold validation in change for the psychiatric or mental condition exhibited by the subject.

22. The method of claim 21, wherein the threshold validation in change for the psychiatric or mental condition exhibited by the subject comprises a threshold change in diagnosis status for the psychiatric or mental condition exhibited by the subject, a threshold change in subjective distress of the subject caused by the corresponding challenge, a threshold change in cognitive symptoms of the subject, a threshold change in mindfulness state of the subject, or a combination thereof.

23. The method of claim 1, wherein the psychiatric or mental condition is a clinically diagnosed mental disorder or a sub-clinically diagnosed mental disorder.

24. The method of claim 23, wherein the psychiatric or mental condition comprises being stressed in a social setting, fearing a social setting, or being overwhelmed in a social setting.

25. The method of claim 23, wherein the psychiatric or mental condition is a clinically diagnosed mental disorder, and wherein the clinically diagnosed mental disorder is an anxiety disorder, a mood disorder, a psychotic disorder, an eating disorder, an impulse control disorder, an addiction disorder, a personality disorder, an obsessive-compulsive disorder, or a post-traumatic stress disorder.

26. The method of claim 23, wherein the psychiatric or mental condition is a clinically diagnosed mental disorder, and wherein the clinically diagnosed mental disorder is an anxiety disorder, and wherein the anxiety disorder comprises a separation anxiety disorder, a selective mutism, a specific phobia, a social anxiety disorder, a panic disorder, an agoraphobia, a generalized anxiety disorder, a substance-induced anxiety disorder, or an anxiety disorder due to a medical condition of the subject.

27. The method of claim 23, wherein the psychiatric or mental condition is a clinically diagnosed mental disorder, and wherein the clinically diagnosed mental disorder is a mood disorder, and wherein the mood disorder comprises a depression disorder, a bipolar disorder, or a cyclothymic disorder.

28. The method of claim 27, wherein the depression disorder is major depressive disorder.

29. The method of claim 23, wherein the psychiatric or mental condition is a clinically diagnosed mental disorder, and wherein the clinically diagnosed mental disorder is a psychotic disorder, and wherein the psychotic disorder comprises a schizophrenia disorder, a delusion disorder, or a hallucination disorder.

30. The method of claim 23, wherein the psychiatric or mental condition is a clinically diagnosed mental disorder, and wherein the clinically diagnosed mental disorder is an eating disorder, and wherein the eating disorder comprises anorexia nervosa, bulimia nervosa, or binge eating disorder.

31. The method of claim 23, wherein the psychiatric or mental condition is a clinically diagnosed mental disorder, and wherein the clinically diagnosed mental disorder is an impulse control disorder, and wherein the impulse control disorder comprises a pyromania disorder, a kleptomania disorder, or a compulsive gambling disorder.

32. The method of claim 23, wherein the psychiatric or mental condition is a clinically diagnosed mental disorder, and wherein the clinically diagnosed mental disorder is an addiction disorder, and wherein the addiction disorder comprises an alcohol use disorder or a substance abuse disorder.

33. The method of claim 23, wherein the psychiatric or mental condition is a clinically diagnosed mental disorder, and wherein the clinically diagnosed mental disorder is a personality disorder, and wherein the personality disorder comprises an antisocial personality disorder, an obsessive-compulsive personality disorder, or a paranoid personality disorder.

34. The method of claim 1, wherein the determining is further performed by one or more models and/or a medical practitioner associated with the subject.

35. The method of claim 1, wherein the determining is further performed by one or more models, wherein the one or more models comprises a logistic regression model, a neural network model, a support vector machine model, a Naive Bayes model, a nearest neighbor model, a random forest model, a decision tree model, a boosted trees model, a multinomial logistic regression model, a linear model, a linear regression model, a Gradient Boosting model, a mixture model, a hidden Markov model, a Gaussian model, a linear discriminant model, or any combinations thereof.

36. The method of claim 1, wherein the determining is further performed by one or more models, wherein the one or models is a concordance-index model.

37. The method of claim 1, wherein the threshold condition comprises an absence, a presence, a deactivation, an activation, or a value for one or more physiological markers.

38. The method of claim 37, wherein the one or more physiological markers comprises a threshold value for skin conductance (SC), a threshold heart rate (HR), a threshold blood volume pulse (BVP), or any combination thereof.

39. The method of claim 37, wherein the threshold condition comprises a deactivation of the parasympathetic nervous system (PNS).

40. The method of claim 37, wherein the threshold condition comprises an activation of the sympathetic nervous system (SNS).

41. A computer system for implementing an exposure progression that improves an ability of a subject to manage a psychiatric or mental condition of the subject, the computer system comprising one or more processors, a display, and a memory coupled to the one or more processors, the memory comprising one or more programs configured to be executed by the one or more processors, thereby causing the computer system to perform a method comprising
  presenting, on the display, an interactive digital reality (DR) scene comprising (i) a first affordance region associated with a plurality of interactive DR activities and (ii) a second affordance region different from the first affordance region and associated with a ledger of activity performed by the subject during the plurality of interactive DR activities and persistently displayed during the plurality of interactive DR activities, and a first interactive DR activity in the plurality of interactive DR activities comprises:
    detecting, by the one or more processors, a selection by the subject of a respective recording object in one or more recording objects at the first affordance region,
    forming, by the one or more processors, a first corresponding evidence construct associated with the subject in one or more evidence constructs, wherein the first corresponding evidence construct is associated with a first statement uttered by the subject during the first interactive DR activity,
    presenting, on the display, at the first affordance region, a first visualization of the first corresponding evidence construct, and
    updating, on the display, at the second affordance region, the ledger with a second visualization of the first corresponding evidence construct different from the first visualization of the first corresponding evidence construct;
  further presenting, on the display, at the first affordance region, a second interactive DR activity in the plurality of interactive DR activities;
  determining whether the subject satisfies a threshold condition associated with each interactive DR activity in the plurality of interactive DR activities, wherein each respective threshold condition defines a criterion that must be achieved in order for the respective threshold condition to be deemed satisfied;
  obtaining, on the display, at the second affordance region, when the subject is deemed to satisfy the threshold condition associated with each interactive DR activity in the plurality of interactive DR activities, by the one or more recording objects, a second corresponding evidence construct associated with a second statement uttered by the subject in the one or more evidence constructs, wherein the second statement is a reframing of the first statement; and
  further updating, by the one or more processors, on the display, at the second affordance region, the ledger with a third visualization of the second corresponding evidence construct associated and, at a user profile associated with the subject, a historical record of the ledger, wherein the third visualization is displayed adjacent to the first visualization, thereby indicating an improvement in the management of the psychiatric or mental condition by the subject.

42. A non-transitory computer readable storage medium storing one or more programs, the one or more programs comprising instructions, which when executed by a computer system cause the computer system to perform a method comprising
  presenting, on the display, an interactive digital reality (DR) scene comprising (i) a first affordance region associated with a plurality of interactive DR activities and (ii) a second affordance region different from the first affordance region and associated with a ledger of activity performed by the subject during the plurality of interactive DR activities and persistently displayed during the plurality of interactive DR activities, and a first interactive DR activity in the plurality of interactive DR activities comprises:
    detecting, by the one or more processors, a selection by the subject of a respective recording object in one or more recording objects at the first affordance region,
    forming, by the one or more processors, a first corresponding evidence construct associated with the subject in one or more evidence constructs, wherein the first corresponding evidence construct is associated with a first statement uttered by the subject during the first interactive DR activity,
    presenting, on the display, at the first affordance region, a first visualization of the first corresponding evidence construct, and
    updating, on the display, at the second affordance region, the ledger with a second visualization of the first corresponding evidence construct different from the first visualization of the first corresponding evidence construct;
  further presenting, on the display, at the first affordance region, a second interactive DR activity in the plurality of interactive DR activities;
  determining whether the subject satisfies a threshold condition associated with each interactive DR activity in the plurality of interactive DR activities, wherein each respective threshold condition defines a criterion that must be achieved in order for the respective threshold condition to be deemed satisfied;
  obtaining, on the display, at the second affordance region, when the subject is deemed to satisfy the threshold condition associated with each interactive DR activity in the plurality of interactive DR activities, by the one or more recording objects, a second corresponding evidence construct associated with a second statement uttered by the subject in the one or more evidence constructs, wherein the second statement is a reframing of the first statement; and
  further updating, by the one or more processors, on the display, at the second affordance region, the ledger with a third visualization of the second corresponding evidence construct associated and, at a user profile associated with the subject, a historical record of the ledger, wherein the third visualization is displayed adjacent to the first visualization, thereby indicating an improvement in the management of the psychiatric or mental condition by the subject.

43. A device for implementing management of a psychiatric or mental condition, the device comprising one or more processors and a memory coupled to the one or more processors, the memory comprising one or more programs configured to be executed by the one or more processors, thereby causing the device to perform a method comprising
  presenting, on the display, an interactive digital reality (DR) scene comprising (i) a first affordance region associated with a plurality of interactive DR activities and (ii) a second affordance region different from the first affordance region and associated with a ledger of activity performed by the subject during the plurality of interactive DR activities and persistently displayed during the plurality of interactive DR activities, and a first interactive DR activity in the plurality of interactive DR activities comprises:

detecting, by the one or more processors, a selection by the subject of a respective recording object in one or more recording objects at the first affordance region,
  forming, by the one or more processors, a first corresponding evidence construct associated with the subject in one or more evidence constructs, wherein the first corresponding evidence construct is associated with a first statement uttered by the subject during the first interactive DR activity,
  presenting, on the display, at the first affordance region, a first visualization of the first corresponding evidence construct, and
  updating, on the display, at the second affordance region, the ledger with a second visualization of the first corresponding evidence construct different from the first visualization of the first corresponding evidence construct;

further presenting, on the display, at the first affordance region, a second interactive DR activity in the plurality of interactive DR activities;

determining whether the subject satisfies a threshold condition associated with each interactive DR activity in the plurality of interactive DR activities, wherein each respective threshold condition defines a criterion that must be achieved in order for the respective threshold condition to be deemed satisfied;

obtaining, on the display, at the second affordance region, when the subject is deemed to satisfy the threshold condition associated with each interactive DR activity in the plurality of interactive DR activities, by the one or more recording objects, a second corresponding evidence construct associated with a second statement uttered by the subject in the one or more evidence constructs, wherein the second statement is a reframing of the first statement; and further updating, by the one or more processors, on the display, at the second affordance region, the ledger with a third visualization of the second corresponding evidence construct associated and, at a user profile associated with the subject, a historical record of the ledger, wherein the third visualization is displayed adjacent to the first visualization, thereby indicating an improvement in the management of the psychiatric or mental condition by the subject.

44. A computer system for implementing a cognitive restructuring regimen, the computer system comprising one or more processors, a display, and a memory coupled to the one or more processors, the memory comprising one or more programs configured to be executed by the one or more processors, thereby causing the computer system to perform a method comprising:

obtaining, in electronic form, an identification of a first statement provided by a subject; and
  providing, via the display, one or more interactive DR activities, wherein each interactive DR activity in the one or more interactive DR activities is configured to help the subject to reframe a respective cognitive pattern associated with a formation of the first statement by the subject with a second cognitive pattern associated with a formation of a second statement, thereby implementing the cognitive restructuring regimen.

* * * * *